United States Patent
Kolkman et al.

(10) Patent No.: US 11,866,713 B2
(45) Date of Patent: *Jan. 9, 2024

(54) COMPOSITIONS AND METHODS FOR INCREASED PROTEIN PRODUCTION IN BACILLUS LICHENIFORMIS

(71) Applicant: DANISCO US INC, Palo Alto, CA (US)

(72) Inventors: Marc Anton Bernhard Kolkman, Oegstgeest (NL); Steven D. Doig, Wilmington, DE (US); Ryan L. Frisch, Newark, DE (US); Hongxian He, Wilmington, DE (US); Frank Wouter Koopman, Utrecht (NL); Chris Leeflang, Twisk (NL)

(73) Assignee: DANISCO US INC., Palo Alto, CA (US)

( * ) Notice: Subject to any disclaimer, the term of this patent is extended or adjusted under 35 U.S.C. 154(b) by 1047 days.

This patent is subject to a terminal disclaimer.

(21) Appl. No.: 16/486,892

(22) PCT Filed: Feb. 22, 2018

(86) PCT No.: PCT/US2018/019140
§ 371 (c)(1),
(2) Date: Aug. 19, 2019

(87) PCT Pub. No.: WO2018/156705
PCT Pub. Date: Aug. 30, 2018

(65) Prior Publication Data
US 2020/0056193 A1 Feb. 20, 2020

Related U.S. Application Data

(60) Provisional application No. 62/463,268, filed on Feb. 24, 2017.

(51) Int. Cl.
*C12N 15/75* (2006.01)
*C07K 14/32* (2006.01)
*C12P 21/02* (2006.01)

(52) U.S. Cl.
CPC .............. *C12N 15/75* (2013.01); *C07K 14/32* (2013.01); *C12P 21/02* (2013.01)

(58) Field of Classification Search
None
See application file for complete search history.

(56) References Cited

FOREIGN PATENT DOCUMENTS

| WO | 200229113 A2 | 4/2002 |
| WO | 2008066931 A2 | 6/2008 |

OTHER PUBLICATIONS

Veith et al. The Complete Genome Sequence of Bacillus licheniformis DSM13, an Organism with Great Industrial Potential J Mol Microbiol Biotechnol 2004;7:204-211 (Year: 2004).*
Accession No. AAU42468 HTH-type transcriptional regulator RghR [Bacillus licheniformis DSM 13 = ATCC 14580] 2015. (Year: 2015).*
Accession No. AE017333 Bacillus licheniformis DSM 13 = ATCC 14580, complete genome (Year: 2015).*
Dischinger J, Josten M, Szekat C, Sahl H-G, Bierbaum G (2009) Production of the Novel Two-Peptide Lantibiotic Lichenicidin by Bacillus licheniformis DSM 13. PLoS One 4(8): e6788. https://doi.org/10.1371/journal.pone.0006788 (Year: 2009).*
GenBank: AE017333.1 Bacillus licheniformis DSM 13 = ATCC 14580, complete genome, 2015 (Year: 2015).*
And GenBank: AAU42468.1 HTH-type transcriptional regulator RghR [Bacillus licheniformis DSM 13 = ATCC 14580], 2015 (Year: 2015).*
International Search Report from PCT Application No. PCT/US2018/019140 dated Jun. 11, 2018, 5 pages.
Written Opinion from PCT Application No. PCT/US2018/019140 dated Jun. 11, 2018, 6 pages.
International Preliminary Report on Patentability from PCT/US2018/019140 dated Aug. 27, 2019, 7 pages.
Hayashi et al., "Bacillus subtilis RghR (YvaN) represses rapG and rapH, which encode inhibitors of expression of the srfA operon", Molecular Microbiology 59 (6), 1714-1729, 2006.

* cited by examiner

*Primary Examiner* — Samuel C Woolwine
*Assistant Examiner* — Tiffany Nicole Grooms

(57) ABSTRACT

The present disclosure is generally related to compositions and methods for obtaining *Bacillus licheniformis* cells/strains having increased protein production capabilities. Certain embodiments of the disclosure are related to genetically modified *Bacillus licheniformis* cells/strains derived from parental *B. licheniformis* cells/strains comprising a variant rghR2 gene.

4 Claims, 9 Drawing Sheets

Specification includes a Sequence Listing.

```
                                  1                                                50
(SEQ ID NO: 4)RghR2 Bra7  (1)   MAMTRFGERLKELREQRSLSVNQLAMYAGVSAAAISRAAAISRIENGHRG
(SEQ ID NO: 2)RghR2 DSM13 (1)   MAMTRFGERLKELREQRSLSVNQLAMYAGVSAAAISR------IENGHRG 51                                               100
(SEQ ID NO: 4)RghR2 Bra7  (51)  VPKPATIRKLAEALKMPYEQLMDIAGYMRADEIREQPRGYVTMQEIAAKH
(SEQ ID NO: 2)RghR2 DSM13 (45)  VPKPATIRKLAEALKMPYEQLMDIAGYMRADEIREQPRGYVTMQEIAAKH 101                          140
(SEQ ID NO: 4)RghR2 Bra7 (101)  GVEDLWLFKPEKWDCLSREDLLNLEQYFHFLVNEAKKRQS
(SEQ ID NO: 2)RghR2 DSM13 (95)  GVEDLWLFKPEKWDCLSREDLLNLEQYFHFLVNEAKKRQS
```

COMPOSITIONS AND METHODS FOR INCREASED PROTEIN PRODUCTION IN BACILLUS LICHENIFORMIS

FIELD

The present disclosure is generally related to the fields of bacteriology, microbiology, genetics, molecular biology, enzymology, industrial protein production the like. More particularly, the present disclosure is related to compositions and methods for obtaining *Bacillus licheniformis* cells/strains (e.g., a protein production host; cell factory) having increased protein production capabilities. Thus, certain embodiments of the disclosure are related to modified *B. licheniformis* cells derived from parental *B. licheniformis* cells comprising a chromosomal rghR2 gene (variant) encoding a RghR2 protein of SEQ ID NO: 4, wherein the modified cells comprise a genetic modification of the rghR2 gene which encodes a RghR2 protein of SEQ ID NO: 2.

CROSS-REFERENCE TO RELATED APPLICATIONS

The present application claims priority to U.S. Provisional Patent Application Ser. No. 62/463,268, filed Feb. 24, 2017, which is hereby incorporated by reference in its entirety.

REFERENCE TO A SEQUENCE LISTING

The contents of the electronic submission of the text file Sequence Listing, named "NB41203USPCT_SequenceListing.txt" was created on Aug. 26, 2020 and is 183 KB in size, which is hereby incorporated by reference in its entirety.

BACKGROUND

Gram-positive bacteria such as *Bacillus subtilis, Bacillus licheniformis* and *Bacillus amyloliquefaciens* are frequently used as microbial factories for the production of industrial relevant proteins, due to their excellent fermentation properties and high yields (e.g., up to 25 grams per liter culture; Van Dijl and Hecker, 2013). For example, *B. subtilis* is well known for its production of α-amylases (Jensen et al., 2000; Raul et al., 2014) and proteases (Brode et al., 1996) necessary for food, textile, laundry, medical instrument cleaning, pharmaceutical industries and the like (Westers et al., 2004). Because these non-pathogenic Gram-positive bacteria produce proteins that completely lack toxic by-products (e.g., lipopolysaccharides; LPS, also known as endotoxins) they have obtained the "Qualified Presumption of Safety" (QPS) status of the European Food Safety Authority, and many of their products gained a "Generally Recognized As Safe" (GRAS) status from the US Food and Drug Administration (Olempska-Beer et al., 2006; Earl et al., 2008; Caspers et al., 2010).

Thus, the production of proteins (e.g., enzymes, antibodies, receptors, etc.) in microbial host cells is of particular interest in the biotechnological arts. Likewise, the optimization of *Bacillus* host cells for the production and secretion of one or more protein(s) of interest is of high relevance, particularly in the industrial biotechnology setting, wherein small improvements in protein yield are quite significant when the protein is produced in large industrial quantities. More particularly, *B. licheniformis* is a *Bacillus* species host cell of high industrial importance, and as such, the ability to modify and engineer *B. licheniformis* host cells for enhanced/increased protein expression/production is highly desirable for construction of new and improved *B. licheniformis* production strains. The present disclosure is thus related to the highly desirable and unmet need for obtaining and constructing *B. licheniformis* cells (e.g., protein production host cells) having increased protein production capabilities.

SUMMARY

The present disclosure is generally related to compositions and methods for obtaining *B. licheniformis* cells (e.g., a protein production host; cell factory) having increased protein production capabilities. Certain embodiments of the disclosure are related to a modified *Bacillus licheniformis* cell derived from a parental *B. licheniformis* cell comprising a rghR2 gene encoding a RghR2 protein comprising 90% sequence identity to SEQ ID NO: 4, wherein the modified cell comprises a genetic modification of the rghR2 gene which encodes a RghR2 protein comprising 90% sequence identity to SEQ ID NO: 2, wherein the modified host cell produces an increased amount of a protein of interest (relative to the unmodified parental cell). In certain embodiments, the RghR2 protein comprising 90% sequence identity to SEQ ID NO: 4 is substantially inactive as a transcriptional regulatory protein, relative to the RghR2 protein comprising 90% sequence identity to SEQ ID NO: 2. In other embodiments, the parental cell comprising the rghR2 gene encoding the RghR2 protein comprising 90% sequence identity to SEQ ID NO: 4 comprises an 18-nucleotide duplication in the rghR2 gene (rghR2$^{dup}$) which corresponds to a repeat of amino acids AAAISR at amino acid positions 38-43 of the RghR2 protein comprising 90% sequence identity to SEQ ID NO: 4, and wherein the modified cell comprises a modification which deletes of the 18-nucleotide duplication in the rghR2 gene (rghR2$_{rest}$), thereby encoding a RghR2 protein comprising 90% sequence identity to SEQ ID NO: 2. In certain other embodiments, the rghR2 gene encoding the RghR2 protein comprising 90% sequence identity to SEQ ID NO: 4 comprises a nucleic acid sequence having at least 90% sequence identity to SEQ ID NO:3 and comprises an 18 nucleotide duplication encoding a repeat of amino acids AAAISR at amino acid positions 38-43 of the RghR2 protein of SEQ ID NO: 4. In other embodiments, the rghR2 gene encoding the RghR2 protein of SEQ ID NO: 2 comprises a nucleic acid sequence comprising 90% sequence identity to the rghR2 gene of SEQ ID NO: 1. In yet another embodiment, the increased amount of a protein of interest is at least 1.0% increased relative to the parental cell. In certain other embodiments, the modified cell further comprising a genetic modification which disrupts, deletes, inactivates or down-regulates at least one endogenous *B. licheniformis* gene selected from the group consisting of abrB1, rpmJ, rpIM, BLi00412, rapK, phrK, BLi00753, yfjT, BLi00828, yhdX, yhzC, terf2, zosA, abbA, speG, yppF, BLi02543, mntR, BLi02768, sspA, BLi03127, BLi03635, mrgA, BLi03644, yvzC, rghR1, spo0F, ywjG, ywq12, BLi04199, BLi04200, licT, bglH and bglP. In certain embodiments, the modified cell comprises a genetic modification which deletes, disrupts or down-regulates an endogenous *B. licheniformis* gene selected from yvzC, Bli03644, AbrB1 and abh (AbrB2), or at least two endogenous *B. licheniformis* genes selected from the group consisting of yvzC, Bli03644, AbrB1 and abh (AbrB2), or at least three endogenous *B. licheniformis* genes selected from the group consisting of yvzC, Bli03644, AbrB1 and abh (AbrB2) or all four endogenous *B. licheniformis* genes yvzC, Bli03644, AbrB1 and abh (AbrB2). In another embodiment, the increased amount of a protein of interest is a heterologous protein. Thus, in certain embodiments, the modified cell comprises an expression construct encoding a heterologous protein of interest. Such expression constructs encoding heterologous proteins of interest may be introduced (e.g., transformed) into the parental *B. licheniformis* cell prior to the one or more genetic modifications described above, introduced (e.g., transformed) into the modified *B. licheniformis* (daughter) cell during the one or more genetic modifications described above, or introduced (e.g., transformed) into the modified *B. licheniformis* (daughter) after performing the one or more genetic modifications described above. In certain other embodiments, the protein of interest is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases and hexose oxidases.

In another embodiment, the disclosure is directed to a modified *B. licheniformis* cell derived from a parental *B. licheniformis* cell comprising a rghR2$_{dup}$ gene encoding a RghR2 protein of SEQ ID NO: 4, wherein the modified cell comprises a rghR2$_{rest}$ gene encoding a RghR2 protein of SEQ ID NO: 2, wherein the modified cell produces an increased amount of a protein of interest relative to the unmodified parental cell.

In certain other embodiments, the disclosure is related to a modified *B. licheniformis* cell derived from a parental *B. licheniformis* cell comprising a rghR2 gene encoding a RghR2 protein comprising 90% sequence identity to SEQ ID NO: 4, wherein the modified cell comprises a polynucleotide construct introduced therein comprising a 5' promoter region operably linked to a nucleic acid sequence encoding a RghR2 protein comprising 90% sequence identity to SEQ ID NO: 2, wherein the modified cell produces an increased amount of a protein of interest relative to the unmodified parental cell. In certain embodiments, the RghR2 protein comprising 90% sequence identity to SEQ ID NO: 4 is substantially inactive as a transcriptional regulatory protein relative to the RghR2 protein comprising 90% sequence identity to SEQ ID NO: 2. In another embodiment, the parental cell comprising the rghR2 gene encoding the RghR2 protein comprising 90% sequence identity to SEQ ID NO: 4 comprises an 18-nucleotide duplication in the rghR2 gene which corresponds to a repeat of amino acids AAAISR at amino acid positions 38-43 of the RghR2 protein comprising 90% sequence identity to SEQ ID NO: 4. In other embodiments, the modified cell further comprises a genetic modification which deletes, disrupts, inactivates or down-regulates the endogenous rghR2 gene encoding the RghR2 protein comprising 90% sequence identity to SEQ ID NO: 4. In other embodiments, the rghR2 gene encoding the RghR2 protein comprising 90% sequence identity to SEQ ID NO: 2 comprises a nucleic acid sequence having at least 90% sequence identity to SEQ ID NO: 1. In another embodiment, the modified cell further comprises a genetic modification which deletes, disrupts or down-regulates at least one endogenous *B. licheniformis* gene selected from the group consisting of yvzC, Bli03644, AbrB1 and abh (AbrB2). In certain other embodiments, the polynucleotide construct comprising a 5' promoter region operably linked to a nucleic acid sequence encoding a RghR2 protein comprising 90% sequence identity to SEQ ID NO: is comprised within a vector. In certain embodiments, the vector is a plasmid. In certain other embodiments, the vector is integrated into the *B. licheniformis* genome. In another embodiment, the vector integrates into the *B. licheniformis* genome at the native rghR2 chromosomal locus, thereby deleting or disrupting the gene encoding the RghR2 protein comprising 90% sequence identity to SEQ ID NO: 4 and inserting therefore the introduced polynucleotide construct comprising the 5' promoter region operably linked to the nucleic acid sequence encoding the RghR2 protein comprising 90% sequence identity to SEQ ID NO: 2. In other embodiments, the increased amount of a protein of interest is a heterologous protein. In another embodiment, the modified cell comprises an expression construct encoding a heterologous protein of interest. In certain embodiments, a protein of interest is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases and hexose oxidases. In other embodiments, the increased amount of a protein of interest is at least 1.0% increased relative to the parental host cell. In another embodiment, the modified cell further comprises an expression construct comprising allele glcT1 (SEQ ID NO: 144), encoding a variant GlcT protein comprising a Leucine (L) to Phenylalanine (F) substitution at amino acid position 67 of the variant GlcT protein.

In other embodiments, the disclosure is related to a modified *B. licheniformis* cell derived from a parental *B. licheniformis* cell, the modified cell comprising a genetic modification which deletes, disrupts or down-regulates an endogenous *B. licheniformis* yvzC gene encoding a YvzC protein comprising 90% sequence identity to SEQ ID NO: 18, wherein the modified cell produces an increased amount of a protein of interest relative to the unmodified parental cell.

In other embodiments, the disclosure is related to a modified *B. licheniformis* cell derived from a parental *B. licheniformis* cell, the modified cell comprising a genetic modification which deletes, disrupts or down-regulates an endogenous *B. licheniformis* Bli03644 gene encoding a Bli03644 protein comprising 90% sequence identity to SEQ ID NO: 20, wherein the modified cell produces an increased amount of a protein of interest relative to the unmodified parental cell.

In other embodiments, the disclosure is related to a modified *B. licheniformis* cell derived from a parental *B. licheniformis* cell, the modified cell comprising a genetic modification which deletes, disrupts or down-regulates an endogenous *B. licheniformis* AbrB1 gene encoding a AbrB1 protein comprising 90% sequence identity to SEQ ID NO: 22, wherein the modified cell produces an increased amount of a protein of interest relative to the unmodified parental cell.

In other embodiments, the disclosure is related to a modified *B. licheniformis* cell derived from a parental *B. licheniformis* cell, the modified cell comprising a genetic modification which deletes, disrupts or down-regulates an endogenous *B. licheniformis* abh (AbrB2) gene encoding a abh (AbrB2) protein comprising 90% sequence identity to SEQ ID NO: 24, wherein the modified cell produces an increased amount of a protein of interest relative to the unmodified parental cell.

In certain other embodiments, the disclosure is directed to a modified *B. licheniformis* cell derived from a parental *B. licheniformis* cell comprising a rghR2 gene encoding a RghR2 protein comprising 90% sequence identity to SEQ ID NO: 2, wherein the modified cell comprises a genetic modification which deletes, disrupts or down-regulates at least one endogenous *B. licheniformis* gene selected from the group consisting of yvzC, Bli03644, AbrB1 and abh (AbrB2), wherein the modified cell produces an increased amount of a protein of interest relative to the unmodified parental cell. In certain embodiments, the rghR2 gene encoding the RghR2 protein comprising 90% sequence identity to SEQ ID NO: 2, comprises a nucleic acid sequence having at least 90% sequence identity to SEQ ID NO: 1. In another embodiment, the aforementioned modified cells further comprise an expression construct comprising allele glcT1 (SEQ ID NO: 144), encoding a variant GlcT protein comprising a Leucine (L) to Phenylalanine (F) substitution at amino acid position 67 of the variant GlcT protein.

In another embodiment, the disclosure is related to a modified *B. licheniformis* cell derived from a parental *B. licheniformis* cell comprising a rghR2 gene encoding a RghR2 protein comprising 90% sequence identity to SEQ ID NO: 4, wherein the modified cell comprises a genetic modification which deletes, disrupts or down-regulates at least one endogenous *B. licheniformis* gene selected from the group consisting of yvzC, Bli03644, AbrB1 and abh (AbrB2), wherein the modified cell produces an increased amount of a protein of interest relative to the unmodified parental cell. In certain embodiments, the rghR2 gene encoding the RghR2 protein comprising 90% sequence identity to SEQ ID NO: 4, comprises a nucleic acid sequence having at least 90% sequence identity to SEQ ID NO: 3. In other embodiments, the RghR2 protein comprising 90% sequence identity to SEQ ID NO: 4 is substantially inactive as a transcriptional regulatory protein relative to the RghR2 protein comprising 90% sequence identity to SEQ ID NO: 2. In other embodiments, the parental cell comprising the rghR2 gene encoding the RghR2 protein comprising 90% sequence identity to SEQ ID NO: 4, comprises an 18-nucleotide duplication in the rghR2 gene which corresponds to a repeat of amino acids AAAISR at amino acid positions 38-43 of the RghR2 protein comprising 90% sequence identity to SEQ ID NO: 4. In certain other embodiments the increased expression of a protein of interest is a heterologous protein of interest.

In certain other embodiments, the disclosure is related to a method for restoring the activity of a substantially inactive RghR2 protein in a parental *B. licheniformis* cell, wherein the parental cell comprises a rghR2 gene encoding a substantially inactive RghR2 protein comprising 90% sequence identity to SEQ ID NO: 4, the method comprising: (a) obtaining a parental *B. licheniformis* cell comprising a gene encoding a RghR2 protein comprising 90% sequence identity to SEQ ID NO: 4, wherein gene encoding the RghR2 protein comprising 90% sequence identity to SEQ ID NO: 4 comprises an 18-nucleotide duplication in the rghR2 gene which corresponds to a repeat of amino acids AAAISR at amino acid positions 38-43 of the RghR2 protein of SEQ ID NO: 4, and (b) modifying the cell of step (a) by deleting the 18-nucleotide duplication in the rghR2 gene to yield a rghR2$_{rest}$ gene, wherein the rghR2$_{rest}$ gene thereby encodes an active RghR2 protein comprising 90% sequence identity to SEQ ID NO: 2. In certain embodiments of the method, the modified cell of step (b) further comprises an introduced polynucleotide expression construct encoding a heterologous protein of interest. In another embodiment of the method, deleting the 18-nucleotide duplication in the rghR2 gene of step (b) comprises deleting the nucleotide duplication by a method selected from homologous recombination, site directed mutagenesis, CRISPR-Cas9 gene editing, TALEN gene editing, homing endonuclease gene editing and ZFN gene editing. In certain embodiments, the rghR2 gene encoding the RghR2 protein comprising 90% sequence identity to SEQ ID NO: 4 comprises a nucleic acid sequence comprising 90% sequence identity to SEQ ID NO: 3, wherein the 18-nucleotide duplication at nucleotides 111-129 of SEQ ID NO: 3 are deleted. In other embodiments, the modified cell of step (b) further comprises a genetic modification which deletes, disrupts, or down-regulates at least one endogenous *B. licheniformis* gene selected from the group consisting of yvzC, Bli03644, AbrB1 and abh (AbrB2). In certain embodiments of the method, the genetic modification which deletes at least one endogenous *B. licheniformis* gene is a complete gene deletion or a partial deletion. In certain embodiments, a partial gene deletion comprises deleting the gene's operator, deleting the gene's promoter, deleting the gene's enhancer, deleting the gene's 5' UTR, deleting the gene's start codon, deleting the gene's encoded ribosomal binding site (RBS), deleting the gene's 3' UTR, deleting the 10% of the gene's coding sequence, deleting the 25% of the gene's coding sequence, deleting the 50% of the gene's coding sequence, deleting the 75% of the gene's coding sequence or any combination thereof.

In another embodiment, the disclosure is related to a method for restoring the activity of a substantially inactive RghR2 protein in a parental *B. licheniformis* cell, wherein the parental cell comprises a rghR2$_{dup}$ gene encoding a substantially inactive RghR2 protein comprising 90% sequence identity to SEQ ID NO: 4, the method comprising: (a) obtaining a parental *B. licheniformis* cell comprising a rghR2$_{dup}$ gene encoding a RghR2 protein comprising at least 90% sequence identity to SEQ ID NO: 4, wherein the rghR2$_{dup}$ gene encoding the RghR2 protein of SEQ ID NO: 4 comprises an 18-nucleotide duplication in the rghR2 gene which corresponds to a repeat of amino acids AAAISR at amino acid positions 38-43 of the RghR2 protein of SEQ ID NO: 4, (b) modifying the parental cell of step (a) by introducing therein a polynucleotide construct comprising a 5' promoter region operably linked to a rghR2$_{rest}$ nucleic acid sequence encoding a RghR2 protein comprising 90% sequence identity to SEQ ID NO: 2, and (c) expressing the polynucleotide construct introduced into the modified cell of step (b) encoding the active RghR2 protein comprising 90% sequence identity to SEQ ID NO: 2. In particular embodiments, the modified cell comprises an introduced polynucleotide expression construct encoding a heterologous protein of interest. In another embodiment, the modified cell comprises a genetic modification which deletes, disrupts, or down-regulates at least one endogenous *B. licheniformis* gene selected from the group consisting of yvzC, Bli03644, AbrB1 and abh (AbrB2). In another embodiment, the genetic modification which deletes at least one endogenous *B. licheniformis* gene is a complete gene deletion or a partial deletion. In certain embodiments, a partial gene deletion comprises deleting the gene's operator, deleting the gene's promoter, deleting the gene's enhancer, deleting the gene's 5' UTR, deleting the gene's start codon, deleting the gene's encoded ribosomal binding site (RBS), deleting the gene's 3' UTR, deleting the 10% of the gene's coding sequence, deleting the 25% of the gene's coding sequence, deleting the 50% of the gene's coding sequence, deleting the 75% of the gene's coding sequence or any combination thereof.

In other embodiments, the disclosure is related to a method for increasing the production of an endogenous protein of interest in *B. licheniformis* cells comprising: (a) obtaining a parental *B. licheniformis* cell comprising a gene encoding a RghR2 protein comprising at least 90% sequence identity to SEQ ID NO: 4, wherein gene encoding the RghR2 protein of SEQ ID NO: 4 comprises an 18-nucleotide duplication in the rghR2 gene which corresponds to a repeat of amino acids AAAISR at amino acid positions 38-43 of the RghR2 protein of SEQ ID NO: 4, (b) modifying the cell of step (a) by deleting the 18-nucleotide duplication in the rghR2 gene, wherein the rghR2 gene thereby encodes a RghR2 protein comprising 90% sequence identity to SEQ ID NO: 2, (c) cultivating the modified cell of step (b) in a medium suitable for the production of the endogenous protein, and (d) recovering the endogenous protein produced in step (c) from the cultivation medium or cell lysate, wherein the modified *B. licheniformis* cell of step (b) produces an increased amount of the endogenous protein, relative to the parental *B. licheniformis* cell obtained in step (a), when both the cells of step (a) and the cells of step (b) are cultivated under the same conditions. In certain embodiments, the rghR2 gene encoding the RghR2 protein comprising 90% sequence identity to SEQ ID NO: 4 comprises a nucleic acid sequence comprising 90% sequence identity to SEQ ID NO: 3, wherein the 18-nucleotide duplication at nucleotides 111-129 of SEQ ID NO: 3 are deleted. In certain embodiments, the genetic modification which deletes at least one endogenous *B. licheniformis* gene is a complete gene deletion or a partial gene deletion. In certain embodiments, a partial gene deletion comprises deleting the gene's operator, deleting the gene's promoter, deleting the gene's enhancer, deleting the gene's 5' UTR, deleting the gene's start codon, deleting the gene's encoded ribosomal binding site (RBS), deleting the gene's 3' UTR, deleting 10% of the gene's coding sequence, deleting 25% of the gene's coding sequence, deleting 50% of the gene's coding sequence, deleting 75% of the gene's coding sequence or any combination thereof.

In yet other embodiments the disclosure is directed to a method for increasing the production of a heterologous protein of interest in *B. licheniformis* cells comprising: (a) obtaining a parental *B. licheniformis* cell comprising a gene encoding a RghR2 protein comprising at least 90% sequence identity to SEQ ID NO: 4, wherein gene encoding the RghR2 protein of SEQ ID NO: 4 comprises an 18-nucleotide duplication in the rghR2 gene which corresponds to a repeat of amino acids AAAISR at amino acid positions 38-43 of the RghR2 protein of SEQ ID NO: 4, (b) modifying the cell of step (a) by deleting the 18-nucleotide duplication in the rghR2 gene, wherein the rghR2 gene thereby encodes a RghR2 protein comprising 90% sequence identity to SEQ ID NO: 2, (c) introducing an expression construct encoding a heterologous protein into the modified *B. licheniformis* cell of step (b), (d) cultivating the modified cell of step (c) in a medium suitable for the production of the heterologous protein, and (e) recovering the heterologous protein produced in step (d) from the cultivation medium or cell lysate, wherein the modified *B. licheniformis* cell of step (b) produces an increased amount of the heterologous protein relative to the parental *B. licheniformis* cell obtained in step (a), comprising the same introduced expression construct encoding the heterologous protein, when both the cells of step (a) and cells of step (b) are cultivated under the same conditions. In certain embodiments, the rghR2 gene encoding the RghR2 protein comprising 90% sequence identity to SEQ ID NO: 4 comprises a nucleic acid sequence comprising 90% sequence identity to SEQ ID NO: 3, wherein the 18-nucleotide duplication at nucleotides 111-129 of SEQ ID NO: 3 are deleted.

In certain other embodiments, the disclosure is related to a method for restoring the activity of a substantially inactive RghR2 protein in a parental *B. licheniformis* cell, wherein the parental cell comprises a rghR2 gene encoding a substantially inactive RghR2 protein comprising 90% sequence identity to SEQ ID NO: 4, the method comprising: (a) obtaining a parental *B. licheniformis* cell comprising a gene encoding a RghR2 protein comprising at least 90% sequence identity to SEQ ID NO: 4, wherein gene encoding the RghR2 protein of SEQ ID NO: 4 comprises an 18-nucleotide duplication in the rghR2 gene which corresponds to a repeat of amino acids AAAISR at amino acid positions 38-43 of the RghR2 protein of SEQ ID NO: 4, and (b) modifying the parental cell of step (a) by: (i) deleting the 18-nucleotide duplication in the rghR2 gene, or (ii) by deleting, disrupting, or down-regulating the rghR2 gene, and (c) deleting, disrupting, or down-regulating at least one endogenous *B. licheniformis* gene selected from the group consisting of yvzC, Bli03644, AbrB1 and abh (AbrB2), wherein the modified cell produces an increased amount of a protein of interest relative to the unmodified parental cell.

In other embodiments, the disclosure is directed to isolated (modified) *B. licheniformis* cell produced by the methods disclosed herein.

In other embodiments, the disclosure is related to a method for identifying a *B. licheniformis* strain comprising a variant rghR2 gene encoding a substantially inactive RghR2 protein, the method comprising: (a) obtaining a *B. licheniformis* strain and sequencing the rghR2 gene therein, (b) aligning and comparing the sequenced rghR2 gene with the native rghR2 gene of SEQ ID NO: 1, wherein a *B. licheniformis* strain comprising a sequenced rghR2 gene comprising an insertion, deletion, substitution and/or duplication of one or more nucleotides in the HTH domain of the rghR2 gene of SEQ ID NO: 1 comprises a variant rghR2 gene encoding a substantially inactive RghR2 protein. In certain embodiments, the HTH domain of a native rghR2 protein of SEQ ID NO: 2 is comprised within amino acid residues 5-58 of SEQ ID NO: 2. In another embodiment, the insertion of one or more nucleotides in the HTH domain of the rghR2 gene of is between nucleotides 111 and 112 of SEQ ID NO: 1. In another embodiment, the *B. licheniformis* strain comprising a variant rghR2 gene encoding a substantially inactive RghR2 protein comprises a six amino acid repeat present in the RghR2 variant protein of SEQ ID NO: 4.

Thus, certain embodiments of the disclosure are related to modified *Bacillus licheniformis* cells (i.e., daughter cells) derived from parental *B. licheniformis* cells, wherein the modified (daughter) cells are capable of expressing/producing increased amounts of one or more proteins of interest, particularly industrially relevant proteins (enzymes) such as amylases, proteases, lipases, esterases and the like.

BRIEF DESCRIPTION OF DRAWINGS

FIG. 1 shows an amino acid sequence alignment of the RghR2 protein (SEQ ID NO: 2) of *B. licheniformis* DSM13 strain and the RghR2 protein of *B. licheniformis* Bra7 strain. As presented in FIG. 1, the RghR2 protein (SEQ ID NO: 4) from *B. licheniformis* isolates Bra7, a Bra7 derived isolate, T5, ATCC-6598 and ATCC-9789 (e.g., see the full length variant RghR2 protein of SEQ ID NO: 4), each comprise a direct repeat of amino acids "Ala-Ala-Ala-Ile-Ser-Arg". For example, as presented in FIG. 1, the variant RghR2 proteins from *B. licheniformis* isolates Bra7, Bra7 derivative, T5, ATCC-6598 and ATCC-9789 (SEQ ID NO: 4) comprise the six (6) amino acid repeat "AAISR" inserted as follows: $Ala_{32}$-$Ala_{33}$-$Ala_{34}$-$Ile_{35}$-$Ser_{36}$-$Arg_{37}$-$Ala_{38}$-$Ala_{39}$-$Ala_{40}$-$Ile_{41}$-$Ser_{42}$-$Arg_{43}$ (SEQ ID NO: 6). In contrast, as presented in FIG. 1, the native RghR2 proteins from *B. licheniformis* isolates such as DSM13, ATCC-27811 and DSM603, do not comprise the repeated "Ala-Ala-Ala-Ile-Ser-Arg" sequence set forth in SEQ ID NO: 6 (e.g., see full length native RghR2 protein of SEQ ID NO: 2).

FIG. 8 shows codons in the DSM13 rghR2 gene (SEQ ID NO: 1), indicated in bold, encoding residues involved in DNA binding. The 18-bp sequence duplicated in the rghR2 gene of *B. licheniformis* strains Bra7, T5, ATCC-9789 and ATCC-6598 is located in a region predicted to encode a sequence-specific DNA binding site.

BRIEF DESCRIPTION OF THE BIOLOGICAL SEQUENCES

Figure 2:
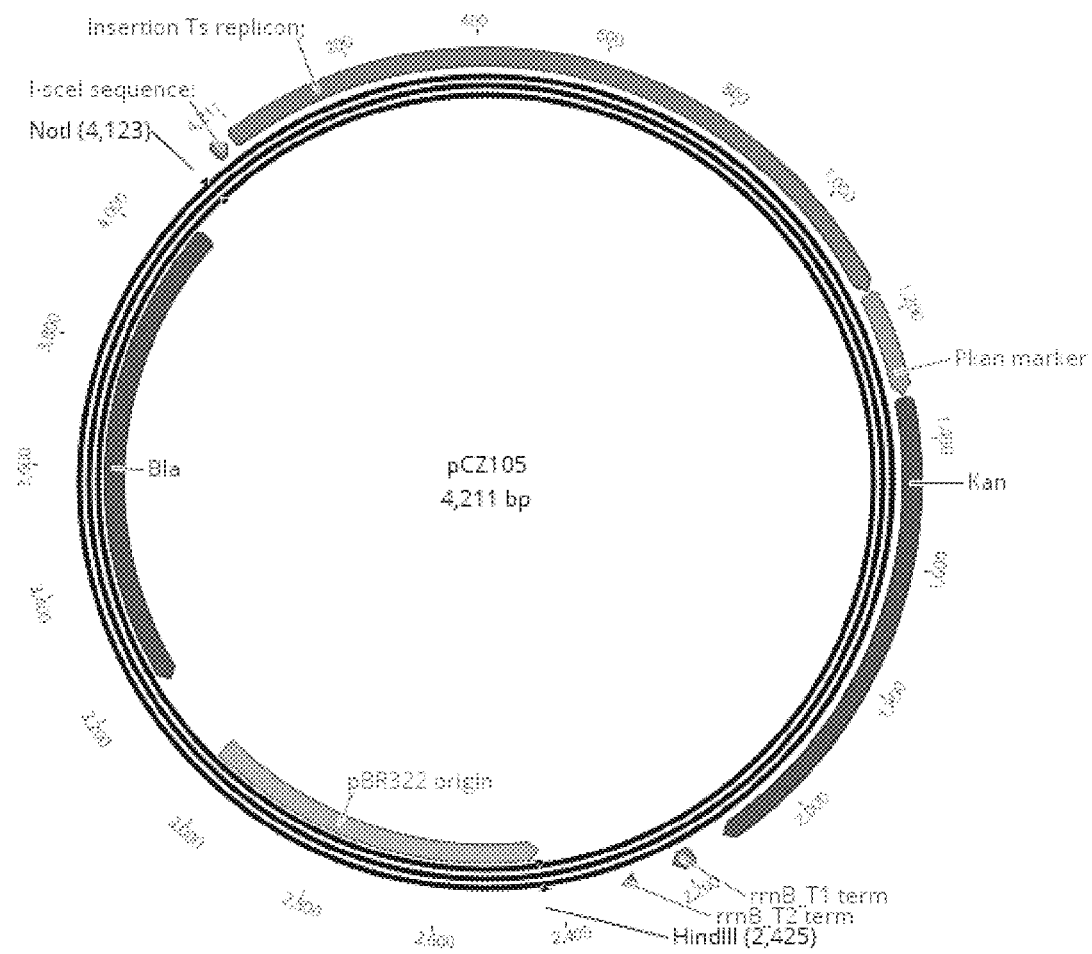
FIG. 2 shows plasmid "pCZ105", which comprises various restriction enzyme sites, amongst which are the HindIII and NotI, a pE194 temperature sensitive replicon (Ts replicon), a kanamycin coding sequence (Kan), a kanamycin promoter (pKan marker), a ribosomal terminator sequence (Term rrnB), a β-lactamase ("Bla") gene and an I-Sce site are present.

SEQ ID NO: 1 is a nucleic acid sequence encoding a native *Bacillus licheniformis* RghR2 protein of SEQ ID NO: 2.

SEQ ID NO: 2 is the amino acid sequence of the native *B. licheniformis* RghR2 protein encoded by nucleic acid sequence of SEQ ID NO: 1.

SEQ ID NO: 3 is a variant *B. licheniformis* nucleic acid sequence encoding a variant *B. licheniformis* RghR2 protein of SEQ ID NO: 4. More particularly, the variant nucleic acid sequence of SEQ ID NO: 3 comprises an 18-base pair (bp) nucleotide duplication, which is not present in the nucleic acid sequence of SEQ ID NO: 1.

SEQ ID NO: 4 is the amino acid sequence of the variant RghR2 protein encoded by the nucleic acid sequence of SEQ ID NO: 3. More particularly, the variant RghR2 protein of SEQ ID NO: 4 comprises a six (6) amino acid residue repeat of "Ala-Ala-Ala-Ile-Ser-Arg" at amino acid residues 36-41 (of SEQ ID NO: 4), wherein the native RghR2 protein of SEQ ID NO: 2 does not comprise the six (6) amino acid residue repeat of "Ala-Ala-Ala-Ile-Ser-Arg" at amino acid residues 36-41.

SEQ ID NO: 5 shows amino acid residues 30-35 ($Ala_{30}$-$Ala_{31}$-$Ala_{32}$-$Ile_{33}$-$Ser_{34}$-$Arg_{35}$) of the native *B. licheniformis* RghR2 protein (i.e., encoded by SEQ ID NO: 1).

SEQ ID NO: 6 shows amino acid residues 30-41 ($Ala_{30}$-$Ala_{31}$-$Ala_{32}$-$Ile_{33}$-$Ser_{34}$-$Arg_{35}$-$Ala_{36}$-$Ala_{37}$-$Ala_{38}$-$Ile_{39}$-$Ser_{40}$-$Arg_{41}$) of the variant *B. licheniformis* RghR2 protein encoded by SEQ ID NO: 3), which comprises a repeat of SEQ ID NO: 5 at amino acid positions 36-41 in SEQ ID NO: 4. Thus, the 18-bp nucleotide duplication set forth in SEQ ID NO: 3 encodes a 6-amino acid repeat of Ala-Ala-Ala-Ile-Ser-Arg, which is represented herein as "Ala-Ala-Ala-Ile-Ser-Arg-Ala-Ala-Ala-Ile-Ser-Arg" as set forth in SEQ ID NO: 6.

SEQ ID NO: 7 is a nucleic acid sequence of primer 369.
SEQ ID NO: 8 is a nucleic acid sequence of primer 378.
SEQ ID NO: 9 is a nucleic acid sequence of primer 379.
SEQ ID NO: 10 is a nucleic acid sequence of primer 380.
SEQ ID NO: 11 is a nucleic acid sequence of primer 381.
SEQ ID NO: 12 is a nucleic acid sequence of primer 384.
SEQ ID NO: 13 is a nucleic acid sequence of primer 752.
SEQ ID NO: 14 is a nucleic acid sequence of primer 753.
SEQ ID NO: 15 is a nucleic acid sequence encoding a native *Bacillus licheniformis* RghR1 protein of SEQ ID NO: 16.

SEQ ID NO: 16 is the amino acid sequence of the native *B. licheniformis* RghR1 protein encoded by nucleic acid sequence of SEQ ID NO: 15.

SEQ ID NO: 17 is the nucleic acid sequence encoding the *B. licheniformis* YvzC protein of SEQ ID NO: 18.

SEQ ID NO: 18 is the amino acid sequence of the *B. licheniformis* YvzC protein encoded by nucleic acid sequence of SEQ ID NO: 17.

SEQ ID NO: 19 is the nucleic acid sequence encoding the *B. licheniformis* Bli03644 protein of SEQ ID NO: 20.

SEQ ID NO: 20 is the amino acid sequence of the *B. licheniformis* Bli03644 protein encoded by nucleic acid sequence of SEQ ID NO: 19.

SEQ ID NO: 21 is the nucleic acid sequence encoding the *B. licheniformis* AbrB1 protein of SEQ ID NO: 22.

SEQ ID NO: 22 is the amino acid sequence of the *B. licheniformis* AbrB1 protein encoded by nucleic acid sequence of SEQ ID NO: 21.

SEQ ID NO: 23 is the nucleic acid sequence encoding the *B. licheniformis* Abh (AbrB2) protein of SEQ ID NO: 24.

SEQ ID NO: 24 is the amino acid sequence of the *B. licheniformis* Abh (AbrB2) protein encoded by nucleic acid sequence of SEQ ID NO: 23.

SEQ ID NO: 25 is the nucleic acid sequence encoding the *B. licheniformis* RpmJ protein of SEQ ID NO: 26.

SEQ ID NO: 26 is the amino acid sequence of the *B. licheniformis* RpmJ protein encoded by nucleic acid sequence of SEQ ID NO: 25.

SEQ ID NO: 27 is the nucleic acid sequence encoding the *B. licheniformis* RplM protein of SEQ ID NO: 28.

SEQ ID NO: 28 is the amino acid sequence of the *B. licheniformis* RplM protein encoded by nucleic acid sequence of SEQ ID NO: 27.

SEQ ID NO: 29 is the nucleic acid sequence encoding the *B. licheniformis* BLi00412 protein of SEQ ID NO: 30.

SEQ ID NO: 30 is the amino acid sequence of the *B. licheniformis* BLi00412 protein encoded by nucleic acid sequence of SEQ ID NO: 29.

SEQ ID NO: 31 is the nucleic acid sequence encoding the *B. licheniformis* RapK protein of SEQ ID NO: 32.

SEQ ID NO: 32 is the amino acid sequence of the *B. licheniformis* RapK protein encoded by nucleic acid sequence of SEQ ID NO: 31.

SEQ ID NO: 33 is the nucleic acid sequence encoding the *B. licheniformis* PhrK protein of SEQ ID NO: 34.

SEQ ID NO: 34 is the amino acid sequence of the *B. licheniformis* PhrK protein encoded by nucleic acid sequence of SEQ ID NO: 33.

SEQ ID NO: 35 is the nucleic acid sequence encoding the *B. licheniformis* BLi00753 protein of SEQ ID NO: 36.

SEQ ID NO: 36 is the amino acid sequence of the *B. licheniformis* BLi00753 protein encoded by nucleic acid sequence of SEQ ID NO: 35.

SEQ ID NO: 37 is the nucleic acid sequence encoding the *B. licheniformis* YfjT protein of SEQ ID NO: 38.

SEQ ID NO: 38 is the amino acid sequence of the *B. licheniformis* YfjT protein encoded by nucleic acid sequence of SEQ ID NO: 37.

SEQ ID NO: 39 is the nucleic acid sequence encoding the *B. licheniformis* BLi00828 protein of SEQ ID NO: 40.

SEQ ID NO: 40 is the amino acid sequence of the *B. licheniformis* BLi00828 protein encoded by nucleic acid sequence of SEQ ID NO: 39.

SEQ ID NO: 41 is the nucleic acid sequence encoding the *B. licheniformis* YhdX protein of SEQ ID NO: 42.

SEQ ID NO: 42 is the amino acid sequence of the *B. licheniformis* YhdX protein encoded by nucleic acid sequence of SEQ ID NO: 41.

SEQ ID NO: 43 is the nucleic acid sequence encoding the *B. licheniformis* YhzC protein of SEQ ID NO: 44.

SEQ ID NO: 44 is the amino acid sequence of the *B. licheniformis* YhzC protein encoded by nucleic acid sequence of SEQ ID NO: 43.

SEQ ID NO: 45 is the nucleic acid sequence encoding the *B. licheniformis* Terf2 protein of SEQ ID NO: 46.

SEQ ID NO: 46 is the amino acid sequence of the *B. licheniformis* Terf2 protein encoded by nucleic acid sequence of SEQ ID NO: 45.

SEQ ID NO: 47 is the nucleic acid sequence encoding the *B. licheniformis* ZosA protein of SEQ ID NO: 48.

SEQ ID NO: 48 is the amino acid sequence of the *B. licheniformis* ZosA protein encoded by nucleic acid sequence of SEQ ID NO: 47.

SEQ ID NO: 49 is the nucleic acid sequence encoding the *B. licheniformis* AbbA protein of SEQ ID NO: 50.

SEQ ID NO: 50 is the amino acid sequence of the *B. licheniformis* AbbA protein encoded by nucleic acid sequence of SEQ ID NO: 49.

SEQ ID NO: 51 is the nucleic acid sequence encoding the *B. licheniformis* SpeG protein of SEQ ID NO: 52.

SEQ ID NO: 52 is the amino acid sequence of the *B. licheniformis* SpeG protein encoded by nucleic acid sequence of SEQ ID NO: 51.

SEQ ID NO: 53 is the nucleic acid sequence encoding the *B. licheniformis* YppF protein of SEQ ID NO: 54.

SEQ ID NO: 54 is the amino acid sequence of the *B. licheniformis* YppF protein encoded by nucleic acid sequence of SEQ ID NO: 53.

SEQ ID NO: 55 is the nucleic acid sequence encoding the *B. licheniformis* BLi02543 protein of SEQ ID NO: 56.

SEQ ID NO: 56 is the amino acid sequence of the *B. licheniformis* BLi02543 protein encoded by nucleic acid sequence of SEQ ID NO: 55.

SEQ ID NO: 57 is the nucleic acid sequence encoding the *B. licheniformis* MntR protein of SEQ ID NO: 58.

SEQ ID NO: 58 is the amino acid sequence of the *B. licheniformis* MntR protein encoded by nucleic acid sequence of SEQ ID NO: 57.

SEQ ID NO: 59 is the nucleic acid sequence encoding the *B. licheniformis* BLi02768 protein of SEQ ID NO: 60.

SEQ ID NO: 60 is the amino acid sequence of the *B. licheniformis* BLi02768 protein encoded by nucleic acid sequence of SEQ ID NO: 59.

SEQ ID NO: 61 is the nucleic acid sequence encoding the *B. licheniformis* SspA protein of SEQ ID NO: 62.

SEQ ID NO: 62 is the amino acid sequence of the *B. licheniformis* SspA protein encoded by nucleic acid sequence of SEQ ID NO: 61.

SEQ ID NO: 63 is the nucleic acid sequence encoding the *B. licheniformis* BLi03127 protein of SEQ ID NO: 64.

SEQ ID NO: 64 is the amino acid sequence of the *B. licheniformis* BLi03127 protein encoded by nucleic acid sequence of SEQ ID NO: 63.

SEQ ID NO: 65 is the nucleic acid sequence encoding the *B. licheniformis* BLi03635 protein of SEQ ID NO: 66.

SEQ ID NO: 66 is the amino acid sequence of the *B. licheniformis* BLi03635 protein encoded by nucleic acid sequence of SEQ ID NO: 65.

SEQ ID NO: 67 is the nucleic acid sequence encoding the *B. licheniformis* MrgA protein of SEQ ID NO: 68.

SEQ ID NO: 68 is the amino acid sequence of the *B. licheniformis* MrgA protein encoded by nucleic acid sequence of SEQ ID NO: 67.

SEQ ID NO: 69 is the nucleic acid sequence encoding the *B. licheniformis* Spo0F protein of SEQ ID NO: 70.

SEQ ID NO: 70 is the amino acid sequence of the *B. licheniformis* Spo0F protein encoded by nucleic acid sequence of SEQ ID NO: 69.

SEQ ID NO: 71 is the nucleic acid sequence encoding the *B. licheniformis* YwjG protein of SEQ ID NO: 72.

SEQ ID NO: 72 is the amino acid sequence of the *B. licheniformis* YwjG protein encoded by nucleic acid sequence of SEQ ID NO: 71.

SEQ ID NO: 73 is the nucleic acid sequence encoding the *B. licheniformis* YwqI2 protein of SEQ ID NO: 74.

SEQ ID NO: 74 is the amino acid sequence of the *B. licheniformis* YwqI2 protein encoded by nucleic acid sequence of SEQ ID NO: 73.

SEQ ID NO: 75 is the nucleic acid sequence encoding the *B. licheniformis* BLi04199 protein of SEQ ID NO: 76.

SEQ ID NO: 76 is the amino acid sequence of the *B. licheniformis* BLi04199 protein encoded by nucleic acid sequence of SEQ ID NO: 75.

SEQ ID NO: 77 is the nucleic acid sequence encoding the *B. licheniformis* BLi04200 protein of SEQ ID NO: 78.

SEQ ID NO: 78 is the amino acid sequence of the *B. licheniformis* BLi04200 protein encoded by nucleic acid sequence of SEQ ID NO: 77.

SEQ ID NO: 79 is the nucleic acid sequence encoding the *B. licheniformis* LicT protein of SEQ ID NO: 80.

SEQ ID NO: 80 is the amino acid sequence of the *B. licheniformis* LicT protein encoded by nucleic acid sequence of SEQ ID NO: 79.

SEQ ID NO: 81 is the nucleic acid sequence encoding the *B. licheniformis* BglH protein of SEQ ID NO: 82.

SEQ ID NO: 82 is the amino acid sequence of the *B. licheniformis* BglH protein encoded by nucleic acid sequence of SEQ ID NO: 81.

SEQ ID NO: 83 is the nucleic acid sequence encoding the *B. licheniformis* BglP protein of SEQ ID NO: 84.

SEQ ID NO: 84 is the amino acid sequence of the *B. licheniformis* BglP protein encoded by nucleic acid sequence of SEQ ID NO: 83.

SEQ ID NO: 85 is the nucleic acid sequence encoding the *B. licheniformis* ComK protein of SEQ ID NO: 86.

SEQ ID NO: 86: is the amino acid sequence of the *B. licheniformis* ComK protein encoded by nucleic acid sequence of SEQ ID NO: 85.

SEQ ID NO: 87 is the nucleotide sequence of the *B. licheniformis* Bra7 strain 18-bp duplication.

SEQ ID NO: 88 is the amino acid sequence of the *S. pyogenes* Cas9 protein.

SEQ ID NO: 89 is the amino acid sequence of the *Acidominococcus* sp. Cpf1 protein.

SEQ ID NO: 90 is the amino acid sequence of the N gregoryi Ago protein.

SEQ ID NO: 91 is the nucleic acid sequence encoding the *S. pyogenes* Cas9 protein of SEQ ID NO: 88.

SEQ ID NO: 92 is a codon optimized nucleic acid sequence encoding the *S. pyogenes* Cas9 protein of SEQ ID NO: 88.

SEQ ID NO: 93 is the nucleic acid sequence of the *B. subtilis* aprE promoter.

SEQ ID NO: 94 is the nucleic acid sequence of the *B. subtilis* xylA promoter.

SEQ ID NO: 95 is a spac promoter nucleic acid sequence.

SEQ ID NO: 96 is a Hyper-spank promoter nucleic acid sequence.

SEQ ID NO: 97 is the nucleic acid sequence of the *B. subtilis* veg promoter.

SEQ ID NO: 98 is the nucleic acid sequence of the *B. subtilis* nprE promoter.

SEQ ID NO: 99 is the nucleic acid sequence of the T5 phage N25 promoter.

SEQ ID NO: 100 is the nucleic acid sequence of the *B. subtilis* groE promoter.

SEQ ID NO: 101 is the nucleic acid sequence of the *B. subtilis* AraA promoter.

SEQ ID NO: 102 is the nucleic acid sequence of the *B. subtilis* AraA2 promoter.

SEQ ID NO: 103 is the nucleic acid sequence of a lambda phage T0 terminator.

SEQ ID NO: 104 is a nucleic acid sequence of a Cas9 expression cassette.

SEQ ID NO: 105 is the nucleic acid sequence of the *B. licheniformis* (Bra7) 18-bp duplication.

SEQ ID NO: 106 is a nucleic acid sequence of a 17-bp VT.

SEQ ID NO: 107 is a nucleic acid sequence of an 18-bp VT.

SEQ ID NO: 108 is a nucleic acid sequence of a 19-bp VT.

SEQ ID NO: 109 is a nucleic acid sequence of a 20-bp VT.

SEQ ID NO: 110 is a nucleic acid sequence encoding a Cas9 endonuclease recognition domain.

SEQ ID NO: 111 is a nucleic acid sequence encoding a guide-RNA (gRNA) targeting the 18-bp duplication.

SEQ ID NO: 112 is a nucleic acid sequence encoding a gRNA expression cassette.

SEQ ID NO: 113 is a 500-bp nucleic acid sequence which is 5' (upstream) of the 18-bp duplication.

SEQ ID NO: 114 is a 500-bp nucleic acid sequence which is 3' (downstream) of the 18-bp duplication.

SEQ ID NO: 115 is a rghR2 (18-bp duplication) editing template nucleic acid sequence.

SEQ ID NO: 116 is the *B. licheniformis* (Bra7) nucleic acid sequence comprising the rghR2 gene.

SEQ ID NO: 117 is a forward primer sequence directed to the rghR2 gene locus.

SEQ ID NO: 118 is a reverse primer sequence directed to the rghR2 gene locus.

SEQ ID NO: 119 is a nucleic acid sequence comprising the edited rghR2 locus.

SEQ ID NO: 120 is an rghR2 sequencing primer.

SEQ ID NO: 121 is a *B. licheniformis* yvc target site 1 nucleic acid sequence.

SEQ ID NO 122 is a *B. licheniformis* yvc target site 2 nucleic acid sequence.

SEQ ID NO: 123 is a *B. licheniformis* yvc target site 3 nucleic acid sequence.

SEQ ID NO: 124 is a *B. licheniformis* yvc target site 4 nucleic acid sequence.

SEQ ID NO: 125 is a *B. licheniformis* yvc target site 5 nucleic acid sequence.

SEQ ID NO: 126 is a *B. licheniformis* yvc target site 6 nucleic acid sequence.

SEQ ID NO: 127 is a *B. licheniformis* yvc target site 7 nucleic acid sequence.

SEQ ID NO: 128 is a *B. licheniformis* yvc target site 8 nucleic acid sequence.

SEQ ID NO: 129 is a *B. licheniformis* yvc target site 9 nucleic acid sequence.

SEQ ID NO: 130 is a *B. licheniformis* yvc target site 10 nucleic acid sequence.

SEQ ID NO: 131 is a *B. licheniformis* yvc target site 11 nucleic acid sequence.

SEQ ID NO: 132 is a *B. licheniformis* yvc target site 12 nucleic acid sequence.

SEQ ID NO: 133 is a *B. licheniformis* yvc target site 13 nucleic acid sequence.

SEQ ID NO: 134 is a *B. licheniformis* yvc target site 14 nucleic acid sequence.

SEQ ID NO: 135 is a *B. licheniformis* yvc target site 15 nucleic acid sequence.

SEQ ID NO: 136 is a *B. licheniformis* yvc target site 16 nucleic acid sequence.

SEQ ID NO: 137 is a *B. licheniformis* yvc target site 17 nucleic acid sequence.

SEQ ID NO: 138 is a *B. licheniformis* yvc target site 18 nucleic acid sequence.

SEQ ID NO: 139 is a *B. licheniformis* yvc target site 19 nucleic acid sequence.

SEQ ID NO: 140 is a nucleic acid sequence comprising a *Cytophaga* sp. variant #1 α-amylase expression cassette.

SEQ ID NO: 141 is a nucleic acid sequence comprising a *Geobacillus stearothermophilus* variant α-amylase expression cassette.

SEQ ID NO: 142 is a nucleic acid sequence comprising a *Pseudomonas* sp. AM1 variant α-amylase expression cassette.

SEQ ID NO: 143 is a nucleic acid sequence comprising a *Cytophaga* sp. variant #2 α-amylase expression cassette.

SEQ ID NO: 144 is a synthetic nucleic acid sequence comprising allele glcT1 (C199T).

DETAILED DESCRIPTION

The present disclosure is generally related to compositions and methods for obtaining *Bacillus licheniformis* cells/strains having increased protein production capabilities. Certain embodiments of the disclosure are related to genetically modified *Bacillus licheniformis* cells/strains derived from parental *B. licheniformis* cells/strains comprising a variant rghR2 gene. Thus, certain other embodiments of the disclosure are related to modified *B. licheniformis* cells derived from parental *B. licheniformis* cells comprising a chromosomal rghR2 gene (variant) encoding a RghR2 protein of SEQ ID NO: 4, wherein the modified cells comprise a genetic modification of the rghR2 gene which encodes a RghR2 protein of SEQ ID NO: 2. Certain other embodiments of the disclosure are related to modified *B. licheniformis* cells derived from parental *B. licheniformis* cells comprising a rghR2 gene encoding a RghR2 protein comprising 90% sequence identity to SEQ ID NO: 4, wherein the modified cells comprise a genetic modification of the rghR2 gene which encodes a RghR2 protein comprising 90% sequence identity to SEQ ID NO: 2, wherein the modified cells produce an increased amount of a protein of interest (i.e., relative to the unmodified parental cells).

In other embodiments, the disclosure is related to modified *B. licheniformis* cells derived from parental *B. licheniformis* cells comprising a rghR2 gene encoding a RghR2 protein comprising 90% sequence identity to SEQ ID NO: 4, wherein the modified cells comprise a polynucleotide construct introduced therein comprising a 5' promoter region operably linked to a nucleic acid sequence encoding a RghR2 protein comprising 90% sequence identity to SEQ ID NO: 2, wherein the modified cells produce an increased amount of a protein of interest (relative to the unmodified parental cells).

In other embodiments, the disclosure is related to modified *B. licheniformis* cells derived from parental *B. licheniformis* cells comprising a rghR2 gene encoding a RghR2 protein comprising 90% sequence identity to SEQ ID NO: 2, wherein the modified cell comprises a genetic modification which deletes, disrupts, inactivates or down-regulates at least one endogenous *B. licheniformis* gene selected from yvzC, BLi03644, AbrB1 and abh (AbrB2), wherein the modified cells produce an increased amount of a protein of interest (relative to the unmodified parental cells).

In other embodiments, the disclosure is related to modified *B. licheniformis* cells derived from parental *B. licheniformis* cells comprising a rghR2 gene encoding a RghR2 protein comprising 90% sequence identity to SEQ ID NO: 4, wherein the modified cell comprises a genetic modification which deletes, disrupts, inactivates or down-regulates at least one endogenous *B. licheniformis* gene selected from yvzC, BLi03644, AbrB1 and abh (AbrB2), wherein the modified cells produce an increased amount of a protein of interest (relative to the unmodified parental cells).

In certain other embodiments, the disclosure is related to modified *B. licheniformis* cells derived from parental *B. licheniformis* cells comprising a rghR2 gene encoding a RghR2 protein comprising 90% sequence identity to SEQ ID NO: 4, wherein the modified cells comprise a genetic modification which deletes the 18-nucleotide (18-bp) duplication in the rghR2 gene.

In other embodiments, the disclosure is related to modified *B. licheniformis* cells derived from parental *B. licheniformis* cells comprising a rghR2 gene encoding a RghR2 protein comprising 90% sequence identity to SEQ ID NO: 4, wherein the modified cells comprise a genetic modification which deletes, disrupts, inactivates or down-regulates the rghR2 gene.

In other embodiments, the disclosure is related to a modified *B. licheniformis* cell derived from a parental *B. licheniformis* cell, wherein the modified cell comprises a genetic modification which deletes, disrupts, inactivates or down-regulates at least one endogenous *B. licheniformis* gene encoding a YvzC protein (SEQ ID NO: 18), a BLi03644 protein (SEQ ID NO: 20), an AbrB1 protein (SEQ ID NO: 22) and/or an Abh (AbrB2) protein (SEQ ID NO: 24), wherein the modified cell produces an increased amount of a protein of interest (relative to the unmodified parental cell).

In other embodiments, a modified *B. licheniformis* cell derived from a parental *B. licheniformis* cell comprises a restored rghR2 gene of SEQ ID NO: 2 and a genetic modification which deletes, disrupts, inactivates or down-regulates at least one endogenous *B. licheniformis* gene encoding a YvzC protein (SEQ ID NO: 18), a BLi03644 protein (SEQ ID NO: 20), an AbrB1 protein (SEQ ID NO: 22) and/or an Abh (AbrB2) protein (SEQ ID NO: 24), wherein the modified cell produces an increased amount of a protein of interest (relative to the unmodified parental cell).

In certain other embodiments, modified *B. licheniformis* cells derived from parental *B. licheniformis* cells, comprise a rghR2$_{rest}$ gene and a nucleic acid construct (SEQ ID NO: 143) comprising allele glcT1 (C199T), encoding a variant GlcT (transcriptional anti-termination) protein comprising a leucine (L) to phenylalanine (F) substitution at amino acid position 67 (L67F) of the variant GlcT protein.

Other embodiments of the disclosure are related to methods for restoring the activity of inactive RghR2 proteins in parental *B. licheniformis* cells. Certain other embodiments of the disclosure are related to such compositions and methods for increasing the production of proteins of interest in modified *B. licheniformis* cells. In other embodiments, the disclosure is related to isolated *B. licheniformis* (daughter) cells modified and produced by the methods of the disclosure.

I. Definitions

In view of the modified *B. licheniformis* cells of the disclosure and methods thereof described herein, the following terms and phrases are defined. Terms not defined herein should be accorded their ordinary meaning as used in the art.

Unless defined otherwise, all technical and scientific terms used herein have the same meaning as commonly understood by one of ordinary skill in the art to which the present compositions and methods apply. Although any methods and materials similar or equivalent to those described herein can also be used in the practice or testing of the present compositions and methods, representative illustrative methods and materials are now described. All publications and patents cited herein are incorporated by reference in their entirety.

It is further noted that the claims may be drafted to exclude any optional element. As such, this statement is intended to serve as antecedent basis for use of such exclusive terminology as "solely," "only", "excluding", "not including" and the like, in connection with the recitation of claim elements, or use of a "negative" limitation or proviso thereof.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein, a "native *Bacillus licheniformis* chromosomal rghR2 gene" comprises a nucleotide sequence encoding a RghR2 protein of SEQ ID NO: 2 (e.g., see TABLE 1 and FIG. 1).

As used herein, a "variant-18-BP" *B. licheniformis* chromosomal rghR2 gene comprises a nucleotide sequence encoding a variant RghR2 protein of SEQ ID NO: 4 (e.g., see TABLE 1 and FIG. 1).

As used herein, a "variant-18-BP *B. licheniformis* chromosomal rghR2 gene" comprising a nucleotide sequence encoding a variant RghR2 protein of SEQ ID NO: 4 may be abbreviated as "rghR2$_{dup}$" and the variant RghR2 protein thereof (comprising the six amino acid repeat "AAASIR") may be abbreviated as "RghR2$_{dup}$".

A used herein, a "variant *B. licheniformis* chromosomal rghR2 gene" includes any *B. licheniformis* chromosomal rghR2 gene encoding a variant RghR2 protein comprising one or more nucleotide insertions, one or more nucleotide deletions, one or more nucleotide duplications and/or one or more nucleotide substitutions in the helix-turn-helix (HTH) domain of the encoded RghR2 protein, which one or more nucleotide insertions, nucleotide deletions, nucleotide duplications and/or nucleotide substitutions in the HTH domain of the encoded RghR2 protein substantially inactivate the RghR2 protein as a transcriptional regulatory protein.

As defined herein, the "HTH domain" of the native *B. licheniformis* RghR2 protein of SEQ ID NO: 2 is comprised within amino residues 5-58 of SEQ ID NO: 2.

For example, in certain embodiments, one skilled in the art may readily screen/sequence rghR2 genes against the native rghR2 gene sequence of SEQ ID NO: 1, and identify "variant *B. licheniformis* chromosomal rghR2 gene" sequences encoding variant RghR2 proteins comprising mutations (e.g., nucleotide insertions, deletions, substitutions, duplications, and the like) in the HTH domain of the encoded RghR2 protein.

Thus, in certain embodiments, the disclosure is related to parental *B. licheniformis* cells comprising a "variant *B. licheniformis* chromosomal rghR2 gene" sequence (i.e., encoding a variant RghR2 protein comprising a mutation in the HTH domain). In other embodiments, the disclosure is related to a modified *B. licheniformis* cell derived from a parental cell *B. licheniformis* comprising a "variant *B. licheniformis* chromosomal rghR2 gene" sequence (i.e., encoding a variant RghR2 protein comprising a mutation in the HTH domain), wherein the modified cell comprises a restored rghR2 gene encoding a native RghR2 protein of SEQ ID NO: 2.

As used herein, a modified *B. licheniformis* cell derived from a parental *B. licheniformis* cell comprising either (i) a "variant-18-BP *B. licheniformis* chromosomal rghR2 gene" (SEQ ID NO: 3) or (ii) a "variant *B. licheniformis* chromosomal rghR2 gene" (i.e., comprising a mutation in the HTH domain of the encoded RghR2 protein comprised within amino residues 5-58 of SEQ ID NO: 2), wherein the modified *B. licheniformis* cell comprises a restored rghR2 gene encoding a native RghR2 protein of SEQ ID NO: 2, the "restored rghR2 gene in the modified cell" may be abbreviated herein as "rghR2$_{rest}$" and the encoded native protein thereof may be abbreviated as "RghR2$_{rest}$".

TABLE 1

RghR2 NATIVE AND RghR2$_{dup}$ PROTEIN SEQUENCES

| SEQ | RghR2 AMINO ACID SEQUENCE |
|---|---|
| 2 | MAMTRFGERLKELREQRSLSVNQLAMYAGVSA$_{32}$A$_{33}$A$_{34}$I$_{35}$S$_{36}$R$_{37}$IENGHRGVPKPATIRKLAEALKMPYEQLMDIAGYMRADEIREQPRGYVTMQEIAAKHGVEDLWLFKPEKWDCLSREDLLNLEQYFHFLVNEAKKRQS |
| 4 | MAMTRFGERLKELREQRSLSVNQLAMYAGVSA$_{32}$A$_{33}$A$_{34}$I$_{35}$S$_{36}$R$_{37}$A$_{38}$A$_{39}$A$_{40}$I4$_{1}$S$_{42}$R$_{43}$IENGHRGVPKPATIRKLAEALKMPYEQLMDIAGYMRADEIREQPRGYVTMQEIAAKHGVEDLWLFKPEKWDCLSREDLLNLEQYFHFLVNEAKKRQS |

More specifically, as presented above in TABLE 1, a "variant-18-BP *B. licheniformis* chromosomal rghR2 gene" of the disclosure (SEQ ID NO: 3) comprises an 18-nucleotide (18-bp) duplication encoding a consecutive repeat of six (6) amino acids which are "Ala-Ala-Ala-Ile-Ser-Arg" (hereinafter "AAAISR"), wherein the primary (1°) amino acid sequence of the encoded variant RghR2 protein is set forth as SEQ ID NO: 4 (see, TABLE 1 and FIG. 1) comprises a linear (consecutive) repeat of these six (6) amino acids as follows: "Ala-Ala-Ala-Ile-Ser-Arg-Ala-Ala-Ala-Ile-Ser-Arg"; hereinafter, "AAAISRAAAISR" (SEQ ID NO: 6). For example, the six amino acid repeat present in RghR2$_{dup}$ protein (SEQ ID NO: 4) is presented in TABLE 1, wherein the repeated amino acid residues of this 140 amino acid protein comprise the bold text amino acids at positions A$_{38}$ to R$_{43}$ of SEQ ID NO: 4.

In contrast, a "native *B. licheniformis* chromosomal rghR2 gene" of the disclosure (SEQ ID NO: 1) does not comprise this 18-nucleotide (18-bp) duplication. Thus, the native rghR2 gene encodes the native RghR2 protein of SEQ ID NO: 2 (which does not comprise the consecutive repeat "AAAISR", as presented in SEQ ID NO: 6). For example, the primary (1°) amino acid sequence of the encoded native RghR2 protein is presented in TABLE 1, wherein the six amino acid repeat of "AAAISR" is not present at positions 38-43 (SEQ ID NO: 2) of this 134 amino acid protein.

As defined herein, a *B. licheniformis* strain Bra7 (or Bra7 strain) is a *B. licheniformis* host cell developed/derived from a wild-type *B. licheniformis* parental strain using classical genetic improvements methods. Although certain embodiments and descriptions of the present disclosure are related to *B. licheniformis* strain Bra7, the compositions and methods of the instant disclosure are not limited to a specific *Bacillus* species, nor are the compositions and methods of the instant disclosure limited to a specific strain of *B. licheniformis* host cells.

As used herein, a "*B. licheniformis* derivative of strain Bra7", specifically refers to a *B. licheniformis* (daughter) cell derived from a parental *B. licheniformis* Bra7 (strain) host cell. More particularly, as used herein, a "*B. licheniformis* derivative of strain Bra7" is a *B. licheniformis* host cell derived from the *B. licheniformis* strain Bra7 parent which comprises a five (5) gene deletion (Δcat, ΔamyL, Δspo, ΔaprL, ΔendoGluC) as described in International PCT Publication No. WO2008/024372.

As used herein, a heterologous *Peanibacillus curdlanolyticus* variant α-amylase (e.g., see, Examples 2 and 4), optionally abbreviated herein as "PcuAmyl-v6", is disclosed in PCT Publication No. WO2014/164834.

As used herein, a *Cytophaga* sp. variant α-amylase referred to herein as "*Cytophaga* sp. α-amylase variant #1" (e.g., see, Example 5) and "*Cytophaga* sp. α-amylase variant #2" (e.g., see, Examples 11 and 12) are disclosed in International PCT Publication Nos. WO2014/164777; WO2012/164800 and WO2014/164834.

As used herein, a "variant *Geobacillus stearothermophilus* amylase" (e.g., see, Example 5) is a variant *G. stearothermophilus* α-amylase disclosed in International PCT Publication No. WO2009/149130.

As used herein, a "variant alkaline α-amylases" (e.g., see, Example 9), referred to herein as alkaline α-amylase "variant 1", alkaline α-amylase "variant 2", alkaline α-amylase "variant 3" and alkaline α-amylase "variant 4", which are variant α-amylase derived from *Bacillus* sp. No. 707 comprising improved alkaline performance/stability thereof, are generally disclosed in International PCT Publication No. WO2008/153805 and US Patent Publication No. US2014/0057324.

As used herein, a "G4 amylase (variant)" of *Pseudomonas* sp. AM1 (e.g., see, Example 8) is disclosed in International PCT Publication No. WO2010/133644.

As used herein, a heterologous DNA/nucleic acid sequence "encoding an enzyme comprising lipase/esterase activity" (e.g., see, Example 10), such DNA/nucleic acid sequence encodes an enzyme commission number "EC 3.1.1.3" enzyme" comprising lipase/esterase activity.

As used herein, a *B. licheniformis* (daughter) cell comprising allele glcT1 (e.g., see, Example 12), allele glcT1 encodes a variant GlcT (transcriptional anti-termination) protein comprising a phenylalanine (F) at amino acid position 67 (F67) of the variant GlcT protein, as described in U.S. Provisional Patent Application Ser. No. 62/613,339, filed Jan. 3, 2018.

Thus, in certain embodiments, a "native *B. licheniformis* chromosomal rghR2 gene" comprises a nucleotide sequence encoding a RghR2 protein comprising at least 90% sequence identity to SEQ ID NO: 2. In other embodiments, a "native *B. licheniformis* chromosomal rghR2 gene" comprises a nucleotide sequence encoding a RghR2 protein comprising at least 90% sequence identity to SEQ ID NO: 2, with the proviso that the RghR2 protein comprising 90% sequence identity to SEQ ID NO: 2 is active as a transcriptional regulatory protein in *B. licheniformis* cells. In certain other embodiments, a "native *B. licheniformis* chromosomal rghR2 gene" comprises a nucleotide sequence encoding a RghR2 protein comprising at least 90% sequence identity to SEQ ID NO: 2, with the proviso that the RghR2 protein comprising 90% sequence identity to SEQ ID NO: 2 does not comprise a repeat of amino acids AAAISR as set forth in SEQ ID NO: 6.

In certain embodiments, a rghR2$_{dup}$ gene comprises a nucleotide sequence encoding a RghR2 protein of SEQ ID NO: 4. In certain embodiments, a rghR2$_{dup}$ gene comprises a nucleotide sequence encoding a RghR2 protein comprising at least 90% sequence identity to SEQ ID NO: 4. In certain embodiments, a rghR2$_{dup}$ gene comprises a nucleotide sequence encoding a RghR2 protein comprising at least 90% sequence identity to SEQ ID NO: 4, with the proviso that the RghR2 protein comprising 90% sequence identity to SEQ ID NO: 4 is substantially inactive as a transcriptional regulatory protein in *B. licheniformis* cells. In certain other embodiments, a rghR2$_{dup}$ gene comprises a nucleotide sequence encoding a RghR2 protein comprising at least 90% sequence identity to SEQ ID NO: 4, with the proviso that the RghR2 protein comprising 90% sequence identity to SEQ ID NO: 4 comprises a repeat of amino acids AAAISR as set forth in SEQ ID NO: 6.

In other embodiments, a variant rghR2 gene of the disclosure comprises any *B. licheniformis* rghR2 gene comprising at least one, two, three, four, five, ten, eighteen, twenty, etc. nucleotides inserted, deleted, duplicated and the like in the native rghR2 gene's nucleic acid sequence between nucleotide positions 111 and 112 of SEQ ID NO: 1, thereby converting the native rghR2 gene into a variant rghR2 gene comprising at least one, two, three, four, five, ten, eighteen, twenty, etc. nucleotides inserted into the native rghR2 gene's nucleic acid sequence.

Thus, in other embodiments, a RghR2 protein which is substantially inactive further includes variant RghR2 proteins comprising at least one, two, three, four, five, six, seven, etc. amino acids inserted between amino acid residues 37 and 38 of the RghR2 protein (i.e., with reference to the active RghR2 protein sequence of SEQ ID NO: 2), wherein such amino acid insertions (i.e., between residues 37 and 38) render the RghR2 protein substantially inactive as transcriptional regulatory protein.

Thus, in certain embodiments, a variant RghR2 protein encoded by a variant rghR2 gene is substantially "inactive as a transcriptional regulatory protein" in *B. licheniformis* cells.

As defined herein, an "RghR2$_{dup}$ protein of SEQ ID NO: 4, comprising a 6-amino acid repeat of amino acids AAAISR" is substantially "inactive as transcriptional regulatory protein" in *B. licheniformis* cells.

As defined herein, a "variant rghR2 gene encoding a variant rghR2 protein comprising a mutation in the HTH domain" of the encoded RghR2 of SEQ ID NO: 2 is substantially "inactive as transcriptional regulatory protein" in *B. licheniformis* cells relative to the native RghR2 protein of SEQ ID NO: 2.

In certain embodiments, a rghR2 gene encoding a variant RghR2 protein which is substantially "inactive as a transcriptional regulatory protein" is determined by screening variant RghR2 proteins (relative to native RghR2 protein; SEQ ID NO: 2) in DNA binding assays known to one skilled in the art.

For example, it is contemplated herein that the RghR2 protein, a transcriptional regulatory protein comprising the HTH domain set forth above, must sufficiently bind to DNA to exert its transcriptional regulatory activity thereof. Thus, by comparing DNA binding affinities of the native RghR2 protein relative to one or more variant RghR2 proteins (i.e., comprising a mutated HTH domain), a reduced DNA binding affinity of a variant RghR2 protein vis-à-vis the native RghR2 protein serves as a corollary for such variant RghR2 proteins which are substantially "inactive as transcriptional regulatory proteins". For example, as contemplated herein, a variant RghR2 protein (i.e. comprising a mutated HTH domain) having a significantly reduced DNA binding affinity (or a complete loss of DNA binding) will have a substantial reduction (or complete loss) of transcriptional regulatory protein activity, relative to the native RghR2 protein, which is substantially active as transcriptional regulatory protein.

Figure 8:
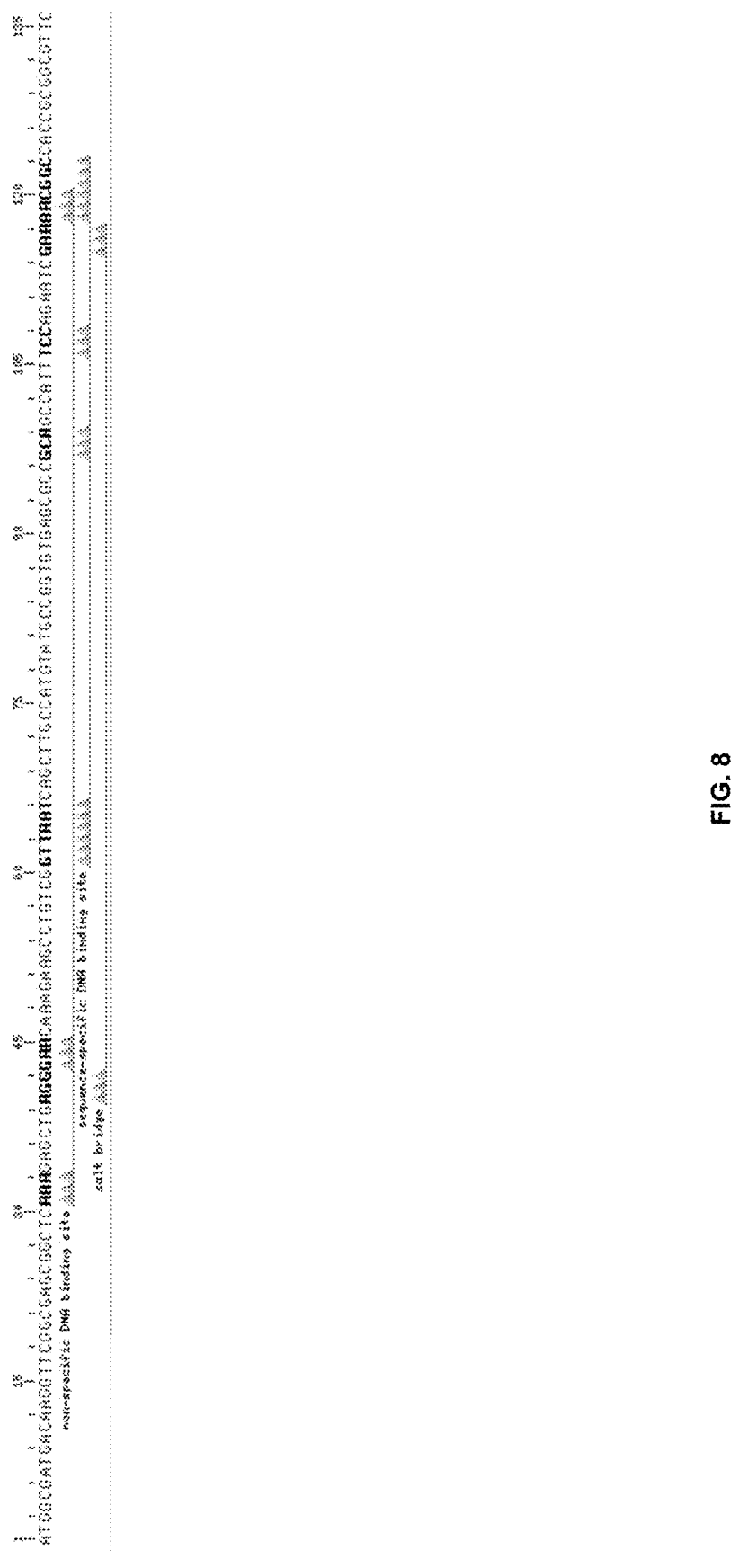

Thus, in certain embodiments, a variant rghR2 gene of the disclosure includes any *B. licheniformis* rghR2 gene variant comprising an insertion, duplication, deletion, non-synonymous substitution, and the like, of the nucleotides in these (DNA binding) regions of the rghR2 gene, as presented in FIG. 8. For example, FIG. 8 of the instant disclosure shows certain rghR2 codons (i.e., the bold text nucleotides in FIG. 8) predicted to encode amino acid residues in the RghR2 protein involved in DNA binding. Thus, in certain embodiments, a variant rghR2 gene of the disclosure is a variant rghR2 gene comprising an insertion, duplication, deletion, non-synonymous substitution, and the like of one or more nucleotides in these (DNA binding) regions of the rghR2 gene. More particularly, in certain embodiments, a variant rghR2 gene comprising an insertion, duplication, deletion, non-synonymous substitution, and the like of the nucleotides in the DNA binding regions of the rghR2 gene encodes a substantially inactive RghR2 protein.

The phrase a RghR2 protein which is substantially "inactive as a transcriptional regulatory protein" includes variant RghR2 proteins encoded by variant rghR2 genes comprising an insertion, duplication, deletion, non-synonymous substitution (and the like) of one or more nucleotides in these (DNA binding) regions of the rghR2 gene, wherein the encoded variant proteins are substantially inactive as transcriptional regulatory proteins.

As used herein, the term "equivalent positions" mean the amino acid residue positions after alignment with the RghR2 polypeptide sequence of SEQ ID NO: 4, particularly from amino acid residues 32 to 43 of SEQ ID NO: 4. The twelve (12) contiguous amino acids residues (i.e., equivalent positions) described above for SEQ ID NO: 4 (i.e., residues 32 to 43 of SEQ ID NO: 4) are presented in the amino acid sequence of SEQ ID NO: 6 ("AAAISRAAAISR). Thus, in certain embodiments, a gene or ORF encoding a variant RghR2 protein of the disclosure may be identified by comparison of the equivalent positions of the encoded RghR2 protein's amino acid sequence to the repeat amino acid sequence set forth in SEQ ID NO: 6, wherein the presence of the SEQ ID NO: 6 repeat sequence indicates a variant RghR2 protein of the disclosure.

The terms "modification" and "genetic modification" are used interchangeably and include: (a) the introduction, substitution, or removal of one or more nucleotides in a gene (or an ORF thereof), or the introduction, substitution, or removal of one or more nucleotides in a regulatory element required for the transcription or translation of the gene or ORF thereof, (b) a gene disruption, (c) a gene conversion, (d) a gene deletion, (e) the down-regulation of a gene, (f) specific mutagenesis and/or (g) random mutagenesis of any one or more of the genes disclosed herein. For example, as used herein a genetic modification includes, but is not limited to, a modification of one or more genes selected from the group consisting of rghR2, rghR1, abrB1, rpmJ, rpIM, BLi00412, rapK, phrK, BLi00753, yfjT, BLi00828, yhdX, yhzC, terf2, zosA, abbA, speG, yppF, BLi02543, mntR, BLi02768, sspA, BLi03127, BLi03635, mrgA, BLi03644, yvzC, spo0F, ywjG, ywq12, BLi04199, BLi04200, licT, bglH and bglP.

As used herein, "disruption of a gene", "gene disruption", "inactivation of a gene" and "gene inactivation" are used interchangeably and refer broadly to any genetic modification that substantially prevents a host cell from producing a functional gene product (e.g., a protein). Exemplary methods of gene disruptions include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and any combinations and variations thereof which disrupt/inactivate the target gene(s) and substantially reduce or prevent the production of the functional gene product (i.e., a protein).

As used herein, the terms "down-regulation" of gene expression and "up-regulation" of gene expression include any method that results in lower (down-regulated) or higher (up-regulated) expression of a gene. For example, the down-regulation of a gene can be achieved by RNA-induced gene silencing, genetic modifications of control elements such as the promoter, ribosomal binding site (RBS)/Shine-Dalgarno sequences, untranslated regions (UTRs), codon changes, and the like.

As used herein, the phrases "deleting the 18-nucleotide duplication", or "deleting the 18-bp duplication" or "modifying the cell by deleting the 18-nucleotide duplication" particularly refer to a genetic modification of a parental *Bacillus* cell comprising a variant rghR2 gene comprising an 18-nucleotide duplication (rghR2$_{dup}$), which duplication encodes a repeat of amino acids "AAAISR" (SEQ ID NO: 6) in the variant RghR2 protein (RghR2$_{dup}$; e.g., see SEQ ID NO: 4, wherein amino acids "AAAISR" at positions 32-37 of SEQ ID NO: 4 are consecutively repeated at positions 38-43 of SEQ ID NO: 4).

Thus, in certain embodiments, a modified *Bacillus* cell of the disclosure is derived from a parental *Bacillus* cell comprising a variant chromosomal rghR2 gene (e.g., rghR2$_{dup}$; SEQ ID NO: 3) comprising an 18-nucleotide duplication encoding the "AAAISR" repeated sequence of SEQ ID NO: 6, wherein the modified *Bacillus* cell is modified by "deleting the 18-nucleotide duplication", thereby resulting in a modified *Bacillus* cell comprising a "restored" rghR2 gene sequence (rghR2$_{rest}$; SEQ ID NO: 1) encoding a native rghR2 protein. Methods for deleting the 18-nuclotide duplication in the parental *Bacillus* cell include, but are not limited to, homologous recombination, CRSIPR-Cas9 gene editing, mega-nuclease gene editing, TALEN gene editing, Zinc-Finger Nuclease (ZFN) editing and the like, which are further described below in Section IV. Thus, in certain embodiments, the disclosure is directed to modified *Bacillus* cells comprising a "restored" rghR2 gene".

As used herein, "host cell" refers to a cell that has the capacity to act as a host or expression vehicle for a newly introduced DNA sequence. This, in certain embodiments of the disclosure, the host cells are *Bacillus* sp. or *E. coli* cells.

As defined herein, a "parental cell", a "parental host cell" or a "parental *B. licheniformis* (host) cell", may be used interchangeably and refer to "unmodified" parental *B. licheniformis* cells. For example, a "parental" cell refers to any cell or strain of microorganism in which the genome of the "parental" cell is altered (e.g., via one or more mutations introduced into the parental cell) to generate a modified "daughter" cell.

As defined herein, a "modified cell", a "modified host cell" or a "modified *B. licheniformis* (host) cell", may be used interchangeably and refer to recombinant *B. licheniformis* (host) cells that comprise at least one genetic modification which is not present in the "parental" *B. licheniformis* host cell from which the modified *B. licheniformis* (daughter) cell is derived. For example, in certain embodiments a "parental *B. licheniformis* (host) cell" of the disclosure comprises a chromosomal rghR2 gene of SEQ ID NO: 3 (rghR2$_{dup}$) encoding a variant RghR2 protein of SEQ ID NO: 4, and a "modified" *B. licheniformis* host cell the disclosure (i.e., derived from the parental *B. licheniformis* host cell comprising the chromosomal rghR2 gene of SEQ ID NO: 3) comprises a genetic modification which deletes the 18-nucleotide duplication in SEQ ID NO: 3, thereby resulting in a modified (restored) *B. licheniformis* host cell comprising a native rghR2 gene (rghR2$_{rest}$) encoding a native RghR2 protein of SEQ ID NO: 2.

In certain embodiments, the "unmodified" *B. licheniformis* (parental) cell may be referred to as a "control cell", particularly when being compared with, or relative to, a "modified" *B. licheniformis* (daughter) cell. As used herein, when the expression and/or production of a protein of interest (POI) in an "unmodified" (parental) cell (i.e., a control cell) is being compared to the expression and/or production of the same POI in a "modified" (daughter) cell, it will be understood that the "modified" and "unmodified" cells are grown/cultivated/fermented under the same conditions (e.g., the same conditions such as media, temperature, pH and the like).

As used herein, "the genus *Bacillus*" includes all species within the genus "*Bacillus*'∞ as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulars, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus,* which is now named "*Geobacillus stearothermophilus*".

As defined herein, the terms "increased expression", "enhanced expression", "increased expression of a POI", "increased production", "increased production of a POI" and the like refer to a "modified" *B. licheniformis* (daughter) cell, wherein the "increase" is always relative (vis-à-vis) to an "unmodified" *B. licheniformis* (parental) cell expressing/producing the same POI.

As used herein, the term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the production of the polypeptide including, but not limited to, transcription, post-transcriptional modification, translation, post-translational modification, secretion and the like.

As defined herein, the combined term "expresses/produces", as used in phrases such as "a modified host cell expresses/produces an increased amount of a protein of interest relative to the (unmodified) parental host cell", the term ("expresses/produces") is meant to include any steps involved in the expression and production of a protein of interest in host cell of the disclosure.

Likewise, as used herein, an "increased amount", when used in phrases such as "a modified host cell 'expresses/produces an increased amount' of one or more proteins of interest relative to the (unmodified) parental host cell", particularly refers to an "increased amount" of any protein of interest (POI) expressed/produced in the modified host cell, which "increased amount" is always relative to the (unmodified) parental *B. licheniformis* cells expressing/producing the same POI, wherein the modified and unmodified cells are grown/cultured/fermented under the same conditions (e.g., the same conditions such as media, temperature, pH and the like). For example, an increased amount of a POI may be an endogenous *B. licheniformis* POI or a heterologous POI expressed in a modified *B. licheniformis* cell of the disclosure.

Thus, as used herein, "increasing" protein production or "increased" protein production is meant an increased amount of protein produced (e.g., a protein of interest). The protein may be produced inside the host cell, or secreted (or transported) into the culture medium. In certain embodiments, the protein of interest is produced (secreted) into the culture medium. Increased protein production may be detected for example, as higher maximal level of protein or enzymatic activity (e.g., such as protease activity, amylase activity, cellulase activity, hemicellulase activity and the like), or total extracellular protein produced as compared to the parental host cell.

As used herein, "nucleic acid" refers to a nucleotide or polynucleotide sequence, and fragments or portions thereof, as well as to DNA, cDNA, and RNA of genomic or synthetic origin, which may be double-stranded or single-stranded, whether representing the sense or antisense strand. It will be understood that as a result of the degeneracy of the genetic code, a multitude of nucleotide sequences may encode a given protein.

It is understood that the polynucleotides (or nucleic acid molecules) described herein include "genes", "vectors" and "plasmids".

Accordingly, the term "gene", refers to a polynucleotide that codes for a particular sequence of amino acids, which comprise all, or part of a protein coding sequence, and may include regulatory (non-transcribed) DNA sequences, such as promoter sequences, which determine for example the conditions under which the gene is expressed. The transcribed region of the gene may include untranslated regions (UTRs), including introns, 5'-untranslated regions (UTRs), and 3'-UTRs, as well as the coding sequence.

As used herein, the term "coding sequence" refers to a nucleotide sequence, which directly specifies the amino acid sequence of its (encoded) protein product. The boundaries of the coding sequence are generally determined by an open reading frame (hereinafter, "ORF"), which usually begins with an ATG start codon. The coding sequence typically includes DNA, cDNA, and recombinant nucleotide sequences.

As defined herein, the term "open reading frame" (hereinafter, "ORF") means a nucleic acid or nucleic acid sequence (whether naturally occurring, non-naturally occurring, or synthetic) comprising an uninterrupted reading frame consisting of (i) an initiation codon, (ii) a series of two (2) or more codons representing amino acids, and (iii) a termination codon, the ORF being read (or translated) in the 5' to 3' direction.

The term "promoter" as used herein refers to a nucleic acid sequence capable of controlling the expression of a coding sequence or functional RNA. In general, a coding sequence is located 3' (downstream) to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" as used herein refers to the association of nucleic acid sequences on a single nucleic acid fragment so that the function of one is affected by the other. For example, a promoter is operably linked with a coding sequence (e.g., an ORF) when it is capable of affecting the expression of that coding sequence (i.e., that the coding sequence is under the transcriptional control of the promoter). Coding sequences can be operably linked to regulatory sequences in sense or antisense orientation.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, "a functional promoter sequence controlling the expression of a gene of interest (or open reading frame thereof) linked to the gene of interest's protein coding sequence" refers to a promoter sequence which controls the transcription and translation of the coding sequence in *Bacillus*. For example, in certain embodiments, the present disclosure is directed to a polynucleotide comprising a 5' promoter (or 5' promoter region, or tandem 5' promoters and the like), wherein the promoter region is operably linked to a nucleic acid sequence encoding an RghR2 protein of SEQ ID NO: 2. Thus, in certain embodiments, a functional promoter sequence controls the expression of an rghR2 gene encoding a RghR2 protein of SEQ ID NO: 2. In other embodiments, a functional promoter sequence controls the expression of a heterologous gene (or endogenous gene) encoding a protein of interest in a *Bacillus* cell, more particularly in a *B. licheniformis* host cell.

As defined herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As defined herein, the term "introducing", as used in phrases such as "introducing into a bacterial cell" or "introducing into a *B. licheniformis* cell at least one polynucleotide open reading frame (ORF), or a gene thereof, or a vector thereof, includes methods known in the art for introducing polynucleotides into a cell, including, but not limited to protoplast fusion, natural or artificial transformation (e.g., calcium chloride, electroporation), transduction, transfection, conjugation and the like (e.g., see Ferrari et al., 1989).

As used herein, "transformed" or "transformation" mean a cell has been transformed by use of recombinant DNA techniques. Transformation typically occurs by insertion of one or more nucleotide sequences (e.g., a polynucleotide, an ORF or gene) into a cell. The inserted nucleotide sequence may be a heterologous nucleotide sequence (i.e., a sequence that is not naturally occurring in cell that is to be transformed). For example, in certain embodiments of the disclosure, a parental *B. licheniformis* cell comprising a variant rghR2 gene encoding a variant RghR2 protein of SEQ ID NO: 4 is modified (e.g., transformed) by introducing into the parental cell a polynucleotide construct comprising a promoter operably linked to a nucleic acid sequence encoding a native RghR2 protein of SEQ ID NO: 2, thereby resulting in a modified *B. licheniformis* (daughter) host cell derived from the "unmodified" (parental) cell.

As used herein, "transformation" refers to introducing an exogenous DNA into a host cell so that the DNA is maintained as a chromosomal integrant or a self-replicating extra-chromosomal vector. As used herein, "transforming DNA", "transforming sequence", and "DNA construct" refer to DNA that is used to introduce sequences into a host cell or organism. Transforming DNA is DNA used to introduce sequences into a host cell or organism. The DNA may be generated in vitro by PCR or any other suitable techniques. In some embodiments, the transforming DNA comprises an incoming sequence, while in other embodiments it further comprises an incoming sequence flanked by homology boxes. In yet a further embodiment, the transforming DNA comprises other non-homologous sequences, added to the ends (i.e., stuffer sequences or flanks). The ends can be closed such that the transforming DNA forms a closed circle, such as, for example, insertion into a vector.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., 1989).

As used herein "an incoming sequence" refers to a DNA sequence that is introduced into the *Bacillus* chromosome. In some embodiments, the incoming sequence is part of a DNA construct. In other embodiments, the incoming sequence encodes one or more proteins of interest. In some embodiments, the incoming sequence comprises a sequence that may or may not already be present in the genome of the cell to be transformed (i.e., it may be either a homologous or heterologous sequence). In some embodiments, the incoming sequence encodes one or more proteins of interest, a gene, and/or a mutated or modified gene. In alternative embodiments, the incoming sequence encodes a functional wild-type gene or operon, a functional mutant gene or operon, or a nonfunctional gene or operon. In some embodiments, the non-functional sequence may be inserted into a gene to disrupt function of the gene. In another embodiment, the incoming sequence includes a selective marker. In a further embodiment the incoming sequence includes two homology boxes.

As used herein, "homology box" refers to a nucleic acid sequence, which is homologous to a sequence in the *Bacillus* chromosome. More specifically, a homology box is an upstream or downstream region having between about 80 and 100% sequence identity, between about 90 and 100% sequence identity, or between about 95 and 100% sequence identity with the immediate flanking coding region of a gene or part of a gene to be deleted, disrupted, inactivated, down-regulated and the like, according to the invention. These sequences direct where in the *Bacillus* chromosome a DNA construct is integrated and directs what part of the *Bacillus* chromosome is replaced by the incoming sequence. While not meant to limit the present disclosure, a homology box may include about between 1 base pair (bp) to 200 kilobases (kb). Preferably, a homology box includes about between 1 bp and 10.0 kb; between 1 bp and 5.0 kb; between 1 bp and 2.5 kb; between 1 bp and 1.0 kb, and between 0.25 kb and 2.5 kb. A homology box may also include about 10.0 kb, 5.0 kb, 2.5 kb, 2.0 kb, 1.5 kb, 1.0 kb, 0.5 kb, 0.25 kb and 0.1 kb. In some embodiments, the 5' and 3' ends of a selective marker are flanked by a homology box wherein the homology box comprises nucleic acid sequences immediately flanking the coding region of the gene.

In still another embodiment of the disclosure, the deletion, disruption, inactivation or down-regulation of a gene active at an inappropriate time, as determined by DNA array analysis (e.g., transcriptome analysis, as described herein) provides enhanced expression of a protein of interest. As used herein, "transcriptome analysis" refers to the analysis of gene transcription.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell which allows for ease of selection of those hosts containing the vector. Examples of such selectable markers include, but are not limited to, antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation.

A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, the marker can be an antimicrobial resistance marker (e.g., $amp^R$, $phleo^R$, $spec^R$, $kan^R$, $ery^R$, $tet^R$, $cmp^R$ and $neo^R$ (see e.g., Guerot-Fleury, 1995; Palmeros et al., 2000; and Trieu-Cuot et al., 1983). In some embodiments, the present invention provides a chloramphenicol resistance gene (e.g., the gene present on pC194, as well as the resistance gene present in the *Bacillus licheniformis* genome). This resistance gene is particularly useful in the present invention, as well as in embodiments involving chromosomal amplification of chromosomally integrated cassettes and integrative plasmids (See e.g., Albertini and Galizzi, 1985; Stahl and Ferrari, 1984). Other markers useful in accordance with the invention include, but are not limited to auxotrophic markers, such as serine, lysine, tryptophan; and detection markers, such as β-galactosidase.

As defined herein, a host cell "genome", a bacterial (host) cell "genome", or a *B. licheniformis* (host) cell "genome" includes chromosomal and extrachromosomal genes.

As used herein, the terms "plasmid", "vector" and "cassette" refer to extrachromosomal elements, often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A used herein, a "transformation cassette" refers to a specific vector comprising a gene (or ORF thereof), and having elements in addition to the foreign gene that facilitate transformation of a particular host cell.

As used herein, the term "vector" refers to any nucleic acid that can be replicated (propagated) in cells and can carry new genes or DNA segments into cells. Thus, the term refers to a nucleic acid construct designed for transfer between different host cells. Vectors include viruses, bacteriophage, pro-viruses, plasmids, phagemids, transposons, and artificial chromosomes such as YACs (yeast artificial chromosomes), BACs (bacterial artificial chromosomes), PLACs (plant artificial chromosomes), and the like, that are "episomes" (i.e., replicate autonomously or can integrate into a chromosome of a host organism).

An "expression vector" refers to a vector that has the ability to incorporate and express heterologous DNA in a cell. Many prokaryotic and eukaryotic expression vectors are commercially available and know to one skilled in the art. Selection of appropriate expression vectors is within the knowledge of one skilled in the art.

As used herein, the terms "expression cassette" and "expression vector" refer to a nucleic acid construct generated recombinantly or synthetically, with a series of specified nucleic acid elements that permit transcription of a particular nucleic acid in a target cell (i.e., these are vectors or vector elements, as described above). The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, DNA constructs also include a series of specified nucleic acid elements that permit transcription of a particular nucleic acid in a target cell. In certain embodiments, a DNA construct of the disclosure comprises a selective marker and an inactivating chromosomal or gene or DNA segment as defined herein.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing mutations into the chromosome of a host cell through homologous recombination. In some embodiments, the targeting vector comprises other non-homologous sequences, e.g., added to the ends (i.e., stuffer sequences or flanking sequences). The ends can be closed such that the targeting vector forms a closed circle, such as, for example, insertion into a vector. For example, in certain embodiments, a parental *B. licheniformis* (host) cell comprising a variant rghR2 gene encoding a variant RghR2 protein of SEQ ID NO: 4, is modified (e.g., transformed) by introducing into the parental cell one or more "targeting vectors" which are designed to delete the 18-nucleotde duplication of the endogenous *B. licheniformis* variant rghR2 gene, such that modified host cell comprising the "restored" native rghR2 gene encodes a native RghR2 protein of SEQ ID NO: 2. Selection and/or construction of appropriate vectors (e.g., for the deletion of the 18-nucleotide duplication in the rghR2 gene) is well within the knowledge of those having skill in the art.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell.

As used herein, the term "protein of interest" or "POI" refers to a polypeptide of interest that is desired to be expressed in a modified *B. licheniformis* (daughter) host cell, wherein the POI is preferably expressed at increased levels (i.e., relative to the "unmodified" (parental) cell). Thus, as used herein, a POI may be an enzyme, a substrate-binding protein, a surface-active protein, a structural protein, a receptor protein, and the like. In certain embodiments, a modified cell of the disclosure produces an increased amount of a heterologous protein of interest or an endogenous protein of interest relative to the parental cell. In particular embodiments, an increased amount of a protein of interest produced by a modified cell of the disclosure is at least a 0.5% increase, at least a 1.0% increase, at least a 5.0% increase, or a greater than 5.0% increase, relative to the parental cell.

Similarly, as defined herein, a "gene of interest" or "GOI" refers a nucleic acid sequence (e.g., a polynucleotide, a gene or an ORF) which encodes a POI. A "gene of interest" encoding a "protein of interest" may be a naturally occurring gene, a mutated gene or a synthetic gene.

As used herein, the terms "polypeptide" and "protein" are used interchangeably, and refer to polymers of any length comprising amino acid residues linked by peptide bonds. The conventional one (1) letter or three (3) letter codes for amino acid residues are used herein. The polypeptide may be linear or branched, it may comprise modified amino acids, and it may be interrupted by non-amino acids. The term polypeptide also encompasses an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

In certain embodiments, a gene of the instant disclosure encodes a commercially relevant industrial protein of interest, such as an enzyme (e.g., a acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof).

As used herein, a "variant" polypeptide refers to a polypeptide that is derived from a parent (or reference) polypeptide by the substitution, addition, or deletion of one or more amino acids, typically by recombinant DNA techniques. Variant polypeptides may differ from a parent polypeptide by a small number of amino acid residues and may be defined by their level of primary amino acid sequence homology/identity with a parent (reference) polypeptide.

Preferably, variant polypeptides have at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a parent (reference) polypeptide sequence. As used herein, a "variant" polynucleotide refers to a polynucleotide encoding a variant polypeptide, wherein the "variant polynucleotide" has a specified degree of sequence homology/identity with a parent polynucleotide, or hybridizes with a parent polynucleotide (or a complement thereof) under stringent hybridization conditions. Preferably, a variant polynucleotide has at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity with a parent (reference) polynucleotide sequence.

As used herein, a "mutation" refers to any change or alteration in a nucleic acid sequence. Several types of mutations exist, including point mutations, deletion mutations, silent mutations, frame shift mutations, splicing mutations and the like. Mutations may be performed specifically (e.g., via site directed mutagenesis) or randomly (e.g., via chemical agents, passage through repair minus bacterial strains).

As used herein, in the context of a polypeptide or a sequence thereof, the term "substitution" means the replacement (i.e., substitution) of one amino acid with another amino acid.

As defined herein, an "endogenous gene" refers to a gene in its natural location in the genome of an organism.

As defined herein, a "heterologous" gene, a "non-endogenous" gene, or a "foreign" gene refer to a gene (or ORF) not normally found in the host organism, but that is introduced into the host organism by gene transfer. As used herein, the term "foreign" gene(s) comprise native genes (or ORFs) inserted into a non-native organism and/or chimeric genes inserted into a native or non-native organism.

As defined herein, a "heterologous" nucleic acid construct or a "heterologous" nucleic acid sequence has a portion of the sequence which is not native to the cell in which it is expressed.

As defined herein, a "heterologous control sequence", refers to a gene expression control sequence (e.g., a promoter or enhancer) which does not function in nature to regulate (control) the expression of the gene of interest. Generally, heterologous nucleic acid sequences are not endogenous (native) to the cell, or a part of the genome in which they are present, and have been added to the cell, by infection, transfection, transformation, microinjection, electroporation, and the like. A "heterologous" nucleic acid construct may contain a control sequence/DNA coding (ORF) sequence combination that is the same as, or different, from a control sequence/DNA coding sequence combination found in the native host cell.

As used herein, the terms "signal sequence" and "signal peptide" refer to a sequence of amino acid residues that may participate in the secretion or direct transport of a mature protein or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "derived" encompasses the terms "originated" "obtained," "obtainable," and "created," and generally indicates that one specified material or composition finds its origin in another specified material or composition, or has features that can be described with reference to the another specified material or composition.

As used herein, the term "homology" relates to homologous polynucleotides or polypeptides. If two or more polynucleotides or two or more polypeptides are homologous, this means that the homologous polynucleotides or polypeptides have a "degree of identity" of at least 60%, more preferably at least 70%, even more preferably at least 85%, still more preferably at least 90%, more preferably at least 95%, and most preferably at least 98%. Whether two polynucleotide or polypeptide sequences have a sufficiently high degree of identity to be homologous as defined herein, can suitably be investigated by aligning the two sequences using a computer program known in the art, such as "GAP" provided in the GCG program package (Program Manual for the Wisconsin Package, Version 8, August 1994, Genetics Computer Group, 575 Science Drive, Madison, Wisconsin, USA 53711) (Needleman and Wunsch, (1970). Using GAP with the following settings for DNA sequence comparison: GAP creation penalty of 5.0 and GAP extension penalty of 0.3.

As used herein, the term "percent (%) identity" refers to the level of nucleic acid or amino acid sequence identity between the nucleic acid sequences that encode a polypeptide or the polypeptide's amino acid sequences, when aligned using a sequence alignment program.

As used herein, "specific productivity" is total amount of protein produced per cell per time over a given time period.

As defined herein, the terms "purified", "isolated" or "enriched" are meant that a biomolecule (e.g., a polypeptide or polynucleotide) is altered from its natural state by virtue of separating it from some, or all of, the naturally occurring constituents with which it is associated in nature. Such isolation or purification may be accomplished by art-recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to a purified or isolated biomolecule composition which provide additional benefits, for example, activating agents, anti-inhibition agents, desirable ions, compounds to control pH or other enzymes or chemicals.

As used herein, the term "ComK polypeptide" is defined as the product of a comK gene; a transcription factor that acts as the final auto-regulatory control switch prior to competence development; involved with activation of the expression of late competence genes involved in DNA-binding and uptake and in recombination (Liu and Zuber, 1998, Hamoen et al., 1998). Exemplary ComK nucleic acid and polypeptide sequences are set forth in SEQ ID NO: 85 and SEQ ID NO: 86, respectively.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "orthologue" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, 1981; Needleman and Wunsch, 1970; Pearson and Lipman, 1988; programs such as GAP, BESTFIT, FASTA, and TFASTA in the Wisconsin Genetics Software Package (Genetics Computer Group, Madison, WI) and Devereux et. al., 1984).

As used herein, an "analogous sequence" is one wherein the function of the gene is essentially the same as the gene derived from a *Bacillus licheniformis* cell. Additionally, analogous genes include at least 60%, 65%, 70%, 75%, 80%, 85%, 90%, 95%, 97%, 98%, 99% or 100% sequence identity with the sequence of the *Bacillus licheniformis* cell. Analogous sequences are determined by known methods of sequence alignment. A commonly used alignment method is BLAST, although there are other methods that also find use in aligning sequences.

As used herein, the term "hybridization" refers to the process by which a strand of nucleic acid joins with a complementary strand through base pairing, as known in the art. A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature ($T_m$) of the nucleic acid binding complex or probe. For example, "maximum stringency" typically occurs at about $T_m$ −5° C. (5° below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Functionally, maximum stringency conditions may be used to identify sequences having strict identity or near-strict identity with the hybridization probe; while an intermediate or low stringency hybridization can be used to identify or detect polynucleotide sequence homologs. Moderate and high stringency hybridization conditions are well known in the art. An example of high stringency conditions includes hybridization at about 42° C. in 50% formamide, 5×SSC, 5×Denhardt's solution, 0.5% SDS and 100 pg/ml denatured carrier DNA, followed by washing two times in 2×SSC and 0.5% SDS at room temperature (RT) and two additional times in 0. 1×SSC and 0.5% SDS at 42° C. An example of moderate stringent conditions including overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination", "recombining" or generating a "recombined" nucleic acid is generally the assembly of two or more nucleic acid fragments wherein the assembly gives rise to a chimeric gene.

As used herein, a "flanking sequence" refers to any sequence that is either upstream or downstream of the sequence being discussed (e.g., for genes A-B-C, gene B is flanked by the A and C gene sequences). In certain embodiments, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. The sequence of each homology box is homologous to a sequence in the *Bacillus* chromosome. These sequences direct where in the *Bacillus* chromosome the new construct gets integrated and what part of the *Bacillus* chromosome will be replaced by the incoming sequence. In other embodiments, the 5' and 3' ends of a selective marker are flanked by a polynucleotide sequence comprising a section of the inactivating chromosomal segment. In some embodiments, a flanking sequence is present on only a single side (either 3' or 5'), while in other embodiments, it is present on each side of the sequence being flanked.

As used herein, the term "stuffer sequence" refers to any extra DNA that flanks homology boxes (typically vector sequences). However, the term encompasses any non-homologous DNA sequence. Not to be limited by any theory, a stuffer sequence provides a non-critical target for a cell to initiate DNA uptake.

II. *B. licheniformis* Rghr1/Rghr2 Transcriptional Regulators

The *Bacillus subtilis* yvaN gene was identified as a repressor of rapG, rapH (Hayashi et al., 2006) and rapD (Ogura & Fujita, 2007), and renamed rghR (rapG and rapH Repressor). Downstream of rghR lies a gene yvaO, with an unknown function, but based on sequence homology encodes a HTH-type (helix-turn-helix) transcriptional regulator. The amino acid sequence identity between "RghR" and "YvaO" is approximately 52%. Upstream of the *B. subtilis* rghR are the genes yvzC and yvaM. The yvzC gene also encodes a putative HTH-type transcriptional regulator, while the translation product of yvaM is a putative hydrolase.

More particularly, *Bacillus licheniformis* encodes two homologs of *Bacillus subtilis* RghR/YvaO, which are named "RghR1" and "RghR2". The amino acid sequence identity between the *B. subtilis* (strain 168) "RghR" protein and *B. licheniformis* (strain DSM 13) "RghR1" protein is approximately 59%; and the amino acid sequence identity between *B. subtilis* (strain 168) "RghR" and *B. licheniformis* (strain DSM 13) "RghR2" is approximately 57%.

Upstream of the *B. licheniformis* rghR1 are two genes, yvzC (BLi03645; SEQ ID NO: 17) and BLi03644 (SEQ ID NO: 19) transcriptional regulators. The *B. licheniformis* YvzC is a homolog of *B. subtilis* YvzC. However, Bli03644 belongs to the AbrB family of transcriptional regulators, and is not a homolog of the putative hydrolase YvaM.

More particularly, as presented and discussed in the Examples section below, *B. licheniformis* (strain DSM13=ATTC 14580) contains a gene, designated rghR2 (KEGG Genome T00200 *B. licheniformis* DSM13 Gene ID No. BLi03647), encoding a putative HTH-type transcriptional regulator. The nucleic acid sequence of rghR2 of *B. licheniformis* (DSM13) is presented in SEQ ID NO: 1 and the encoded amino acid sequence of the RghR2 protein of *Bacillus licheniformis* (DSM13) is presented in SEQ ID NO: 2.

For example, Applicant of the present disclosure sequenced (1) the genome of *B. licheniformis* strain Bra7, (2) the genome of a *B. licheniformis* derivative of strain Bra7, (3) the genome of *B. licheniformis* strain ATCC-9789 (www.atcc.org/Products/All/9789.aspx), and (4) the genome of *B. licheniformis* strain ATCC-6598 (www.atcc.org/en/Products/All/6598.aspx), which revealed that all of these *B. licheniformis* strains have a duplication (i.e., a repeat) of 18 nucleotides (18-bp) in the rghR2 gene (e.g., see SEQ ID NO: 3, wherein nucleotides "GCCGCAGCCATTTCCAGA" are repeated twice in consecutive order, which nucleotide duplication is set forth in SEQ ID NO: 87) and wherein this 18-nucleotide sequence encodes amino acids "AAAISR" (SEQ ID NO: 5) such that the variant RghR2 protein of SEQ ID NO: 4 comprises a repeat of "AAAISR" (i.e., AAAISR-AAAISR; as presented in SEQ ID NO: 6).

Thus, the amino acid sequence of the RghR2 protein of the *B. licheniformis* Bra7 strain (SEQ ID NO: 4) is identical to the sequence of RghR2 of the *B. licheniformis* Bra7 derivative, the *B. licheniformis* strain ATCC-9789 and the *B. licheniformis* strain ATCC-6598, as presented in SEQ ID NO: 4.

An alignment of the *B. licheniformis* Bra7 strain RghR2 protein amino acid sequence (SEQ ID NO: 4) and the *B. licheniformis* DSM13 strain RghR2 protein amino acid sequence (SEQ ID NO: 2) is presented FIG. 1, illustrating the repeat (AAAISR) in SEQ ID NO: 4. The insertion (repeat) of the sequence "AAAISR" is in the helix-turn-helix (HTH) domain and near the sequence-specific DNA-binding site of the RghR2 protein as shown in FIG. 8.

For example, a RghR2 protein of SEQ ID NO: 4 (e.g., encoded by a rghR2$_{dup}$ gene) comprises 140 amino acid residues, a molecular weight of ~16.1 kDa, a theoretical net charge of +4.5 and theoretical isoelectric point ($P_t$) of 9.38 (molecular weight, net charge and $P_t$ calculation based on 1° amino acid sequence), whereas a RghR2 protein of SEQ ID NO: 2 (e.g., encoded by a native or rghR2$_{rest}$ gene) comprises 134 amino acid residues, a molecular weight of ~15.6 kDa, a theoretical net charge of +3.5 and a theoretical isoelectric point ($P_t$) of 8.85 (molecular weight, net charge and $P_t$ calculation based on 1° amino acid sequence). Likewise, assessment of RghR2 protein sequence using Pfam analysis (version 31.0) indicates that the Rgh2 protein comprises a helix-turn-helix (HTH) domain of HTH family_31 (HTH_31; clan-0123), which HTH domain is comprised within amino residues 5-58 of the RghR2 protein of SEQ ID NO: 2. For example, the rghR2 gene of the *B. licheniformis* Bra7 strain, encoding the variant RghR2 protein of SEQ ID NO: 4, comprises a duplication of the six amino acid repeat "AAAISR" (FIG. 1), which six amino acid repeat is located approximately in the middle of the HTH domain (amino acid) sequence.

Figure 4:
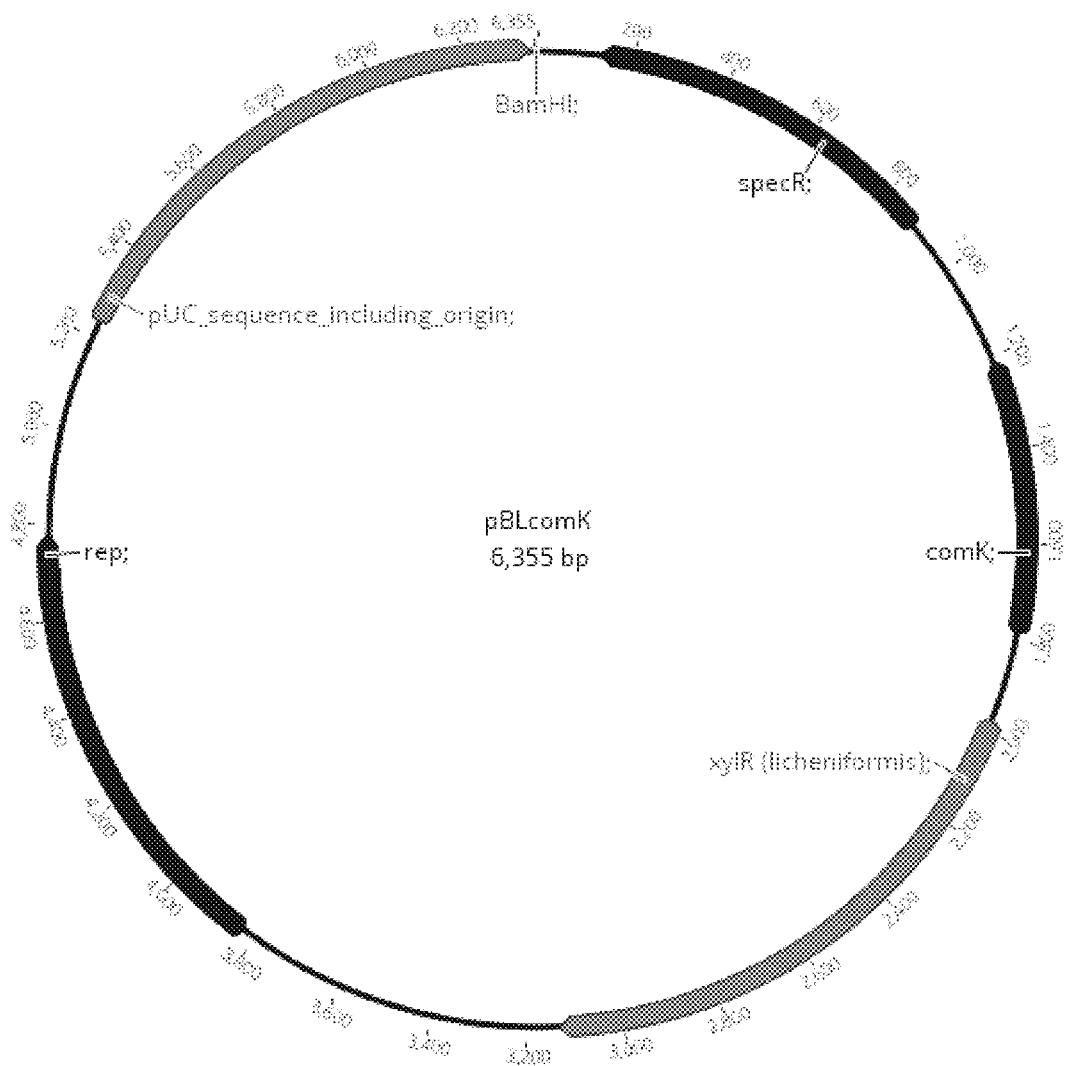
FIG. 4 shows a map of plasmid "pBLComK". This plasmid includes DNA sequences encoding the pBR322 origin of replication, the *Enterococcus faecalis* Spectinomycin resistance (Spec) gene spc (also called aad9), the *B. subtilis* (natto) plasmid pTA1060 rep gene for replication in Bacilli, the *B. licheniformis* comK gene (controlled by the *B. subtilis* xylA promoter), and the *B. subtilis* xylR gene.

Without wishing to be bound by a particular theory, mechanism or mode of operation, it is contemplated herein that the insertion (repeat) of the sequence "AAAISR" in SEQ ID NO: 4, significantly affects, or even completely abolishes, the function of the RghR2 protein as a transcriptional regulator. For example, as a transcription regulator, RghR2 will directly and indirectly regulate the expression of several other genes (e.g., see Example 3). Thus, inactivation of RghR2 by this 18-bp nucleotide duplication encoding the "AAAISR" amino acid repeat set forth in SEQ ID NO: 6 is contemplated to affect the physiology of the cell and as such, may impact factors like cell growth and heterologous protein production. More particularly, the impact of this 18-bp nucleotide duplication present in SEQ ID NO: 3 was further studied in the Example 2, by removing (e.g., deleting) the 18-bp duplication in the rghR2 gene in the *B. licheniformis* derivative of Bra7 (strain) cells producing various heterologous enzymes. More particularly, as presented in FIG. 4, deletion of the rhgR2 18-bp duplication showed a decrease in biomass when cultured, but at the same time demonstrated an improved amylase production titer (i.e., increased production of a protein of interest). Thus, as presented in FIG. 5, the specific productivity (enzyme production/$OD_{600}$) improved by at least a factor 2 in the rghR2 restored (i.e., 418-bp duplication) strain.

III. Transcriptome Analysis of Genes Up-Regulated and Down-Regulated in *B. licheniformis* Rghr2 Variant and Rghr2 Restored Cells As set forth in Example 3, transcriptome analysis of the *B. licheniformis* derivative of Bra7 strain cells (i.e., comprising rghR2 with the 18-bp duplication; SEQ ID NO: 3) and the rghR2 restored variant of this strain (i.e., via removal of the 18-bp duplication; SEQ ID NO: 1), revealed that the transcription of several genes are regulated by RghR2. For example, the transcription of genes upregulated and downregulated by at least two-fold in the rghR2 restored strain (i.e., relative to the rghR2 inactive strain comprising the 18-bp duplication) are indicated in Example 3, TABLE 2 and TABLE 3, respectively.

Figure 7:
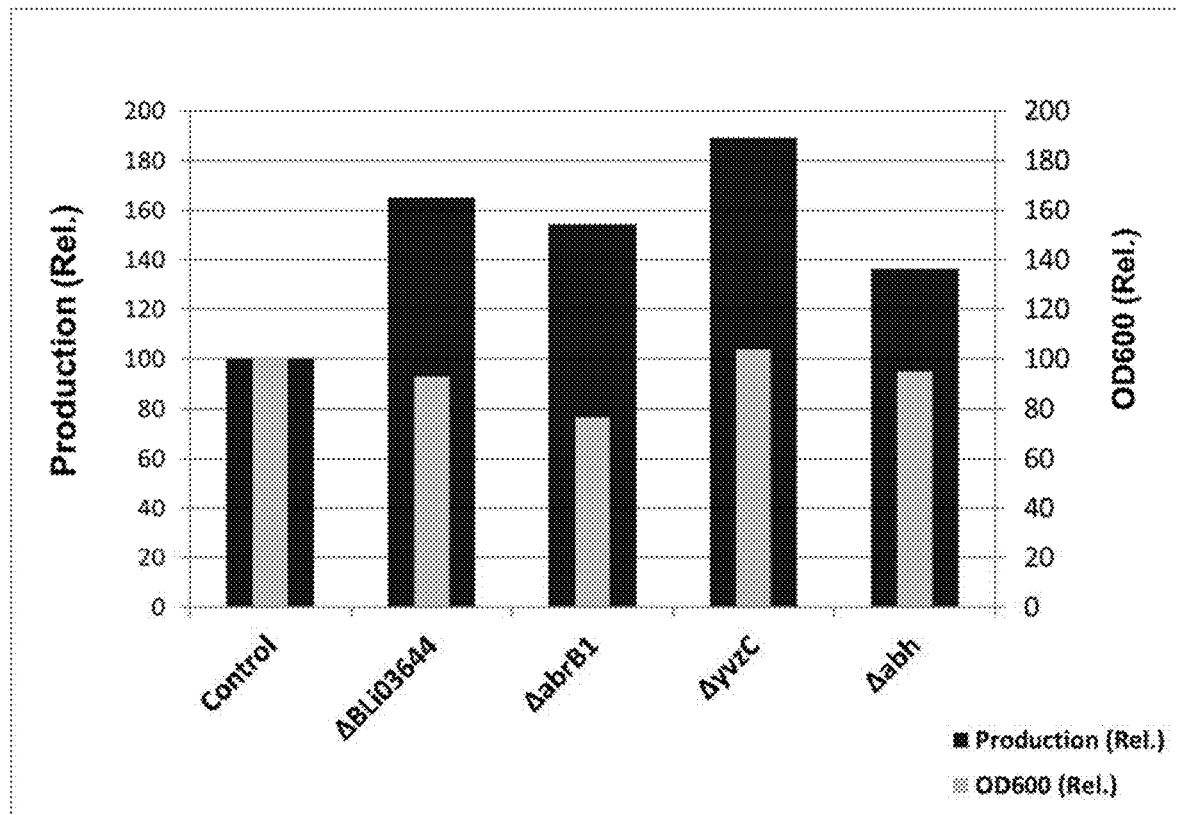
FIG. 7 shows the (protein) production of a *P. curdlanolyticus* α-amylase (black bars) expressed in modified *B. licheniformis* host cells comprising a disrupted BLi03644 gene (ΔBLi03644), a disrupted abrB1 gene (ΔabrB1), a disrupted yvzC gene (ΔyvzC) or a disrupted abh gene (Δabh), relative to the (parental) control host cell. The $OD_{600}$ of these cell cultures are presented as grey bars in FIG. 7.

More particularly, it is contemplated herein that the deletion, disruption, inactivation or down-regulation of one or more the genes in TABLE 3, in either rghR2 restored *B. licheniformis* strains (i.e., comprising the rghR2 gene encoding the RghR2 protein of SEQ ID NO: 2) or rghR2 inactivated *B. licheniformis* strains (i.e., comprising the rghR2 gene encoding the RghR2 protein of SEQ ID NO: 4) will have a positive effect on protein production in these modified host cells, similar to the effect observed by re-activation of rghR2 gene (i.e., via removal/deletion of the 18-bp repeat in the rghR2 gene). Thus, as presented in Example 4, the effect of inactivation (e.g., a deletion, disruption or down-regulation) of a subset of these genes (i.e., Bli03644 (SEQ ID NO: 19); yvzC (SEQ ID NO: 17); abrB1 (SEQ ID NO: 21) and abh (SEQ ID NO: 23)) on heterologous protein production was explored. For example, the Bli03644, abrB1, yvzC and abh genes were inactivated by insertion of antibiotic marker in a *B. licheniformis* Bra7 derivative producing a heterologous α-amylase. Thus, the amylase production was determined in four single knock-out strains (i.e., ΔBLi03644, ΔabrB1, ΔyvzC and Δabh) and compared to the parental strain as control (as described in Example 2). More particularly, as presented in FIG. 7, inactivation of Bli03644, abrB1, yvzC and abh resulted in improved α-amylase production, while cell growth ($OD_{600}$) was less affected (i.e., demonstrating an increased specific productivity, Qp).

IV. Molecular Biology

As set forth above, certain embodiments of the disclosure are related to modified *B. licheniformis* cells derived from parental *B. licheniformis* cells comprising a rghR2 gene encoding a RghR2 protein comprising 90% sequence identity to SEQ ID NO: 4, wherein the modified cells comprise a genetic modification of the rghR2 gene which encodes a RghR2 protein comprising 90% sequence identity to SEQ ID NO: 2. In other embodiments the disclosure is related to modified *B. licheniformis* cells derived from parental *B. licheniformis* cells comprising a rghR2 gene encoding a RghR2 protein of SEQ ID NO: 4, wherein the modified cells comprise a restored rghR2 gene encoding a RghR2 protein of SEQ ID NO: 2. In another embodiment the disclosure is related to modified *B. licheniformis* cells derived from parental *B. licheniformis* cells comprising a rghR2 gene encoding a RghR2 protein comprising 90% sequence identity to SEQ ID NO: 2 and a genetic modification which deletes, disrupts, inactivates or down-regulates at least one endogenous *B. licheniformis* gene selected from the group consisting of abrB1, rpmJ, rpIM, BLi00412, rapK, phrK, BLi00753, yfiT, BLi00828, yhdX, yhzC, terf2, zosA, abbA, speG, yppF, BLi02543, mntR, BLi02768, sspA, BLi03127, BLi03635, mrgA, BLi03644, yvzC, rghR1, spo0F, ywjG, ywq12, BLi04199, BLi04200, licT, bglH and bglP. In another embodiment the disclosure is related to modified *B. licheniformis* cells derived from parental *B. licheniformis* cells comprising a rghR2 gene encoding a RghR2 protein comprising 90% sequence identity to SEQ ID NO: 4 and a genetic modification which deletes, disrupts, inactivates or down-regulates at least one endogenous *B. licheniformis* gene selected from the group consisting of abrB1, rpmJ, rpIM, BLi00412, rapK, phrK, BLi00753, yfjT, BLi00828, yhdX, yhzC, terf2, zosA, abbA, speG, yppF, BLi02543, mntR, BLi02768, sspA, BLi03127, BLi03635, mrgA, BLi03644, yvzC, rghR1, spo0F, ywjG, ywq12, BLi04199, BLi04200, licT, bglH and bglP. Other embodiments are related to genetic modifications which alter the coding sequence of an RghR2 protein's HTH domain.

Thus, certain embodiments of the disclosure provide compositions and methods for genetically modifying (altering) a parental *B. licheniformis* cell of the disclosure to generate modified (rghR2$_{rest}$) cells, and more particularly, modified *B. licheniformis* (rghR2$_{rest}$) cells which produce an increased amount of an endogenous or heterologous protein of interest (i.e., relative to the (unmodified) parental *B. licheniformis* cells).

Thus, certain embodiments of the disclosure are directed to methods for genetically modifying *Bacillus* cells, wherein the modification comprises, but is not limited to, (a) the introduction, substitution, or removal of one or more nucleotides in a gene (or an ORF thereof), or the introduction, substitution, or removal of one or more nucleotides in a regulatory element required for the transcription or translation of the gene or ORF thereof, (b) a gene disruption, (c) a gene conversion, (d) a gene deletion, (e) a gene down-regulation, (f) site specific mutagenesis and/or (g) random mutagenesis. For example, as used herein a genetic modification includes, but is not limited to, a modification of one or more genes selected from the group consisting of rghR1, rghR2, abrB1, rpmJ, rpIM, BLi00412, rapK, phrK, BLi00753, yfjT, BLi00828, yhdX, yhzC, terf2, zosA, abbA, speG, yppF, BLi02543, mntR, BLi02768, sspA, BLi03127, BLi03635, mrgA, BLi03644, yvzC, spo0F, ywjG, ywq12, BLi04199, BLi04200, licT, bglH and bglP.

In certain embodiments, a modified *Bacillus* cell of the disclosure is constructed by reducing or eliminating the expression of a gene set forth above, using methods well known in the art, for example, insertions, disruptions, replacements, or deletions. The portion of the gene to be modified or inactivated may be, for example, the coding region or a regulatory element required for expression of the coding region.

An example of such a regulatory or control sequence may be a promoter sequence or a functional part thereof, (i.e., a part which is sufficient for affecting expression of the nucleic acid sequence). Other control sequences for modification include, but are not limited to, a leader sequence, a propeptide sequence, a signal sequence, a transcription terminator, a transcriptional activator and the like.

In certain other embodiments a modified *Bacillus* cell is constructed by gene deletion to eliminate or reduce the expression of at least one of the aforementioned genes of the disclosure. Gene deletion techniques enable the partial or complete removal of the gene(s), thereby eliminating their expression, or expressing a non-functional (or reduced activity) protein product. In such methods, the deletion of the gene(s) may be accomplished by homologous recombination using a plasmid that has been constructed to contiguously contain the 5' and 3' regions flanking the gene. The contiguous 5' and 3' regions may be introduced into a *Bacillus* cell, for example, on a temperature-sensitive plasmid, such as pE194, in association with a second selectable marker at a permissive temperature to allow the plasmid to become established in the cell. The cell is then shifted to a non-permissive temperature to select for cells that have the plasmid integrated into the chromosome at one of the homologous flanking regions. Selection for integration of the plasmid is effected by selection for the second selectable marker. After integration, a recombination event at the second homologous flanking region is stimulated by shifting the cells to the permissive temperature for several generations without selection. The cells are plated to obtain single colonies and the colonies are examined for loss of both selectable markers (see, e.g., Perego, 1993). Thus, a person of skill in the art (e.g., by reference to the rghR1, rghR2, abrB1, rpmJ, rpIM, BLi00412, rapK, phrK, BLi00753, yfjT, BLi00828, yhdX, yhzC, terf2, zosA, abbA, speG, yppF, BLi02543, mntR, BLi02768, sspA, BLi03127, BLi03635, mrgA, BLi03644, yvzC, spo0F, ywjG, ywq12, BLi04199, BLi04200, licT, bglH and bglP gene (nucleic acid) sequences and the encoded protein sequences thereof), may readily identify nucleotide regions in the gene's coding sequence and/or the gene's non-coding sequence suitable for complete or partial deletion.

In other embodiments, a modified *Bacillus* cell of the disclosure is constructed by introducing, substituting, or removing one or more nucleotides in the gene or a regulatory element required for the transcription or translation thereof. For example, nucleotides may be inserted or removed so as to result in the introduction of a stop codon, the removal of the start codon, or a frame-shift of the open reading frame. Such a modification may be accomplished by site-directed mutagenesis or PCR generated mutagenesis in accordance with methods known in the art (e.g., see, Botstein and Shortle, 1985; Lo et al., 1985; Higuchi et al., 1988; Shimada, 1996; Ho et al., 1989; Horton et al., 1989 and Sarkar and Sommer, 1990). Thus, in certain embodiments, a gene of the disclosure is inactivated by complete or partial deletion.

In another embodiment, a modified *Bacillus* cell is constructed by the process of gene conversion (e.g., see Iglesias and Trautner, 1983). For example, in the gene conversion method, a nucleic acid sequence corresponding to the gene(s) is mutagenized in vitro to produce a defective nucleic acid sequence, which is then transformed into the parental *Bacillus* cell to produce a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (Perego, 1993). Alternatively, the defective nucleic acid sequence may contain an insertion, substitution, or deletion of one or more nucleotides of the gene, as described below.

In other embodiments, a modified *Bacillus* cell is constructed by established anti-sense techniques using a nucleotide sequence complementary to the nucleic acid sequence of the gene (Parish and Stoker, 1997). More specifically, expression of the gene by a *Bacillus* cell may be reduced (down-regulated) or eliminated by introducing a nucleotide sequence complementary to the nucleic acid sequence of the gene, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. Such anti-sense methods include, but are not limited to RNA interference (RNAi), small interfering RNA (siRNA), microRNA (miRNA), antisense oligonucleotides, and the like, all of which are well known to the skilled artisan.

In other embodiments, a modified *Bacillus* cell is produced/constructed via CRISPR-Cas9 editing. For example, a gene encoding rghR1, rghR2, abrB1, rpmJ, rpIM, BLi00412, rapK, phrK, BLi00753, yfjT, BLi00828, yhdX, yhzC, terf2, zosA, abbA, speG, yppF, BLi02543, mntR, BLi02768, sspA, BLi03127, BLi03635, mrgA, BLi03644, yvzC, spo0F, ywjG, ywq12, BLi04199, BLi04200, licT, bglH and/or bglP can be disrupted (or deleted or down-regulated) by means of nucleic acid guided endonucleases, that find their target DNA by binding either a guide RNA (e.g., Cas9) and Cpf1 or a guide DNA (e.g., NgAgo), which recruits the endonuclease to the target sequence on the DNA, wherein the endonuclease can generate a single or double stranded break in the DNA. This targeted DNA break becomes a substrate for DNA repair, and can recombine with a provided editing template to disrupt or delete the gene. For example, the gene encoding the nucleic acid guided endonuclease (for this purpose Cas9 from *S. pyogenes*) or a codon optimized gene encoding the Cas9 nuclease is operably linked to a promoter active in the *Bacillus* cell and a terminator active in *Bacillus* cell, thereby creating a *Bacillus* Cas9 expression cassette. Likewise, one or more target sites unique to the gene of interest are readily identified by a person skilled in the art. For example, to build a DNA construct encoding a gRNA-directed to a target site within the gene of interest, the variable targeting domain (VT) will comprise nucleotides of the target site which are 5' of the (PAM) protospacer adjacent motif (TGG), which nucleotides are fused to DNA encoding the Cas9 endonuclease recognition domain for *S. pyogenes* Cas9 (CER). The combination of the DNA encoding a VT domain and the DNA encoding the CER domain thereby generate a DNA encoding a gRNA. Thus, a *Bacillus* expression cassette for the gRNA is created by operably linking the DNA encoding the gRNA to a promoter active in *Bacillus* cells and a terminator active in *Bacillus* cells.

In certain embodiments, the DNA break induced by the endonuclease is repaired/replaced with an incoming sequence. For example, to precisely repair the DNA break generated by the Cas9 expression cassette and the gRNA expression cassette described above, a nucleotide editing template is provided, such that the DNA repair machinery of the cell can utilize the editing template. For example, about 500 bp 5' of targeted gene can be fused to about 500 bp 3' of the targeted gene to generate an editing template, which template is used by the *Bacillus* host's machinery to repair the DNA break generated by the RGEN.

The Cas9 expression cassette, the gRNA expression cassette and the editing template can be co-delivered to filamentous fungal cells using many different methods (e.g., protoplast fusion, electroporation, natural competence, or induced competence). The transformed cells are screened by PCR amplifying the target gene locus, by amplifying the locus with a forward and reverse primer. These primers can amplify the wild-type locus or the modified locus that has been edited by the RGEN. These fragments are then sequenced using a sequencing primer to identify edited colonies (e.g., see Examples 6 and 7 below).

In yet other embodiments, a modified *Bacillus* cell is constructed by random or specific mutagenesis using methods well known in the art, including, but not limited to, chemical mutagenesis (see, e.g., Hopwood, 1970) and transposition (see, e.g., Youngman et al., 1983). Modification of the gene may be performed by subjecting the parental cell to mutagenesis and screening for mutant cells in which expression of the gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG), O-methyl hydroxylamine, nitrous acid, ethyl methane sulphonate (EMS), sodium bisulphite, formic acid, and nucleotide analogues. When such agents are used, the mutagenesis is typically performed by incubating the parental cell to be mutagenized in the presence of the mutagenizing agent of choice under suitable conditions, and selecting for mutant cells exhibiting reduced or no expression of the gene.

In certain other embodiments, a modified *Bacillus* cell comprises a deletion of an endogenous gene selected from rghR1, rghR2, abrB1, rpmJ, rpIM, BLi00412, rapK, phrK, BLi00753, yfjT, BLi00828, yhdX, yhzC, terf2, zosA, abbA, speG, yppF, BLi02543, mntR, BLi02768, sspA, BLi03127, BLi03635, mrgA, BLi03644, yvzC, spo0F, ywjG, ywq12, BLi04199, BLi04200, licT, bglH and bglP. Thus, in certain of these embodiments, the modified *Bacillus* cell is constructed as described above.

In other embodiments, a modified *Bacillus* cell comprises a disruption of an endogenous gene selected from rghR1, rghR2, abrB1, rpmJ, rpIM, BLi00412, rapK, phrK, BLi00753, yfjT, BLi00828, yhdX, yhzC, terf2, zosA, abbA, speG, yppF, BLi02543, mntR, BLi02768, sspA, BLi03127, BLi03635, mrgA, BLi03644, yvzC, spo0F, ywjG, ywq12, BLi04199, BLi04200, licT, bglH and bglP. In certain embodiments, a polynucleotide disruption cassette of the disclosure comprises a marker gene.

In other embodiments, a modified *Bacillus* cell comprises a down-regulated endogenous gene selected from rghR1, rghR2, abrB1, rpmJ, rpIM, BLi00412, rapK, phrK, BLi00753, yfjT, BLi00828, yhdX, yhzC, terf2, zosA, abbA, speG, yppF, BLi02543, mntR, BLi02768, sspA, BLi03127, BLi03635, mrgA, BLi03644, yvzC, spo0F, ywjG, ywq12, BLi04199, BLi04200, licT, bglH and bglP. For example, in certain embodiments, down-regulating one or more genes set forth above comprises deleting or disrupting the gene's upstream or downstream regulatory elements.

International PCT Publication No. WO2003/083125 discloses methods for modifying *Bacillus* cells, such as the creation of *Bacillus* deletion strains and DNA constructs using PCR fusion to bypass *E. coli*. PCT Publication No. WO2002/14490 discloses methods for modifying *Bacillus* cells including (1) the construction and transformation of an integrative plasmid (pComK), (2) random mutagenesis of coding sequences, signal sequences and pro-peptide sequences, (3) homologous recombination, (4) increasing transformation efficiency by adding non-homologous flanks to the transformation DNA, (5) optimizing double crossover integrations, (6) site directed mutagenesis and (7) marker-less deletion.

Those of skill in the art are well aware of suitable methods for introducing polynucleotide sequences into bacterial cells (e.g., *E. coli* and *Bacillus* spp.) (e.g., Ferrari et al., 1989; Saunders et al., 1984; Hoch et al., 1967; Mann et al., 1986; Holubova, 1985; Chang et al., 1979; Vorobjeva et al., 1980; Smith et al., 1986; Fisher et. al., 1981 and McDonald, 1984). Indeed, such methods as transformation including protoplast transformation and congression, transduction, and protoplast fusion are known and suited for use in the present disclosure. Methods of transformation are particularly preferred to introduce a DNA construct of the present disclosure into a host cell.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell, without insertion into a plasmid or vector. Such methods include, but are not limited to, calcium chloride precipitation, electroporation, naked DNA, liposomes and the like. In additional embodiments, DNA constructs are co-transformed with a plasmid without being inserted into the plasmid. In further embodiments, a selective marker is deleted or substantially excised from the modified *Bacillus* strain by methods known in the art (e.g., Stahl et al., 1984 and Palmeros et al., 2000). In some embodiments, resolution of the vector from a host chromosome leaves the flanking regions in the chromosome, while removing the indigenous chromosomal region.

Promoters and promoter sequence regions for use in the expression of genes, open reading frames (ORFs) thereof and/or variant sequences thereof in *Bacillus* cells are generally known on one of skill in the art. Promoter sequences of the disclosure of the disclosure are generally chosen so that they are functional in the *Bacillus* cells (e.g., *B. licheniformis* cells, *B. subtilis* cells and the like). Certain exemplary *Bacillus* promoter sequences are presented in TABLE 6. Likewise, promoters useful for driving gene expression in *Bacillus* cells include, but are not limited to, the *B. subtilis* alkaline protease (aprE) promoter (Stahl et al., 1984), the α-amylase promoter of *B. subtilis* (Yang et al., 1983), the α-amylase promoter of *B. amyloliquefaciens* (Tarkinen et al., 1983), the neutral protease (nprE) promoter from *B. subtilis* (Yang et al., 1984), a mutant aprE promoter (PCT Publication No. WO2001/51643) or any other promoter from *B. licheniformis* or other related Bacilli. In certain other embodiments, the promoter is a ribosomal protein promoter or a ribosomal RNA promoter (e.g., the rrnI promoter) disclosed in U.S. Patent Publication No. 2014/0329309. Methods for screening and creating promoter libraries with a range of activities (promoter strength) in *Bacillus* cells is describe in PCT Publication No. WO2003/089604.

V. Culturing Modified Cells for Production of a Protein of Interest

In other embodiments, the present disclosure provides methods for increasing the protein productivity of a modified *Bacillus* cell, as compared (i.e., relative) to an unmodified (parental) cell. In certain embodiments, the instant disclosure is directed to methods of producing a protein of interest (POI) comprising fermenting/cultivating a modified bacterial cell, wherein the modified cell secrets the POI into the culture medium. Fermentation methods well known in the art can be applied to ferment the modified and unmodified *Bacillus* cells of the disclosure.

In some embodiments, the cells are cultured under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within typical batch cultures, cells can progress through a static lag phase to a high growth log phase, and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Thus, in certain embodiments, a POI produced by a transformed (modified) host cell may be recovered from the culture medium by conventional procedures including separating the host cells from the medium by centrifugation or filtration, or if necessary, disrupting the cells and removing the supernatant from the cellular fraction and debris. Typically, after clarification, the proteinaceous components of the supernatant or filtrate are precipitated by means of a salt, e.g., ammonium sulfate. The precipitated proteins are then solubilized and may be purified by a variety of chromatographic procedures, e.g., ion exchange chromatography, gel filtration.

VI. Proteins of Interest Produced by Modified (Host) Cells

A protein of interest (POI) of the instant disclosure can be any endogenous or heterologous protein, and it may be a variant of such a POI. The protein can contain one or more disulfide bridges or is a protein whose functional form is a monomer or a multimer, i.e., the protein has a quaternary structure and is composed of a plurality of identical (homologous) or non-identical (heterologous) subunits, wherein the POI or a variant POI thereof is preferably one with properties of interest.

For example, as set forth in the Examples below, the modified (rghR2$_{rest}$) *Bacillus* cells of the disclosure produce increased amounts of heterologous POIs (e.g., heterologous amylases set forth in Examples 2 and 5), while showing a decrease in biomass when cultured. Thus, in certain embodiments, a modified cell of the disclosure expresses an endogenous POI, a heterologous POI or a combination of one or more thereof. For example, in certain embodiments, a modified Bacillus cell of the disclosure produces at least about 0.1% more, at least about 0.5% more, at least about 1% more, at least about 5% more, at least about 6% more, at least about 7% more, at least about 8% more, at least about 9% more, or at least about 10% or more of a POI, relative to its unmodified (parental) cell.

In certain embodiments, a modified Bacillus cell of the disclosure exhibits an increased specific productivity (Qp) of a POI relative the (unmodified) parental Bacillus cell. For example, the detection of specific productivity (Qp) is a suitable method for evaluating protein production. The specific productivity (Qp) can be determined using the following equation:

$$Qp = gP/gDCW \cdot hr$$

wherein, "gP" is grams of protein produced in the tank; "gDCW" is grams of dry cell weight (DCW) in the tank and "hr" is fermentation time in hours from the time of inoculation, which includes the time of production as well as growth time.

Thus, in certain other embodiments, a modified Bacillus cell of the disclosure comprises a specific productivity (Qp) increase of at least about 0.1%, at least about 1%, at least about 5%, at least about 6%, at least about 7%, at least about 8%, at least about 9%, or at least about 10% or more, relative to the unmodified (parental) cell.

In certain embodiments, a POI or a variant POI thereof is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

Thus, in certain embodiments, a POI or a variant POI thereof is an enzyme selected from Enzyme Commission (EC) Number EC 1, EC 2, EC 3, EC 4, EC 5 or EC 6.

For example, in certain embodiments a POI is an oxidoreductase enzyme, including, but not limited to, an EC 1 (oxidoreductase) enzyme selected from EC 1.10.3.2 (e.g., a laccase), EC 1.10.3.3 (e.g., L-ascorbate oxidase), EC 1.1.1.1 (e.g., alcohol dehydrogenase), EC 1.11.1.10 (e.g., chloride peroxidase), EC 1.11.1.17 (e.g., peroxidase), EC 1.1.1.27 (e.g., L-lactate dehydrogenase), EC 1.1.1.47 (e.g., glucose 1-dehydrogenase), EC 1.1.3.X (e.g., glucose oxidase), EC 1.1.3.10 (e.g., pyranose oxidase), EC 1.13.11.X (e.g., dioxygenase), EC 1.13.11.12 (e.g., lineolate 13S-lipozygenase), EC 1.1.3.13 (e.g., alcohol oxidase), EC 1.14.14.1 (e.g., monooxygenase), EC 1.14.18.1 (e.g., monophenol monooxigenase) EC 1.15.1.1 (e.g., superoxide dismutase), EC 1.1.5.9 (formerly EC 1.1.99.10, e.g., glucose dehydrogenase), EC 1.1.99.18 (e.g., cellobiose dehydrogenase), EC 1.1.99.29 (e.g., pyranose dehydrogenase), EC 1.2.1.X (e.g., fatty acid reductase), EC 1.2.1.10 (e.g., acetaldehyde dehydrogenase), EC 1.5.3.X (e.g., fructosyl amine reductase), EC 1.8.1.X (e.g., disulfide reductase) and EC 1.8.3.2 (e.g., thiol oxidase).

In certain embodiments a POI is a transferase enzyme, including, but not limited to, an EC 2 (transferase) enzyme selected from EC 2.3.2.13 (e.g., transglutaminase), EC 2.4.1.X (e.g., hexosyltransferase), EC 2.4.1.40 (e.g., alternasucrase), EC 2.4.1.18 (e.g., 1,4 alpha-glucan branching enzyme), EC 2.4.1.19 (e.g., cyclomaltodextrin glucanotransferase), EC 2.4.1.2 (e.g., dextrin dextranase), EC 2.4.1.20 (e.g., cellobiose phosphorylase), EC 2.4.1.25 (e.g., 4-alpha-glucanotransferase), EC 2.4.1.333 (e.g., 1,2-beta-oligoglucan phosphor transferase), EC 2.4.1.4 (e.g., amylosucrase), EC 2.4.1.5 (e.g., dextransucrase), EC 2.4.1.69 (e.g., galactoside 2-alpha-L-fucosyl transferase), EC 2.4.1.9 (e.g., inulosucrase), EC 2.7.1.17 (e.g., xylulokinase), EC 2.7.7.89 (formerly EC 3.1.4.15, e.g., [glutamine synthetase]-adenylyl-L-tyrosine phosphorylase), EC 2.7.9.4 (e.g., alpha glucan kinase) and EC 2.7.9.5 (e.g., phosphoglucan kinase).

In other embodiments a POI is a hydrolase enzyme, including, but not limited to, an EC 3 (hydrolase) enzyme selected from EC 3.1.X.X (e.g., an esterase), EC 3.1.1.1 (e.g., pectinase), EC 3.1.1.14 (e.g., chlorophyllase), EC 3.1.1.20 (e.g., tannase), EC 3.1.1.23 (e.g., glycerol-ester acylhydrolase), EC 3.1.1.26 (e.g., galactolipase), EC 3.1.1.32 (e.g., phospholipase A1), EC 3.1.1.4 (e.g., phospholipase A2), EC 3.1.1.6 (e.g., acetylesterase), EC 3.1.1.72 (e.g., acetylxylan esterase), EC 3.1.1.73 (e.g., feruloyl esterase), EC 3.1.1.74 (e.g., cutinase), EC 3.1.1.86 (e.g., rhamnogalacturonan acetylesterase), EC 3.1.1.87 (e.g., fumosin B1 esterase), EC 3.1.26.5 (e.g., ribonuclease P), EC 3.1.3.X (e.g., phosphoric monoester hydrolase), EC 3.1.30.1 (e.g., Aspergillus nuclease S1), EC 3.1.30.2 (e.g., Serratia marcescens nuclease), EC 3.1.3.1 (e.g., alkaline phosphatase), EC 3.1.3.2 (e.g., acid phosphatase), EC 3.1.3.8 (e.g., 3-phytase), EC 3.1.4.1 (e.g., phosphodiesterase I), EC 3.1.4.11 (e.g., phosphoinositide phospholipase C), EC 3.1.4.3 (e.g., phospholipase C), EC 3.1.4.4 (e.g., phospholipase D), EC 3.1.6.1 (e.g., arylsufatase), EC 3.1.8.2 (e.g., diisopropyl-fluorophosphatase), EC 3.2.1.10 (e.g., oligo-1, 6-glucosidase), EC 3.2.1.101 (e.g., mannan endo-1,6-alpha-mannosidase), EC 3.2.1.11 (e.g., alpha-1,6-glucan-6-glucanohydrolase), EC 3.2.1.131 (e.g., xylan alpha-1,2-glucuronosidase), EC 3.2.1.132 (e.g., chitosan N-acetylglucosaminohydrolase), EC 3.2.1.139 (e.g., alpha-glucuronidase), EC 3.2.1.14 (e.g., chitinase), EC 3.2.1.151 (e.g., xyloglucan-specific endo-beta-1,4-glucanase), EC 3.2.1.155 (e.g., xyloglucan-specific exo-beta-1,4-glucanase), EC 3.2.1.164 (e.g., galactan endo-1,6-beta-galactosidase), EC 3.2.1.17 (e.g., lysozyme), EC 3.2.1.171 (e.g., rhamnogalacturonan hydrolase), EC 3.2.1.174 (e.g., rhamnogalacturonan rhamnohydrolase), EC 3.2.1.2 (e.g., beta-amylase), EC 3.2.1.20 (e.g., alpha-glucosidase), EC 3.2.1.22 (e.g., alpha-galactosidase), EC 3.2.1.25 (e.g., beta-mannosidase), EC 3.2.1.26 (e.g., beta-fructofuranosidase), EC 3.2.1.37 (e.g., xylan 1,4-beta-xylosidase), EC 3.2.1.39 (e.g., glucan endo-1,3-beta-D-glucosidase), EC 3.2.1.40 (e.g., alpha-L-rhamnosidase), EC 3.2.1.51 (e.g., alpha-L-fucosidase), EC 3.2.1.52 (e.g., beta-N-Acetylhexosaminidase), EC 3.2.1.55 (e.g., alpha-N-arabinofuranosidase), EC 3.2.1.58 (e.g., glucan 1,3-beta-glucosidase), EC 3.2.1.59 (e.g., glucan endo-1,3-alpha-glucosidase), EC 3.2.1.67 (e.g., galacturan 1,4-alpha-galacturonidase), EC 3.2.1.68 (e.g., isoamylase), EC 3.2.1.7 (e.g., 1-beta-D-fructan fructanohydrolase), EC 3.2.1.74 (e.g., glucan 1,4-β-glucosidase), EC 3.2.1.75 (e.g., glucan endo-1,6-beta-glucosidase), EC 3.2.1.77 (e.g., mannan 1,2-(1,3)-alpha-mannosidase), EC 3.2.1.80 (e.g., fructan beta-fructosidase), EC 3.2.1.82 (e.g., exo-poly-alpha-galacturonosidase), EC 3.2.1.83 (e.g., kappa-carrageenase), EC 3.2.1.89 (e.g., arabinogalactan endo-1,4-beta-galactosidase), EC 3.2.1.91 (e.g., cellulose 1,4-beta-cellobiosidase), EC 3.2.1.96 (e.g., mannosyl-glycoprotein endo-beta-N-acetyl-glucosaminidase), EC 3.2.1.99 (e.g., arabinan endo-1,5-alpha-L-arabinanase), EC 3.4.X.X (e.g., peptidase), EC 3.4.11.X (e.g., aminopeptidase), EC 3.4.11.1 (e.g., leucyl aminopeptidase), EC 3.4.11.18 (e.g., methionyl aminopeptidase), EC 3.4.13.9 (e.g., Xaa-Pro dipeptidase), EC 3.4.14.5 (e.g., dipeptidyl-peptidase IV), EC 3.4.16.X (e.g., serine-type carboxypeptidase), EC 3.4.16.5 (e.g., carboxypeptidase C), EC 3.4.19.3 (e.g., pyroglutamyl-peptidase I), EC 3.4.21.X (e.g., serine endopeptidase), EC 3.4.21.1 (e.g., chymotrypsin), EC 3.4.21.19 (e.g., glutamyl endopeptidase), EC 3.4.21.26 (e.g., prolyl oligopeptidase), EC 3.4.21.4 (e.g., trypsin), EC 3.4.21.5 (e.g., thrombin), EC 3.4.21.63 (e.g., oryzin), EC 3.4.21.65 (e.g., thermomycolin), EC 3.4.21.80 (e.g., streptogrisin A), EC 3.4.22.X (e.g., cysteine endopeptidase), EC 3.4.22.14 (e.g., actinidain), EC 3.4.22.2 (e.g., papain), EC 3.4.22.3 (e.g., ficain), EC 3.4.22.32 (e.g., stem bromelain), EC 3.4.22.33 (e.g., fruit bromelain), EC 3.4.22.6 (e.g., chymopapain), EC 3.4.23.1 (e.g., pepsin A), EC 3.4.23.2 (e.g., pepsin B), EC 3.4.23.22 (e.g., endothiapepsin), EC 3.4.23.23 (e.g., mucorpepsin), EC 3.4.23.3 (e.g., gastricsin), EC 3.4.24.X (e.g., metalloendopeptidase), EC 3.4.24.39 (e.g., deuterolysin), EC 3.4.24.40 (e.g., serralysin), EC 3.5.1.1 (e.g., asparaginase), EC 3.5.1.11 (e.g., penicillin amidase), EC 3.5.1.14 (e.g., N-acyl-aliphatic-L-amino acid amidohydrolase), EC 3.5.1.2 (e.g., L-glutamine amidohydrolase), EC 3.5.1.28 (e.g., N-acetylmuramoyl-L-alanine amidase), EC 3.5.1.4 (e.g., amidase), EC 3.5.1.44 (e.g., protein-L-glutamine amidohydrolase), EC 3.5.1.5 (e.g., urease), EC 3.5.1.52 (e.g., peptide-N(4)-(N-acetyl-beta-glucosaminyl)asparagine amidase), EC 3.5.1.81 (e.g., N-Acyl-D-amino-acid deacylase), EC 3.5.4.6 (e.g., AMP deaminase) and EC 3.5.5.1 (e.g., nitrilase).

In other embodiments a POI is a lyase enzyme, including, but not limited to, an EC 4 (lyase) enzyme selected from EC 4.1.2.10 (e.g., mandelonitrile lyase), EC 4.1.3.3 (e.g., N-acetylneuraminate lyase), EC 4.2.1.1 (e.g., carbonate dehydratase), EC 4.2.2.- (e.g., rhamnogalacturonan lyase), EC 4.2.2.10 (e.g., pectin lyase), EC 4.2.2.22 (e.g., pectate trisaccharide-lyase), EC 4.2.2.23 (e.g., rhamnogalacturonan endolyase) and EC 4.2.2.3 (e.g., mannuronate-specific alginate lyase).

In certain other embodiments a POI is an isomerase enzyme, including, but not limited to, an EC 5 (isomerase) enzyme selected from EC 5.1.3.3 (e.g., aldose 1-epimerase), EC 5.1.3.30 (e.g., D-psicose 3-epimerase), EC 5.4.99.11 (e.g., isomaltulose synthase) and EC 5.4.99.15 (e.g., (1→4)-α-D-glucan 1-α-D-glucosylmutase).

In yet other embodiments, a POI is a ligase enzyme, including, but not limited to, an EC 6 (ligase) enzyme selected from EC 6.2.1.12 (e.g., 4-coumarate:coenzyme A ligase) and EC 6.3.2.28 (e.g., L-amino-acid alpha-ligase)9

Thus, in certain embodiments, industrial protease producing *Bacillus* host cells provide particularly preferred expression hosts. Likewise, in certain other embodiments, industrial amylase producing *Bacillus* host cells provide particularly preferred expression hosts.

For example, there are two general types of proteases which are typically secreted by *Bacillus* spp., namely neutral (or "metalloproteases") and alkaline (or "serine") proteases. For example, *Bacillus* subtilisin proteins (enzymes) are exemplary serine proteases for use in the present disclosure. A wide variety of *Bacillus* subtilisins have been identified and sequenced, for example, subtilisin 168, subtilisin BPN', subtilisin Carlsberg, subtilisin DY, subtilisin 147 and subtilisin 309 (e.g., WO 1989/06279 and Stahl et al., 1984). In some embodiments of the present disclosure, the modified *Bacillus* cells produce mutant (i.e., variant) proteases. Numerous references provide examples of variant proteases, such as PCT Publication Nos. WO1999/20770; WO1999/20726; WO1999/20769; WO1989/06279; U.S. RE34,606; U.S. Pat. Nos. 4,914,031; 4,980,288; 5,208,158; 5,310,675; 5,336,611; 5,399,283; 5,441,882; 5,482,849; 5,631,217; 5,665,587; 5,700,676; 5,741,694; 5,858,757; 5,880,080; 6,197,567 and 6,218,165. Thus, in certain embodiments, a modified *Bacillus* cells of the disclosure comprises an expression construct encoding a protease.

In certain other embodiments, a modified *Bacillus* cells of the disclosure comprises an expression construct encoding an amylase. A wide variety of amylase enzymes and variants thereof are known to one skilled in the art. For example, International PCT Publication NO. WO2006/037484 and WO 2006/037483 describe variant α-amylases having improved solvent stability, Publication No. WO1994/18314 discloses oxidatively stable α-amylase variants, Publication No. WO1999/19467, WO2000/29560 and WO2000/60059 disclose Termamyl-like α-amylase variants, Publication No. WO2008/112459 discloses α-amylase variants derived from *Bacillus* sp. number 707, Publication No. WO1999/43794 discloses maltogenic α-amylase variants, Publication No. WO1990/11352 discloses hyper-thermostable α-amylase variants, Publication No. WO2006/089107 discloses α-amylase variants having granular starch hydrolyzing activity.

In other embodiments, a POI or variant POI expressed and produced in a modified cell of the disclosure is a peptide, a peptide hormone, a growth factor, a clotting factor, a chemokine, a cytokine, a lymphokine, an antibody, a receptor, an adhesion molecule, a microbial antigen (e.g., HBV surface antigen, HPV E7, etc.), variants thereof, fragments thereof and the like. Other types of proteins (or variants thereof) of interest may be those that are capable of providing nutritional value to a food or to a crop. Non-limiting examples include plant proteins that can inhibit the formation of anti-nutritive factors and plant proteins that have a more desirable amino acid composition (e.g., a higher lysine content than a non-transgenic plant).

There are various assays known to those of ordinary skill in the art for detecting and measuring activity of intracellularly and extracellularly expressed proteins. In particular, for proteases, there are assays based on the release of acid-soluble peptides from casein or hemoglobin measured as absorbance at 280 nm or colorimetrically, using the Folin method (e.g., Bergmeyer et al., 1984). Other assays involve the solubilization of chromogenic substrates (See e.g., Ward, 1983). Other exemplary assays include succinyl-Ala-Ala-Pro-Phe-para-nitroanilide assay (SAAPFpNA) and the 2,4, 6-trinitrobenzene sulfonate sodium salt assay (TNBS assay). Numerous additional references known to those in the art provide suitable methods (See e.g., Wells et al., 1983; Christianson et al., 1994 and Hsia et al., 1999).

International PCT Publication No. WO2014/164777 discloses Ceralpha α-amylase activity assays useful for amylase activities described herein.

Means for determining the levels of secretion of a protein of interest in a host cell and detecting expressed proteins include the use of immunoassays with either polyclonal or monoclonal antibodies specific for the protein. Examples include enzyme-linked immunosorbent assay (ELISA), radioimmunoassay (RIA), fluorescence immunoassay (FIA), and fluorescent activated cell sorting (FACS).

EXAMPLES

Certain aspects of the present invention may be further understood in light of the following examples, which should not be construed as limiting. Modifications to materials and methods will be apparent to those skilled in the art.

Example 1

Duplication of 18-Bp Sequence in the Rghr2 Gene of Bacillus Licheniformis Strains Bacillus licheniformis strain DSM13 (ATTC 14580) contains a gene, designated rghR2 (BLi03647), encoding a putative HTH-type transcriptional regulator. The rghR2 nucleic acid sequence of B. licheniformis DSM13 is depicted in SEQ ID NO: 1 and the encoded amino acid sequence of the RghR2 protein of Bacillus licheniformis DSM13 is depicted in SEQ ID NO: 2.

Sequencing of the genomes of (a) B. licheniformis strain Bra7, (b) a B. licheniformis Bra7 derivative, (c) B. licheniformis strain ATCC-9789 (www.atcc.org/Products/All/9789.aspx) and (d) B. licheniformis strain ATCC-6598 (www.atcc.org/en/Products/All/6598.aspx) revealed that all of these B. licheniformis strains have a duplication of 18 nucleotides in the rghR2 gene, wherein the 18 nucleotide duplication is presented in SEQ ID NO: 3: GCCGCAGCCATTTCCAGA.

Thus, the nucleotide sequence of (a) the B. licheniformis Bra7 strain rghR2 gene (SEQ ID NO: 3) is identical to the nucleotide sequence of the rghR2 gene of (b) B. licheniformis Bra7 derivative, (c) ATCC-9789, and (d) ATCC-6598, as presented in SEQ ID NO: 3. Likewise, the amino acid sequence of the RghR2 protein of B. licheniformis Bra7 strain (SEQ ID NO: 5) is identical to the amino acid sequence of RghR2 of Bacillus licheniformis Bra7 derivative, ATCC-9789 and ATCC-6598, as presented in SEQ ID NO: 4.

An alignment of the B. licheniformis Bra7 strain RghR2 amino acid sequence (SEQ ID NO: 4) and the B. licheniformis DSM13 strain RghR2 amino acid sequence (SEQ ID NO: 2), illustrating the repeat amino acids (AAAISR) is shown in FIG. 1. The insertion of the sequence "AAAISR" is in the helix-turn-helix (HTH) domain and near the sequence-specific DNA-binding site as shown in FIG. 8. One may expect that the insertion has a significant effect on, or even completely abolishes, the "function" of the RghR2 transcription regulator (i.e., a substantially inactive transcriptional regulatory protein). For example, as a transcription regulator, RghR2 will directly and indirectly regulate the expression of several other genes. It is contemplated herein that the inactivation of RghR2 (e.g., by the 18-bp duplication set forth in SEQ ID NO: 5 encoding the "AAAISR" amino acid repeat set forth in SEQ ID NO: 6) affects cell physiology and consequently, may impact factors like growth and heterologous protein production thereof. Thus, the impact on growth and heterologous protein production were further studied by removing the 18-bp duplication in the rghR2 gene in B. licheniformis Bra7 derivative cells producing various heterologous enzymes.

Example 2

Figure 3:
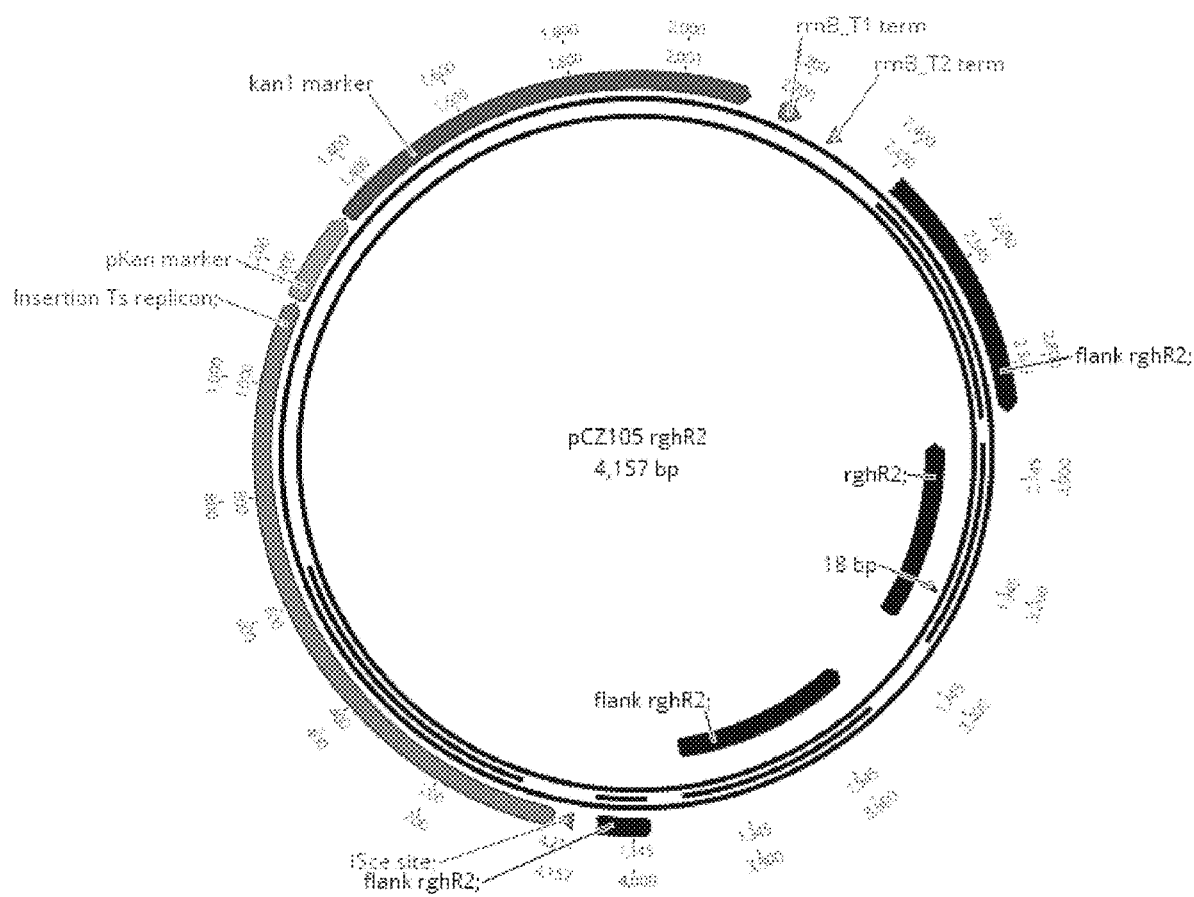
FIG. 3 shows the engineered "pCZ105 rghR2" plasmid. This plasmid comprises a pE194 temperature sensitive replicon (Ts replicon), a kanamycin coding sequence (Kan), a kanamycin promoter (pKan marker), a ribosomal terminator sequence (Term rrnB), an I-Sce site, an eighteen base-pair (18-bp) deleted rghR2 gene and rghR2 flanking regions.

Removal of the 18-Bp Duplication in Rghr2 and its Effect on Cell Growth and Heterologous Enzyme Production To remove the 18-bp duplication in the rghR2 gene in B. licheniformis Bra7 derivative strain (and strains related or derived from this host strain), two PCR amplifications were performed on the genomic DNA of Bra7. One PCR amplification was performed using primers 378 and 379 (TABLE 2) and a second PCR amplification was performed on genomic DNA of Bra7 using primers 380 and 381 (TABLE 2). Both fragments were gel purified and used in a fusion PCR using primer 378 and 381 to yield a rghR2 fragment with the 18-bp duplication deleted. This fragment was digested using HindIII and NotI and after gel purification ligated into a HindIII and NotI digested and gel purified temperature sensitive integration plasmid pCZ105 (FIG. 2) yielding the plasmid "pZC105_rghR2" (FIG. 3).

TABLE 2

PCR Primers

| Primer # | Nucleotide Sequence | SEQ ID NO |
|---|---|---|
| 369 | GAGACTAGTGAGCTCGCATCACACGC | 7 |
| 378 | GACTGCGGCCGCACCATGATTACTCCCCTTTCTAATCT | 8 |
| 379 | TCTGGAAATGGCTGCGGCGCTCACACCGGCATACATGG | 9 |
| 380 | GCCGCAGCCATTTCCAGAATCGAAAACGGCCACCGCGG | 10 |
| 381 | GACTAAGCTTCGCCGTCTTGATGCTTGT | 11 |
| 384 | GTACGGCATTTTCAGAGCCTC | 12 |
| 752 | TGAATCATCTTTCCGATCACAAGTTG | 13 |
| 753 | AAGGAGGGGATGACAAATGGAAG | 14 |

Plasmid pZC105_rghR2 was rolling circle amplified (GE Healthcare Europe GmbH, Eindhoven, The Netherlands) and transformed in a B. licheniformis (Bra7 derivative) strain that lacks the native B. licheniformis amylase (AmyL) gene, but carries an expression cassette encoding a heterologous Peanibacillus curdlanolyticus variant α-amylase. Thus, the expression cassette comprises a gene encoding a P. curdlanolyticus variant α-amylase behind a strong promoter and is integrated in the B. licheniformis genome. The sequence of the heterologous P. curdlanolyticus variant α-amylase, is disclosed in PCT Publication No. WO2014/164834 (i.e., SEQ ID NO: 35), specifically incorporated herein by reference in its entirety.

Cells were made competent using plasmid pBLComK (FIG. 4) as previously described in PCT International Application No. PCT/US2016/059078, filed Oct. 27, 2016. Cells were plated onto Luria agar containing 30 mg/l kanamycin and cultured over night at 37° C. Formed colonies were re-streaked onto fresh Luria agar and cultured over-night at 37° C. Single colonies were picked and cultured in Luria broth at 42° C. over-night while shaking to promote integration in the genome. Subsequently, cells were plated onto Luria agar containing 30 mg/l kanamycin and cultured over night at 37° C. After verification of integration in the genome by PCR using primer 369 and 384, the correct clones were cultured in Luria broth over-night at 37° C. followed by plating onto Luria agar. Single colonies were re-streaked onto LB agar plates and LB agar plates containing 30 mg/l kanamycin and cultured over night at 37° C. to verify the removal of the vector part from the genome by a double crossover event. Colonies unable to grow in the presence of kanamycin were subjected to PCR using primer 752 and 753 (TABLE 2) and the obtained fragment was sequenced. This confirmed removal of the 18-bp duplication in the rghR2 gene.

One of the verified clones, clone 197, was used for further studies. Clone 197, expressing *P. curdlanolyticus* α-amylase in a rghR2 restored host (i.e., rghR2$_{rest}$, removal off 18-bp duplication) and the parental control strain (i.e., comprising rghR2 with the 18-bp duplication) expressing *P. curdlanolyticus* α-amylase, were inoculated in tryptone soy broth (TSB) medium and cultured over night at 37° C. while shaking. Main cultures were inoculated from this pre-culture at an OD$_{660}$ of 0.1 in an amylase production medium using glucose slow release microtiter plates (srMTP; PS Biotech GmbH, Herzogenrath, Germany). Plates were cultured for 72 hours while shaking at 37° C.

After 72 hours, the OD$_{600}$ was measured (FIG. 5) and 100 ul of cells was diluted 1:1 with 50% propylene glycol (Sigma Aldrich, Zwijndrecht, The Netherlands) and incubated for 1 hour at 40° C. while shaking. After incubation, the amylase activity was measured using the Ceralpha reagent (Megazyme, Wicklow, Ireland) as described in the instructions of Megazyme, and as disclosed in PCT International Application No. PCT/US2016/059078.

Figure 5:
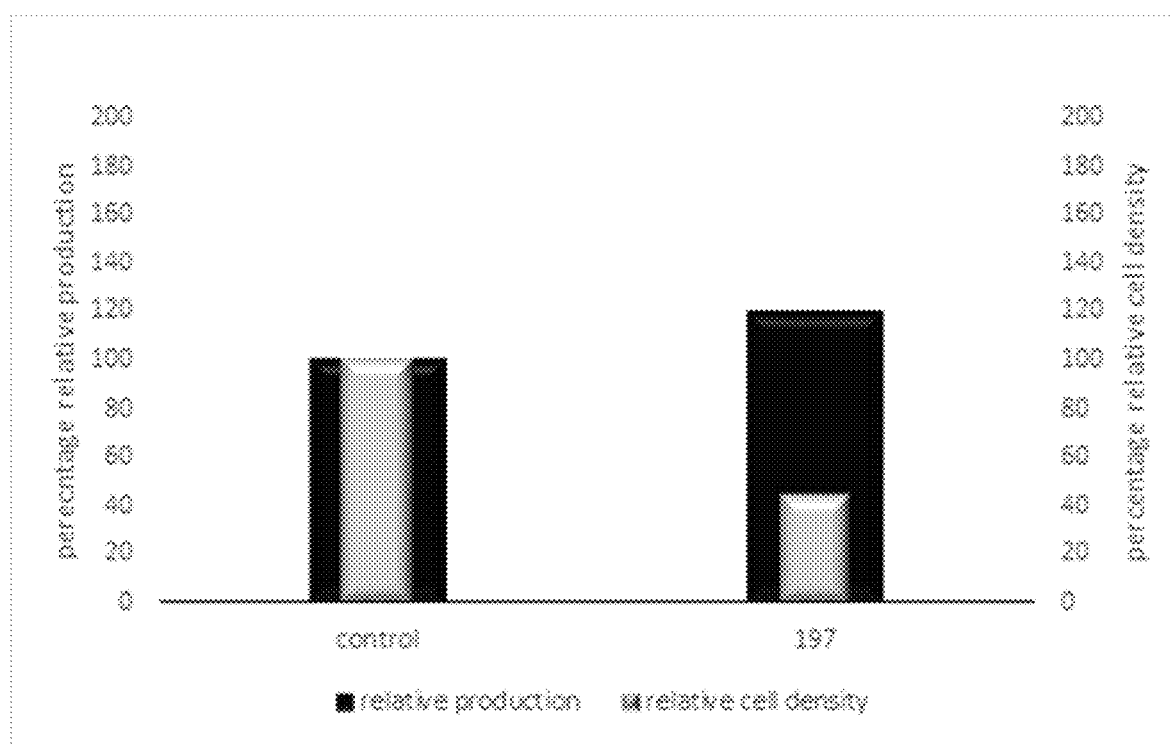
FIG. 5 shows a bar graph representing results of a slow release microtiter plate experiment (see, Example 2) of control (parental) *B. licheniformis* host cells (i.e., *B. licheniformis* cells comprising the 18-bp rghR2 duplication; $rghR2_{dup}$) and *B. licheniformis* clone 197 (i.e., *B. licheniformis* daughter cells comprising a restored rghR2 gene ($rghR2_{rest}$). More particularly, as presented in FIG. 5, the light grey bars represent the relative optical density (cell density) to the control, and the black bars represent the relative production titers of a heterologous *Peanibacillus curdlanolyticus* variant α-amylase relative to the control.
Figure 6:
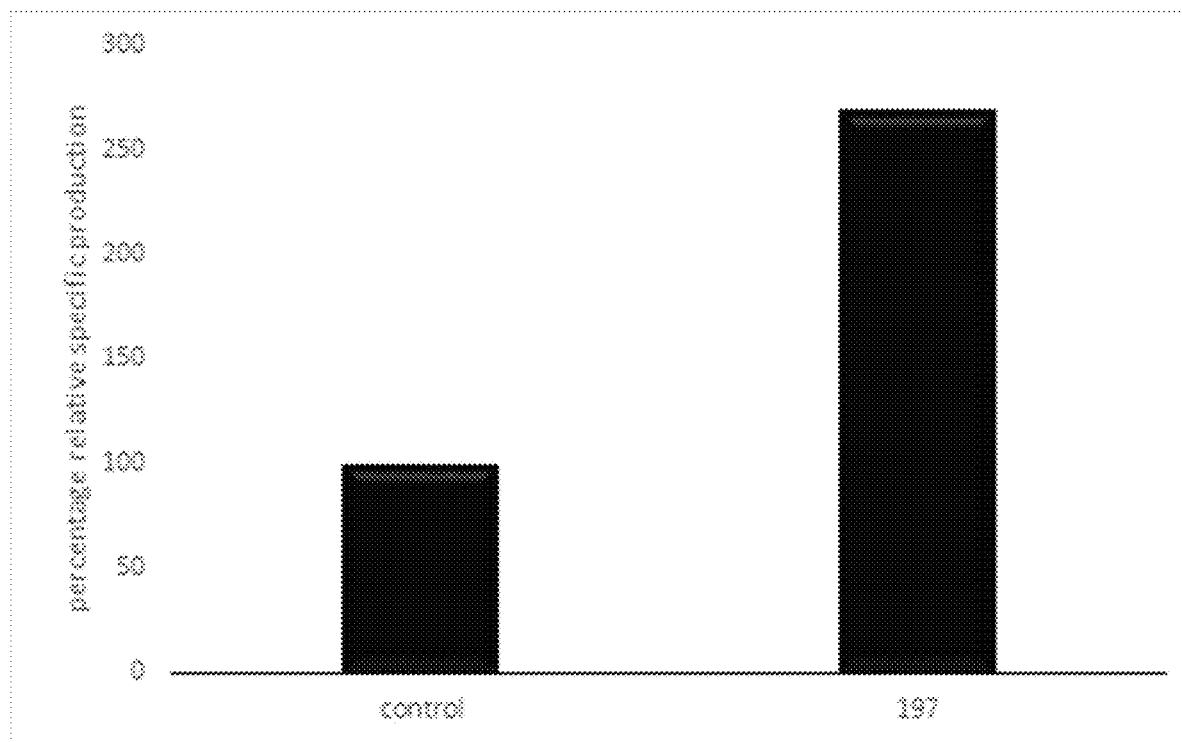
FIG. 6 shows the specific relative protein production (i.e., *P. curdlanolyticus* α-amylase) of the *B. licheniformis* $rghR2_{rest}$ strain (i.e., daughter cell, clone 197) compared to the control (parental; $rghR2_{dup}$) strain.

As presented in FIG. 5, deletion of the rhgR2 18-bp duplication showed a decrease in biomass when cultured, but at the same time demonstrated an improved amylase production titer. For example, FIG. 6 shows that the specific productivity (enzyme production/OD$_{600}$) of the heterologous α-amylase improved by at least a factor 2 in the rghR2 restored strain.

Example 3

RghR2 Regulated Genes

Transcriptome analysis of a Bra7 production strain (i.e., comprising rghR2 with the 18-bp duplication) and the rghR2 restored (rghR2$_{rest}$) variant of this strain (i.e., removal of the 18-bp duplication), revealed that transcription of several genes are regulated by RghR2 (TABLE 3). Transcription of genes downregulated by at least two-fold in the rghR2 restored strain (i.e., relative to the rghR2 inactive strain comprising the 18-bp duplication) are indicated in TABLE 4. One can expect that (further) down-regulation of these genes, or deletion of these genes, in both rghR2 restored strains and rghR2 inactivated strains (e.g., via the 18-bp insertion) has a positive effect on protein production. This would be a similar effect as seen by re-activation of rghR2 by removal of the 18-bp repeat. Therefore, the effect of inactivation of a subset of these genes (Bli03644, yvzC, abrB1, abh) on heterologous protein production was explored as described below in Example 4.

TABLE 3

GENES UPREGULATED BY A FACTOR 2 OR MORE IN A rghR2 RESTORED STRAIN

| ID | Gene_Name | Product |
|---|---|---|
| BLi00340 | blaSE | glutamyl endopeptidase blase (mpr) |
| BLi00343 | BLi00343 | hypothetical protein |
| BLi00373 | ycgM, putB | proline dehydrogenase YcgM |
| BLi00374 | rocA | 1-pyrroline-5-carboxylate dehydrogenase |
| BLi00401 | lchAA | lichenysin synthase LchAA |
| BLi00403 | lchAC | lichenysin synthase LchAC |
| BLi00404 | lchAD | lichenysin synthase LchAD |
| BLi01250 | catE | catechol-2,3-dioxygenase subunit CatE |
| BLi00947 | BLi00947 | hypothetical protein |
| BLi00950 | BLi00950 | hypothetical protein |
| BLi00976 | yhcM | protein YhcM |
| BLi00977 | BLi00977 | hypothetical protein |

TABLE 3-continued

GENES UPREGULATED BY A FACTOR 2 OR MORE IN A rghR2 RESTORED STRAIN

| ID | Gene_Name | Product |
|---|---|---|
| BLi01109 | apr | subtilisin Carlsberg |
| BLi01295 | abnA1 | arabinan endo-1,5-alpha-L-arabinosidase AbnA |
| BLi01337 | xkdK | phage tail sheath protein XkdK |
| BLi01364 | ggt | gamma-glutamyltranspeptidase |
| BLi02599 | isp | intracellular serine protease Isp |
| BLi01748 | bpr1 | bacillopeptidase F |
| BLi02215 | BLi02215 | hypothetical protein |
| BLi02255 | yvgO | stress response protein YvgO |
| BLi02264 | cwlS | D-gamma-glutamyl-meso-diaminopimelic acid endopeptidase CwlS |
| BLi02271 | yoaJ | extracellular endoglucanase |
| BLi02544 | BLi02544 | hypothetical protein |
| BLi05030 | BLi05030 | hypothetical protein |
| BLi02827 | sacC | levanase SacC |
| BLi02828 | levG | fructose-specific phosphotransferase system EIID component LevG |
| BLi02830 | levE | trigger enzyme fructose-specific phosphotransferase enzyme IIB component LevE |
| BLi02831 | levD | PTS system fructose-specific transporter subunits IIA |
| BLi05031 | BLi05031 | hypothetical protein |
| BLi03176 | ytvB | transmembrane protein YtvB |
| BLi03197 | pckA | phosphoenolpyruvate carboxykinase |
| BLi03566 | yvmC | cyclodipeptide synthase YvmC |
| BLi03567 | cypX | cytochrome P450 cyclo-l-leucyl-l-leucyl dipeptide oxidase CypX |
| BLi03981 | BLi03981 | hypothetical protein |
| BLi03989 | pobA | 4-hydroxybenzoate 3-monooxygenase |
| BLi03991 | BLi03991 | oxidoreductase |
| BLi03992 | BLi03992 | 4-oxalocrotonate tautomerase |
| BLi03999 | yuaB | hypothetical protein |
| BLi04032 | BLi04032 | ABC transporter ATP binding/permease protein |
| BLi04124 | lanP | peptidase LanP |
| BLi04125 | lanT | lichenicidin processing transporter LanT |
| BLi04126 | lanM1 | lichenicidin modifying enzyme LanM |
| BLi05042 | lanA1 | lichenicidin prepeptide LanA |
| BLi04127 | lanA2 | lichenicidin prepeptide LanA |
| BLi04128 | lanM2 | lichenicidin modifying enzyme LanM |

Gene IDs from KEGG GENOME T00200 (*Bacillus licheniformis* DSM 13 = ATCC 14580)

TABLE 4

GENES DOWNREGULATED BY A FACTOR 2 OR MORE IN A rghR2 RESTORED STRAIN

| ID | Gene_Name | Product |
|---|---|---|
| BLi00050 | abrB1 | transition state transcriptional regulator AbrB |
| BLi00158 | rpmJ | 50S ribosomal protein L36 |
| BLi00167 | rplM | 50S ribosomal protein L13 |
| Bli00412 | BLi00412 | ABC transporter ATP-binding protein |
| BLi00751 | rapK | response regulator aspartate phosphatase RapK |
| BLi05046 | phrK | response regulator aspartate phosphatase RapK regulator PhrK |
| BLi00753 | BLi00753 | SAM methyltransferase |
| BLi00826 | yfjT | protein YfjT |
| BLi00828 | BLi00828 | glycerol dehydrogenase |
| BLi01035 | yhdX | protein YhdX |
| BLi01118 | yhzC | protein YhzC |
| — | terf2 | Telomeric repeat-binding factor 2 |
| BLi01593 | zosA | zinc-transporting ATPase ZosA |
| BLi01626 | abbA | AbrB inhibitor AbbA |
| BLi02012 | speG | spermidine N(1)-acetyltransferase SpeG |
| BLi02362 | yppF | protein YppF |
| BLi02543 | BLi02543 | hypothetical protein |
| BLi02623 | mntR | manganese transport transcriptional regulator |
| BLi02768 | BLi02768 | hypothetical protein |
| BLi03099 | sspA | small acid-soluble spore protein SspA |
| BLi03127 | BLi03127 | hypothetical protein |
| BLi03635 | BLi03635 | phage protein |
| BLi00972 | metQ | methionine ABC transporter substrate-binding protein MetQ |

TABLE 4-continued

GENES DOWNREGULATED BY A FACTOR 2 OR MORE
IN A rghR2 RESTORED STRAIN

| ID | Gene_Name | Product |
|---|---|---|
| BLi03478 | BLi03478 | D-alanyl-D-alanine carboxypeptidase |
| BLi03480 | mrgA | metalloregulation DNA-binding stress protein MrgA |
| BLi03644 | BLi03644 | transcriptional regulator |
| BLi03645 | yvzC | HTH-type transcriptional regulator YvzC |
| BLi03646 | rghR1 | HTH-type transcriptional regulator RghR |
| BLi03961 | spo0F | phosphotransferase Spo0F |
| BLi03962 | ywjG | hypothetical protein |
| BLi04055 | ywql2 | hypothetical protein |
| BLi04199 | BLi04199 | family 1 glycoside hydrolase |
| BLi04200 | BLi04200 | PTS system beta-glucoside-specific transporter subunit IIABC |
| BLi04201 | licT | transcriptional antiterminator LicT |
| BLi04214 | bglH | phospho-beta-glucosidase BglH |
| BLi04215 | bglP | trigger enzyme beta-glucoside-specific phosphotransferase system EIIBCA component |

Gene IDs from KEGG GENOME T00200 (*Bacillus licheniformis* DSM 13 = ATCC 14580)

Example 4

Inactivation of Rghr2 Regulated Genes and Their Effect on Heterologous Protein Production The Bli03644, abrB1, yvzC and abh genes were inactivated by insertion of antibiotic marker in a Bra7 strain producing a heterologous α-amylase (i.e., the heterologous *P. curdlanolyticus* α-amylase disclosed in PCT Publication No. WO2014/164834), wherein the heterologous α-amylase production was determined in the four single knock-out strains (ΔBLi03644, ΔabrB1, ΔyvzC and Δabh) and compared to the parental (control) strain as described in Example 2. For example, as presented in FIG. 7, inactivation of Bli03644, abrB1, yvzC and abh resulted in improved heterologous α-amylase production, while cell growth ($OD_{600}$) was less affected.

Example 5

Enhanced Production of Amylases in Modified Cells Comprising Rghr2$_{Rest}$

In the present example, both *B. licheniformis* cells comprising rghR2 gene having the 18-bp duplication (SEQ ID NO: 3) and *B. licheniformis* cells comprising the rghR2 gene lacking the 18-bp duplication (rghR2$_{rest}$; SEQ ID NO: 1) comprise a single copy of either: (a) a heterologous *Cytophaga* sp. variant #1 α-amylase expression cassette integrated in the *B. licheniformis* genome (SEQ ID NO: 140) or (b) a variant *Geobacillus stearothermophilus* α-amylase expression cassette (SEQ ID NO: 141) integrated into the *B. licheniformis* genome, which were inoculated from a frozen vial (1 mL, 20% glycerol) in 10 mL seed medium (15 g/L Yeast extract, 5.5 g/L Dextrose, 3 g/L Potassium phosphate, 1 g/L Magnesium sulfate). Cultures were grown at 38° C. in a vented 100 mL flask at 310 RPM until the $OD_{600}$ was approximately 2. From each culture 0.25 mL was transferred to 25 mL of production medium (30 g/L 2-(N-morpholino) ethanesulfonic acid (MES), 6.7 g/L Yeast Nitrogen Base with ammonium sulfate without amino acids, 1.7 g/L Yeast Nitrogen Base without ammonium sulfate or amino acids, 0.7 g/L Soytone, pH 6.8 with Ammonium hydroxide) in a 100 mL vented flask and two 14 mm glucose feed beads were added and the flask incubated at 38° C., 310 RPM for 84 hours with periodic replacement of evaporated water losses.

After 84 hours, a sample was taken from each flask and centrifuged. One tenth (0.1) mL of the supernatant was mixed with 0.9 mL of Bradford reagent. Color was measured as absorbance of 595 nm wavelength and compared to a standard curve to determine protein concentration. The pellet was resuspended in propylene glycol, warmed for 30 minutes and also assayed with Bradford as above. The amylase titer was determined by the aggregate of the two measurements are presented in TABLE 5.

TABLE 5

AMYLASE TITER FROM rghR2 RESTORED STRAINS

| Heterologous Amylase | rghR2 allele | Amylase titer (g/L ± range) | Fold difference compared to rghR2 18-bp duplication (SEQ ID NO: 3) |
|---|---|---|---|
| *Cytophaga* sp. α-amylase (V1) | rghR2 18-bp dup (SEQ ID NO: 3) | 2.0 ± 0.1 | 1.0 |
| *Cytophaga* sp. α-amylase (V1) | rghR2$_{rest}$ (SEQ ID NO: 1) | 2.2 ± 0.2 | 1.1 |
| *G. stearothermophilus* α-amylase | rghR2 18-bp dup (SEQ ID NO: 3) | 3.9 ± 0.2 | 1.0 |
| *G. stearothermophilus* α-amylase | rghR2$_{rest}$ (SEQ ID NO: 1) | 4.3 ± 0.1 | 1.1 |

Thus, as presented above in TABLE 5, both *B. licheniformis* strains comprising the rghR2$_{rest}$ allele show improvement in amylase titer of at least 10%, indicating that removing the natively existing 18-bp duplication in rghR2 gene is beneficial for production of multiple heterologous amylase molecules.

Example 6

Crispr-Cas9 Editing and Deletion of the 18-Nucleotide Duplication in the Rghr2 Gene In the present example, a gene encoding a nucleic acid guided endonuclease (e.g., Cas9 from *S. pyogenes* (SEQ ID NO: 91)) or a codon optimized gene thereof (e.g., Cas9 nuclease of SEQ ID NO: 92) is operably linked to a promoter active in *B. licheniformis* (e.g., see, TABLE 6 below) and a terminator active in *B. licheniformis* (e.g., SEQ ID NO: 103), thereby creating a *B. licheniformis* Cas9 expression cassette (SEQ ID NO: 104).

TABLE 6

LIST OF EXAMPLARY PROMOTERS ACTIVE IN
B. LICHENIFORMIS

| Promoter Name | SEQ ID NO |
|---|---|
| aprEp | 93 |
| xylAp | 94 |
| spac | 95 |
| Hyper spank | 96 |
| Vegp | 97 |
| nprEp | 98 |
| N25 promoter | 99 |
| groE promoter | 100 |
| AraAp | 101 |
| AraA2p | 102 |

A target site unique to the 18-bp duplication allele of rghR2 (SEQ ID NO: 105), such that the rghR2 gene lacking the 18-bp duplication does not contain the target site, can be identified.

Likewise, to build a DNA construct encoding a guide RNA (gRNA) targeting the unique target site within the 18-bp duplication (SEQ ID NO: 105), the variable targeting domain (VT), comprising the target site nucleotides of SEQ ID NO: 106, SEQ ID NO: 107, SEQ ID NO: 108, or SEQ ID NO: 109 (which nucleotides are upstream (5') of the proto-spacer adjacent motif (PAM) nucleotides "TGG", are fused to DNA encoding the Cas9 endonuclease recognition domain for S. pyogenes Cas9 (CER, SEQ ID NO: 110).

The combination (fusion) of the DNA encoding the VT domain and the DNA encoding the CER domain generate a DNA encoding a gRNA (for example the DNA encoding the gRNA targeting the target site from the 18-bp duplication within rghR2 (SEQ ID NO:105) to generate SEQ ID NO: 111.

A B. licheniformis expression cassette for the gRNA is created by operably linking the DNA encoding the gRNA (SEQ ID NO: 111) to a promoter active in B. licheniformis (e.g., TABLE 6) and a terminator active in B. licheniformis (e.g., SEQ ID NO: 103) which creates a gRNA expression cassette (spac-gRNA-t0 SEQ ID NO: 112). In order to precisely repair the DNA break generated by the Cas9 expression cassette (SEQ ID NO: 104) and the gRNA expression cassette (SEQ ID NO: 112), an editing template to be used by the DNA repair machinery of the cell must be provided. For example, the 500 bp upstream (5') of the 18-bp duplication (SEQ ID NO: 113) is fused to the 500 bp downstream (3') of the 18-bp duplication (SEQ ID NO: 114) to generate an editing template (SEQ ID NO: 115) that can be used by the B. licheniformis host machinery to repair the DNA break generated by the RGEN.

The Cas9 expression cassette (SEQ ID NO: 104), the gRNA expression cassette (SEQ ID NO: 112) and the editing template (SEQ ID NO: 115) are co-delivered to B. licheniformis cells using many different methods (e.g., protoplast fusion, electroporation, natural competence, or induced competence). Transformed cells are screened by PCR amplifying the rghR2 locus (SEQ ID NO:116) by amplifying the locus with a forward primer (SEQ ID NO: 117) and reverse primer (SEQ ID NO: 118). These primers amplify the wild-type locus (SEQ ID NO: 116) or the restored locus that had been edited by the RGEN (SEQ ID NO: 119). These fragments are then sequenced using a sequencing primers (SEQ ID NO: 120) to identify edited colonies.

Thus, as described in this Example, any of the genes in the rghR2 regulon can be edited in a similar manner to inactivate, enhance, down-regulated or delete the gene.

Example 7

Crispr-Cas9 Editing and Gene Down-Regulation

The instant Example describes the modulation (e.g., down-regulation) of a gene of interest via CRSIPR-Cas9 editing. An exemplary method to modulate gene expression level is the use of nuclease-defective variants (e.g., Cas9 D 10A/N863A or D 10A/H840A) of nucleotide-guided endonucleases to enhance or antagonize transcription of target gene(s). These Cas9 variants are inactive for all nuclease domains present in the protein sequence. These Cas9 variants therefore retain the RNA-guided DNA binding activity, but are unable to cleave either strand of DNA when bound to the cognate target site.

For example, the nuclease-defective Cas9 protein can be expressed as a B. licheniformis expression cassette (constructed as described in Example 6), and when combined with a B. licheniformis gRNA expression cassette, the Cas9 protein is directed to a specific target sequence within the cell. The binding of the Cas9 (variant) protein to specific target sites can block the binding or movement of transcription machinery on the DNA of the cell, thereby decreasing the amount of a gene product produced.

Additionally, the binding activity could enhance transcription by locally melting the DNA in the region allowing the transcription machinery to bind or elongate the gene more readily which would increase the amount of gene product produced. Thus, any gene in the rghR2 regulon (or any other gene in the B. licheniformis cell) can be targeted for modulation (up- or down-regulated) of gene expression using this method.

For example, to target the yvcZ gene with a nuclease defective Cas9 protein, there are 19 unique target sites within the yvcZ ORF that can be targeted (SEQ ID NO: 121 to 139). These target sequences can be made into gRNA expression cassettes, as described in Example 6.

Co-delivery of a nuclease-defective Cas9 expression cassette (e.g., constructed as described above in Example 6) with a gRNA expression cassette for the target gene allows for gene dosage changes (modulation) by silencing or activating transcription within the gene. By delivering multiple gRNA expression cassettes simultaneously, the targeting and modulation of multiple genes at the same is possible. The gene modulation (up-regulation or down-regulation) are readily monitored in cells containing the nuclease-defective Cas9 expression cassette and the gRNA expression cassette(s), by using methods such known to the skilled artisan, such as RNAseq.

Example 8

Enhanced Production of a Heterologous G4 Amylase in Modified Cells Comprising Rghr2$_{Rest}$ In the present example, B. licheniformis cells comprising a rghR2 gene having the 18-bp duplication (SEQ ID NO: 3) and B. licheniformis cells comprising the rghR2 gene lacking the 18-bp duplication (rghR2$_{rest}$; SEQ ID NO: 1), both comprise a single copy of an expression cassette (SEQ ID NO: 142) encoding a heterologous G4 amylase (variant) of Pseudomonas sp. AM1 (e.g., see PCT Publication No. WO2010/133644, specifically incorporated herein by reference in its entirety). Both strains were cultivated as described in Example 2 and samples taken after 48 hours were assayed with Ceralpha reagent as described. The fold difference in specific productivity (G4 amylase production/

OD$_{600}$) in the rghR2$_{rest}$ strain relative to the strain comprising the 18-bp duplication in rghR2 is presented in TABLE 7.

TABLE 7

SPECIFIC PRODUCTIVITY OF G4 AMYLASE FROM rghR2$_{rest}$ CELLS

| Heterologous Amylase | rghR2 allele in B. licheniformis host | Fold difference in Qp compared to rghR2 w/ 18-bp duplication (SEQ ID NO: 3) |
|---|---|---|
| Pseudomonas sp. α-amylase | rghR2$_{rest}$ (SEQ ID NO: 1) | 1.25 |

Thus, as presented above in TABLE 7, the specific productivity (Qp) of the heterologous G4 amylase is significantly improved in the B. licheniformis rghR2$_{rest}$ cells vis-à-vis the B. licheniformis cells comprising the 18-bp duplication in the rghR2 gene.

Example 9

Enhanced Production of Alkaline Amylases in Modified Cells Comprising Rghr2$_{Rest}$ In the present example, B. licheniformis cells comprising rghR2 gene having the 18-bp duplication (SEQ ID NO: 3) and B. licheniformis cells comprising the rghR2$_{rest}$ (SEQ ID NO: 1) comprise either a single copy of: (1) an expression cassette for alkaline α-amylase variant 1 integrated in the B. licheniformis genome, (2) an expression cassette of alkaline α-amylase variant 2 integrated in the B. licheniformis genome, (3) an expression cassette for alkaline α-amylase variant 3 integrated into the B. licheniformis genome or (4) an expression cassette for alkaline α-amylase variant 4 integrated into the B. licheniformis genome. Strains were fermented in a fed-batch system and at the end of the fermentations, samples were taken and assayed for alpha-amylase activity using the Ceralpha reagent of Megazyme as described in Example 2. The fold difference in amylase production in strains without the 18-bp duplication in rghR2 compared to strains with the 18-bp duplication in rghR2 is presented in TABLE 8.

TABLE 8

ALKALINE AMYLASE PRODUCTION FROM rghR2$_{rest}$ STRAINS IN FED BATCH CULTURES

| Amylase | rghR2 allele | Fold difference compared to rghR2 w/ 18-bp duplication (SEQ ID NO: 3) |
|---|---|---|
| Variant 1 | rghR2$_{rest}$ (SEQ ID NO: 1) | 1.8 |
| Variant 2 | rghR2$_{rest}$ (SEQ ID NO: 1) | 2.3 |
| Variant 3 | rghR2$_{rest}$ (SEQ ID NO: 1) | 1.6 |
| Variant 4 | rghR2$_{rest}$ (SEQ ID NO: 1) | 1.9 |

Thus, as presented above in TABLE 8, the production of alkaline amylases in fed batch cultures is improved in the B. licheniformis rghR2$_{rest}$ cells vis-à-vis the B. licheniformis cells comprising the 18-bp duplication in the rghR2 gene.

Example 10

Enhanced Lipase Production in Bacillus Cells Comprising Rghr2$_{Rest}$

Figure 9:
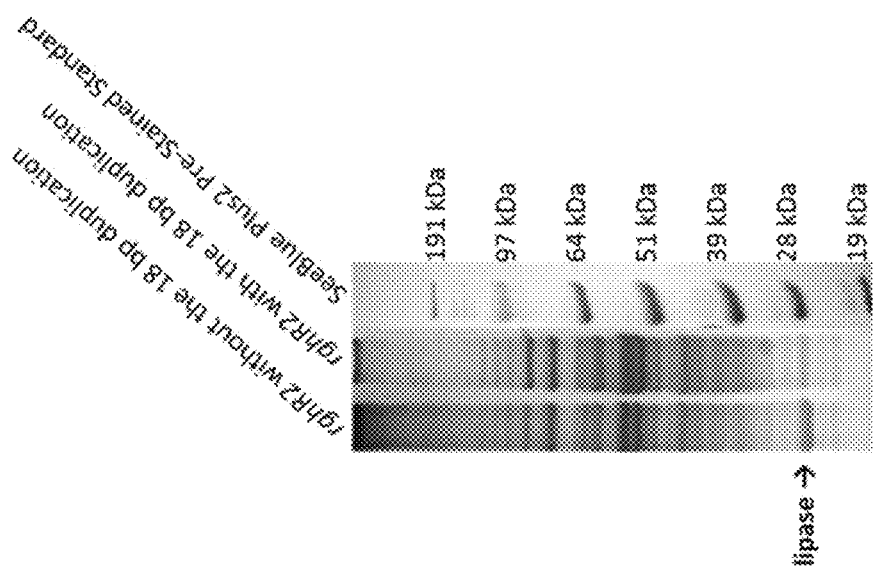
FIG. 9 shows the production of a heterologous EC 3.1.1.3 enzyme comprising lipase/esterase activity. As presented in the FIG. 9 SDS-PAGE, production of the heterologous EC 3.1.1.3 enzyme comprising lipase/esterase activity is improved in the *B. licheniformis* $rghR2_{rest}$ cells vis-à-vis the *B. licheniformis* cells comprising the rghR2 gene having the 18-bp duplication ($rghR2_{dup}$).

In the present example, B. licheniformis cells comprising the rghR2 gene having the 18-bp duplication (SEQ ID NO: 3) and B. licheniformis cells comprising the rghR2$_{rest}$ gene (SEQ ID NO: 1) both comprise a single copy of an expression cassette encoding a heterologous EC 3.1.1.3 enzyme comprising lipase/esterase activity. Thus, both strains were cultivated as described in Example 2 and equal amounts of sample taken after 48 hours were subjected to SDS-PAGE (Invitrogen 4-12% NuPAGE Bis-Tris gel of ThermoFischer) according to the instructions of the supplier. The stained SDS-PAGE protein gel (FIG. 9) shows an increased level of the EC 3.1.1.3 enzyme (~28 kDa) produced by the B. licheniformis rghR2$_{rest}$ strain (see, FIG. 9, lane 1). Thus, as presented in FIG. 9, the production of heterologous lipase/esterase enzymes is improved in the B. licheniformis rghR2$_{rest}$ cells relative to the B. licheniformis cells comprising the rghR2 gene having the 18-bp duplication.

Example 11

Enhanced Production of Alpha Amylase in Rghr2$_{Rest}$ Strains in Fed Batch Culture In the present example, B. licheniformis cells comprising rghR2 having the 18-bp duplication (SEQ ID NO: 3) and B. licheniformis cells comprising the rghR2$_{rest}$ gene (SEQ ID NO: 1), both comprise a single copy of an expression cassette (SEQ ID NO: 143) encoding a heterologous Cytophaga sp. variant #2 α-amylase described in PCT Publication No. WO2014/164834. Both strains were grown under standard fed-batch fermentation conditions. Amylase activity was monitored throughout the fermentation using Ceralpha reagent of Megazyme as described in Example 2. The fold difference in the specific productivity of the B. licheniformis rghR2$_{rest}$ cells relative to the B. licheniformis cells comprising the 18-bp duplication in the rghR2 gene is presented below in TABLE 9.

TABLE 9

HETEROLOGOUS AMYLASE PRODUCTION FROM rghR2$_{rest}$ STRAINS IN FED BATCH CULTURES

| Heterologous Amylase | rghR2 allele | Fold difference in Qp compared to rghR2 w/ 18-bp duplication (SEQ ID NO 3) |
|---|---|---|
| Cytophaga sp. variant #2 | rghR2$_{rest}$ (SEQ ID NO: 1) | 1.10 |

Thus, as presented in the TABLE 9, the specific productivity for the B. licheniformis cells producing the heterologous Cytophaga sp. variant #2 α-amylase is improved by 10% in the cells comprising the rghR2$_{rest}$ gene relative to cells comprising the rghR2 gene having the 18-bp duplication.

Example 12

Enhanced Amylase Production in Modified B. Licheniformis Cells Comprising Alleles Rghr2$_{Rest}$ and Glct1

In the present example, a heterologous α-amylase expression cassette was introduced into parental and modified B. licheniformis cells BF62 and BF169. More particularly, the parental B. licheniformis host, transformed with the heterologous α-amylase expression cassette, was named "BF134". Likewise, the B. licheniformis (daughter) cell "BF62", comprising a rghR2$_{rest}$ gene, transformed with the heterologous α-amylase expression cassette, was named "BF165" and the *B. licheniformis* (daughter) cell "BF169", comprising allele glcT1 and a rghr2$_{rest}$ gene, was named "BF260", as set forth below in TABLE 10.

The *B. licheniformis* allele glcT1 encodes a variant GlcT (transcriptional anti-termination) protein comprising a phenylalanine (F) at amino acid position 67 (F67) of the variant GlcT protein, as described in U.S. Provisional Patent Application Ser. No. 62/613,339, filed Jan. 3, 2018, which is incorporated herein by reference in its entirety.

TABLE 10

*B. LICHENIFORMIS* PARENT/DAUGHTER CELL MODIFICATIONS

| Strain Name | Genetic Modification | Strain Name Transformed w/ Cassette |
|---|---|---|
| *B. licheniformis* (parent) | n/a | BF134 |
| BF62 (daughter) cell | rghr2$_{rest}$ | BF165 |
| BF169 (daughter) cell | glcT1 + rghR2$_{rest}$ | BF260 |

Thus, the parental and modified *B. licheniformis* BF62 and BF169 cells (TABLE 10), comprising a plasmid carrying a xylose-inducible comK expression cassette, were grown overnight at 37° C. and 250 RPM in fifteen (15) ml of L broth (1% (w/v) Tryptone, 0.5% Yeast extract (w/v), 1% NaCl (w/v)), containing one hundred (100) μg/ml spectinomycin dihydrochloride in a 125 ml baffled flask. The overnight culture was diluted to 0.7 (OD$_{600}$ units) in 25 ml fresh L broth containing one hundred (100) μg/ml spectinomycin dihydrochloride in a two hundred fifty (250) ml baffle flask. Cells were grown for one (1) hour at 37° C. (250 RPM). D-xylose was added to 0.1% (w/v) from a 50% (w/v) stock. Cells were grown for an additional four (4) hours at 37° C. (250 RPM) and pelleted at 1700×g for seven (7) minutes.

The cells were resuspended in one fourth (¼) volume of original culture using the spent medium. One hundred (100) μl of concentrated cells were mixed with approximately one (1) μg of an expression cassette comprising (in the 5' to 3' direction) the same 5' catH homology arm, catH gene and spoVGrrnIp hybrid promoter, operably linked to a wild-type *B. subtilis* aprE 5'-UTR (WT-5'-UTR), wherein the WT-5'-UTR was operably linked to DNA encoding the lat signal sequence, followed by DNA (ORF) encoding a variant *G. stearothermophilus* α-amylase. The 3' end of the DNA (ORF) encoding the variant *G. stearothermophilus* α-amylase, was operably linked to the lat terminator, which was operably linked to the 3' catH homology arm. Transformation reactions were incubated at 37° C., 1000 RPM for approximately ninety (90) minutes.

Transformation mixes were plated on petri plates filled with L-broth containing ten (10) μg/ml chloramphenicol solidified with 1.5% (w/v) agar. Plates were incubated at 37° C. for two (2) days. Colonies were streak purified on petri plates filled with L-broth containing 1% (w/v) insoluble corn starch solidified with 1.5% (w/v) agar. Plates were incubated at 37° C. for twenty-four (24) hours until colonies had formed. Starch hydrolysis was indicated by clearing of the insoluble starch surrounding the colony, forming a halo, and was used to select transformants expressing the variant *G. stearothermophilus* α-amylase protein. Colony PCR was used to amplify the catH locus from halo producing colonies using standard techniques, and the forward and reverse primer pairs. Sequence verified *B. licheniformis* (daughter) cells comprising the expression cassette were stored and named as shown in the 3$^{rd}$ column of TABLE 10.

Thus, *B. licheniformis* strains named BF165 (i.e., rghr2$_{rest}$) and BF260 (i.e., rghr2$_{rest}$+glcT1), comprising the α-amylase expression cassette, were assessed for α-amylase production under small scale conditions. The strains were streak purified on L agar plates containing 1% (w·v$^{-1}$) insoluble starch and grown for approximately twenty-four (24) hours at 37° C. A single halo positive colony was inoculated into 15 ml of Tryptic Soy Broth (1.7% (w·v$^{-1}$) Tryptone, 0.3% (w·v$^{-1}$) soytone, 0.25% (w·v$^{-1}$) glucose, 0.5% (w·v$^{-1}$) sodium chloride, 0.25% (w·v$^{-1}$) Dipotassium phosphate) and grown at 37° C. (250 RPM) for 6 hours. Subsequently, 0.025 ml of this seed culture was inoculated into 25 ml of flask growth medium (4% (w·v$^{-1}$) MES, 0.1% (w·v$^{-1}$) Monopotassium phosphate, 0.05% (w·v$^{-1}$) sodium chloride, 0.03% (w·v$^{-1}$) soytone, containing trace metals, pH 6.8 with Ammonium hydroxide). A single high glucose release feed bead (Kuhner) was added (feed rate 57 mg/L·hr). The cultures were grown at 42° C. (250 RPM) for 90 hours. The total secreted protein production was determined using the method of Bradford with a BSA standard. The relative α-amylase production averaged from repeat measurements of at least two independent flasks for each strain is shown in TABLE 11 below.

TABLE 11

SMALL SCALE PRODUCTION OF α-AMYLASE

| *B. licheniformis* cell | Modification | Relative expression ± SEM |
|---|---|---|
| BF165 | rghR2$_{rest}$ | 1.00 ± 0.02 |
| BF260 | rghR2$_{rest}$ + glcT1 | 1.09 ± 0.04 |

Thus, as presented in TABLE 11, the *Bacillus* BF260 cells (comprising a rghR2$_{rest}$ and allele glcT1) demonstrate an approximately 9% increase in relative α-amylase production when compared (vis-à-vis) to *Bacillus* host cells BF165 (comprising rghR2$_{rest}$ and a wild-type glcT gene). Thus, in certain embodiments modified *B. licheniformis* cells of the disclosure comprising a restored rghR2 gene (rghR2$_{rest}$), further comprises a nucleic acid construct comprising allele glcT1 (SEQ ID NO: 144), encoding a variant GlcT protein comprising a Leucine (L) to Phenylalanine (F) substitution at amino acid position 67 of the variant GlcT protein.

REFERENCES

Albertini and Galizzi, *Bacteriol.*, 162:1203-1211, 1985.
Bergmeyer et al., "*Methods of Enzymatic Analysis*" vol. 5, *Peptidases, Proteinases and their Inhibitors, Verlag Chemie*, Weinheim, 1984.
Botstein and Shortie, *Science* 229: 4719, 1985.
Brode et al., "Subtilisin BPN' variants: increased hydrolytic activity on surface-bound substrates via decreased surface activity", *Biochemistry*, 35(10):3162-3169, 1996.
Caspers et al., "Improvement of Sec-dependent secretion of a heterologous model protein in *Bacillus subtilis* by saturation mutagenesis of the N-domain of the AmyE signal peptide", *Appl. Microbiol. Biotechnol.*, 86(6):1877-1885, 2010.
Chang et al., *Mol. Gen. Genet.*, 168:11-115, 1979.
Christianson et al., *Anal. Biochem.*, 223:119-129, 1994.
Devereux et at, *Nucl. Acid Res.*, 12: 387-395, 1984.
Earl et al., "Ecology and genomics of *Bacillus subtilis*", *Trends in Microbiology.*, 16(6):269-275, 2008.

Ferrari et al., "Genetics," in Harwood et al. (ed), *Bacillus*, Plenum Publishing Corp., 1989.
Fisher et. al., *Arch. Microbiol.*, 139:213-217, 1981.
Guerot-Fleury, *Gene*, 167:335-337, 1995.
Hamoen et al., "Controlling competence in *Bacillus subtilis*: shared used of regulators", *Microbiology*, 149:9-17, 2003.
Hamoen et al., *Genes Dev.* 12:1539-1550, 1998.
Hampton et al., *Seroloaical Methods, A Laboratory Manual*, APS Press, St. Paul, M N 1990.
Hardwood and Cutting (eds.) *Molecular Biological Methods for Bacillus*, John Wiley & Sons, 1990.
Hayashi et al., *Mol. Microbiol.*, 59(6): 1714-1729, 2006
Higuchi et al., *Nucleic Acids Research* 16: 7351, 1988.
Ho et al., *Gene* 77: 61, 1989.
Hoch et al., *J. Bacteriol.*, 93:1925-1937, 1967.
Holubova, *Folia Microbiol.*, 30:97, 1985.
Hopwood, *The Isolation of Mutants in Methods in Microbiology* (J. R. Norris and D. W. Ribbons, eds.) pp 363-433, Academic Press, New York, 1970.
Horton et al., *Gene* 77: 61, 1989.
Hsia et al., *Anal Biochem.*, 242:221-227, 1999.
Iglesias and Trautner, *Molecular General Genetics* 189: 73-76, 1983.
Jensen et al., "Cell-associated degradation affects the yield of secreted engineered and heterologous proteins in the *Bacillus subtilis* expression system" *Microbiology*, 146 (Pt 10:2583-2594, 2000.
Liu and Zuber, 1998,
Lo et al., *Proceedings of the National Academy of Sciences USA* 81: 2285, 1985.
Maddox et al., *J. Exp. Med.*, 158:1211, 1983.
Mann et al., *Current Microbiol.*, 13:131-135, 1986.
McDonald, *J. Gen. Microbiol.*, 130:203, 1984.
Needleman and Wunsch, *J. Mol. Biol.*, 48: 443, 1970.
Ogura & Fujita, *FEMS Microbiol Lett.*, 268(1): 73-80. 2007.
Olempska-Beer et al., "Food-processing enzymes from recombinant microorganisms—a review'" *Regul. Toxicol. Pharmacol.*, 45(2):144-158, 2006.
Palmeros et al., *Gene* 247:255-264, 2000.
Parish and Stoker, FEMS *Microbiology* Letters 154: 151-157, 1997.
Pearson and Lipman, *Proc. Natl. Acad. Sci. USA* 85: 2444, 1988.
Perego, 1993, In A. L. Sonneshein, J. A. Hoch, and R. Losick, editors, *Bacillus subtilis and Other Gram-Positive Bacteria*, Chapter 42, American Society of Microbiology, Washington, D.C.
Raul et al., "Production and partial purification of alpha amylase from *Bacillus subtilis* (MTCC 121) using solid state fermentation", *Biochemistry Research International*, 2014.
Sarkar and Sommer, *BioTechniques* 8: 404, 1990.
Saunders et al., *J. Bacteriol.*, 157: 718-726, 1984.
Shimada, *Meth. Mol. Biol.* 57: 157; 1996
Smith and Waterman, *Adv. Appl. Math.*, 2: 482, 1981.
Smith et al., *Appl. Env. Microbiol.*, 51:634 1986.
Stahl and Ferrari, *J. Bacteriol.*, 158:411-418, 1984.
Stahl et al, *J. Bacteriol.*, 158:411-418, 1984.
Tarkinen, et al, *J. Biol. Chem.* 258: 1007-1013, 1983.
Trieu-Cuot et al., *Gene*, 23:331-341, 1983.
Van Dijl and Hecker, "*Bacillus subtilis*: from soil bacterium to super-secreting cell factory", *Microbial Cell Factories*, 12(3). 2013.
Vorobjeva et al., *FEMS Microbiol. Lett.*, 7:261-263, 1980.
Ward, "Proteinases," in Fogarty (ed)., *Microbial Enzymes and Biotechnology. Applied Science*, London, pp 251-317, 1983.
Wells et al., *Nucleic Acids Res.* 11:7911-7925, 1983.
Westers et al., "*Bacillus subtilis* as cell factory for pharmaceutical proteins: a biotechnological approach to optimize the host organism", *Biochimica et Biophysica Acta.*, 1694: 299-310, 2004.
Yang et al, *J. Bacteriol.*, 160: 15-21, 1984.
Yang et al., *Nucleic Acids Res.* 11: 237-249, 1983.
Youngman et al., *Proc. Natl. Acad. Sci. USA* 80: 2305-2309, 1983.

The invention claimed is:

1. A *Bacillus licheniformis* cell comprising:

1) A rghR2 gene encoding a RghR2 protein comprising at least 90% sequence identity to SEQ ID NO: 4, wherein the rghR2 gene contains an 18-nucleotide duplication encoding a repeat of amino acids AAAISR at amino acid positions 38-43 of the RghR2 protein of SEQ ID NO: 4, and 2) A targeting vector configured to delete the 18-nucleotide duplication in the rghR2 gene, which upon deletion of the 18-nt duplication results in a modified cell comprising a modified rghR2 gene encoding a RghR2 protein comprising at least 90% sequence identity to SEQ ID NO: 2, wherein the modified cell produces an increased amount of a protein of interest relative to an unmodified cell.

2. The *Bacillus licheniformis* cell of claim 1, wherein the modified rghR2 gene encoding the RghR2 protein comprising at least 90% sequence identity to SEQ ID NO: 2 comprises a nucleic acid sequence comprising at least 90% sequence identity to the rghR2 gene of SEQ ID NO: 1.

3. The *Bacillus licheniformis* cell of claim 1, wherein the increased amount of a protein of interest is at least 1.0% increased relative to the unmodified cell.

4. The modified cell of claim 1, further comprising a genetic modification which disrupts, deletes, inactivates, or down-regulates
   (a) a rghR1 gene encoding a RghR1 protein comprising at least 90% sequence identity to SEQ ID NO: 16,
   (b) a yvzCgene encoding a yvzC protein comprising at least 90% sequence identity to SEQ ID NO: 18, and/or
   (c) a Bli03644 gene encoding a Bli03644 protein comprising at least 90% sequence identity to SEQ ID NO: 20.

* * * * *

SEQUENCE LISTING

```
<160> NUMBER OF SEQ ID NOS: 144

<210> SEQ ID NO 1
<211> LENGTH: 405
<212> TYPE: DNA
<213> ORGANISM: Bacillus licheniformis

<400> SEQUENCE: 1
atggcgatga caaggttcgg cgagcggctc aaagagctga gggaacaaag aagcctgtcg      60
gttaatcagc ttgccatgta tgccggtgtg agcgccgcag ccatttccag aatcgaaaac     120
ggccaccgcg gcgttcccaa gcccgcgacg atcagaaaat tggccgaggc tctgaaaatg     180
ccgtacgagc agctcatgga tattgccggt tatatgagag ctgacgagat tcgcgaacag     240
ccgcgcggct atgtcacgat gcaggagatc gcggccaagc acggcgtcga agacctgtgg     300
ctgtttaaac ccgagaaatg ggactgtttg tcccgcgaag acctgctcaa cctcgaacag     360
tattttcatt ttttggttaa tgaagcgaag aagcgccaat cataa                     405

<210> SEQ ID NO 2
<211> LENGTH: 134
<212> TYPE: PRT
<213> ORGANISM: Bacillus licheniformis

<400> SEQUENCE: 2
```

Met Ala Met Thr Arg Phe Gly Glu Arg Leu Lys Glu Leu Arg Glu Gln
1               5                   10                  15

Arg Ser Leu Ser Val Asn Gln Leu Ala Met Tyr Ala Gly Val Ser Ala
            20                  25                  30

Ala Ala Ile Ser Arg Ile Glu Asn Gly His Arg Gly Val Pro Lys Pro
        35                  40                  45

Ala Thr Ile Arg Lys Leu Ala Glu Ala Leu Lys Met Pro Tyr Glu Gln
    50                  55                  60

Leu Met Asp Ile Ala Gly Tyr Met Arg Ala Asp Glu Ile Arg Glu Gln
65                  70                  75                  80

Pro Arg Gly Tyr Val Thr Met Gln Glu Ile Ala Ala Lys His Gly Val
                85                  90                  95

Glu Asp Leu Trp Leu Phe Lys Pro Glu Lys Trp Asp Cys Leu Ser Arg
            100                 105                 110

Glu Asp Leu Leu Asn Leu Glu Gln Tyr Phe His Phe Leu Val Asn Glu
            115                 120                 125

Ala Lys Lys Arg Gln Ser
        130

<210> SEQ ID NO 3
<211> LENGTH: 423
<212> TYPE: DNA
<213> ORGANISM: Bacillus licheniformis

<400> SEQUENCE: 3
atggcgatga caaggttcgg cgagcggctc aaagagctga gggaacaaag aagcctgtcg    60
gttaatcagc ttgccatgta tgccggtgtg agcgccgcag ccatttccag agccgcagcc   120
atttccagaa tcgaaaacgg ccaccgcggc gttcccaagc ccgcgacgat cagaaaattg   180
gccgaggctc tgaaaatgcc gtacgagcag ctcatggata ttgccggtta tatgagagct   240
gacgagattc gcgaacagcc gcgcggctat gtcacgatgc aggagatcgc ggccaagcac   300
ggcgtcgaag acctgtggct gtttaaaccc gagaaatggg actgtttgtc ccgcgaagac   360
ctgctcaacc tcgaacagta tttttcatttt ttggttaatg aagcgaagaa cgccaatca   420 taa                                                                 423

<210> SEQ ID NO 4
<211> LENGTH: 140
<212> TYPE: PRT
<213> ORGANISM: Bacillus licheniformis

<400> SEQUENCE: 4

Met Ala Met Thr Arg Phe Gly Glu Arg Leu Lys Glu Leu Arg Glu Gln
1               5                   10                  15

Arg Ser Leu Ser Val Asn Gln Leu Ala Met Tyr Ala Gly Val Ser Ala
            20                  25                  30

Ala Ala Ile Ser Arg Ala Ala Ile Ser Arg Ile Glu Asn Gly His
        35                  40                  45

Arg Gly Val Pro Lys Pro Ala Thr Ile Arg Lys Leu Ala Glu Ala Leu
    50                  55                  60

Lys Met Pro Tyr Glu Gln Leu Met Asp Ile Ala Gly Tyr Met Arg Ala
65                  70                  75                  80

Asp Glu Ile Arg Glu Gln Pro Arg Gly Tyr Val Thr Met Gln Glu Ile
                85                  90                  95

Ala Ala Lys His Gly Val Glu Asp Leu Trp Leu Phe Lys Pro Glu Lys

```
            100                 105                 110
Trp Asp Cys Leu Ser Arg Glu Asp Leu Leu Asn Leu Glu Gln Tyr Phe
        115                 120                 125

His Phe Leu Val Asn Glu Ala Lys Lys Arg Gln Ser
    130                 135                 140

<210> SEQ ID NO 5
<211> LENGTH: 6
<212> TYPE: PRT
<213> ORGANISM: Bacillus licheniformis

<400> SEQUENCE: 5

Ala Ala Ala Ile Ser Arg
1               5

<210> SEQ ID NO 6
<211> LENGTH: 12
<212> TYPE: PRT
<213> ORGANISM: Bacillus licheniformis

<400> SEQUENCE: 6

Ala Ala Ala Ile Ser Arg Ala Ala Ala Ile Ser Arg
1               5                   10

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
gagactagtg agctcgcatc acacgc                                          26

<210> SEQ ID NO 8
<211> LENGTH: 38
<212> TYPE: DNA
<213> ORGANISM: Artificial Sequence
<220> FEATURE:
<223> OTHER INFORMATION: primer

<400> SEQUENCE: 8
gactgcggcc gcaccatgat tactcccctt tctaatct                             38

<210> SEQ ID NO 9
<211> LENGTH: 38
<212> TYPE: DNA
<213> ORGANISM: Artificial Sequence
<220> FEATURE:
<223> OTHER INFORMATION: primer

<400> SEQUENCE: 9
tctggaaatg gctgcggcgc tcacaccggc atacatgg                             38

<210> SEQ ID NO 10
<211> LENGTH: 38
<212> TYPE: DNA
<213> ORGANISM: Artificial Sequence
<220> FEATURE:
<223> OTHER INFORMATION: primer

<400> SEQUENCE: 10
gccgcagcca tttccagaat cgaaaacggc caccgcgg                             38
```

```
<210> SEQ ID NO 11
<211> LENGTH: 28
<212> TYPE: DNA
<213> ORGANISM: Artificial Sequence
<220> FEATURE:
<223> OTHER INFORMATION: primer

<400> SEQUENCE: 11
gactaagctt cgccgtcttg atgcttgt                                        28

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
gtacggcatt ttcagagcct c                                               21

<210> SEQ ID NO 13
<211> LENGTH: 26
<212> TYPE: DNA
<213> ORGANISM: Artificial Sequence
<220> FEATURE:
<223> OTHER INFORMATION: primer

<400> SEQUENCE: 13
tgaatcatct ttccgatcac aagttg                                          26

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
aaggagggga tgacaaatgg aag                                             23

<210> SEQ ID NO 15
<211> LENGTH: 402
<212> TYPE: DNA
<213> ORGANISM: Bacillus licheniformis

<400> SEQUENCE: 15
atgacgaact tggacaccca tttacgacaa ttaagggaac ggaaaaaact gaccgtcaat      60
caactggcga tgtattccgg cgtcagttcg gcaggcattt cgcgaatcga aaacggaaag     120
cgcggcgtgc cgaagccggc gacgatcaga aaactggcgg acgctttgaa agtcccgtat     180
gaggaactga tggcatctgc aggctatatc agcgcgtcta cagtccagga agcaagaagc     240
agctatgatt ccatttacga catcgtgtca cagtacgatt tagaggacct ttctctgttt     300
gacagcgaaa agtggaaggt gctttcaaaa aaagacatcg aaaacctgga caaatatttc     360
gactttctcg tgcaggaagc aagcagccga acaaaaaact ga                       402

<210> SEQ ID NO 16
<211> LENGTH: 60
<212> TYPE: PRT
<213> ORGANISM: Bacillus licheniformis

<400> SEQUENCE: 16

Met Thr Asn Phe Gly His His Leu Arg Gln Leu Arg Glu Arg Lys Lys
1               5                   10                  15
```

```
Leu Thr Val Asn Gln Leu Ala Met Tyr Ser Gly Val Ser Ala Gly
             20                  25                  30

Ile Ser Arg Ile Glu Asn Gly Lys Arg Gly Val Pro Lys Pro Ala Thr
         35                  40                  45

Ile Arg Lys Leu Ala Asp Ala Leu Lys Val Pro Tyr
     50                  55                  60

<210> SEQ ID NO 17
<211> LENGTH: 231
<212> TYPE: DNA
<213> ORGANISM: Bacillus licheniformis

<400> SEQUENCE: 17
atggtaaaaa agattcatat caaaagagat tttgttctcc agtacatgat tgaacacaat     60
ctctccttaa atcagcttgc cattgaaatc ggcgtatccc cggcgacact cagcagagtt    120
ttaaatggcg aaaggaggcc cggacaactt gtgatcggaa agatgattca gtatttcaac    180
aaaaaatttg aagatctctt ttattataaa gatgttgaca aaagtcaata a              231

<210> SEQ ID NO 18
<211> LENGTH: 75
<212> TYPE: PRT
<213> ORGANISM: Bacillus licheniformis

<400> SEQUENCE: 18

Met Val Lys Lys Ile His Ile Lys Arg Asp Phe Val Leu Gln Tyr Met
1               5                   10                  15

Ile Glu His Asn Leu Ser Leu Asn Gln Leu Ala Ile Glu Ile Gly Val
             20                  25                  30

Ser Pro Ala Thr Leu Ser Arg Val Leu Asn Gly Glu Arg Arg Pro Gly
         35                  40                  45

Gln Leu Val Ile Gly Lys Met Ile Gln Tyr Phe Asn Lys Lys Phe Glu
     50                  55                  60

Asp Leu Phe Tyr Tyr Lys Asp Val Asp Lys Ser
65                  70                  75

<210> SEQ ID NO 19
<211> LENGTH: 285
<212> TYPE: DNA
<213> ORGANISM: Bacillus licheniformis

<400> SEQUENCE: 19
gtgaaaaata ccgggattgt ccggagaatc gatgagctcg gcagagtcgt tctcccggtc     60
gaaatgcgca gggtgctgaa tatcaatgaa aaggacccgc tcgaaatata ccgacggc     120 gaaaacatca ttttgacaaa atacgccgca acatggcat gtttgatgac cggcgacatc    180
accacgaaaa ataaaacgta tgcgggcggc aaaatcgtac tcagcccgcg cggagcggaa    240
atgctcctgg aagatatgat ggcggcactg tcagaaaaga ataa                     285

<210> SEQ ID NO 20
<211> LENGTH: 93
<212> TYPE: PRT
<213> ORGANISM: Bacillus licheniformis

<400> SEQUENCE: 20

Met Lys Asn Thr Gly Ile Val Arg Arg Ile Asp Glu Leu Gly Arg Val
1               5                   10                  15

Val Leu Pro Val Glu Met Arg Arg Val Leu Asn Ile Asn Glu Lys Asp
```

20                  25                  30

Pro Leu Glu Ile Tyr Thr Asp Gly Glu Asn Ile Ile Leu Thr Lys Tyr
                35                  40                  45

Ala Ala Asn Met Ala Cys Leu Met Thr Gly Asp Ile Thr Thr Lys Asn
            50                  55                  60

Lys Thr Tyr Ala Gly Gly Lys Ile Val Leu Ser Pro Arg Gly Ala Glu
65                  70                  75                  80

Met Leu Leu Glu Asp Met Met Ala Ala Leu Ser Glu Lys
                85                  90

<210> SEQ ID NO 21
<211> LENGTH: 285
<212> TYPE: DNA
<213> ORGANISM: Bacillus licheniformis

<400> SEQUENCE: 21
atgaaatcta caggtattgt acgtaaagtt gatgaactag dacgcgtggt gattccaatc    60
gaacttcgcc gtacgcttgg aatcgcagaa aaagacgctc ttgaaatcta tgtagatgac   120
gaaaaaatca tcttgaaaaa atataaacca acatgactt gccaagttac aggtgaggtt    180
tctgatgaca accttaaact tgcaggcggt aaattggttc ttagccctga aggcgctgag   240
caaatcatta cgaaattca agcacaactt caatctcaaa ataa                     285

<210> SEQ ID NO 22
<211> LENGTH: 94
<212> TYPE: PRT
<213> ORGANISM: Bacillus licheniformis

<400> SEQUENCE: 22

Met Lys Ser Thr Gly Ile Val Arg Lys Val Asp Glu Leu Gly Arg Val
1               5                   10                  15

Val Ile Pro Ile Glu Leu Arg Arg Thr Leu Gly Ile Ala Glu Lys Asp
                20                  25                  30

Ala Leu Glu Ile Tyr Val Asp Asp Glu Lys Ile Ile Leu Lys Lys Tyr
            35                  40                  45

Lys Pro Asn Met Thr Cys Gln Val Thr Gly Glu Val Ser Asp Asp Asn
        50                  55                  60

Leu Lys Leu Ala Gly Gly Lys Leu Val Leu Ser Pro Glu Gly Ala Glu
65                  70                  75                  80

Gln Ile Ile Asn Glu Ile Gln Ala Gln Leu Gln Ser Gln Lys
                85                  90

<210> SEQ ID NO 23
<211> LENGTH: 288
<212> TYPE: DNA
<213> ORGANISM: Bacillus licheniformis

<400> SEQUENCE: 23
ttgaaagcaa taggagttgt gagaaaagta gacgaactcg gcaggatcgt gatgccgatt    60
gaattgagaa gagctttgga tatctcgatc aaggacagca tcgaattctt tgtcgaccaa   120
gataaaatcg tcctgaaaaa atataaaccg cacggtgtgt gtctgatgac cggtgaaatc   180
acttctgaaa accgcgagta tggaaacggg aaaattacgc tcagtcctga aggggccgaa   240
ttgcttttgg aagaaatcaa agctgcctta aacggagtga agcataa                 288

<210> SEQ ID NO 24
<211> LENGTH: 95

```
<212> TYPE: PRT
<213> ORGANISM: Bacillus licheniformis

<400> SEQUENCE: 24

Met Lys Ala Ile Gly Val Val Arg Lys Val Asp Glu Leu Gly Arg Ile
1               5                   10                  15

Val Met Pro Ile Glu Leu Arg Arg Ala Leu Asp Ile Ser Ile Lys Asp
                20                  25                  30

Ser Ile Glu Phe Phe Val Asp Gln Asp Lys Ile Val Leu Lys Lys Tyr
            35                  40                  45

Lys Pro His Gly Val Cys Leu Met Thr Gly Glu Ile Thr Ser Glu Asn
        50                  55                  60

Arg Glu Tyr Gly Asn Gly Lys Ile Thr Leu Ser Pro Glu Gly Ala Glu
65                  70                  75                  80

Leu Leu Leu Glu Glu Ile Lys Ala Ala Leu Asn Gly Val Lys Ala
                85                  90                  95

<210> SEQ ID NO 25
<211> LENGTH: 114
<212> TYPE: DNA
<213> ORGANISM: Bacillus licheniformis

<400> SEQUENCE: 25
atgaaagtga gaccatcagt taaaccgatc tgtgaaaaat gcaaggtcat tcgcagaaaa      60
ggaaaagtaa tggtgatctg tgaaaatcca agcataaac aaaaacaagg ataa            114

<210> SEQ ID NO 26
<211> LENGTH: 37
<212> TYPE: PRT
<213> ORGANISM: Bacillus licheniformis

<400> SEQUENCE: 26

Met Lys Val Arg Pro Ser Val Lys Pro Ile Cys Glu Lys Cys Lys Val
1               5                   10                  15

Ile Arg Arg Lys Gly Lys Val Met Val Ile Cys Glu Asn Pro Lys His
                20                  25                  30

Lys Gln Lys Gln Gly
            35

<210> SEQ ID NO 27
<211> LENGTH: 431
<212> TYPE: DNA
<213> ORGANISM: Bacillus licheniformis

<400> SEQUENCE: 27
atgcgtacaa cacctatggc taacgcaagt aatattgaac gcaagtggtt agttgttgat      60
gctgctggca agacgctagg acgtcttcct actgaagttg catctatcct tcgcggaaaa     120
cataaaccaa cttacacacc acacgttgac actggagatc atgtgatcat catcaacgct     180
gaaaaaatcg agttaactgg taaaaagtta acggacaaaa tctactaccg tcacactcaa     240
catccaggcg gtttaaaatc aagaactgct cttgaaatgc gtacaaacta ccctgagaaa     300
atgcttgaac ttgcgatcaa aggcatgctt ccaaaaggtt ctctaggtcg tcaaatgttc     360
aaaaaattga atgtataccg tggttctgag catccacacc aagcacaaaa acctgaagtt     420
tacgaacttc g                                                          431

<210> SEQ ID NO 28
<211> LENGTH: 143
```

<212> TYPE: PRT
<213> ORGANISM: Bacillus licheniformis

<400> SEQUENCE: 28

Met Arg Thr Thr Pro Met Ala Asn Ala Ser Asn Ile Glu Arg Lys Trp
1               5                   10                  15

Leu Val Val Asp Ala Ala Gly Lys Thr Leu Gly Arg Leu Ser Thr Glu
            20                  25                  30

Val Ala Ser Ile Leu Arg Gly Lys His Lys Pro Thr Tyr Thr Pro His
        35                  40                  45

Val Asp Thr Gly Asp His Val Ile Ile Asn Ala Glu Lys Ile Glu
    50                  55                  60

Leu Thr Gly Lys Lys Leu Thr Asp Lys Ile Tyr Tyr Arg His Thr Gln
65                  70                  75                  80

His Pro Gly Gly Leu Lys Ser Arg Thr Ala Leu Glu Met Arg Thr Asn
                85                  90                  95

Tyr Pro Glu Lys Met Leu Glu Leu Ala Ile Lys Gly Met Leu Pro Lys
            100                 105                 110

Gly Ser Leu Gly Arg Gln Met Phe Lys Lys Leu Asn Val Tyr Arg Gly
        115                 120                 125

Ser Glu His Pro His Gln Ala Gln Lys Pro Glu Val Tyr Glu Leu
    130                 135                 140

<210> SEQ ID NO 29
<211> LENGTH: 915
<212> TYPE: DNA
<213> ORGANISM: Bacillus licheniformis

<400> SEQUENCE: 29
atgggtacaa tagggataaa ctttaaaaac attcaacatc aatatcgtac caaggatgtg      60 ctaaggggg tgagtttcca tgccgatccc tcctccatca cgttcttggc aggcgagaat     120
ggagccggaa agacaacttt gataaaggtt gctctcggct taatcagtcc gaaggcagga     180
aatgcgctgt tcgacgggca aagcgtcggg gaaatccggg agaagatcag ctgcgtgttt     240
gatgagcctc ctgtttatcc taatgaaagt ggtcttgaca atctaaagtt tttatcaggt     300
atacacagcc ttgatcgaaa gtggagtcag gaggtttgtg ccatgctcaa attggatgag     360 ggactttta aacaaaaagc aaaagcgcta tcactgggtc aaagacaccg tttagctgta     420
gcggccgcgt tattgcgcaa acctaaatat ttgtttcttg atgagccgtc aatcggcctc     480
gacccaccgt catggcagct ggtccaaatc gctttaaaac agatgactgc caggggatgt     540
gcaattttga ttacggggca aaattatgac gcgattgaaa atctcgctga caatatagcg     600
attttgcaaa gtgaaaaaat tatcttctcc ggtcctattg taaaacttgt tcaagcattt     660
cccgtatatg ttcgaattgt aactgatgac catcgggaaa tagctgtgca gtttccagaa     720
gctgaacctg attcttccgg aatataccgc atcgtttgcg aatcaggtga acaggcccgc     780
gccgtgattg atcaggtgag gagaagcacc ctgaattttc aagagctatc gactgaaaaa     840
gcgtcaatgg ggaaaatggt gacagatatt tacaaggatg gatttcagtc ggaaaagaga     900
gggttaacgt atgaa                                                      915

<210> SEQ ID NO 30
<211> LENGTH: 304
<212> TYPE: PRT
<213> ORGANISM: Bacillus licheniformis

<400> SEQUENCE: 30

```
Met Gly Thr Ile Gly Ile Asn Phe Lys Asn Ile Gln His Gln Tyr Arg
1               5                   10                  15

Thr Lys Asp Val Leu Arg Gly Val Ser Phe His Ala Asp Pro Ser Ser
            20                  25                  30

Ile Thr Phe Leu Ala Gly Glu Asn Gly Ala Gly Lys Thr Thr Leu Ile
        35                  40                  45

Lys Val Ala Leu Gly Leu Ile Ser Pro Lys Ala Gly Asn Ala Leu Phe
50                  55                  60

Asp Gly Gln Ser Val Gly Glu Ile Arg Glu Lys Ile Ser Cys Val Phe
65                  70                  75                  80

Asp Glu Pro Pro Val Tyr Pro Asn Glu Ser Gly Leu Asp Asn Leu Lys
                85                  90                  95

Phe Leu Ser Gly Ile His Ser Leu Asp Arg Lys Trp Ser Gln Glu Val
            100                 105                 110

Cys Ala Met Leu Lys Leu Asp Glu Gly Leu Leu Lys Gln Lys Ala Lys
        115                 120                 125

Ala Leu Ser Leu Gly Gln Arg His Arg Leu Ala Val Ala Ala Ala Leu
130                 135                 140

Leu Arg Lys Pro Lys Tyr Leu Phe Leu Asp Glu Pro Ser Ile Gly Leu
145                 150                 155                 160

Asp Pro Pro Ser Trp Gln Leu Val Gln Ile Ala Leu Lys Gln Met Thr
                165                 170                 175

Ala Arg Gly Cys Ala Ile Leu Ile Thr Gly Gln Asn Tyr Asp Ala Ile
            180                 185                 190

Glu Asn Leu Ala Asp Asn Ile Ala Ile Leu Gln Ser Gly Lys Ile Ile
        195                 200                 205

Phe Ser Gly Pro Ile Val Lys Leu Val Gln Ala Phe Pro Val Tyr Val
210                 215                 220

Arg Ile Val Thr Asp Asp His Arg Glu Ile Ala Val Gln Phe Pro Glu
225                 230                 235                 240

Ala Glu Pro Asp Ser Ser Gly Ile Tyr Arg Ile Val Cys Glu Ser Gly
                245                 250                 255

Glu Gln Ala Arg Ala Val Ile Asp Gln Val Arg Arg Ser Thr Leu Asn
            260                 265                 270

Phe Gln Glu Leu Ser Thr Glu Lys Ala Ser Met Gly Lys Met Val Thr
        275                 280                 285

Asp Ile Tyr Lys Asp Gly Phe Gln Ser Glu Lys Arg Gly Leu Thr Tyr
290                 295                 300
```

<210> SEQ ID NO 31
<211> LENGTH: 1096
<212> TYPE: DNA
<213> ORGANISM: Bacillus licheniformis

<400> SEQUENCE: 31

| | |
|---|---|
| atgagcaagg tcgcttcaga ggtggttgcg ggggtgttga cgaattccca tttggccatt | 60 |
| aaaaagcacg atactgagca ggcaaagcat cttttttgatg aggcgaagtc gatgttttcc | 120 |
| gagatggaag aggatcagaa tgtgctggct tattttttcgc ttcttgagga gcggtaccgg | 180 |
| atgatgcttt atgatgcgag gggagagcgg ctgccgcggg agtcttattt taatgattcg | 240 |
| cagatcgagt gcatcgagca gacggatcat atgattgatt actattttcta cttttttgag | 300 |
| gcgatgcatg aagcgtacaa caagaatgtt gagcgggcga tcagtctgta caaggttgcc | 360 |
| gagaaaaaac tggcgaaggt gcccgatcag attgaagcgg ccgagtttta ttttaaagtg | 420 |

```
tcctggctgt atatgtctct tcggcaaaat gcggtttctc tcaattatgc gagagacgcg    480
atgaatattt acaaaatgca tgacgggtac gaaaaaaagc tggcgatttc ccaagttgtg    540
atggggacaa attacatgca gatgcagcgc tttaaagatg cggagaagta ctttgaagaa    600
tcgattgaaa tttccaaaaa gattgacgat tcattttag aagcgatgct tcatcacaat    660
atcagcattc tgtattccaa ttccggccgg tctcaggaat gcattctcgc cgtccagcat    720
gctttgagca acgccgaatg gtgcaagtca agctactata tcaactcgct ttacatgctg    780
accagagagt ttttcaaaat cggcgaaaca gaagcggccc tgttctatca taaaaaagga    840
caggaggaat taagaaaaa cgggaataag cattatgaaa agaaaataaa tattatttat    900
gagctgtatt gccatgaaaa cgtaaaaagc atcaaagacg acatccattc cttggacgag    960
atgaatgatt tagacggtgt ctgcgatctt tctttgctca tctcaagcta ttttgagaaa   1020
aaaggagatg acaagaaagc gctggaattt gttaaaatat tcatgaaagc cgaaaacaaa   1080
atgagatcat taggga                                                   1096

<210> SEQ ID NO 32
<211> LENGTH: 364
<212> TYPE: PRT
<213> ORGANISM: Bacillus licheniformis

<400> SEQUENCE: 32

Met Ser Lys Val Ala Ser Glu Val Val Ala Gly Val Leu Asn Glu Phe
1               5                   10                  15

His Leu Ala Ile Lys Lys His Asp Thr Glu Gln Ala Lys His Leu Phe
            20                  25                  30

Asp Glu Ala Lys Ser Met Phe Ser Glu Met Glu Glu Asp Gln Asn Val
        35                  40                  45

Leu Ala Tyr Phe Ser Leu Leu Glu Glu Arg Tyr Arg Met Met Leu Tyr
    50                  55                  60

Asp Ala Arg Gly Glu Arg Leu Pro Arg Glu Ser Tyr Phe Asn Asp Ser
65                  70                  75                  80

Gln Ile Glu Cys Ile Glu Gln Thr Asp His Met Ile Asp Tyr Tyr Phe
                85                  90                  95

Tyr Phe Phe Glu Ala Met His Glu Ala Tyr Asn Lys Asn Val Glu Arg
            100                 105                 110

Ala Ile Ser Leu Tyr Lys Val Ala Glu Lys Lys Leu Ala Lys Val Pro
        115                 120                 125

Asp Gln Ile Glu Ala Ala Glu Phe Tyr Phe Lys Val Ser Trp Leu Tyr
    130                 135                 140

Met Ser Leu Arg Gln Asn Ala Val Ser Leu Asn Tyr Ala Arg Asp Ala
145                 150                 155                 160

Met Asn Ile Tyr Lys Met His Asp Gly Tyr Glu Lys Lys Leu Ala Ile
                165                 170                 175

Ser Gln Val Val Met Gly Thr Asn Tyr Met Gln Met Gln Arg Phe Lys
            180                 185                 190

Asp Ala Glu Lys Tyr Phe Glu Glu Ser Ile Glu Ile Ser Lys Lys Ile
        195                 200                 205

Asp Asp Ser Phe Leu Glu Ala Met Leu His His Asn Ile Ser Ile Leu
    210                 215                 220

Tyr Ser Asn Ser Gly Arg Ser Gln Glu Cys Ile Leu Ala Val Gln His
225                 230                 235                 240

Ala Leu Ser Asn Ala Glu Trp Cys Lys Ser Ser Tyr Tyr Ile Asn Ser
```

```
                 245                 250                 255
Leu Tyr Met Leu Thr Arg Glu Phe Phe Lys Ile Gly Glu Thr Glu Ala
            260                 265                 270

Ala Leu Phe Tyr His Lys Lys Gly Gln Glu Glu Leu Lys Lys Asn Gly
        275                 280                 285

Asn Lys His Tyr Glu Lys Lys Ile Asn Ile Ile Tyr Glu Leu Tyr Cys
    290                 295                 300

His Glu Asn Val Lys Ser Ile Lys Asp Ile His Ser Leu Asp Glu
305                 310                 315                 320

Met Asn Asp Leu Asp Gly Val Cys Asp Leu Ser Leu Leu Ile Ser Ser
                325                 330                 335

Tyr Phe Glu Lys Lys Gly Asp Asp Lys Lys Ala Leu Glu Phe Val Lys
            340                 345                 350

Ile Phe Met Lys Ala Glu Asn Lys Met Arg Ser Leu
            355                 360

<210> SEQ ID NO 33
<211> LENGTH: 121
<212> TYPE: DNA
<213> ORGANISM: Bacillus licheniformis

<400> SEQUENCE: 33
atgaaaaaat taattctttg cttgtcgtta actgctatgg tcttaggcgg agctgcttta      60
tcccaaagcc acaatcaggc gtcaggcggc gttcaaacag cggagctgcc ggttgggggt     120
t                                                                    121

<210> SEQ ID NO 34
<211> LENGTH: 40
<212> TYPE: PRT
<213> ORGANISM: Bacillus licheniformis

<400> SEQUENCE: 34

Met Lys Lys Leu Ile Leu Cys Leu Ser Leu Thr Ala Met Val Leu Gly
1               5                   10                  15

Gly Ala Ala Leu Ser Gln Ser His Asn Gln Ala Ser Gly Gly Val Gln
            20                  25                  30

Thr Ala Glu Leu Pro Val Gly Gly
        35                  40

<210> SEQ ID NO 35
<211> LENGTH: 747
<212> TYPE: DNA
<213> ORGANISM: Bacillus licheniformis

<400> SEQUENCE: 35
atgaatgaca aacatttttt atcattttta aaacacgcag ataagccttt cagcggctgg      60 gattttctt tcattgaaga cacaggacga atgaaaagcg acctgctttc atggtcatac     120
ggaagcatgg ctctgtctct tatccaggat tccgaatcaa tgttggatat ggggacaggc     180
ggcggcgagt ttttatccaa attggggccg tttccttcgt cagcatacgc tactgaatgt     240
tatttgccta atgtgccagt cgccaaggaa cgattgacgc ctttagggt tcaggtcgtt     300 caaattgatg atgatgaaga tcttccattt gaatccggcc aattcgacct gatcatcaat     360
aaacacgaat catattcagt acaagaggtg aggagaatcc tttcaaaagg aggacggttt     420
ctcactcagc aagtcggcgg gcttgattgc aagaaaataa atgaaaaact ggcgtgccg      480 ctaaatgaag aatttaagga ttgggacttg aaacagcgt taaagagat ggaaaagcat     540
```

```
gattttaaga ttttaaaaag cagagaagag tgtccgactc aaaggtttta tgatattggg      600
gctctggtct attatttgaa agccattccc tggcaggcgc tcggttttga agtgaatcaa      660
tataaggatg aattgtacga gattcataaa atgatcgaag aaaagggcta ttttgacgtc      720
acacagtacc ggtttatgat tttagcg                                          747
```

<210> SEQ ID NO 36
<211> LENGTH: 248
<212> TYPE: PRT
<213> ORGANISM: Bacillus licheniformis

<400> SEQUENCE: 36

```
Met Asn Asp Lys Thr Phe Leu Ser Phe Leu Lys His Ala Asp Lys Pro
1               5                   10                  15

Phe Ser Gly Trp Asp Phe Ser Phe Ile Glu Asp Thr Gly Arg Met Lys
            20                  25                  30

Ser Asp Leu Leu Ser Trp Ser Tyr Gly Ser Met Ala Leu Ser Leu Ile
        35                  40                  45

Gln Asp Ser Glu Ser Met Leu Asp Met Gly Thr Gly Gly Glu Phe
    50                  55                  60

Leu Ser Lys Leu Gly Pro Phe Pro Ser Ser Ala Tyr Ala Thr Glu Cys
65                  70                  75                  80

Tyr Leu Pro Asn Val Pro Val Ala Lys Glu Arg Leu Thr Pro Leu Gly
                85                  90                  95

Val Gln Val Val Gln Ile Asp Asp Glu Asp Leu Pro Phe Glu Ser
            100                 105                 110

Gly Gln Phe Asp Leu Ile Ile Asn Lys His Glu Ser Tyr Ser Val Gln
        115                 120                 125

Glu Val Arg Arg Ile Leu Ser Lys Gly Gly Arg Phe Leu Thr Gln Gln
    130                 135                 140

Val Gly Gly Leu Asp Cys Glu Glu Ile Asn Glu Lys Leu Gly Val Pro
145                 150                 155                 160

Leu Asn Glu Glu Phe Lys Asp Trp Asp Leu Glu Thr Ala Leu Lys Glu
                165                 170                 175

Met Glu Lys His Asp Phe Lys Ile Leu Lys Ser Arg Glu Glu Cys Pro
            180                 185                 190

Thr Gln Arg Phe Tyr Asp Ile Gly Ala Leu Val Tyr Tyr Leu Lys Ala
        195                 200                 205

Ile Pro Trp Gln Ala Leu Gly Phe Glu Val Asn Gln Tyr Lys Asp Glu
    210                 215                 220

Leu Tyr Glu Ile His Lys Met Ile Glu Glu Lys Gly Tyr Phe Asp Val
225                 230                 235                 240

Thr Gln Tyr Arg Phe Met Ile Leu
                245
```

<210> SEQ ID NO 37
<211> LENGTH: 183
<212> TYPE: DNA
<213> ORGANISM: Bacillus licheniformis

<400> SEQUENCE: 37

```
atgggtaacg cagtacatga caaagaacag caagtcaatt atttgaaaaa cagattggat      60
atgtttatgt cagtcatcga ttctttagac ccggaatcga ccgaccttga agatattgac     120
agactgatca gcatgctcga cgatttggaa gccaaatacg agcgctttaa aaaagactgg     180
```

<210> SEQ ID NO 38
<211> LENGTH: 61
<212> TYPE: PRT
<213> ORGANISM: Bacillus licheniformis

<400> SEQUENCE: 38

```
Met Gly Asn Ala Val His Asp Lys Glu Gln Gln Val Asn Tyr Leu Lys
1               5                   10                  15

Asn Arg Leu Asp Met Phe Met Ser Val Ile Asp Ser Leu Asp Pro Glu
            20                  25                  30

Ser Thr Asp Leu Glu Asp Ile Asp Arg Leu Ile Ser Met Leu Asp Asp
        35                  40                  45

Leu Glu Ala Lys Tyr Glu Arg Phe Lys Lys Asp Trp Lys
    50                  55                  60
```

<210> SEQ ID NO 39
<211> LENGTH: 1086
<212> TYPE: DNA
<213> ORGANISM: Bacillus licheniformis

<400> SEQUENCE: 39

```
atgtcaaaat cagtaaaatc agtcacatca cctaaaaaat ttattacagg aaaacgactg      60
ctggagaact tgaacgacta cattgaagat tttggcgaca acgcatatat catttgcgat     120
gaattcattt tggaacgcgc tcaaaaagaa gcggggaatt cgattcagaa agccggcaat     180
caagccgttt ttgaaaaatt caattacgaa tgcacacagg aagaaatcga tcgcaaccgg     240
gagcttgcac gcaatgcagg cgctaatatc atcgttggga tcggaggcgg taaaacgctt     300
gataccgcaa aagccaccgc ttattacgag aagctgccgg ttgtgatttt cccgacaatt     360
gcttctacgg atgctccatg tacggccctt gccgtcattt ataaacacga cggatcgttt     420
gaccgctatc tgttttttgcc gacgaaccca gatgtcgttc ttgcggactc tgagattttg     480
gcatccgcgc cgccgcgctt tttcgcagcc ggtatcggtg acgccttggc gacgtatttt     540
gaagcgcgtg cctgctttaa agcaaacggc gataaccctcg tgctgatgaa gccttcaaca     600
actggattgg gacttgcccg tctttgctat gatacgctgt ggaaaacgg tgtgaaagcg     660
atgcaggcgg ttaagcacgg cgtttccaca cgagcggtcg aagatacaat cgaggcgacc     720
atctatttaa gcggcgtcgg tgccgaatca ggcggtcttg ccgccgcaca cgcgatccac     780
aacggaatga cagccgttcc ttctctgcac agggctcagc acggcgaaaa agtcacgttc     840
ggccttttgg cgcagcttgt tcttgaaaac gcgccggccg aagaattgga gaccgttatt     900
gactttatca aaggcgtcgg tcttccgttg acattaaaag acctcggagt cgacgaattt     960
gtcgaagaag aatggcgcca agtcgctcaa agcgcttgcg cggaaggcga cacaatgggc    1020
aacatgccgt tcccagtcac ccctgacgac gtctacaatg cgatcgtcgc cgccaacgcg    1080
attgca                                                               1086
```

<210> SEQ ID NO 40
<211> LENGTH: 361
<212> TYPE: PRT
<213> ORGANISM: Bacillus licheniformis

<400> SEQUENCE: 40

```
Met Ser Lys Ser Val Lys Ser Val Thr Ser Pro Lys Lys Phe Ile Thr
1               5                   10                  15
```

```
Gly Lys Arg Leu Leu Glu Asn Leu Asn Asp Tyr Ile Glu Asp Phe Gly
            20                  25                  30

Asp Asn Ala Tyr Ile Ile Cys Asp Glu Phe Ile Leu Glu Arg Ala Gln
            35                  40                  45

Lys Glu Ala Gly Asn Ser Ile Gln Lys Ala Gly Asn Gln Ala Val Phe
 50                  55                  60

Glu Lys Phe Asn Tyr Glu Cys Thr Gln Glu Glu Ile Asp Arg Asn Arg
 65                  70                  75                  80

Glu Leu Ala Arg Asn Ala Gly Ala Asn Ile Ile Val Gly Ile Gly Gly
                85                  90                  95

Gly Lys Thr Leu Asp Thr Ala Lys Ala Thr Ala Tyr Tyr Glu Lys Leu
            100                 105                 110

Pro Val Val Ile Phe Pro Thr Ile Ala Ser Thr Asp Ala Pro Cys Thr
            115                 120                 125

Ala Leu Ala Val Ile Tyr Lys His Asp Gly Ser Phe Asp Arg Tyr Leu
            130                 135                 140

Phe Leu Pro Thr Asn Pro Asp Val Val Leu Ala Asp Ser Glu Ile Leu
145                 150                 155                 160

Ala Ser Ala Pro Pro Arg Phe Phe Ala Ala Gly Ile Gly Asp Ala Leu
                165                 170                 175

Ala Thr Tyr Phe Glu Ala Arg Ala Cys Phe Lys Ala Asn Gly Asp Asn
            180                 185                 190

Leu Val Leu Met Lys Pro Ser Thr Thr Gly Leu Gly Leu Ala Arg Leu
            195                 200                 205

Cys Tyr Asp Thr Leu Leu Glu Asn Gly Val Lys Ala Met Gln Ala Val
210                 215                 220

Lys His Gly Val Ser Thr Arg Ala Val Glu Asp Thr Ile Glu Ala Thr
225                 230                 235                 240

Ile Tyr Leu Ser Gly Val Gly Ala Glu Ser Gly Gly Leu Ala Ala Ala
                245                 250                 255

His Ala Ile His Asn Gly Met Thr Ala Val Pro Ser Leu His Arg Ala
            260                 265                 270

Gln His Gly Glu Lys Val Thr Phe Gly Leu Leu Ala Gln Leu Val Leu
            275                 280                 285

Glu Asn Ala Pro Ala Glu Glu Leu Glu Thr Val Ile Asp Phe Ile Lys
            290                 295                 300

Gly Val Gly Leu Pro Leu Thr Leu Lys Asp Leu Gly Val Asp Glu Phe
305                 310                 315                 320

Val Glu Glu Glu Trp Arg Gln Val Ala Gln Ser Ala Cys Ala Glu Gly
                325                 330                 335

Asp Thr Met Gly Asn Met Pro Phe Pro Val Thr Pro Asp Asp Val Tyr
            340                 345                 350

Asn Ala Ile Val Ala Ala Asn Ala Ile
            355                 360

<210> SEQ ID NO 41
<211> LENGTH: 110
<212> TYPE: DNA
<213> ORGANISM: Bacillus licheniformis

<400> SEQUENCE: 41
atgatgggta aagggagaat taaagtggaa gaacggatta agatcgaaac cgatgctgaa      60
atgtttaaag cgactctcct tgatcaaaca cagtctcaga agaagaaata                110
```

-continued

```
<210> SEQ ID NO 42
<211> LENGTH: 36
<212> TYPE: PRT
<213> ORGANISM: Bacillus licheniformis

<400> SEQUENCE: 42

Met Met Gly Lys Gly Arg Ile Lys Val Glu Glu Arg Ile Lys Ile Glu
1               5                   10                  15

Thr Asp Ala Glu Met Phe Lys Ala Thr Leu Leu Asp Gln Thr Gln Ser
            20                  25                  30

Gln Lys Lys Lys
        35

<210> SEQ ID NO 43
<211> LENGTH: 231
<212> TYPE: DNA
<213> ORGANISM: Bacillus licheniformis

<400> SEQUENCE: 43
atgaaagaga aaaaatcgta cgctgagctc atgaagtccc gcaataccca aaaggtgaaa       60
gaacttgatg taaccatcac ggatatctac attcaaatgg tccttgatga atcgcttttt      120
aaacggcgtt tgcacacgct gagcaagaag attaatgaag cattagacaa aggagataag      180
caatctttcc ttgagctttc aagagaatat acagcgctga aaaagcacgc a               231

<210> SEQ ID NO 44
<211> LENGTH: 77
<212> TYPE: PRT
<213> ORGANISM: Bacillus licheniformis

<400> SEQUENCE: 44

Met Lys Glu Lys Lys Ser Tyr Ala Glu Leu Met Lys Ser Arg Asn Thr
1               5                   10                  15

Gln Lys Val Lys Glu Leu Asp Val Thr Ile Thr Asp Ile Tyr Ile Gln
            20                  25                  30

Met Val Leu Asp Glu Ser Leu Phe Lys Arg Arg Leu His Thr Leu Ser
        35                  40                  45

Lys Lys Ile Asn Glu Ala Leu Asp Lys Gly Asp Lys Gln Ser Phe Leu
    50                  55                  60

Glu Leu Ser Arg Glu Tyr Thr Ala Leu Lys Lys His Ala
65                  70                  75

<210> SEQ ID NO 45
<211> LENGTH: 627
<212> TYPE: DNA
<213> ORGANISM: Bacillus licheniformis

<400> SEQUENCE: 45
gtgggaaaag aaaaaacaaa aaagccaatt tataagaaat ggtggttttg ttaatcatc        60 gttatcatca tcggggcagc agcatcaaat ggtggaaatt cagagcaagc ttcatcaaca      120
aataaagaaa atccaccga gagtaaaacg actgaaacaa acaagatac gaagaaagaa       180 gaaaaaaagg aagaaccgaa aaagaggaa acaaacccta aatcggtga cgatgttaaa       240 gtcggtgata tgaattataa aatcactggg aagaaaacag cagatcaggt gggaccgtct     300
gcattgcctc aaaaagctag cgataaatac cttgttattg atgtcacatt gaaaataac     360 ggcaatgaaa aagtaacagt agacgcttct ttcttcaagc ttaaacgtgg agaaaaaacc     420
tatgaagctg attctgctgc aagcatgtca gcgaaccaaa gcgaggacgg caatattgac     480
```

```
aataactttt tccttcaaaa cttgaatcct gattctaaaa tcagtggaaa agtagtattt    540
gatgtagctc cggaagttgc taacgcaaaa gacctacaat tacaagtgca gactggtgca    600
tggggaacgg aaaccggaat catcgat                                       627
```

<210> SEQ ID NO 46
<211> LENGTH: 209
<212> TYPE: PRT
<213> ORGANISM: Bacillus licheniformis

<400> SEQUENCE: 46

```
Val Gly Lys Glu Lys Thr Lys Lys Pro Ile Tyr Lys Lys Trp Trp Phe
1               5                   10                  15

Trp Leu Ile Ile Val Ile Ile Ile Gly Ala Ala Ala Ser Asn Gly Gly
            20                  25                  30

Asn Ser Glu Gln Ala Ser Ser Thr Asn Lys Glu Lys Ser Thr Glu Ser
        35                  40                  45

Lys Thr Thr Glu Thr Lys Gln Asp Thr Lys Lys Glu Glu Lys Lys Glu
    50                  55                  60

Glu Pro Lys Lys Glu Glu Thr Asn Pro Lys Ile Gly Asp Asp Val Lys
65                  70                  75                  80

Val Gly Asp Met Asn Tyr Lys Ile Thr Gly Lys Lys Thr Ala Asp Gln
                85                  90                  95

Val Gly Pro Ser Ala Leu Pro Gln Lys Ala Ser Asp Lys Tyr Leu Val
            100                 105                 110

Ile Asp Val Thr Leu Lys Asn Asn Gly Asn Glu Lys Val Thr Val Asp
        115                 120                 125

Ala Ser Phe Phe Lys Leu Lys Arg Gly Glu Lys Thr Tyr Glu Ala Asp
    130                 135                 140

Ser Ala Ala Ser Met Ser Ala Asn Gln Ser Glu Asp Gly Asn Ile Asp
145                 150                 155                 160

Asn Asn Phe Phe Leu Gln Asn Leu Asn Pro Asp Ser Lys Ile Ser Gly
                165                 170                 175

Lys Val Val Phe Asp Val Ala Pro Glu Val Ala Asn Ala Lys Asp Leu
            180                 185                 190

Gln Leu Gln Val Gln Thr Gly Ala Trp Gly Thr Glu Thr Gly Ile Ile
        195                 200                 205

Asp
```

<210> SEQ ID NO 47
<211> LENGTH: 1877
<212> TYPE: DNA
<213> ORGANISM: Bacillus licheniformis

<400> SEQUENCE: 47

```
atgcaattag agatcgggaa gcaatcgcag caaaaccgtc acacgttgca atttgaaaat    60
tggaggcagc acggggaatt gatagctgcg cttttgtcgg gtttgttgat tcttgcaggc    120
tggctgttgt ccggcaatga acattgtcc gttgttctgt ttattttagc ttttttgtatc    180 ggcggctttg ctaaagcgaa agaaggtata caagaaacgc tgtcggaaaa aacgctgaat    240
gttgaactct tgatgatttt tgcggcggtc gggtctgcgc tgatcggcta ctgggctgaa    300
ggggccgtgt taatttttat cttttctctc agcggagcgc ttgaaacgta tacattaaat    360
aaaagcaaac gcgatttgac ttcactgatg aaattggagc cggaggaagc cgttttgctt    420 gaaaagaag gaacaagaac cgtggcggca gccgatcttc aggcgggcga cctcattctt    480
```

```
gtgaagcctg agaacgcat tgcggcagac ggagaaatcg aaaccggaaa acgagtatc      540
gacgaatcgg ctctaacggg cgaatccatc ccagccgaaa aaacactcgg agacgcggtt    600
tttgcgggta cggtcaattt gagcggatcg ctcacggtcc gtgtcacaaa ggcaaatgaa    660
gattcgttgt tcaaaaagat cattcggctc gttgagtctg cgcaaaacag cgtttcaccg    720
tcgcaggcgt tcattgagcg atttgaaaat atttacgtta aaggggtttt gcttgctgtc    780
ggactgctgc tctttctgcc gcatttttttg cttggctgga gctggagcga dacattttac    840
agagcgatgg tgttcatggt cgtcgcttcg ccgtgcgccc ttgtcgcttc aatcatgcct    900
gccgcgctgt cgctgatatc aaatggcgca agaaacggcc tgcttgtcaa aggcagcgtc    960
tttcttgaaa agcttggcaa cagcaaaatc gttgcattgg ataaaacggg aacgattacg    1020
aacggaaagc ccggcgtgga ggatatgctt ttagctgcag atatcgagga gcgcgaatgc    1080
ttggaggctg ctgctgcgat tgagaagcag tcaggccatc cgcttgccaa agcgattgtc    1140
gagtatgcag aagcaaaagg catcaagccg ccgcgaatg tgtcgattga ggagacgtca     1200
gggtttggcg ttcaggctcg atacaatgga gagacatggc tgatcggcaa agccggattt    1260
gtcggggaag aggcagccgg gcaatttctc acggcggctg ttcaggagct tgccaagcag    1320
ggaaaaacaa ttgtgttcat gaaaaaaggc gaaaaatcg cggggtgttt tgcattaaaa     1380
gaccaaatca gaccggaagc aaaagcggtg gtcgaagagc tgaacgcgct tggcgttcag    1440
acggcgatgc tgacagggga ccagcctgaa accgcagcgg ccatcgcacg agaagcgggc    1500
ttgaaaatcg tcgtttcaga atgccttcct gacagaaaag tagaggaagc gaaaaagctg    1560
aaaaaaacat acgaacaat cgttatggtg ggagacggaa tcaatgatgc accggcccta     1620
gccgccgctg atgtggggat cgcaatgggg ggaggaacag atgtcgcact ggaaacggct    1680
gacgtcgttt taatgaaaaa cgaattgaca ggactgacca aaatgattcg gctctcccgg    1740
aaaatgaata cgatcattaa acaaaacgtc attttctcgc ttgctgtgat ctgtctttta    1800
atctgcagca actttcttca aattcttgat ctgccgctcg gtgtcatcgg gcatgaaggc    1860
agcacgctgc ttgtgat                                                   1877
```

<210> SEQ ID NO 48
<211> LENGTH: 625
<212> TYPE: PRT
<213> ORGANISM: Bacillus licheniformis

<400> SEQUENCE: 48

```
Met Gln Leu Glu Ile Gly Lys Gln Ser Gln Gln Asn Arg His Thr Leu
1               5                   10                  15

Gln Phe Glu Asn Trp Arg Gln His Gly Glu Leu Ile Ala Ala Leu Leu
            20                  25                  30

Ser Gly Leu Leu Ile Leu Ala Gly Trp Leu Leu Ser Gly Asn Glu Thr
        35                  40                  45

Leu Ser Val Val Leu Phe Ile Leu Ala Phe Cys Ile Gly Gly Phe Ala
    50                  55                  60

Lys Ala Lys Glu Gly Ile Gln Glu Thr Leu Ser Glu Lys Thr Leu Asn
65                  70                  75                  80

Val Glu Leu Leu Met Ile Phe Ala Ala Val Gly Ser Ala Leu Ile Gly
                85                  90                  95

Tyr Trp Ala Glu Gly Ala Val Leu Ile Phe Ile Phe Ser Leu Ser Gly
            100                 105                 110

Ala Leu Glu Thr Tyr Thr Leu Asn Lys Ser Lys Arg Asp Leu Thr Ser
        115                 120                 125
```

```
Leu Met Lys Leu Glu Pro Glu Glu Ala Val Leu Leu Glu Lys Glu Gly
    130                 135                 140

Thr Arg Thr Val Ala Ala Ala Asp Leu Gln Ala Gly Asp Leu Ile Leu
145                 150                 155                 160

Val Lys Pro Gly Glu Arg Ile Ala Ala Asp Gly Glu Ile Glu Thr Gly
                165                 170                 175

Lys Thr Ser Ile Asp Glu Ser Ala Leu Thr Gly Glu Ser Ile Pro Ala
            180                 185                 190

Glu Lys Thr Leu Gly Asp Ala Val Phe Ala Gly Thr Val Asn Leu Ser
        195                 200                 205

Gly Ser Leu Thr Val Arg Val Thr Lys Ala Asn Glu Asp Ser Leu Phe
    210                 215                 220

Lys Lys Ile Ile Arg Leu Val Glu Ser Ala Gln Asn Ser Val Ser Pro
225                 230                 235                 240

Ser Gln Ala Phe Ile Glu Arg Phe Gly Asn Ile Tyr Val Lys Gly Val
                245                 250                 255

Leu Leu Ala Val Gly Leu Leu Leu Phe Leu Pro His Phe Leu Leu Gly
            260                 265                 270

Trp Ser Trp Ser Glu Thr Phe Tyr Arg Ala Met Val Phe Met Val Val
        275                 280                 285

Ala Ser Pro Cys Ala Leu Val Ala Ser Ile Met Pro Ala Ala Leu Ser
    290                 295                 300

Leu Ile Ser Asn Gly Ala Arg Asn Gly Leu Leu Val Lys Gly Ser Val
305                 310                 315                 320

Phe Leu Glu Lys Leu Gly Asn Ser Lys Ile Val Ala Leu Asp Lys Thr
                325                 330                 335

Gly Thr Ile Thr Asn Gly Lys Pro Gly Val Glu Asp Met Leu Leu Ala
            340                 345                 350

Ala Asp Ile Glu Glu Arg Glu Cys Leu Glu Ala Ala Ala Ile Glu
        355                 360                 365

Lys Gln Ser Gly His Pro Leu Ala Lys Ala Ile Val Glu Tyr Ala Glu
    370                 375                 380

Ala Lys Gly Ile Lys Pro Ala Ala Asn Val Ser Ile Glu Glu Thr Ser
385                 390                 395                 400

Gly Phe Gly Val Gln Ala Arg Tyr Asn Gly Glu Thr Trp Leu Ile Gly
                405                 410                 415

Lys Ala Gly Phe Val Gly Glu Ala Ala Gly Gln Phe Leu Thr Ala
            420                 425                 430

Ala Val Gln Glu Leu Ala Lys Gln Gly Lys Thr Ile Val Phe Met Lys
        435                 440                 445

Lys Gly Glu Lys Ile Ala Gly Cys Phe Ala Leu Lys Asp Gln Ile Arg
    450                 455                 460

Pro Glu Ala Lys Ala Val Val Glu Glu Leu Asn Ala Leu Gly Val Gln
465                 470                 475                 480

Thr Ala Met Leu Thr Gly Asp Gln Pro Glu Thr Ala Ala Ala Ile Ala
                485                 490                 495

Arg Glu Ala Gly Leu Lys Ile Val Val Ser Glu Cys Leu Pro Asp Arg
            500                 505                 510

Lys Val Glu Glu Ala Lys Lys Leu Lys Lys Thr Tyr Gly Thr Ile Val
        515                 520                 525

Met Val Gly Asp Gly Ile Asn Asp Ala Pro Ala Leu Ala Ala Ala Asp
    530                 535                 540
```

Val Gly Ile Ala Met Gly Gly Gly Thr Asp Val Ala Leu Glu Thr Ala
545                 550                 555                 560

Asp Val Val Leu Met Lys Asn Glu Leu Thr Gly Leu Thr Lys Met Ile
            565                 570                 575

Arg Leu Ser Arg Lys Met Asn Thr Ile Ile Lys Gln Asn Val Ile Phe
        580                 585                 590

Ser Leu Ala Val Ile Cys Leu Leu Ile Cys Ser Asn Phe Leu Gln Ile
    595                 600                 605

Leu Asp Leu Pro Leu Gly Val Ile Gly His Glu Gly Ser Thr Leu Leu
    610                 615                 620

Val
625

<210> SEQ ID NO 49
<211> LENGTH: 178
<212> TYPE: DNA
<213> ORGANISM: Bacillus licheniformis

<400> SEQUENCE: 49
atggaacgct tttcagaaga agagagaaaa ctgttgctga acgtactttt ggaccatgag    60
tatgccgtag agctactaag cagtgagatc aatgatatag aaactggtac aaaaaatgtg   120
gatagcctga catataagaa actggttacc ttatatgacc gtgtccggtc tgaaaatt    178

<210> SEQ ID NO 50
<211> LENGTH: 59
<212> TYPE: PRT
<213> ORGANISM: Bacillus licheniformis

<400> SEQUENCE: 50

Met Glu Arg Phe Ser Glu Glu Arg Lys Leu Leu Leu Asn Val Leu
1               5                   10                  15

Leu Asp His Glu Tyr Ala Val Glu Leu Leu Ser Ser Glu Ile Asn Asp
            20                  25                  30

Ile Glu Thr Gly Thr Lys Asn Val Asp Ser Leu Thr Tyr Lys Lys Leu
        35                  40                  45

Val Thr Leu Tyr Asp Arg Val Arg Ser Glu Asn
    50                  55

<210> SEQ ID NO 51
<211> LENGTH: 537
<212> TYPE: DNA
<213> ORGANISM: Bacillus licheniformis

<400> SEQUENCE: 51
atgattaatc agcttaaatt gcgtccgctt gaaagagaag accttccgtt tgtccaccgt    60
cttaacaacg atgcgaaaat tatgtcatat tggttgaag aaccgtacga acttttgtt    120 gagctgcagg atttatttga caaacacatt cacgaccaaa gcgagcggcg ctttatcata   180
gagaaagaga ctgagatgat cggattggta gagctggtcg aaattgatta tattcacagg   240
cgggcggagt ttcaaatcat aattgatccc gagcatcaag ggaacggtta ttcgtcaagc   300
gcaacatatt tggcaatgaa ctacgcattt tccgtcttga acttgcacaa attgtatttg   360
atcgtcgacg aagataatgc aaaagcgatt cacttgtata aaaaggcagg ttcactatc    420 gagagcgagc tgcaggatga attttttcgtc gacggctatt atcgtaacgc cattagaatg   480
tgcatttttc aggatgagtt tttatcactt aaaaaaagca agaggaagg catgcag      537

<210> SEQ ID NO 52
<211> LENGTH: 178
<212> TYPE: PRT
<213> ORGANISM: Bacillus licheniformis

<400> SEQUENCE: 52

```
Met Ile Asn Gln Leu Lys Leu Arg Pro Leu Glu Arg Glu Asp Leu Pro
1               5                   10                  15

Phe Val His Arg Leu Asn Asn Asp Ala Lys Ile Met Ser Tyr Trp Phe
            20                  25                  30

Glu Glu Pro Tyr Glu Thr Phe Val Glu Leu Gln Asp Leu Phe Asp Lys
        35                  40                  45

His Ile His Asp Gln Ser Glu Arg Arg Phe Ile Ile Glu Lys Glu Thr
    50                  55                  60

Glu Met Ile Gly Leu Val Glu Leu Val Glu Ile Asp Tyr Ile His Arg
65                  70                  75                  80

Arg Ala Glu Phe Gln Ile Ile Ile Asp Pro Glu His Gln Gly Asn Gly
                85                  90                  95

Tyr Ser Ser Ser Ala Thr Tyr Leu Ala Met Asn Tyr Ala Phe Ser Val
            100                 105                 110

Leu Asn Leu His Lys Leu Tyr Leu Ile Val Asp Glu Asp Asn Ala Lys
        115                 120                 125

Ala Ile His Leu Tyr Lys Lys Ala Gly Phe Thr Ile Glu Ser Glu Leu
    130                 135                 140

Gln Asp Glu Phe Phe Val Asp Gly Tyr Tyr Arg Asn Ala Ile Arg Met
145                 150                 155                 160

Cys Ile Phe Gln Asp Glu Phe Leu Ser Leu Lys Lys Ser Lys Glu Glu
                165                 170                 175

Gly Met
```

<210> SEQ ID NO 53
<211> LENGTH: 207
<212> TYPE: DNA
<213> ORGANISM: Bacillus licheniformis

<400> SEQUENCE: 53

```
atgcaccata tgaacgtatc atacttaaga aattgttttg ccgagatgaa acagtatgag    60
acagactgca tgaacaaact gatggatttc gctaagtttt tgtatatcca gggacatctg   120
acattaaacg aatttcgcac aagtatgaaa gttcttgaag cgaatggcgc acagcaccct   180
gcttatgata tgaatacgga cgccagc                                       207
```

<210> SEQ ID NO 54
<211> LENGTH: 69
<212> TYPE: PRT
<213> ORGANISM: Bacillus licheniformis

<400> SEQUENCE: 54

```
Met His His Met Asn Val Ser Tyr Leu Arg Asn Cys Phe Ala Glu Met
1               5                   10                  15

Lys Gln Tyr Glu Thr Asp Cys Met Asn Lys Leu Met Asp Phe Ala Lys
            20                  25                  30

Phe Leu Tyr Ile Gln Gly His Leu Thr Leu Asn Glu Phe Arg Thr Ser
        35                  40                  45

Met Lys Val Leu Glu Ala Asn Gly Ala Gln His Pro Ala Tyr Asp Met
    50                  55                  60

Asn Thr Asp Ala Ser
65
```

<210> SEQ ID NO 55
<211> LENGTH: 69
<212> TYPE: PRT
<213> ORGANISM: Bacillus licheniformis

<400> SEQUENCE: 55

Met His His Met Asn Val Ser Tyr Leu Arg Asn Cys Phe Ala Glu Met
1               5                   10                  15

Lys Gln Tyr Glu Thr Asp Cys Met Asn Lys Leu Met Asp Phe Ala Lys
            20                  25                  30

Phe Leu Tyr Ile Gln Gly His Leu Thr Leu Asn Glu Phe Arg Thr Ser
        35                  40                  45

Met Lys Val Leu Glu Ala Asn Gly Ala Gln His Pro Ala Tyr Asp Met
    50                  55                  60

Asn Thr Asp Ala Ser
65

<210> SEQ ID NO 56
<211> LENGTH: 160
<212> TYPE: PRT
<213> ORGANISM: Bacillus licheniformis

<400> SEQUENCE: 56

Met Lys Lys Ala Ile Leu Gly Phe Ser Leu Ser Ala Ala Leu Leu Val
1               5                   10                  15

Pro Ser Ser Phe Ala Ala Ala Gly Asp Gly Gln Leu Thr Ser Glu
            20                  25                  30

Gln Lys Glu Leu Leu Glu Ala Lys Thr Glu Tyr Val Gln Ser Leu Pro
        35                  40                  45

Glu Gln Ala Ser Val Gln Ser Gly Val Thr Ala Tyr Ala Gly Lys Arg
    50                  55                  60

Leu Thr Ile Lys Arg Gly Ser Phe Leu Ala Trp Ser Lys Asp Tyr Ile
65                  70                  75                  80

Asp Trp Tyr Tyr Asn Gly Lys Lys Val Ser Lys Ser Ser Gly Ser Gln
                85                  90                  95

Asp Val Gly Tyr Val Phe Pro Asn Val Val Arg Ala Lys Gly Ile Lys
            100                 105                 110

Arg Tyr Tyr Lys Ser Ser Gly Leu His Lys Trp Arg Ala Lys Lys Thr
        115                 120                 125

Leu Ser Phe Gly Thr Val Thr Pro Trp Gly Asp Val Glu Leu Ala Ser
    130                 135                 140

Ser Thr Phe Thr Asp Arg Arg Trp Val Asn Lys Lys Gly Lys Tyr Gly
145                 150                 155                 160

<210> SEQ ID NO 57
<211> LENGTH: 422
<212> TYPE: DNA
<213> ORGANISM: Bacillus licheniformis

<400> SEQUENCE: 57
atgacaacac cgagtatgga agattacata gaacaaattt atatgctgat tgaagaaaaa      60
ggatatgcaa gagtctcaga tatagccgaa gctctggccg tccatccctc ctcggttaca     120
aaaatggttc aaaaactcga taagacgaa tatttgattt atgaaaagta tcgcggcctc      180
gtgctgacgc ctaaaggaaa gaaaataggc aagcgtttag tatacagaca tgaattattg     240

```
gagcagtttt tacgaatcat tggtgttgac gaagagaaaa tttatgatga tgttgaagga    300
atcgaacatc atttaagctg aacagcatt gaccgtatcg agatcttgt gcagtatttt     360 gaagacgaca gcaaaagaat cgacgatttg agaagcgtcc aaaaaagaaa cgaacaggaa    420
aa                                                                  422
```

<210> SEQ ID NO 58
<211> LENGTH: 140
<212> TYPE: PRT
<213> ORGANISM: Bacillus licheniformis

<400> SEQUENCE: 58

```
Met Thr Thr Pro Ser Met Glu Asp Tyr Ile Glu Gln Ile Tyr Met Leu
1               5                   10                  15

Ile Glu Glu Lys Gly Tyr Ala Arg Val Ser Asp Ile Ala Glu Ala Leu
            20                  25                  30

Ala Val His Pro Ser Ser Val Thr Lys Met Val Gln Lys Leu Asp Lys
        35                  40                  45

Asp Glu Tyr Leu Ile Tyr Glu Lys Tyr Arg Gly Leu Val Leu Thr Pro
    50                  55                  60

Lys Gly Lys Lys Ile Gly Lys Arg Leu Val Tyr Arg His Glu Leu Leu
65                  70                  75                  80

Glu Gln Phe Leu Arg Ile Ile Gly Val Asp Glu Glu Lys Ile Tyr Asp
                85                  90                  95

Asp Val Glu Gly Ile Glu His His Leu Ser Trp Asn Ser Ile Asp Arg
            100                 105                 110

Ile Gly Asp Leu Val Gln Tyr Phe Glu Asp Asp Ser Lys Arg Ile Asp
        115                 120                 125

Asp Leu Arg Ser Val Gln Lys Arg Asn Glu Gln Glu
    130                 135                 140
```

<210> SEQ ID NO 59
<211> LENGTH: 234
<212> TYPE: DNA
<213> ORGANISM: Bacillus licheniformis

<400> SEQUENCE: 59

```
gtgccggacg gttcaccata tcgtaaacgc tatcaaccag ccggtccggt gcggcagatg    60
aaaaacaaac gtctgttcat actttcgttg attgtgttga gcgtggtcat gatcggagtt   120 caggaaaccct tcccaaacct gctgacgaca gggttaatga ctgtcgttat tgcggcggca   180 gttttttaata ttttaaaaga atcgctgaat aaaaaagatg aaacacacag caaa         234
```

<210> SEQ ID NO 60
<211> LENGTH: 78
<212> TYPE: PRT
<213> ORGANISM: Bacillus licheniformis

<400> SEQUENCE: 60

```
Met Pro Asp Gly Ser Pro Tyr Arg Lys Arg Tyr Gln Pro Ala Gly Pro
1               5                   10                  15

Val Arg Gln Met Lys Asn Lys Arg Leu Phe Ile Leu Ser Leu Ile Val
            20                  25                  30

Leu Ser Val Val Met Ile Gly Val Gln Glu Thr Phe Pro Asn Leu Leu
        35                  40                  45

Thr Thr Gly Leu Met Thr Val Val Ile Ala Ala Ala Val Phe Asn Ile
    50                  55                  60
```

Leu Lys Glu Ser Leu Asn Lys Lys Asp Glu Thr His Ser Lys
 65                  70                  75

<210> SEQ ID NO 61
<211> LENGTH: 210
<212> TYPE: DNA
<213> ORGANISM: Bacillus licheniformis

<400> SEQUENCE: 61
atggctcaaa acaacagaca aagcagttct aaccaactat tggttcctgg tgctgctcaa      60
gctatcgacc aaatgaaatt cgaaatcgct tctgaatttg gcgttaacct tggagcagaa     120
actacttctc gtgcaaacgg ttcagttgga ggagaaatca ctaagcgttt agtttctttc     180
gctcaacagc aaatgggtgg aacacaacaa                                      210

<210> SEQ ID NO 62
<211> LENGTH: 70
<212> TYPE: PRT
<213> ORGANISM: Bacillus licheniformis

<400> SEQUENCE: 62

Met Ala Gln Asn Asn Arg Gln Ser Ser Ser Asn Gln Leu Leu Val Pro
 1               5                  10                  15

Gly Ala Ala Gln Ala Ile Asp Gln Met Lys Phe Glu Ile Ala Ser Glu
            20                  25                  30

Phe Gly Val Asn Leu Gly Ala Glu Thr Thr Ser Arg Ala Asn Gly Ser
        35                  40                  45

Val Gly Gly Glu Ile Thr Lys Arg Leu Val Ser Phe Ala Gln Gln Gln
    50                  55                  60

Met Gly Gly Thr Gln Gln
 65                  70

<210> SEQ ID NO 63
<211> LENGTH: 1502
<212> TYPE: DNA
<213> ORGANISM: Bacillus licheniformis

<400> SEQUENCE: 63
atgagcaaca ctgaacttga tttgctgagg cagcaggcga atgaattaaa cttgcaaata      60
ttaaagctga ttaacgagcg aggaagaatc gttcaggaga ttggaaaagc gaaggaagca     120
caaggcatca accgctacga tcctgtcaga gaaagagcga tgctgaacga aattattgaa     180
aataacgacg accgtttga aaactcgacg atccagcata tcttcaaaga gattttcaaa      240
gccgggcttg aactgcagga agacgatcac agcaaagcgc tgctcgtttc ccgcaagaaa     300
aagcctgaaa atacaatcgt tgatctgaaa ggcgaaaaaa tcggcgacgg agaacaaaga     360
tttatcgtcg gtccgtgtgc ggttgaaagc tacgaacaag tagcggaagt cgcagcggca     420
gctaaaaagc aaggcttgaa actgcttcgc ggcggagctt tcaaaccgcg tacaagcccg     480
tacgacttcc aaggcctcgg cgtggaaggc ctgcaaatct taaagcgtgt tgctgatgag     540
tatgatctgg ccgtcatcag tgagatcgtg aatccgcagc atattgaaga agccattgat     600
tacatcgatg tcatccaaat cggcgcccgc aacatgcaga acttcgagct cttaaaagcg     660
gccggttcag tgaagaagcc ggttctgctg aagcgcggac ttgccgcaac gctgaaggaa     720
ttcatcaatg cagcggagta catcatgtcg cagggcaatg atcaaatcat cctttgtgaa     780
cgcggaatca gaacgtatga acagcgactt agaaatacgc ttgatatctc agctgtgccg     840
atcctgaagc aggaaactca ccttcctgta ttcgtggatg tcactcattc aaccggacgc     900

```
cgcgacctgc ttcttccgac agcaaaagca gcgcttgcga tcggagctga cggtgtcatg    960
gccgaggtcc atcctgatcc ttctgtcgcg ctttccgact cagctcagca aatggatatc   1020
ccgacatttg aaaaatggtt aaatgaactg aagccgctcg ttcaagtaaa agcataattg   1080
aacactgaat taaagtacat gcttcaatcc gttctaaaag aagaattgag tccgatcaat   1140
cagcgccttg atggaatcga caagcgctta gacaaaatcg acgcacgctt cgttgagata   1200
gacaagcgct tcgatgaagt ggacgcacgc ttcgttgaag tagataagcg ctttaacgca   1260
atcgacaagc gcttcaaaga aatagacggg cgcttaaaca aagtagaaaa ccgcttaaac   1320
gcaatggaca gcggctgaa tcggcttgaa acagatatag atgaactgaa agagggcag    1380 gagaggctcc cgaaaacgat catcgagaac atcggacaat ttacggagaa cattgtcgaa   1440
catgccgatg ataaggcggc tgccttgaat gacagggttt ttagcgtcga aaccgcaata   1500
ca                                                                 1502
```

<210> SEQ ID NO 64
<211> LENGTH: 147
<212> TYPE: PRT
<213> ORGANISM: Bacillus licheniformis

<400> SEQUENCE: 64

```
Met Asn Thr Glu Leu Lys Tyr Met Leu Gln Ser Val Leu Lys Glu Glu
1               5                   10                  15

Leu Ser Pro Ile Asn Gln Arg Leu Asp Gly Ile Asp Lys Arg Leu Asp
                20                  25                  30

Lys Ile Asp Ala Arg Phe Val Glu Ile Asp Lys Arg Phe Asp Glu Val
            35                  40                  45

Asp Ala Arg Phe Val Glu Val Asp Lys Arg Phe Asn Ala Ile Asp Lys
        50                  55                  60

Arg Phe Lys Glu Ile Asp Gly Arg Leu Asn Lys Val Glu Asn Arg Leu
65                  70                  75                  80

Asn Ala Met Asp Lys Arg Leu Asn Arg Leu Glu Thr Asp Ile Asp Glu
                85                  90                  95

Leu Lys Arg Gly Gln Glu Arg Leu Pro Lys Thr Ile Ile Glu Asn Ile
            100                 105                 110

Gly Gln Phe Thr Glu Asn Ile Val Glu His Ala Asp Asp Lys Ala Ala
        115                 120                 125

Ala Leu Asn Asp Arg Val Phe Ser Val Glu Thr Ala Ile Gln Arg Ile
    130                 135                 140

Tyr Arg Leu
145
```

<210> SEQ ID NO 65
<211> LENGTH: 375
<212> TYPE: DNA
<213> ORGANISM: Bacillus licheniformis

<400> SEQUENCE: 65

```
atgaaactaa attatgattg tgtccgctca attcttctag aattagagga aaatttaact     60
cttaacgatg gcgtcacttt atatcagctc aaagattttg agacattcaa agagtatggc    120
tatgaaactt ccgtttacgc tttaaccaag ttaatcgaag ctgactttt aaacggttcg     180 gtttcgcgcg cagacaataa gattgactat attggtgttg ctctattac ttgggatgga    240 catcaatttt tagacaacat tcgtgacaat gctgtttggt ctaaaacgaa agatgccgtt    300
```

```
aagtcgttat caagcgtttc cttgtccata ctttcaaatg tcggagaaag catcacgaaa    360
aagcttatcg gttta                                                     375
```

<210> SEQ ID NO 66
<211> LENGTH: 124
<212> TYPE: PRT
<213> ORGANISM: Bacillus licheniformis

<400> SEQUENCE: 66

```
Met Lys Leu Asn Tyr Asp Cys Val Arg Ser Ile Leu Leu Glu Leu Glu
1               5                   10                  15

Glu Asn Leu Thr Leu Asn Asp Gly Val Thr Leu Tyr Gln Leu Lys Asp
            20                  25                  30

Phe Glu Thr Phe Lys Glu Tyr Gly Tyr Glu Thr Ser Val Tyr Ala Leu
        35                  40                  45

Thr Lys Leu Ile Glu Ala Asp Phe Leu Asn Gly Ser Val Ser Arg Ala
    50                  55                  60

Asp Asn Lys Ile Asp Tyr Ile Gly Val Gly Ser Ile Thr Trp Asp Gly
65                  70                  75                  80

His Gln Phe Leu Asp Asn Ile Arg Asp Asn Ala Val Trp Ser Lys Thr
                85                  90                  95

Lys Asp Ala Val Lys Ser Leu Ser Ser Val Ser Leu Ser Ile Leu Ser
            100                 105                 110

Asn Val Gly Glu Ser Ile Thr Lys Lys Leu Ile Gly
        115                 120
```

<210> SEQ ID NO 67
<211> LENGTH: 458
<212> TYPE: DNA
<213> ORGANISM: Bacillus licheniformis

<400> SEQUENCE: 67

```
atgatctctc aacaattaaa acagcaaaat cctgtacttg aaaactcaat gaatacgaat     60
ttgtcaaact ggttcatcct ttacacgaag cttcaccgtt tcactggta cgtaaaaggg    120 ccgcagttct ttaccctaca tgaaaaattt gaagagctat acaaccatgc gtcagaaaca    180
gcagatgtga tcgcggaacg cttgctggcc atcggcggac agccgctcgc cacaatgaaa    240
gaatacattg accacggcac aattgaggaa aacggagccg aaaaaacggc cgaagaaatg    300
gtttccgcac tggtaagcga ttaccgtcaa atccgcgatg aaattcagca taccatcgaa    360
cttgcggaag ataaatcaga tcattctacc gctgaccttt atatcgccct gacagaggaa    420
attgataagc agatttggat gctttcttca tttttgga                            458
```

<210> SEQ ID NO 68
<211> LENGTH: 152
<212> TYPE: PRT
<213> ORGANISM: Bacillus licheniformis

<400> SEQUENCE: 68

```
Met Ile Ser Gln Gln Leu Lys Gln Gln Asn Pro Val Leu Glu Asn Ser
1               5                   10                  15

Met Asn Thr Asn Leu Ser Asn Trp Phe Ile Leu Tyr Thr Lys Leu His
            20                  25                  30

Arg Phe His Trp Tyr Val Lys Gly Pro Gln Phe Phe Thr Leu His Glu
        35                  40                  45

Lys Phe Glu Glu Leu Tyr Asn His Ala Ser Glu Thr Ala Asp Val Ile
    50                  55                  60
```

```
Ala Glu Arg Leu Leu Ala Ile Gly Gly Gln Pro Leu Ala Thr Met Lys
 65                  70                  75                  80

Glu Tyr Ile Asp His Gly Thr Ile Glu Asn Gly Ala Glu Lys Thr
                 85                  90                  95

Ala Glu Glu Met Val Ser Ala Leu Val Ser Asp Tyr Arg Gln Ile Arg
            100                 105                 110

Asp Glu Ile Gln His Thr Ile Glu Leu Ala Glu Asp Lys Ser Asp His
        115                 120                 125

Ser Thr Ala Asp Leu Tyr Ile Ala Leu Thr Glu Glu Ile Asp Lys Gln
    130                 135                 140

Ile Trp Met Leu Ser Ser Phe Leu
145                 150
```

```
<210> SEQ ID NO 69
<211> LENGTH: 373
<212> TYPE: DNA
<213> ORGANISM: Bacillus licheniformis

<400> SEQUENCE: 69
atgaatgaga agattttaat cgtagacgac cagtacggga ttcgggttct gctgaatgaa     60
gttttcaata agaagggta caaaaccttc caggccgcaa acgggattca agcgcttgac    120
attgtgaaaa accagcgccc cgacctcgtt ctgctcgata tgaaaatccc cggaatggac    180
ggaattgaaa ttttaaaaag aatgaagatc atagacgagg ggatccgcgt catcatcatg    240
acggcctacg gagagctcga catgatccag gaatcgaagg agctcggagc cctgacacac    300
tttgctaagc cttttgacat cgacgaaatc cgcgatgccg tcaaaacgta tctgcccata    360
aagtccaacg gat                                                      373

<210> SEQ ID NO 70
<211> LENGTH: 122
<212> TYPE: PRT
<213> ORGANISM: Bacillus licheniformis

<400> SEQUENCE: 70

Met Asn Glu Lys Ile Leu Ile Val Asp Asp Gln Tyr Gly Ile Arg Val
  1               5                  10                  15

Leu Leu Asn Glu Val Phe Asn Lys Glu Gly Tyr Lys Thr Phe Gln Ala
             20                  25                  30

Ala Asn Gly Ile Gln Ala Leu Asp Ile Val Lys Asn Gln Arg Pro Asp
         35                  40                  45

Leu Val Leu Leu Asp Met Lys Ile Pro Gly Met Asp Gly Ile Glu Ile
 50                  55                  60

Leu Lys Arg Met Lys Ile Ile Asp Glu Gly Ile Arg Val Ile Ile Met
 65                  70                  75                  80

Thr Ala Tyr Gly Glu Leu Asp Met Ile Gln Glu Ser Lys Glu Leu Gly
                 85                  90                  95

Ala Leu Thr His Phe Ala Lys Pro Phe Asp Ile Asp Glu Ile Arg Asp
            100                 105                 110

Ala Val Lys Thr Tyr Leu Pro Ile Lys Ser
        115                 120
```

```
<210> SEQ ID NO 71
<211> LENGTH: 523
<212> TYPE: DNA
<213> ORGANISM: Bacillus licheniformis
```

<400> SEQUENCE: 71

```
ttgcttaaaa ttttcaccac tcaattgacg ggaatcttca accggattca agagggcgag      60
gcccaatcga tagaggacgg cgcccgcttg ttggctcagg cggtcatcag tgatcattcg     120
gtttatgtat acggaaaaaa tgaattggaa ggcattttga agaagcgat gtacagttct      180
gaaccgttcc cctcagtcaa accgctgcag aaggacgaag aaaactggcc cgattttgaa     240
atgacggaca aagtgctgat gttctgcgcc ggttcagcgg atgacgaaga actgaaaatg     300
gcggaaaaac tgtatgaaaa aggaatcgga cttgttgtcg tctcccttc gggaaaagac      360
ggcgtcccga tcgcatcctt cgccgatgtc catatcgatt caaagctgag aatgccgctt     420
cttcccgatg aagacggaac aaggtacgga tttccgtccc tgatggtcag cctctatatt     480
tatcatgccc tatcctttac attaaaggaa atcctccagg aat                      523
```

<210> SEQ ID NO 72
<211> LENGTH: 174
<212> TYPE: PRT
<213> ORGANISM: Bacillus licheniformis

<400> SEQUENCE: 72

```
Met Leu Lys Ile Phe Thr Thr Gln Leu Thr Gly Ile Phe Asn Arg Ile
1               5                   10                  15
Gln Glu Gly Glu Ala Gln Ser Ile Glu Asp Gly Ala Arg Leu Leu Ala
            20                  25                  30
Gln Ala Val Ile Ser Asp His Ser Val Tyr Val Tyr Gly Lys Asn Glu
        35                  40                  45
Leu Glu Gly Ile Leu Lys Glu Ala Met Tyr Ser Ser Glu Pro Phe Pro
    50                  55                  60
Ser Val Lys Pro Leu Gln Lys Asp Glu Glu Asn Trp Pro Asp Phe Glu
65                  70                  75                  80
Met Thr Asp Lys Val Leu Met Phe Cys Ala Gly Ser Ala Asp Asp Glu
                85                  90                  95
Glu Leu Lys Met Ala Glu Lys Leu Tyr Glu Lys Gly Ile Gly Leu Val
            100                 105                 110
Val Val Ser Pro Ser Gly Lys Asp Gly Val Pro Ile Ala Ser Phe Ala
        115                 120                 125
Asp Val His Ile Asp Ser Lys Leu Arg Met Pro Leu Leu Pro Asp Glu
    130                 135                 140
Asp Gly Thr Arg Tyr Gly Phe Pro Ser Leu Met Val Ser Leu Tyr Ile
145                 150                 155                 160
Tyr His Ala Leu Ser Phe Thr Leu Lys Glu Ile Leu Gln Glu
                165                 170
```

<210> SEQ ID NO 73
<211> LENGTH: 266
<212> TYPE: DNA
<213> ORGANISM: Bacillus licheniformis

<400> SEQUENCE: 73

```
atgagcaaaa cgattaaact taaccatgca gcggttatga agaagctgga acaagtaagc      60
agcacgcttc aagccgtatc tttaaaaagc ccgccagccg agcgctcgg gcggaacaac     120
cttgatttta cgaaaaagtg gcttgaacga gaagccgaaa tttgcaatat ggtcaaacag     180
tataaagagg ctgttcgtaa aaacattgag gacacccgct caaatgtgga cacgctgaag     240
gaacaggatg aggcgattgc ccgaag                                         266
```

<210> SEQ ID NO 74
<211> LENGTH: 88
<212> TYPE: PRT
<213> ORGANISM: Bacillus licheniformis

<400> SEQUENCE: 74

Met Ser Lys Thr Ile Lys Leu Asn His Ala Ala Val Met Lys Lys Leu
1               5                   10                  15

Glu Gln Val Ser Ser Thr Leu Gln Ala Val Ser Leu Lys Ser Pro Pro
            20                  25                  30

Ala Gly Ala Leu Gly Arg Asn Asn Leu Asp Phe Thr Lys Lys Trp Leu
        35                  40                  45

Glu Arg Glu Ala Glu Ile Cys Asn Met Val Lys Gln Tyr Lys Glu Ala
    50                  55                  60

Val Arg Lys Asn Ile Glu Asp Thr Arg Ser Asn Val Asp Thr Leu Lys
65                  70                  75                  80

Glu Gln Asp Glu Ala Ile Ala Arg
                85

<210> SEQ ID NO 75
<211> LENGTH: 1396
<212> TYPE: DNA
<213> ORGANISM: Bacillus licheniformis

<400> SEQUENCE: 75
atgaaatata aaacattagc tcaatttccg aaagattttt tgtggggcgc gtctacttcc      60
gcttatcaag tggaaggcgc ttgggacgaa gatggaaaag ggccttctgt catcgatgcg     120
cgcgaaagct acccggaagg gacaaccgat tttaaagtcg caagcgacca ttaccagcgc     180
tataaagaag atatcgcttt atttgcggaa atgggcttca aagcgtaccg tttttcgatt     240
gcctggacgc gcatcattcc ggacggggac ggtgatatta tccgaaaggg aatcgaattt     300
tacagccgtt tgatcgatga acttctaaag tatggaatcg aaccaattgt tacgatgtac     360
cactttgatc tgccgaatgc tttgcagaaa aaaggcggct ggtcggacag gccacgatt      420
gatgcttttg aaaagtatgc gaaggtcctt tttgaaagct acggtgaccg cgtcaaatac     480
tggctgacca tcaatgagca aaatatgatg atcctccacg gatctgcact cggtacactc     540
gatccgaact tggaaaatcc gaaaaaagag ctttatcagc aaaaccatca catgctcgtc     600
gcacaggcga aagcgatcaa gctttgccat gagatgctgc cggaagcaaa aatcggtcct     660
gcgccgaata ttgcgctcat ctatcccgct tcttcgaaac cggaggacgt gctggcggct     720
tttaactata atgcgatccg aaactggctt tacttggata tggccgtatt cggacggtac     780
aatacaacag cgtgggcata tatgaaagaa aaaggctgca caccggtcat cgctgaaggg     840
gatatggaca ttctgcggtc ggccaagccg gattttatcg cgtttaacta ctatacatcg     900
caaacgctg aagcaagcag gggtgatggc agcgacacgg ctgctcgagg cggagaccag     960
catttgcaga cgggagaaga aggcgtatat aggggaagca gcaatccgca cctaaagaaa    1020
aacgcatttg gctgggagat cgaccctgtc ggtttccgtt cgacgctgcg cgaaatttac    1080
gaccgctacc agctgccgct gatcgtcact gagaacggcc tcggcgcgtt tgatcagctt    1140
gaagacggag atgtcgtaaa tgacgattac cgcatcgatt atttaaaaga gcatatcaag    1200
caaattcagc tggcaatcac ggatggagtc gatgttttcg gctactcccc atggtctgcc    1260
atcgacttaa tttcgaccca tcaaggctgt tcaaaacgct acggattat ttatgtgaac    1320
cgcgatgaat tgatttgaa agacttgcgc cgcattcgca aaaaaagctt ttactggtat    1380
aaaaacctga ttgcta                                                          1396

<210> SEQ ID NO 76
<211> LENGTH: 465
<212> TYPE: PRT
<213> ORGANISM: Bacillus licheniformis

<400> SEQUENCE: 76

Met Lys Tyr Lys Thr Leu Ala Gln Phe Pro Lys Asp Phe Leu Trp Gly
1               5                   10                  15

Ala Ser Thr Ser Ala Tyr Gln Val Glu Gly Ala Trp Asp Glu Asp Gly
                20                  25                  30

Lys Gly Pro Ser Val Ile Asp Ala Arg Glu Ser Tyr Pro Glu Gly Thr
            35                  40                  45

Thr Asp Phe Lys Val Ala Ser Asp His Tyr Gln Arg Tyr Lys Glu Asp
        50                  55                  60

Ile Ala Leu Phe Ala Glu Met Gly Phe Lys Ala Tyr Arg Phe Ser Ile
65                  70                  75                  80

Ala Trp Thr Arg Ile Ile Pro Asp Gly Asp Gly Asp Ile Asn Pro Lys
                85                  90                  95

Gly Ile Glu Phe Tyr Ser Arg Leu Ile Asp Glu Leu Leu Lys Tyr Gly
            100                 105                 110

Ile Glu Pro Ile Val Thr Met Tyr His Phe Asp Leu Pro Asn Ala Leu
        115                 120                 125

Gln Lys Lys Gly Gly Trp Ser Asp Arg Ala Thr Ile Asp Ala Phe Glu
    130                 135                 140

Lys Tyr Ala Lys Val Leu Phe Glu Ser Tyr Gly Asp Arg Val Lys Tyr
145                 150                 155                 160

Trp Leu Thr Ile Asn Glu Gln Asn Met Met Ile Leu His Gly Ser Ala
                165                 170                 175

Leu Gly Thr Leu Asp Pro Asn Leu Glu Asn Pro Lys Lys Glu Leu Tyr
            180                 185                 190

Gln Gln Asn His His Met Leu Val Ala Gln Ala Lys Ala Ile Lys Leu
        195                 200                 205

Cys His Glu Met Leu Pro Glu Ala Lys Ile Gly Pro Ala Pro Asn Ile
    210                 215                 220

Ala Leu Ile Tyr Pro Ala Ser Ser Lys Pro Glu Asp Val Leu Ala Ala
225                 230                 235                 240

Phe Asn Tyr Asn Ala Ile Arg Asn Trp Leu Tyr Leu Asp Met Ala Val
                245                 250                 255

Phe Gly Arg Tyr Asn Thr Thr Ala Trp Ala Tyr Met Lys Glu Lys Gly
            260                 265                 270

Cys Thr Pro Val Ile Ala Glu Gly Asp Met Asp Ile Leu Arg Ser Ala
        275                 280                 285

Lys Pro Asp Phe Ile Ala Phe Asn Tyr Tyr Thr Ser Gln Thr Ala Glu
    290                 295                 300

Ala Ser Arg Gly Asp Gly Ser Asp Thr Ala Ala Arg Gly Gly Asp Gln
305                 310                 315                 320

His Leu Gln Thr Gly Glu Glu Gly Val Tyr Arg Gly Ser Ser Asn Pro
                325                 330                 335

His Leu Lys Lys Asn Ala Phe Gly Trp Glu Ile Asp Pro Val Gly Phe
            340                 345                 350

Arg Ser Thr Leu Arg Glu Ile Tyr Asp Arg Tyr Gln Leu Pro Leu Ile
        355                 360                 365

| | | | | | | | | | | | |
|---|---|---|---|---|---|---|---|---|---|---|---|
|Val|Thr|Glu|Asn|Gly|Leu|Gly|Ala|Phe|Asp|Gln|Leu|Glu|Asp|Gly|Asp|
| |370| | | |375| | | |380| | | | | | |

Val Val Asn Asp Asp Tyr Arg Ile Asp Tyr Leu Lys Glu His Ile Lys
385                 390                 395                 400

Gln Ile Gln Leu Ala Ile Thr Asp Gly Val Asp Val Phe Gly Tyr Ser
            405                 410                 415

Pro Trp Ser Ala Ile Asp Leu Ile Ser Thr His Gln Gly Cys Ser Lys
        420                 425                 430

Arg Tyr Gly Phe Ile Tyr Val Asn Arg Asp Glu Phe Asp Leu Lys Asp
        435                 440                 445

Leu Arg Arg Ile Arg Lys Lys Ser Phe Tyr Trp Tyr Lys Asn Leu Ile
450                 455                 460

Ala
465

<210> SEQ ID NO 77
<211> LENGTH: 1830
<212> TYPE: DNA
<213> ORGANISM: Bacillus licheniformis

<400> SEQUENCE: 77

```
atgaatgttc aatcaatggc aaaagaaatt ctggcgcgcg tcggcgggga gaagaacgtt      60
gtatcgctag tccattgcgc gacaaggctc cgcttcaaac tgaaagaccg ttccaaagca     120
gacagagaag cgcttgaaaa tacggatggc gtggtaaccg tggtggagag cggcgggcaa     180
tttcaagtcg ttatcggcaa taacgttcct gaagtatata agaaaatcgg ccggatctct     240
caactgttgg aaagttctgc ggccgatcac agtcaaaaag agaaaggaag cctcgccggt     300
agattagtag atgtcgtatc cagcattttc actccgctgc tcggcgtcat ggcgggagcg     360
gggattttaa aaggcctgct tttgatttgc acaaacgccg gctggctctc gccggaagag     420
acgacatata cgattctata cgcggcagcc gacagcctgt tttatttcct gcctttgctg     480
ctcgccgtta cggccgccaa aaaattcgga gcgaacccgt tcatagcgct gacgattgcc     540
ggagcgctga tctatccgac gatactcgaa ctgaaaaaca gcgcgcccca tacggagttt     600
tcggcattc cggtcgtctt gatgaattat acgtcgaccg ttatcccgat tatccttgcg     660
gtatttgtga tgagctatct tgaaagatta tgtatgcgct ttattcatga aagcgtgaag     720
aactttatca ccccctttat tatgcctgacg gtgatggtgc cgttaacttt gatcgtattc     780
ggaccgctcg gcgtttacac aggaaacggg atcgcggcgg cgattctgtc cgttttttgat     840
ttcagcccga ttctggcagg agcgattatt gcggcctat  ggcaaatcct tgtcatcttc     900
gggattcact gggggatcgt ccctgtcatt ttgaacaaca ttgccgtcca ggcaaggac      960
tacattaagc cggcgacggc agccgccgtg tttgcccaaa caggagccgc atttggcgtc    1020
atgctgaaga cgaaaaacaa gaagctgaaa gcattggcag atcagctgc cgttaccggg    1080
atattcggga ttacagagcc ggccgtctac ggggtgacgc tcaggctgaa aaagccgttt    1140
gtatgcggtg tcatcagcgc ggcggcaggc ggagccatta tcggatactc cggcagcgtc    1200
gccctcgctt ccggcgctcc gggcttgttg acgattccga tttttttacgg accgggcttt    1260
ctcggcttca tcatcggcat ttcagtttca tttgttttat cgattttgct cacttacatt    1320
gtcggctttg acgaccctgt ggaggtgaca aaagaggagc ctgttgaaaa aagcgccggt    1380
gaaccgattt acagcccttt gcaaggagaa gtcctgccgt taacagaagt atcagataaa    1440
gtgttcgcat cgggggcgct tggagaggga atcgcggtgg ttccgtcaaa aggcgttgtc    1500
```

-continued

```
accgccsctg cggacggcat cgtgacaacg gcatttccga cgggtcacgc atacggcata    1560
acgaccgaaa gcggagccga gattttgatt catattggaa tggacacagt caggctcgaa    1620
ggaaagcact tcaatcctaa agccgtgcag gggcaaaatg tgaaacgggg tgatatactc    1680
gcagaattcg atctggacgc tttgaaagaa gaagggtttg acgtgaaaac gccgatcatc    1740
gttacaaatt ccggtcaata cacggatgtc attccaacgg atcaaaaaaa ggtgaaaact    1800
gaagaacgga tcatcacttt aatttcatca                                     1830
```

<210> SEQ ID NO 78
<211> LENGTH: 609
<212> TYPE: PRT
<213> ORGANISM: Bacillus licheniformis

<400> SEQUENCE: 78

```
Met Asn Val Gln Ser Met Ala Lys Glu Ile Leu Ala Arg Val Gly Gly
1               5                   10                  15

Glu Lys Asn Val Val Ser Leu Val His Cys Ala Thr Arg Leu Arg Phe
            20                  25                  30

Lys Leu Lys Asp Arg Ser Lys Ala Asp Arg Glu Ala Leu Glu Asn Thr
        35                  40                  45

Asp Gly Val Val Thr Val Val Glu Ser Gly Gly Gln Phe Gln Val Val
    50                  55                  60

Ile Gly Asn Asn Val Pro Glu Val Tyr Lys Glu Ile Gly Arg Ile Ser
65                  70                  75                  80

Gln Leu Leu Glu Ser Ser Ala Ala Asp His Ser Gln Lys Glu Lys Gly
                85                  90                  95

Ser Leu Ala Gly Arg Leu Val Asp Val Val Ser Ser Ile Phe Thr Pro
            100                 105                 110

Leu Leu Gly Val Met Ala Gly Ala Gly Ile Leu Lys Gly Leu Leu Leu
        115                 120                 125

Ile Cys Thr Asn Ala Gly Trp Leu Ser Pro Glu Glu Thr Thr Tyr Thr
    130                 135                 140

Ile Leu Tyr Ala Ala Ala Asp Ser Leu Phe Tyr Phe Leu Pro Leu Leu
145                 150                 155                 160

Leu Ala Val Thr Ala Ala Lys Lys Phe Gly Ala Asn Pro Phe Ile Ala
                165                 170                 175

Leu Thr Ile Ala Gly Ala Leu Ile Tyr Pro Thr Ile Leu Glu Leu Lys
            180                 185                 190

Asn Ser Gly Ala His Thr Glu Phe Phe Gly Ile Pro Val Val Leu Met
        195                 200                 205

Asn Tyr Thr Ser Thr Val Ile Pro Ile Ile Leu Ala Val Phe Val Met
    210                 215                 220

Ser Tyr Leu Glu Arg Leu Cys Met Arg Phe Ile His Glu Ser Val Lys
225                 230                 235                 240

Asn Phe Ile Thr Pro Leu Leu Cys Leu Thr Val Met Val Pro Leu Thr
                245                 250                 255

Leu Ile Val Phe Gly Pro Leu Gly Val Tyr Thr Gly Asn Gly Ile Ala
            260                 265                 270

Ala Ala Ile Leu Ser Val Phe Asp Phe Ser Pro Ile Leu Ala Gly Ala
        275                 280                 285

Ile Ile Ala Ala Leu Trp Gln Ile Leu Val Ile Phe Gly Ile His Trp
    290                 295                 300

Gly Ile Val Pro Val Ile Leu Asn Asn Ile Ala Val His Gly Lys Asp
```

Tyr Ile Lys Pro Ala Thr Ala Ala Val Phe Ala Gln Thr Gly Ala
                325                 330                 335

Ala Phe Gly Val Met Leu Lys Thr Lys Asn Lys Lys Leu Lys Ala Leu
                340                 345                 350

Ala Gly Ser Ala Ala Val Thr Gly Ile Phe Gly Ile Thr Glu Pro Ala
                355                 360                 365

Val Tyr Gly Val Thr Leu Arg Leu Lys Lys Pro Phe Val Cys Gly Val
        370                 375                 380

Ile Ser Ala Ala Ala Gly Gly Ala Ile Ile Gly Tyr Ser Gly Ser Val
385                 390                 395                 400

Ala Leu Ala Ser Gly Ala Pro Gly Leu Leu Thr Ile Pro Ile Phe Tyr
                405                 410                 415

Gly Pro Gly Phe Leu Gly Phe Ile Ile Gly Ile Ser Val Ser Phe Val
                420                 425                 430

Leu Ser Ile Leu Leu Thr Tyr Ile Val Gly Phe Asp Asp Pro Val Glu
            435                 440                 445

Val Thr Lys Glu Glu Pro Val Glu Lys Ser Ala Gly Glu Pro Ile Tyr
        450                 455                 460

Ser Pro Leu Gln Gly Glu Val Leu Pro Leu Thr Glu Val Ser Asp Lys
465                 470                 475                 480

Val Phe Ala Ser Gly Ala Leu Gly Glu Gly Ile Ala Val Val Pro Ser
                485                 490                 495

Lys Gly Val Val Thr Ala Pro Ala Asp Gly Ile Val Thr Thr Ala Phe
            500                 505                 510

Pro Thr Gly His Ala Tyr Gly Ile Thr Thr Glu Ser Gly Ala Glu Ile
        515                 520                 525

Leu Ile His Ile Gly Met Asp Thr Val Arg Leu Glu Gly Lys His Phe
    530                 535                 540

Asn Pro Lys Ala Val Gln Gly Gln Asn Val Lys Arg Gly Asp Ile Leu
545                 550                 555                 560

Ala Glu Phe Asp Leu Asp Ala Leu Lys Glu Glu Gly Phe Asp Val Lys
                565                 570                 575

Thr Pro Ile Ile Val Thr Asn Ser Gly Gln Tyr Thr Asp Val Ile Pro
            580                 585                 590

Thr Asp Gln Lys Lys Val Lys Thr Glu Glu Arg Ile Ile Thr Leu Ile
        595                 600                 605

Ser

<210> SEQ ID NO 79
<211> LENGTH: 821
<212> TYPE: DNA
<213> ORGANISM: Bacillus licheniformis

<400> SEQUENCE: 79
gtgaaaattg ccaaagtgat caacaacaat gtgatcagtg ttttaaatga acagggtcag    60
gaattagtgg tcatgggcag gggaatcgct tttcaaaaaa agcctggcga agcggtggat   120
gaatcgagaa tcgagaagat tttcaggctt gataataaag atgtatcaga aaggtttaag   180
acgctgttgg acgaaattcc aattgaattt atggaaatgt ctgaagaaat tatctcctat   240
gcgaaattaa agctcggcaa aaagctgaat gacagcattt atgtctcgct gaccgaccat   300
attcatttcg ccgtcgaacg gcataaaaag ggactggata ttaaaaatgc cctgctttgg   360
gagacgaaac ggctgtataa agatgagttc gccatcggca agaggcgct ggccatcatt   420

```
gaaaagaaga cggggacagc tcttccggag gatgaagccg cctttatcgc gctccatatc      480
gtaaacgccg agctgaatga agaaatgccg aacatcgtca atattacgaa agtcatgcag      540
gagattttaa gcatcgtcaa gtatcacttt catatcgaat ttgacgaaga atcgcttcac      600
tattaccgct tcattaccca tttgaaattt ttcgcccagc ggctgttcag cggaacctat      660
atggaaagcc gggacgactt tttatttgaa accgtcaaaa ataagtaccg ggacgcttat      720
gtttgtacaa ataaaatcag gcagtatatc gaaaaagaat acggtcatca gctgacaaac      780
gaagagcttc tgtatttgac gattcatatc gagcgagtcg t                          821
```

<210> SEQ ID NO 80
<211> LENGTH: 273
<212> TYPE: PRT
<213> ORGANISM: Bacillus licheniformis

<400> SEQUENCE: 80

```
Met Lys Ile Ala Lys Val Ile Asn Asn Val Ile Ser Val Leu Asn
1               5                   10                  15

Glu Gln Gly Gln Glu Leu Val Val Met Gly Arg Gly Ile Ala Phe Gln
            20                  25                  30

Lys Lys Pro Gly Glu Ala Val Asp Glu Ser Arg Ile Glu Lys Ile Phe
        35                  40                  45

Arg Leu Asp Asn Lys Asp Val Ser Glu Arg Phe Lys Thr Leu Leu Asp
    50                  55                  60

Glu Ile Pro Ile Glu Phe Met Glu Met Ser Glu Ile Ile Ser Tyr
65                  70                  75                  80

Ala Lys Leu Lys Leu Gly Lys Lys Leu Asn Asp Ser Ile Tyr Val Ser
                85                  90                  95

Leu Thr Asp His Ile His Phe Ala Val Glu Arg His Lys Lys Gly Leu
            100                 105                 110

Asp Ile Lys Asn Ala Leu Leu Trp Glu Thr Lys Arg Leu Tyr Lys Asp
        115                 120                 125

Glu Phe Ala Ile Gly Lys Glu Ala Leu Ala Ile Ile Glu Lys Lys Thr
    130                 135                 140

Gly Thr Ala Leu Pro Glu Asp Glu Ala Ala Phe Ile Ala Leu His Ile
145                 150                 155                 160

Val Asn Ala Glu Leu Asn Glu Glu Met Pro Asn Ile Val Asn Ile Thr
                165                 170                 175

Lys Val Met Gln Glu Ile Leu Ser Ile Val Lys Tyr His Phe His Ile
            180                 185                 190

Glu Phe Asp Glu Glu Ser Leu His Tyr Tyr Arg Phe Ile Thr His Leu
        195                 200                 205

Lys Phe Phe Ala Gln Arg Leu Phe Ser Gly Thr Tyr Met Glu Ser Arg
    210                 215                 220

Asp Asp Phe Leu Phe Glu Thr Val Lys Asn Lys Tyr Arg Asp Ala Tyr
225                 230                 235                 240

Val Cys Thr Asn Lys Ile Arg Gln Tyr Ile Glu Lys Tyr Gly His
                245                 250                 255

Gln Leu Thr Asn Glu Glu Leu Leu Tyr Leu Thr Ile His Ile Glu Arg
            260                 265                 270

Val
```

<210> SEQ ID NO 81
<211> LENGTH: 1387

<212> TYPE: DNA
<213> ORGANISM: Bacillus licheniformis

<400> SEQUENCE: 81

```
atgactgaac aaacgaaaaa gtttcctgaa ggttttttat ggggcggagc ggttgccgca      60
aaccaagtgg aaggcgccta taatgtcggc gggaaaggac tctcgacagc cgatgtgtcg     120
ccgaacggcg tcatgtatcc attcgatgag tcgatggagt cattgaacct gtatcatgaa     180
ggcatcgatt tttaccaccg ctacaaagaa gatatcgctc ttttcgccga aatgggattt     240
aaagcattcc ggacatcgat tgcctggacg cggattttc ctaacggcga tgaaactgaa      300
ccgaatgaag agggactcga attttatgat cgcctctttg acgagctatt aaaatacaat     360
attgagccag tggtgacgat ttcccactac gaaatgccgc tcggtctgat taaaaaatac     420
ggcggctgga aaaccggaa agtgatcgat tgctatgagc attatgcgaa acggttttc       480
acccgctata agaaaaagt aaaatactgg atgacattca atgaaatcaa catggttctg      540
catgcgccgt ttacaggcgg aggccttgtg tttgaagaag cgaaaacaa gttaaatgcg      600
atgtaccaag cggcgcatca tctatttgtc gcaagcgctc ttgccgttaa agcggggcac     660
gacatcattc cggacgctaa atcggctgc atgatcgccg caacgacgac atacccgatg      720
acgccaaagc cggaagacgt gctcgctgcg atggagaatg agagaagaac gctgttttc      780
tcggatgtac aggcgcgcgg ggcttatccg ggctatatga gcgcttctt taaggaaaac      840
ggaattacga ttgaaatggc tgaaggtgat gaagacatct aaaggaaaa caccgtcgac      900
tatatcggtt tcagctacta catgtcaatg gtcgcaagca cgagtccgga agacttggca     960
aaaacggaag gcaacctgct cggcggcgtc aaaaatccgt accttgaatc gtccgaatgg    1020
ggctggcaga tcgatcctaa agggatccgc attacgctga atacattgta cgaccgctat    1080
caaaagccgc ttttcattgt tgaaaacggg ctcggcgccg tcgatgtcgt cgaagaagac    1140
ggctccatcc aggatgacta cagaatcaac tatttgcgcg atcatttaaa agaagtaaga    1200
gaagccattg cagacggcgt cgacttaatc ggctacacat catggggccc gatcgacctg    1260
gtcagcgcat ccaccgccga aatgaaaaag cgctacggct atatttacgt cgatcgtgac    1320
aatgaaggaa aaggcacgct ttcaagaacg agaaagaaaa gcttttactg gtataagaaa    1380
gtaatcg                                                              1387
```

<210> SEQ ID NO 82
<211> LENGTH: 462
<212> TYPE: PRT
<213> ORGANISM: Bacillus licheniformis

<400> SEQUENCE: 82

```
Met Thr Glu Gln Thr Lys Lys Phe Pro Glu Gly Phe Leu Trp Gly Gly
1               5                   10                  15

Ala Val Ala Ala Asn Gln Val Glu Gly Ala Tyr Asn Val Gly Gly Lys
            20                  25                  30

Gly Leu Ser Thr Ala Asp Val Ser Pro Asn Gly Val Met Tyr Pro Phe
        35                  40                  45

Asp Glu Ser Met Glu Ser Leu Asn Leu Tyr His Glu Gly Ile Asp Phe
    50                  55                  60

Tyr His Arg Tyr Lys Glu Asp Ile Ala Leu Phe Ala Glu Met Gly Phe
65                  70                  75                  80

Lys Ala Phe Arg Thr Ser Ile Ala Trp Thr Arg Ile Phe Pro Asn Gly
                85                  90                  95
```

Asp Glu Thr Glu Pro Asn Glu Glu Gly Leu Glu Phe Tyr Asp Arg Leu
            100                 105                 110

Phe Asp Glu Leu Leu Lys Tyr Asn Ile Glu Pro Val Val Thr Ile Ser
        115                 120                 125

His Tyr Glu Met Pro Leu Gly Leu Ile Lys Lys Tyr Gly Gly Trp Lys
    130                 135                 140

Asn Arg Lys Val Ile Asp Cys Tyr Glu His Tyr Ala Lys Thr Val Phe
145                 150                 155                 160

Thr Arg Tyr Lys Glu Lys Val Lys Tyr Trp Met Thr Phe Asn Glu Ile
                165                 170                 175

Asn Met Val Leu His Ala Pro Phe Thr Gly Gly Leu Val Phe Glu
            180                 185                 190

Glu Gly Glu Asn Lys Leu Asn Ala Met Tyr Gln Ala Ala His His Leu
        195                 200                 205

Phe Val Ala Ser Ala Leu Ala Val Lys Ala Gly His Asp Ile Ile Pro
    210                 215                 220

Asp Ala Lys Ile Gly Cys Met Ile Ala Ala Thr Thr Thr Tyr Pro Met
225                 230                 235                 240

Thr Pro Lys Pro Glu Asp Val Leu Ala Ala Met Glu Asn Glu Arg Arg
                245                 250                 255

Thr Leu Phe Phe Ser Asp Val Gln Ala Arg Gly Ala Tyr Pro Gly Tyr
            260                 265                 270

Met Lys Arg Phe Phe Lys Glu Asn Gly Ile Thr Ile Glu Met Ala Glu
        275                 280                 285

Gly Asp Glu Asp Ile Leu Lys Glu Asn Thr Val Asp Tyr Ile Gly Phe
    290                 295                 300

Ser Tyr Tyr Met Ser Met Val Ala Ser Thr Ser Pro Glu Asp Leu Ala
305                 310                 315                 320

Lys Thr Glu Gly Asn Leu Leu Gly Gly Val Lys Asn Pro Tyr Leu Glu
                325                 330                 335

Ser Ser Glu Trp Gly Trp Gln Ile Asp Pro Lys Gly Ile Arg Ile Thr
            340                 345                 350

Leu Asn Thr Leu Tyr Asp Arg Tyr Gln Lys Pro Leu Phe Ile Val Glu
        355                 360                 365

Asn Gly Leu Gly Ala Val Asp Val Val Glu Glu Asp Gly Ser Ile Gln
    370                 375                 380

Asp Asp Tyr Arg Ile Asn Tyr Leu Arg Asp His Leu Lys Glu Val Arg
385                 390                 395                 400

Glu Ala Ile Ala Asp Gly Val Asp Leu Ile Gly Tyr Thr Ser Trp Gly
                405                 410                 415

Pro Ile Asp Leu Val Ser Ala Ser Thr Ala Glu Met Lys Lys Arg Tyr
            420                 425                 430

Gly Tyr Ile Tyr Val Asp Arg Asp Asn Glu Gly Lys Gly Thr Leu Ser
        435                 440                 445

Arg Thr Arg Lys Lys Ser Phe Tyr Trp Tyr Lys Lys Val Ile
    450                 455                 460

<210> SEQ ID NO 83
<211> LENGTH: 1820
<212> TYPE: DNA
<213> ORGANISM: Bacillus licheniformis

<400> SEQUENCE: 83
atggattata ataaagtatc gaaggacatt ttacaactcg tgggcggtga agagaacgta        60

```
cagagcgtga ttcactgcat gacaagactg cgtttcaatc tttatgacaa tgcgaaggca    120
gaccgcgcga aactggaaag tcttccggct gtaatgggca ccaacatcag cggccagcag    180
tttcaaatca tcattggaaa tgatgtccct aaggtgtata aagcgatcat tgccaacagc    240
gggctcagcg atgaaaaagc gggcgagcag caagctggca aaagaaaaa cgtgctgtcc    300 gccatttttg atgtgatatc aggcgtattt acgccgattc tcccggcgat cgccggagcg    360
ggtatgatca aggggatcat tgcaatcgcc gtcacgttcg gctggatgag cgaaactagc    420
caggtccaca ccatttttatc cgccatcggc gacggagcat tttacttcct gccgattttg    480
ctggcggtca gtgccgcgag aaaattcggc agtaatcctt atgttgcggc ggcgatcgga    540
gcggcgattc tgcatcccga tctgacagcg cttctcggtt cagggaaaag catttccttt    600
gtcggattgc ctgtaaccgc tgccacttat tcgtcgaccg tcattccgat cctgctcgcg    660
atttggattg catcttacgt tgagaaatgg attgacaaag tcaccccgac ttcgttgaag    720 atgattttg taccgacgct gacgctgctg gttgtcgtgc ctgtcacatt aattacggtc    780
ggtccgctcg gtgcgattgc agggaactat ctgtcaatcg gtgtgaacgg tttatttgaa    840
aatgccggtt taatcacgat gatccttta gcaggaacgt tctcgctgat cgtcatgaca    900
ggaatgcact atgctttcat tccggttatg ttcaacaaca ttacgcaaaa cggctacgat    960
tacttgatac ctgcgatgtt cttggcgaat atgggcagg ctggcgcgtc atttgccgtc   1020
ttcctgcgat ccagaaataa gaaattcaaa tcattgtcgc tgacgacaag catcacggct   1080
ttgatgggga ttacagagcc ggcgatgtac ggtgtcaaca tgaggctgaa aaagccgttt   1140
gtatccgcgc ttctcggcgc cgctgtcgga ggagcatttt acggcatcac cggcgtagca   1200
gcatatatta ttggcggaaa cgtcggtttg ccgggaatta cgacgtttat cggcccgact   1260
tttatacagg caatgatcgg tatcgtcatc gcgttctttg ccgcaacggc gtttgctttt   1320
gtattggggt ttgaagacat tccttcagat gaagccgctg aacaaggagc cgctccatct   1380
gaagcgggcg cggagagat cattcaaagc ccgctgaaag cgaagtcaa agcattgagt   1440 gaagtggatg atgcgacatt ttctggagaa gtcatgggaa aaggcgtcgc cattgagcct   1500
gaagaaggca aagtggtgtc gccggtatca ggcacgatca caaccgtttt tcaaacgaag   1560
cacgccctcg gcattacaag cgacaatggg gcggaaatta ttatccatat cggaatcgac   1620
acggtgaaat tgaacggcga gcactttacc gtgcatgtca ataaaggcga cgctgtaaaa   1680
ccgggagacg agcttgtctc atttgatatg gatgcgatta aggatgcagg ctatcagttg   1740
atcacgccgg ttatcatcac aaatacggac cggtaccagt cgatcaaacc tttgaaatca   1800
gatgaaagcg ttgacattga                                               1820
```

<210> SEQ ID NO 84
<211> LENGTH: 604
<212> TYPE: PRT
<213> ORGANISM: Bacillus licheniformis

<400> SEQUENCE: 84

Met Asp Tyr Asn Lys Val Ser Lys Asp Ile Leu Gln Leu Val Gly Gly
1               5                   10                  15

Glu Glu Asn Val Gln Ser Val Ile His Cys Met Thr Arg Leu Arg Phe
            20                  25                  30

Asn Leu Tyr Asp Asn Ala Lys Ala Asp Arg Ala Lys Leu Glu Ser Leu
        35                  40                  45

Pro Ala Val Met Gly Thr Asn Ile Ser Gly Gln Gln Phe Gln Ile Ile
    50                  55                  60

```
Ile Gly Asn Asp Val Pro Lys Val Tyr Lys Ala Ile Ala Asn Ser
 65                  70                  75                  80

Gly Leu Ser Asp Glu Lys Ala Gly Glu Gln Ala Gly Lys Lys Lys
                 85                  90                  95

Asn Val Leu Ser Ala Ile Phe Asp Val Ile Ser Gly Val Phe Thr Pro
                100                 105                 110

Ile Leu Pro Ala Ile Ala Gly Ala Gly Met Ile Lys Gly Ile Ala
            115                 120                 125

Ile Ala Val Thr Phe Gly Trp Met Ser Glu Thr Ser Gln Val His Thr
130                 135                 140

Ile Leu Ser Ala Ile Gly Asp Gly Ala Phe Tyr Phe Leu Pro Ile Leu
145                 150                 155                 160

Leu Ala Val Ser Ala Ala Arg Lys Phe Gly Ser Asn Pro Tyr Val Ala
                165                 170                 175

Ala Ala Ile Gly Ala Ala Ile Leu His Pro Asp Leu Thr Ala Leu Leu
                180                 185                 190

Gly Ser Gly Lys Ser Ile Ser Phe Val Gly Leu Pro Val Thr Ala Ala
            195                 200                 205

Thr Tyr Ser Ser Thr Val Ile Pro Ile Leu Leu Ala Ile Trp Ile Ala
            210                 215                 220

Ser Tyr Val Glu Lys Trp Ile Asp Lys Val Thr Pro Thr Ser Leu Lys
225                 230                 235                 240

Met Ile Phe Val Pro Thr Leu Thr Leu Leu Val Val Pro Val Thr
                245                 250                 255

Leu Ile Thr Val Gly Pro Leu Gly Ala Ile Ala Gly Asn Tyr Leu Ser
                260                 265                 270

Ile Gly Val Asn Gly Leu Phe Glu Asn Ala Gly Leu Ile Thr Met Ile
            275                 280                 285

Leu Leu Ala Gly Thr Phe Ser Leu Ile Val Met Thr Gly Met His Tyr
290                 295                 300

Ala Phe Ile Pro Val Met Phe Asn Asn Ile Thr Gln Asn Gly Tyr Asp
305                 310                 315                 320

Tyr Leu Ile Pro Ala Met Phe Leu Ala Asn Met Gly Gln Ala Gly Ala
                325                 330                 335

Ser Phe Ala Val Phe Leu Arg Ser Arg Asn Lys Lys Phe Lys Ser Leu
                340                 345                 350

Ser Leu Thr Thr Ser Ile Thr Ala Leu Met Gly Ile Thr Glu Pro Ala
            355                 360                 365

Met Tyr Gly Val Asn Met Arg Leu Lys Lys Pro Phe Val Ser Ala Leu
            370                 375                 380

Leu Gly Ala Ala Val Gly Gly Ala Phe Tyr Gly Ile Thr Gly Val Ala
385                 390                 395                 400

Ala Tyr Ile Ile Gly Gly Asn Val Gly Leu Pro Gly Ile Thr Thr Phe
                405                 410                 415

Ile Gly Pro Thr Phe Ile Gln Ala Met Ile Gly Ile Val Ile Ala Phe
            420                 425                 430

Phe Ala Ala Thr Ala Phe Ala Phe Val Leu Gly Phe Glu Asp Ile Pro
435                 440                 445

Ser Asp Glu Ala Ala Glu Gln Gly Ala Ala Pro Ser Glu Ala Gly Ala
    450                 455                 460

Gly Glu Ile Ile Gln Ser Pro Leu Lys Gly Glu Val Lys Ala Leu Ser
465                 470                 475                 480
```

```
Glu Val Asp Asp Ala Thr Phe Ser Gly Glu Val Met Gly Lys Gly Val
                485                 490                 495

Ala Ile Glu Pro Glu Glu Gly Lys Val Val Ser Pro Ser Gly Thr
            500                 505                 510

Ile Thr Thr Val Phe Gln Thr Lys His Ala Leu Gly Ile Thr Ser Asp
            515                 520                 525

Asn Gly Ala Glu Ile Ile Ile His Ile Gly Ile Asp Thr Val Lys Leu
            530                 535                 540

Asn Gly Glu His Phe Thr Val His Val Asn Lys Gly Asp Ala Val Lys
545                 550                 555                 560

Pro Gly Asp Glu Leu Val Ser Phe Asp Met Asp Ala Ile Lys Asp Ala
                565                 570                 575

Gly Tyr Gln Leu Ile Thr Pro Val Ile Ile Thr Asn Thr Asp Arg Tyr
            580                 585                 590

Gln Ser Ile Lys Pro Leu Lys Ser Asp Glu Ser Val
            595                 600
```

```
<210> SEQ ID NO 85
<211> LENGTH: 570
<212> TYPE: DNA
<213> ORGANISM: Bacillus licheniformis

<400> SEQUENCE: 85
atgagcacag aggatatgac aaaggatacg tatgaagtaa acagttcgac aatggctgtc      60
ctgcctctgg gagaggggga gaaacccgcc tcaaaaatac ttgagaccga caggactttc     120
cgcgtcaata tgaagccgtt tcaaattatc gaaagaagct gccgctattt cggatcgagc     180
tatgcgggaa gaaaagcggg cacatatgaa gtcattaaag tttcccataa accgccgatc     240
atggtggatc actcaaacaa catttttctt ttccccacat tttcctcaac tcgtcctcag     300
tgcgggtggc tttcccatgc gcatgttcac gagttttgcg cggcaaagta tgacaacacg     360
tttgtcacgt ttgtcaacgg ggaaacgctg gagctgcccg tatccatctc atctttcgaa     420
aaccaggttt accgaacggc atggctgaga acaaaattta tcgacaggat tgaaggaaac     480
cccatgcaga agaaacagga atttatgctc tatccgaaag aagaccggaa tcagctgata     540
tacgaattca tcctcaggga gctgaaaaag                                      570
```

```
<210> SEQ ID NO 86
<211> LENGTH: 189
<212> TYPE: PRT
<213> ORGANISM: Bacillus licheniformis

<400> SEQUENCE: 86

Met Ser Thr Glu Asp Met Thr Lys Asp Thr Tyr Glu Val Asn Ser Ser
1               5                   10                  15

Thr Met Ala Val Leu Pro Leu Gly Glu Gly Glu Lys Pro Ala Ser Lys
            20                  25                  30

Ile Leu Glu Thr Asp Arg Thr Phe Arg Val Asn Met Lys Pro Phe Gln
        35                  40                  45

Ile Ile Glu Arg Ser Cys Arg Tyr Phe Gly Ser Ser Tyr Ala Gly Arg
    50                  55                  60

Lys Ala Gly Thr Tyr Glu Val Ile Lys Val Ser His Lys Pro Pro Ile
65                  70                  75                  80

Met Val Asp His Ser Asn Asn Ile Phe Leu Phe Pro Thr Phe Ser Ser
                85                  90                  95

Thr Arg Pro Gln Cys Gly Trp Leu Ser His Ala His Val His Glu Phe
```

```
                100                 105                 110
Cys Ala Ala Lys Tyr Asp Asn Thr Phe Val Thr Phe Val Asn Gly Glu
            115                 120                 125

Thr Leu Glu Leu Pro Val Ser Ile Ser Ser Phe Glu Asn Gln Val Tyr
130                 135                 140

Arg Thr Ala Trp Leu Arg Thr Lys Phe Ile Asp Arg Ile Glu Gly Asn
145                 150                 155                 160

Pro Met Gln Lys Lys Gln Glu Phe Met Leu Tyr Pro Lys Glu Asp Arg
                165                 170                 175

Asn Gln Leu Ile Tyr Glu Phe Ile Leu Arg Glu Leu Lys
            180                 185

<210> SEQ ID NO 87
<211> LENGTH: 36
<212> TYPE: DNA
<213> ORGANISM: Bacillus licheniformis

<400> SEQUENCE: 87
gccgcagcca tttccagagc cgcagccatt tccaga                                  36

<210> SEQ ID NO 88
<211> LENGTH: 1368
<212> TYPE: PRT
<213> ORGANISM: Streptococcus pyogenes

<400> SEQUENCE: 88

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240
```

-continued

```
Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655
```

-continued

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val

-continued

```
             1070                1075                1080

Arg Lys Val Leu Ser Met Pro Gln Val Asn Ile Val Lys Lys Thr
     1085                1090                1095

Glu Val Gln Thr Gly Gly Phe Ser Lys Glu Ser Ile Leu Pro Lys
     1100                1105                1110

Arg Asn Ser Asp Lys Leu Ile Ala Arg Lys Lys Asp Trp Asp Pro
     1115                1120                1125

Lys Lys Tyr Gly Gly Phe Asp Ser Pro Thr Val Ala Tyr Ser Val
     1130                1135                1140

Leu Val Val Ala Lys Val Glu Lys Gly Lys Ser Lys Lys Leu Lys
     1145                1150                1155

Ser Val Lys Glu Leu Leu Gly Ile Thr Ile Met Glu Arg Ser Ser
     1160                1165                1170

Phe Glu Lys Asn Pro Ile Asp Phe Leu Glu Ala Lys Gly Tyr Lys
     1175                1180                1185

Glu Val Lys Lys Asp Leu Ile Ile Lys Leu Pro Lys Tyr Ser Leu
     1190                1195                1200

Phe Glu Leu Glu Asn Gly Arg Lys Arg Met Leu Ala Ser Ala Gly
     1205                1210                1215

Glu Leu Gln Lys Gly Asn Glu Leu Ala Leu Pro Ser Lys Tyr Val
     1220                1225                1230

Asn Phe Leu Tyr Leu Ala Ser His Tyr Glu Lys Leu Lys Gly Ser
     1235                1240                1245

Pro Glu Asp Asn Glu Gln Lys Gln Leu Phe Val Glu Gln His Lys
     1250                1255                1260

His Tyr Leu Asp Glu Ile Ile Glu Gln Ile Ser Glu Phe Ser Lys
     1265                1270                1275

Arg Val Ile Leu Ala Asp Ala Asn Leu Asp Lys Val Leu Ser Ala
     1280                1285                1290

Tyr Asn Lys His Arg Asp Lys Pro Ile Arg Glu Gln Ala Glu Asn
     1295                1300                1305

Ile Ile His Leu Phe Thr Leu Thr Asn Leu Gly Ala Pro Ala Ala
     1310                1315                1320

Phe Lys Tyr Phe Asp Thr Thr Ile Asp Arg Lys Arg Tyr Thr Ser
     1325                1330                1335

Thr Lys Glu Val Leu Asp Ala Thr Leu Ile His Gln Ser Ile Thr
     1340                1345                1350

Gly Leu Tyr Glu Thr Arg Ile Asp Leu Ser Gln Leu Gly Gly Asp
     1355                1360                1365

<210> SEQ ID NO 89
<211> LENGTH: 1307
<212> TYPE: PRT
<213> ORGANISM: Acidomiococcus sp.

<400> SEQUENCE: 89

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60
```

Cys Leu Gln Leu Val Gln Leu Asp Trp Glu Asn Leu Ser Ala Ala Ile
 65                  70                  75                  80

Asp Ser Tyr Arg Lys Glu Lys Thr Glu Thr Arg Asn Ala Leu Ile
                 85                  90                  95

Glu Glu Gln Ala Thr Tyr Arg Asn Ala Ile His Asp Tyr Phe Ile Gly
                100                 105                 110

Arg Thr Asp Asn Leu Thr Asp Ala Ile Asn Lys Arg His Ala Glu Ile
                115                 120                 125

Tyr Lys Gly Leu Phe Lys Ala Glu Leu Phe Asn Gly Lys Val Leu Lys
                130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Lys Glu Asn Cys His Ile Phe
                195                 200                 205

Thr Arg Leu Ile Thr Ala Val Pro Ser Leu Arg Glu His Phe Glu Asn
210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
                275                 280                 285

Asp Glu Thr Ala His Ile Ile Ala Ser Leu Pro His Arg Phe Ile Pro
                290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
                370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
                450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe

-continued

```
                485                 490                 495
Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
                530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
                595                 600                 605

Ser Thr Gln Leu Lys Ala Val Thr Ala His Phe Gln Thr His Thr Thr
                610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
                675                 680                 685

Lys Thr Thr Ser Ile Asp Leu Ser Ser Leu Arg Pro Ser Ser Gln Tyr
                690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
                740                 745                 750

Gly His His Gly Lys Pro Asn Leu His Thr Leu Tyr Trp Thr Gly Leu
                755                 760                 765

Phe Ser Pro Glu Asn Leu Ala Lys Thr Ser Ile Lys Leu Asn Gly Gln
                770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
                820                 825                 830

Arg Leu Ser His Asp Leu Ser Asp Glu Ala Arg Ala Leu Leu Pro Asn
                835                 840                 845

Val Ile Thr Lys Glu Val Ser His Glu Ile Ile Lys Asp Arg Arg Phe
                850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
                900                 905                 910
```

```
Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
        995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
    1295                1300                1305
```

<210> SEQ ID NO 90
<211> LENGTH: 887
<212> TYPE: PRT
<213> ORGANISM: N. gregoryi

<400> SEQUENCE: 90

```
Met Thr Val Ile Asp Leu Asp Ser Thr Thr Ala Asp Glu Leu Thr
1               5                   10                  15

Ser Gly His Thr Tyr Asp Ile Ser Val Thr Leu Thr Gly Val Tyr Asp
            20                  25                  30

Asn Thr Asp Glu Gln His Pro Arg Met Ser Leu Ala Phe Glu Gln Asp
        35                  40                  45

Asn Gly Glu Arg Arg Tyr Ile Thr Leu Trp Lys Asn Thr Thr Pro Lys
    50                  55                  60

Asp Val Phe Thr Tyr Asp Tyr Ala Thr Gly Ser Thr Tyr Ile Phe Thr
65                  70                  75                  80

Asn Ile Asp Tyr Glu Val Lys Asp Gly Tyr Glu Asn Leu Thr Ala Thr
                85                  90                  95

Tyr Gln Thr Thr Val Glu Asn Ala Thr Ala Gln Glu Val Gly Thr Thr
            100                 105                 110

Asp Glu Asp Glu Thr Phe Ala Gly Gly Glu Pro Leu Asp His His Leu
        115                 120                 125

Asp Asp Ala Leu Asn Glu Thr Pro Asp Ala Glu Thr Glu Ser Asp
    130                 135                 140

Ser Gly His Val Met Thr Ser Phe Ala Ser Arg Asp Gln Leu Pro Glu
145                 150                 155                 160

Trp Thr Leu His Thr Tyr Thr Leu Thr Ala Thr Asp Gly Ala Lys Thr
                165                 170                 175

Asp Thr Glu Tyr Ala Arg Arg Thr Leu Ala Tyr Thr Val Arg Gln Glu
            180                 185                 190

Leu Tyr Thr Asp His Asp Ala Ala Pro Val Ala Thr Asp Gly Leu Met
        195                 200                 205

Leu Leu Thr Pro Glu Pro Leu Gly Glu Thr Pro Leu Asp Leu Asp Cys
    210                 215                 220

Gly Val Arg Val Glu Ala Asp Glu Thr Arg Thr Leu Asp Tyr Thr Thr
225                 230                 235                 240

Ala Lys Asp Arg Leu Leu Ala Arg Glu Leu Val Glu Glu Gly Leu Lys
                245                 250                 255

Arg Ser Leu Trp Asp Asp Tyr Leu Val Arg Gly Ile Asp Glu Val Leu
            260                 265                 270

Ser Lys Glu Pro Val Leu Thr Cys Asp Glu Phe Asp Leu His Glu Arg
        275                 280                 285

Tyr Asp Leu Ser Val Glu Val Gly His Ser Gly Arg Ala Tyr Leu His
    290                 295                 300

Ile Asn Phe Arg His Arg Phe Val Pro Lys Leu Thr Leu Ala Asp Ile
305                 310                 315                 320

Asp Asp Asp Asn Ile Tyr Pro Gly Leu Arg Val Lys Thr Thr Tyr Arg
                325                 330                 335

Pro Arg Arg Gly His Ile Val Trp Gly Leu Arg Asp Glu Cys Ala Thr
            340                 345                 350

Asp Ser Leu Asn Thr Leu Gly Asn Gln Ser Val Val Ala Tyr His Arg
        355                 360                 365

Asn Asn Gln Thr Pro Ile Asn Thr Asp Leu Leu Asp Ala Ile Glu Ala
    370                 375                 380
```

-continued

```
Ala Asp Arg Arg Val Val Glu Thr Arg Arg Gln Gly His Gly Asp Asp
385                 390                 395                 400

Ala Val Ser Phe Pro Gln Glu Leu Leu Ala Val Glu Pro Asn Thr His
            405                 410                 415

Gln Ile Lys Gln Phe Ala Ser Asp Gly Phe His Gln Ala Arg Ser
        420                 425                 430

Lys Thr Arg Leu Ser Ala Ser Arg Cys Ser Glu Lys Ala Gln Ala Phe
            435                 440                 445

Ala Glu Arg Leu Asp Pro Val Arg Leu Asn Gly Ser Thr Val Glu Phe
        450                 455                 460

Ser Ser Glu Phe Phe Thr Gly Asn Asn Glu Gln Gln Leu Arg Leu Leu
465                 470                 475                 480

Tyr Glu Asn Gly Glu Ser Val Leu Thr Phe Arg Asp Gly Ala Arg Gly
                485                 490                 495

Ala His Pro Asp Glu Thr Phe Ser Lys Gly Ile Val Asn Pro Pro Glu
            500                 505                 510

Ser Phe Glu Val Ala Val Val Leu Pro Glu Gln Gln Ala Asp Thr Cys
        515                 520                 525

Lys Ala Gln Trp Asp Thr Met Ala Asp Leu Leu Asn Gln Ala Gly Ala
530                 535                 540

Pro Pro Thr Arg Ser Glu Thr Val Gln Tyr Asp Ala Phe Ser Ser Pro
545                 550                 555                 560

Glu Ser Ile Ser Leu Asn Val Ala Gly Ala Ile Asp Pro Ser Glu Val
                565                 570                 575

Asp Ala Ala Phe Val Val Leu Pro Pro Asp Gln Glu Gly Phe Ala Asp
            580                 585                 590

Leu Ala Ser Pro Thr Glu Thr Tyr Asp Glu Leu Lys Lys Ala Leu Ala
        595                 600                 605

Asn Met Gly Ile Tyr Ser Gln Met Ala Tyr Phe Asp Arg Phe Arg Asp
610                 615                 620

Ala Lys Ile Phe Tyr Thr Arg Asn Val Ala Leu Gly Leu Leu Ala Ala
625                 630                 635                 640

Ala Gly Gly Val Ala Phe Thr Thr Glu His Ala Met Pro Gly Asp Ala
                645                 650                 655

Asp Met Phe Ile Gly Ile Asp Val Ser Arg Ser Tyr Pro Glu Asp Gly
            660                 665                 670

Ala Ser Gly Gln Ile Asn Ile Ala Ala Thr Ala Thr Ala Val Tyr Lys
        675                 680                 685

Asp Gly Thr Ile Leu Gly His Ser Ser Thr Arg Pro Gln Leu Gly Glu
690                 695                 700

Lys Leu Gln Ser Thr Asp Val Arg Asp Ile Met Lys Asn Ala Ile Leu
705                 710                 715                 720

Gly Tyr Gln Gln Val Thr Gly Glu Ser Pro Thr His Ile Val Ile His
                725                 730                 735

Arg Asp Gly Phe Met Asn Glu Asp Leu Asp Pro Ala Thr Glu Phe Leu
            740                 745                 750

Asn Glu Gln Gly Val Glu Tyr Asp Ile Val Glu Ile Arg Lys Gln Pro
        755                 760                 765

Gln Thr Arg Leu Leu Ala Val Ser Asp Val Gln Tyr Asp Thr Pro Val
        770                 775                 780

Lys Ser Ile Ala Ala Ile Asn Gln Asn Glu Pro Arg Ala Thr Val Ala
785                 790                 795                 800
```

```
Thr Phe Gly Ala Pro Glu Tyr Leu Ala Thr Arg Asp Gly Gly Leu
                805                 810                 815

Pro Arg Pro Ile Gln Ile Glu Arg Val Ala Gly Glu Thr Asp Ile Glu
            820                 825                 830

Thr Leu Thr Arg Gln Val Tyr Leu Leu Ser Gln Ser His Ile Gln Val
        835                 840                 845

His Asn Ser Thr Ala Arg Leu Pro Ile Thr Thr Ala Tyr Ala Asp Gln
    850                 855                 860

Ala Ser Thr His Ala Thr Lys Gly Tyr Leu Val Gln Thr Gly Ala Phe
865                 870                 875                 880

Glu Ser Asn Val Gly Phe Leu
                885

<210> SEQ ID NO 91
<211> LENGTH: 12203
<212> TYPE: DNA
<213> ORGANISM: Streptococcus pyogenes

<400> SEQUENCE: 91
```

| | | | | | |
|---|---|---|---|---|---|
| atggataaga | aatactcaat | aggcttagat | atcggcacaa | atagcgtcgg | atgggcggtg | 60 |
| atcactgatg | aatataaggt | tccgtctaaa | aagttcaagg | ttctgggaaa | tacagaccgc | 120 |
| cacagtatca | aaaaaatct | tatagggggct | cttttatttg | acagtggaga | gacagcggaa | 180 |
| gcgactcgtc | tcaaacggac | agctcgtaga | aggtatacac | gtcggaagaa | tcgtatttgt | 240 |
| tatctacagg | agattttttc | aaatgagatg | gcgaaagtag | atgatagttt | ctttcatcga | 300 |
| cttgaagagt | cttttttggt | ggaagaagac | aagaagcatg | aacgtcatcc | tatttttgga | 360 |
| aatatagtag | atgaagttgc | ttatcatgag | aaatatccaa | ctatctatca | tctgcgaaaa | 420 |
| aaattggtag | attctactga | taaagcggat | ttgcgcttaa | tctatttggc | cttagcgcat | 480 |
| atgattaagt | tcgtggtca | ttttttgatt | gagggagatt | taaatcctga | taatagtgat | 540 |
| gtggacaaac | tatttatcca | gttggtacaa | acctacaatc | aattatttga | agaaaaccct | 600 |
| attaacgcaa | gtggagtaga | tgctaaagcg | attctttctg | cacgattgag | taaatcaaga | 660 |
| cgattagaaa | atctcattgc | tcagctcccc | ggtgagaaga | aaaatggctt | atttgggaat | 720 |
| ctcattgctt | tgtcattggg | tttgaccct | aattttaaat | caaattttga | tttggcagaa | 780 |
| gatgctaaat | tacagctttc | aaaagatact | tacgatgatg | atttagataa | tttattggcg | 840 |
| caaattggag | atcaatatgc | tgatttgttt | ttggcagcta | agaatttatc | agatgctatt | 900 |
| ttactttcag | atatcctaag | agtaaatact | gaaataacta | aggctcccct | atcagcttca | 960 |
| atgattaaac | gctacgatga | acatcatcaa | gacttgactc | ttttaaaagc | tttagttcga | 1020 |
| caacaacttc | cagaaaagta | taaagaaatc | tttttttgatc | aatcaaaaaa | cggatatgca | 1080 |
| ggttatattg | atgggggagc | tagccaagaa | gaattttata | aatttatcaa | accaatttta | 1140 |
| gaaaaaatgg | atggtactga | ggaattattg | gtgaaactaa | atcgtgaaga | tttgctgcgc | 1200 |
| aagcaacgga | cctttgacaa | cggctctatt | ccccatcaaa | ttcacttggg | tgagctgcat | 1260 |
| gctatttga | aagacaagaa | agactttat | ccatttttaa | aagacaatcg | tgagaagatt | 1320 |
| gaaaaaatct | tgacttttcg | aattccttat | tatgttggtc | cattggcgcg | tggcaatagt | 1380 |
| cgttttgcat | ggatgactcg | gaagtctgaa | gaaacaatta | ccccatggaa | ttttgaagaa | 1440 |
| gttgtcgata | aggtgcttc | agctcaatca | tttattgaac | gcatgacaaa | ctttgataaa | 1500 |
| aatcttccaa | atgaaaaagt | actaccaaaa | catagtttgc | tttatgagta | ttttacggtt | 1560 |
| tataacgaat | tgacaaaggt | caaatatgtt | actgaaggaa | tgcgaaaacc | agcatttctt | 1620 |

```
tcaggtgaac agaagaaagc cattgttgat ttactcttca aaacaaatcg aaaagtaacc    1680
gttaagcaat taaagaaga ttatttcaaa aaaatagaat gttttgatag tgttgaaatt    1740
tcaggagttg aagatagatt taatgcttca ttaggtacct accatgattt gctaaaaatt    1800
attaaagata aagattttt ggataatgaa gaaaatgaag atatcttaga ggatattgtt    1860
ttaacattga ccttatttga agatagggag atgattgagg aaagacttaa acatatgct    1920
cacctctttg atgataaggt gatgaaacag cttaaacgtc gccgttatac tggttgggga    1980
cgtttgtctc gaaaattgat taatggtatt agggataagc aatctggcaa aacaatatta    2040
gatttttga aatcagatgg ttttgccaat cgcaatttta tgcagctgat ccatgatgat    2100
agtttgacat ttaaagaaga cattcaaaaa gcacaagtgt ctggacaagg cgatagttta    2160
catgaacata ttgcaaattt agctggtagc cctgctatta aaaaggtat tttacagact    2220
gtaaaagttg ttgatgaatt ggtcaaagta atggggcggc ataagccaga aaatatcgtt    2280
attgaaatgg cacgtgaaaa tcagacaact caaaagggcc agaaaaattc gcgagagcgt    2340
atgaaacgaa tcgaagaagg tatcaaagaa ttaggaagtc agattcttaa agagcatcct    2400
gttgaaaata ctcaattgca aaatgaaaag ctctatctct attatctcca aaatggaaga    2460
gacatgtatg tggaccaaga attagatatt aatcgtttaa gtgattatga tgtcgatcac    2520
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta agtgattac cttaaaatct    2880
aaattagttt ctgacttccg aaaagatttc caattctata aagtacgtga gattaacaat    2940
taccatcatg cccatgatgc gtatctaaat gccgtcgttg gaactgcttt gattaagaaa    3000
tatccaaaac ttgaatcgga gtttgtctat ggtgattata agtttatga tgttcgtaaa    3060
atgattgcta agtctgagca agaaataggc aaagcaaccg caaaatattt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttat    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatggaa agaagttcct ttgaaaaaaa tccgattgac    3540
tttttagaag ctaaaggata taaggaagtt aaaaaagact taatcattaa actacctaaa    3600
tatagtcttt ttgagttaga aaacggtcgt aaacggatgc tggctagtgc cggagaatta    3660
caaaaaggaa atgagctggc tctgccaagc aaatatgtga attttttata tttagctagt    3720
cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
```

```
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgactgaatg gataagaaat actcaatagg cttagatatc    4140
ggcacaaata gcgtcggatg ggcggtgatc actgatgaat ataaggttcc gtctaaaaag    4200
ttcaaggttc tgggaaatac agaccgccac agtatcaaaa aaaatcttat aggggctctt    4260
ttatttgaca gtgagagac agcggaagcg actcgtctca aacggacagc tcgtagaagg    4320
tatacacgtc ggaagaatcg tatttgttat ctacaggaga ttttttcaaa tgagatggcg    4380
aaagtagatg atagtttctt tcatcgactt gaagagtctt ttttggtgga agaagacaag    4440
aagcatgaac gtcatcctat ttttggaaat atagtagatg aagttgctta tcatgagaaa    4500
tatccaacta tctatcatct gcgaaaaaaa ttggtagatt ctactgataa agcggatttg    4560
cgcttaatct atttggcctt agcgcatatg attaagtttc gtggtcattt tttgattgag    4620
ggagatttaa atcctgataa tagtgatgtg gacaaactat ttatccagtt ggtacaaacc    4680
tacaatcaat tatttgaaga aaaccctatt aacgcaagtg gagtagatgc taaagcgatt    4740
ctttctgcac gattgagtaa atcaagacga ttagaaaatc tcattgctca gctccccggt    4800
gagaagaaaa atggcttatt tgggaatctc attgctttgt cattgggttt gacccctaat    4860
tttaaatcaa attttgattt ggcagaagat gctaaattac agctttcaaa agatacttac    4920
gatgatgatt tagataattt attggcgcaa attggagatc aatatgctga tttgttttg    4980 gcagctaaga atttatcaga tgctatttta ctttcagata tcctaagagt aaatactgaa    5040
ataactaagg ctcccctatc agcttcaatg attaaacgct acgatgaaca tcatcaagac    5100
ttgactcttt taaaagcttt agttcgacaa caacttccag aaaagtataa agaaatcttt    5160
tttgatcaat caaaaaacgg atatgcaggt tatattgatg ggggagctag ccaagaagaa    5220
ttttataaat ttatcaaacc aattttagaa aaaatggatg gtactgagga attattggtg    5280
aaactaaatc gtgaagattt gctgcgcaag caacggacct ttgacaacgg ctctattccc    5340
catcaaattc acttgggtga gctgcatgct attttgagaa gacaagaaga cttttatcca    5400
tttttaaaag acaatcgtga gaagattgaa aaaatcttga cttttcgaat tccttattat    5460
gttggtccat tggcgcgtgg caatagtcgt tttgcatgga tgactcggaa gtctgaagaa    5520
acaattaccc catggaattt tgaagaagtt gtcgataaag gtgcttcagc tcaatcattt    5580
attgaacgca tgacaaactt tgataaaaat cttccaaatg aaaaagtact accaaaacat    5640
agtttgcttt atgagtattt tacggtttat aacgaattga caaaggtcaa atatgttact    5700
gaaggaatgc gaaaaccagc atttctttca ggtgaacaga agaaagccat tgttgattta    5760
ctcttcaaaa caaatcgaaa agtaaccgtt aagcaattaa aagaagatta tttcaaaaaa    5820
atagaatgtt ttgatagtgt tgaaatttca ggagttgaag atagatttaa tgcttcatta    5880
ggtacctacc atgatttgct aaaaattatt aaagataaag attttttgga taatgaagaa    5940
aatgaagata tcttagagga tattgtttta acattgacct tatttgaaga tagggagatg    6000
attgaggaaa gacttaaaac atatgctcac ctctttgatg ataaggtgat gaaacagctt    6060
aaacgtcgcc gttatactgg ttggggacgt ttgtctcgaa aattgattaa tggtattagg    6120
gataagcaat ctggcaaaac aatattagat ttttgaaat cagatggttt tgccaatcgc    6180
aattttatgc agctgatcca tgatgatagt ttgacattta agaagacat tcaaaaagca    6240 caagtgtctg gacaaggcga tagtttacat gaacatatt caaatttagc tggtagccct    6300
gctattaaaa aaggtatttt acagactgta aaagttgttg atgaattggt caaagtaatg    6360
```

```
gggcggcata agccagaaaa tatcgttatt gaaatggcac gtgaaaatca gacaactcaa   6420
aagggccaga aaaattcgcg agagcgtatg aaacgaatcg aagaaggtat caaagaatta   6480
ggaagtcaga ttcttaaaga gcatcctgtt gaaaatactc aattgcaaaa tgaaaagctc   6540
tatctctatt atctccaaaa tggaagagac atgtatgtgg accaagaatt agatattaat   6600
cgtttaagtg attatgatgt cgatcacatt gttccacaaa gtttccttaa agacgattca   6660
atagacaata aggtcttaac gcgttctgat aaaaatcgtg gtaaatcgga taacgttcca   6720
agtgaagaag tagtcaaaaa gatgaaaaac tattggagac aacttctaaa cgccaagtta   6780
atcactcaac gtaagtttga taatttaacg aaagctgaac gtggaggttt gagtgaactt   6840
gataaagctg gttttatcaa acgccaattg gttgaaactc gccaaatcac taagcatgtg   6900
gcacaaattt tggatagtcg catgaatact aaatacgatg aaaatgataa acttattcga   6960
gaggttaaag tgattacctt aaaatctaaa ttagtttctg acttccgaaa agatttccaa   7020
ttctataaag tacgtgagat taacaattac catcatgccc atgatgcgta tctaaatgcc   7080
gtcgttggaa ctgctttgat taagaaatat ccaaaacttg aatcggagtt tgtctatggt   7140
gattataaag tttatgatgt tcgtaaaatg attgctaagt ctgagcaaga aataggcaaa   7200
gcaaccgcaa atatttctt ttactctaat atcatgaact tcttcaaaac agaaattaca   7260
cttgcaaatg gagagattcg caaacgccct ctaatcgaaa ctaatgggga aactggagaa   7320
attgtctggg ataaagggcg agattttgcc acagtgcgca agtattgtc catgccccaa   7380 gtcaatattg tcaagaaaac agaagtacag acaggcggat tctccaagga gtcaattta   7440 ccaaaaagaa attcggacaa gcttattgct cgtaaaaaag actgggatcc aaaaaaatat   7500
ggtggttttg atagtccaac ggtagcttat tcagtcctag tggttgctaa ggtggaaaaa   7560
gggaaatcga agaagttaaa atccgttaaa gagttactag ggatcacaat tatggaagaa   7620
agttcctttg aaaaaaatcc gattgacttt ttagaagcta aaggatataa ggaagttaaa   7680
aaagacttaa tcattaaact acctaaatat agtcttttg agttagaaaa cggtcgtaaa   7740
cggatgctgg ctagtgccgg agaattacaa aaaggaaatg agctggctct gccaagcaaa   7800
tatgtgaatt ttttatattt agctagtcat tatgaaaagt tgaagggtag tccagaagat   7860
aacgaacaaa aacaattgtt tgtggagcag cataagcatt atttagatga gattattgag   7920
caaatcagtg aattttctaa gcgtgttatt ttagcagatg ccaatttaga taagttctt   7980 agtgcatata acaaacatag agacaaacca atacgtgaac aagcagaaaa tattattcat   8040
ttatttacgt tgacgaatct ggagctcccc gctgctttta aatattttga tacaacaatt   8100
gatcgtaaac gatatacgtc tacaaaagaa gttttagatg ccactcttat ccatcaatcc   8160
atcactggtc tttatgaaac acgcattgat ttgagtcagc taggaggtga ctgaatggat   8220
aagaaatact caataggctt agatatcggc acaaatagcg tcggatgggc ggtgatcact   8280
gatgaatata aggttccgtc taaaaagttc aaggttctgg aaatacaga ccgccacagt   8340 atcaaaaaaa atcttatagg ggctctttta tttgacagtg gagagacagc ggaagcgact   8400
cgtctcaaac ggacagctcg tagaaggtat acacgtcgga agaatcgtat ttgttatcta   8460
caggagattt tttcaaatga gatggcgaaa gtagatgata gtttctttca tcgacttgaa   8520
gagtcttttt tggtggaaga agacaagaag catgaacgtc atcctatttt tggaaatata   8580
gtagatgaag ttgcttatca tgagaaatat ccaactatct atcatctgcg aaaaaaattg   8640
gtagattcta ctgataaagc ggatttgcgc ttaatctatt tggccttagc gcatatgatt   8700
```

```
aagtttcgtg gtcattttt  gattgaggga gatttaaatc ctgataatag tgatgtggac   8760
aaactattta tccagttggt acaaacctac aatcaattat ttgaagaaaa ccctattaac   8820
gcaagtggag tagatgctaa agcgattctt tctgcacgat tgagtaaatc aagacgatta   8880
gaaaatctca ttgctcagct ccccggtgag aagaaaaatg gcttatttgg gaatctcatt   8940
gctttgtcat tgggtttgac ccctaatttt aaatcaaatt ttgatttggc agaagatgct   9000
aaattacagc tttcaaaaga tacttacgat gatgatttag ataatttatt ggcgcaaatt   9060
ggagatcaat atgctgattt gttttttggca gctaagaatt tatcagatgc tattttactt   9120
tcagatatcc taagagtaaa tactgaaata actaaggctc ccctatcagc ttcaatgatt   9180
aaacgctacg atgaacatca tcaagacttg actcttttaa aagctttagt tcgacaacaa   9240
cttccagaaa agtataaaga aatctttttt gatcaatcaa aaaacggata tgcaggttat   9300
attgatgggg gagctagcca agaagaattt tataaattta tcaaaccaat tttagaaaaa   9360
atggatggta ctgaggaatt attggtgaaa ctaaatcgtg aagatttgct gcgcaagcaa   9420
cggacctttg acaacggctc tattccccat caaattcact tgggtgagct gcatgctatt   9480
ttgagaagac aagaagactt ttatccattt ttaaaagaca atcgtgagaa gattgaaaaa   9540
atcttgactt tcgaattcc  ttattatgtt ggtccattgg cgcgtggcaa tagtcgtttt   9600
gcatggatga ctcggaagtc tgaagaaaca attaccccat ggaattttga agaagttgtc   9660
gataaaggtg cttcagctca atcatttatt gaacgcatga caaactttga taaaaatctt   9720
ccaaatgaaa aagtactacc aaaacatagt ttgctttatg agtattttac ggtttataac   9780
gaattgacaa aggtcaaata tgttactgaa ggaatgcgaa accagcatt  tctttcaggt   9840
gaacagaaga aagccattgt tgatttactc ttcaaaacaa atcgaaaagt aaccgttaag   9900
caattaaaag aagattattt caaaaaaata gaatgttttg atagtgttga atttcagga   9960
gttgaagata gatttaatgc ttcattaggt acctaccatg atttgctaaa aattattaaa  10020
gataaagatt ttttggataa tgaagaaaat gaagatatct tagaggatat tgttttaaca  10080
ttgaccttat ttgaagatag ggagatgatt gaggaaagac ttaaaacata tgctcacctc  10140
tttgatgata aggtgatgaa acagcttaaa cgtcgccgtt atactggttg gggacgtttg  10200
tctcgaaaat tgattaatgg tattagggat aagcaatctg gcaaaacaat attagatttt  10260
ttgaaatcag atggttttgc caatcgcaat tttatgcagc tgatccatga tgatagtttg  10320
acatttaaag aagacattca aaaagcacaa gtgtctggac aaggcgatag tttacatgaa  10380
catattgcaa atttagctgg tagccctgct attaaaaaag gtattttaca gactgtaaaa  10440
gttgttgatg aattggtcaa agtaatgggg cggcataagc cagaaaatat cgttattgaa  10500
atggcacgtg aaaatcagac aactcaaaag ggccagaaaa attcgcgaga gcgtatgaaa  10560
cgaatcgaag aaggtatcaa agaattagga agtcagattc ttaaagagca tcctgttgaa  10620
aatactcaat tgcaaaatga aaagctctat ctctattatc tccaaaatgg aagagacatg  10680
tatgtggacc aagaattaga tattaatcgt ttaagtgatt atgatgtcga tcacattgtt  10740
ccacaaagtt tccttaaaga cgattcaata gacaataagg tcttaacgcg ttctgataaa  10800
aatcgtggta atcggataaa cgttccaagt gaagaagtag tcaaaagat gaaaaactat  10860
tggagacaac ttctaaacgc caagttaatc actcaacgta agtttgataa tttaacgaaa  10920
gctgaacgtg gaggtttgag tgaacttgat aaagctggtt ttatcaaacg ccaattggtt  10980
gaaactcgcc aaatcactaa gcatgtggca caaattttgg atagtcgcat gaatactaaa  11040
tacgatgaaa atgataaact tattcgagag gttaaagtga ttaccttaaa atctaaatta  11100
```

```
gtttctgact tccgaaaaga tttccaattc tataaagtac gtgagattaa caattaccat   11160
catgcccatg atgcgtatct aaatgccgtc gttggaactg ctttgattaa gaaatatcca   11220
aaacttgaat cggagtttgt ctatggtgat tataaagttt atgatgttcg taaaatgatt   11280
gctaagtctg agcaagaaat aggcaaagca accgcaaaat atttctttta ctctaatatc   11340
atgaacttct tcaaaacaga attacactt gcaaatggag agattcgcaa acgccctcta   11400
atcgaaacta atggggaaac tggagaaatt gtctgggata aagggcgaga ttttgccaca   11460
gtgcgcaaag tattgtccat gccccaagtc aatattgtca agaaaacaga agtacagaca   11520
ggcggattct ccaaggagtc aattttacca aaaagaaatt cggacaagct tattgctcgt   11580
aaaaaagact gggatccaaa aaaatatggt ggttttgata gtccaacggt agcttattca   11640
gtcctagtgg ttgctaaggt ggaaaaaggg aaatcgaaga agttaaaatc cgttaaagag   11700
ttactaggga tcacaattat ggaagaagt tcctttgaaa aaaatccgat tgactttta   11760 gaagctaaag gatataagga agttaaaaaa gacttaatca ttaaactacc taaatatagt   11820 cttttttgagt tagaaaacgg tcgtaaacgg atgctggcta gtgccggaga attacaaaaa   11880
ggaaatgagc tggctctgcc aagcaaatat gtgaatttt tatatttagc tagtcattat   11940
gaaaagttga agggtagtcc agaagataac gaacaaaaac aattgtttgt ggagcagcat   12000
aagcattatt tagatgagat tattgagcaa atcagtgaat tttctaagcg tgttatttta   12060
gcagatgcca atttagataa agttcttagt gcatataaca aacatagaga caaaccaata   12120
cgtgaacaag cagaaaatat tattcattta tttacgttga cgaatcttgg agctcccgct   12180
gcttttaaat attttgatac aac                                          12203
```

<210> SEQ ID NO 92
<211> LENGTH: 4107
<212> TYPE: DNA
<213> ORGANISM: Artificial Sequence
<220> FEATURE:
<223> OTHER INFORMATION: codon optimized S. pyogenes Cas9

<400> SEQUENCE: 92

```
atggataaaa aatacagcat tggtctggat atcggaacca acagcgttgg gtgggcagta     60
ataacagatg aatacaaagt gccgtcaaaa aaatttaagg ttctggggaa tacagatcgc    120
cacagcataa aaagaatct gattggggca ttgctgtttg attcgggtga cagctgag      180 gccacgcgtc tgaaacgtac agcaagaaga cgttacacac gtcgtaaaaa tcgtatttgc    240
tacttacagg aaatttttc taacgaaatg gccaaggtag atgatagttt cttccatcgt    300
ctcgaagaat cttttctggt tgaggaagat aaaaaacacg aacgtcaccc tatctttggc    360
aatatcgtgg atgaagtggc ctatcatgaa aaataccta cgatttatca tcttcgcaag    420
aagttggttg atagtacgga caaagcggat ctgcgtttaa tctatcttgc gttagcgcac    480
atgatcaaat tcgtggtca tttcttaatt gaaggtgatc tgaatcctga taactctgat    540
gtggacaaat tgtttataca attagtgcaa acctataatc agctgttcga ggaaaacccc    600
attaatgcct ctggagttga tgccaaagcg attttaagcg cgagactttc taagtcccgg    660
cgtctggaga atctgatcgc ccagttacca ggggaaaaga aaatggtct gtttggtaat    720 ctgattgccc tcagtctggg gcttaccccg aacttcaaat ccaattttga cctggctgag    780
gacgcaaagc tgcagctgag caaagatact tatgatgatg acctcgacaa tctgctcgcc    840
cagattggtg accaatatgc ggatctgttt ctggcagcga gaatctttc ggatgctatc    900
```

```
ttgctgtcgg atattctgcg tgttaatacc gaaatcacca aagcgcctct gtctgcaagt      960
atgatcaaga gatacgacga gcaccaccag gacctgactc ttcttaaggc actggtacgc     1020
caacagcttc cggagaaata caaagaaata ttcttcgacc agtccaagaa tggttacgcg     1080
ggctacatcg atggtggtgc atcacaggaa gagttctata aatttattaa accaatcctt     1140
gagaaaatgg atggcacgga agagttactt gttaaactta accgcgaaga cttgcttaga     1200
aagcaacgta cattcgacaa cggctccatc ccacaccaga ttcatttagg tgaacttcac     1260
gccatcttgc gcagacaaga agatttctat cccttcttaa aagacaatcg ggagaaaatc     1320
gagaagatcc tgacgttccg cattccctat tatgtcggtc ccctggcacg tggtaattct     1380
cggtttgcct ggatgacgcg caaaagtgag gaaaccatca ccccttggaa ctttgaagaa     1440
gtcgtggata aggtgctag cgcgcagtct tttatagaaa gaatgacgaa cttcgataaa     1500
aacttgccca acgaaaaagt cctgcccaag cactctcttt tatatgagta ctttactgtg     1560
tacaacgaac tgactaaagt gaaatacgtt acggaaggta tgcgcaaacc tgcctttctt     1620
agtggcgagc agaaaaaagc aattgtcgat cttctcttta aaacgaatcg caaggtaact     1680
gtaaaacagc tgaaggaaga ttatttcaaa aagatcgaat gctttgattc tgtcgagatc     1740
tcgggtgtcg aagatcgttt caacgcttcc ttagggacct atcatgattt gctgaagata     1800
ataaagacaa aagactttct cgacaatgaa gaaaatgaag atattctgga ggatattgtt     1860
ttgaccttga ccttattcga agatagagag atgatcgagg agcgcttaaa aacctatgcc     1920
cacctgtttg atgacaaagt catgaagcaa ttaaagcgcc gcagatatac ggggtggggc     1980
cgcttgagcc gcaagttgat taacggtatt agagacaagc agagcggaaa aactatcctg     2040
gatttcctca aatctgacgg atttgcgaac cgcaatttta tgcagcttat acatgatgat     2100
tcgcttacat tcaaagagga tattcagaag gctcaggtgt ctgggcaagg tgattcactc     2160
cacgaacata tagcaaattt ggccggctct cctgcgatta agaaggggat cctgcaaaca     2220
gttaaagttg tggatgaact tgtaaaagta atgggccgcc acaagccgga gaatatcgtg     2280
atagaaatgg cgcgcgagaa tcaaacgaca caaaaaggtc aaaagaactc aagagagaga     2340
atgaagcgca ttgaggaggg gataaaggaa cttggatctc aaattctgaa agaacatcca     2400
gttgaaaaca ctcagctgca aaatgaaaaa ttgtacctgt actacctgca gaatggaaga     2460
gacatgtacg tggatcagga attggatatc aatagactct cggactatga cgtagatcac     2520
attgtccctc agagcttcct caaggatgat tctatagata ataaagtact tacgagatcg     2580
gacaaaaatc gcggtaaatc ggataacgtc ccatcggagg aagtcgttaa aaagatgaaa     2640
aactattggc gtcaactgct gaacgccaag ctgatcacac agcgtaagtt tgataatctg     2700
actaaagccg aacgcggtgg tcttagtgaa ctcgataaag caggatttat aaaacggcag     2760
ttagtagaaa cgcgccaaat tacgaaacac gtggctcaga tcctcgattc tagaatgaat     2820
acaaagtacg atgaaaacga taactgatc cgtgaagtaa aagtcattac cttaaaatct     2880
aaacttgtgt ccgatttccg caaagatttt cagttttaca aggtccggga atcaataac      2940 tatcaccatg cacatgatgc atatttaaat gcggttgtag gcacggccct tattaagaaa     3000
taccctaaac tcgaaagtga gtttgtttat ggggattata agtgtatga cgttcgcaaa       3060 atgatcgcga aatcagaaca ggaaatcggt aaggctaccg ctaaatactt ttttattcc       3120 aacattatga ttttttttaa gaccgaaata actctcgcga atggtgaaat ccgtaaacgg     3180
cctcttatag aaaccaatgg tgaacgggga gaaatcgttt gggataaagg tcgtgacttt     3240
gccaccgttc gtaaagtcct ctcaatgccg caagttaaca ttgtcaagaa gacggaagtt     3300
```

```
caaacagggg gattctccaa agaatctatc ctgccgaagc gtaacagtga taaacttatt    3360
gccagaaaaa aagattggga tccaaaaaaa tacggaggct tgattcccc taccgtcgcg     3420 tatagtgtgc tggtggttgc taaagtcgag aagggaaaa gcaagaaatt gaaatcagtt     3480
aaagaactgc tgggtattac aattatggaa agatcgtcct ttgagaaaaa tccgatcgac    3540 ttttagagg ccaagggta taggaagtg aaaaagatc tcatcatcaa attaccgaag       3600
tatagtcttt ttgagctgga aaacggcaga aaaagaatgc tggcctccgc gggcgagtta    3660
cagaagggaa atgagctggc gctgccttcc aaatatgtta attttctgta ccttgccagt    3720
cattatgaga aactgaaggg cagccccgaa gataacgaac agaaacaatt attcgtggaa    3780
cagcataagc actatttaga tgaaattata gagcaaatta gtgaattttc taagcgcgtt    3840
atcctcgcgg atgctaattt agacaaagta ctgtcagctt ataataaaca tcgggataag    3900
ccgattagag aacaggccga aaatatcatt catttgttta ccttaaccaa ccttggagca    3960
ccagctgcct tcaaatattt cgataccaca attgatcgta aacggtatac aagtacaaaa    4020
gaagtcttgg acgcaaccct cattcatcaa tctattactg gattatatga gacacgcatt    4080
gatctttcac agctgggcgg agactaa                                        4107

<210> SEQ ID NO 93
<211> LENGTH: 607
<212> TYPE: DNA
<213> ORGANISM: Bacillus subtilis

<400> SEQUENCE: 93
attcctccat ttcttctgc tatcaaaata acagactcgt gattttccaa acgagctttc      60 aaaaagcct ctgccccttg caaatcggat gcctgtctat aaaattcccg atattggtta    120
aacagcggcg caatggcggc cgcatctgat gtctttgctt ggcgaatgtt catcttattt    180
cttcctccct ctcaataatt ttttcattct atccctttc tgtaaagttt attttcaga     240 atacttttat catcatgctt tgaaaaaata tcacgataat atccattgtt ctcacggaag    300
cacacgcagg tcatttgaac gaattttttc gacaggaatt tgccgggact caggagcatt    360
taacctaaaa aagcatgaca tttcagcata atgaacattt actcatgtct attttcgttc    420
ttttctgtat gaaaatagtt atttcgagtc tctacggaaa tagcgagaga tgatatacct    480
aaatagagat aaaatcatct caaaaaatg ggtctactaa aatattattc catctattac    540
aataaattca cagaatagtc ttttaagtaa gtctactctg aattttttta aaggagagg    600 gtaacta                                                              607

<210> SEQ ID NO 94
<211> LENGTH: 138
<212> TYPE: DNA
<213> ORGANISM: Bacillus subtilis

<400> SEQUENCE: 94
tattgaaaat actgacgagg ttatataaga tgaaaataag ttagtttgtt taaacaacaa     60
actaataggt gatgtactta ctatatgaaa taaaatgcat ctgtatttga atgaatttat    120
ttttaagggg gaaatcac                                                  138

<210> SEQ ID NO 95
<211> LENGTH: 177
<212> TYPE: DNA
<213> ORGANISM: Artificial Sequence
<220> FEATURE:
```

<223> OTHER INFORMATION: spac promoter

<400> SEQUENCE: 95

| | | | | |
|---|---|---|---|---|
| ggtagcccttt | gcctacctag | cttccaagaa | agatatccta | acagcacaag agcggaaaga | 60 |
| tgttttgttc | tacatccaga | acaacctctg | ctaaaattcc | tgaaaaattt tgcaaaaagt | 120 |
| tgttgactttt | atctacaagg | tgtggcataa | atgtgtggaat | tgtgagcgct cacaatt | 177 |

<210> SEQ ID NO 96
<211> LENGTH: 100
<212> TYPE: DNA
<213> ORGANISM: Artificial Sequence
<220> FEATURE:
<223> OTHER INFORMATION: hyper-spank promoter

<400> SEQUENCE: 96

| | | | | |
|---|---|---|---|---|
| ctcgagggta | aatgtgagca | ctcacaattc | attttgcaaa | agttgttgac tttatctaca | 60 |
| aggtgtggca | taatgtgtgt | aattgtgagc | ggataacaat | | 100 |

<210> SEQ ID NO 97
<211> LENGTH: 237
<212> TYPE: DNA
<213> ORGANISM: Bacillus subtilis

<400> SEQUENCE: 97

| | | | | |
|---|---|---|---|---|
| ggagttctga | gaattggtat | gccttataag | tccaattaac | agttgaaaac ctgcatagga | 60 |
| gagctatgcg | ggttttttat | tttacataat | gatacataat | ttaccgaaac ttgcggaaca | 120 |
| taattgagga | atcatagaat | tttgtcaaaa | taatttatt | gacaacgtct tattaacgtt | 180 |
| gatataattt | aaatttatt | tgacaaaaat | gggctcgtgt | tgtacaataa atgtagt | 237 |

<210> SEQ ID NO 98
<211> LENGTH: 270
<212> TYPE: DNA
<213> ORGANISM: Bacillus subtilis

<400> SEQUENCE: 98

| | | | | |
|---|---|---|---|---|
| gaattcgagc | tcggtaccga | tcttaacatt | tttccctat | cattttccg tcttcatttg | 60 |
| tcattttttc | cagaaaaat | cgcgtcattc | gactcatgtc | taatccaaca cgtgtctctc | 120 |
| ggcttatccc | ctgacaccgc | ccgccgacag | cccgcatggg | acgattctat caattcagcc | 180 |
| gcggagtcta | gttttatatt | gcagaatgcg | agattgctgg | tttattataa caatataagt | 240 |
| tttcattatt | ttcaaaaagg | gggatttatt | | | 270 |

<210> SEQ ID NO 99
<211> LENGTH: 56
<212> TYPE: DNA
<213> ORGANISM: T5 phage

<400> SEQUENCE: 99

| | | | | |
|---|---|---|---|---|
| aagaatcata | aaaaatttat | ttgctttcag | gaaaattttt | ctgtataata gattca | 56 |

<210> SEQ ID NO 100
<211> LENGTH: 173
<212> TYPE: DNA
<213> ORGANISM: Bacillus subtilis

<400> SEQUENCE: 100

| | | | | |
|---|---|---|---|---|
| gctattgtaa | cataatcggt | acggggtga | aaaagctaac | ggaaaggga gcggaaaaga | 60 |
| atgatgtaag | cgtgaaaaat | tttttatctt | atcacttgaa | attggaaggg agattcttta | 120 | ttataagaat tgtggaattg tgagcggata acaattccca attaaaggag gaa         173

<210> SEQ ID NO 101
<211> LENGTH: 231
<212> TYPE: DNA
<213> ORGANISM: Bacillus subtilis

<400> SEQUENCE: 101
aagcttctca tcaatgattt gaattggagc tcgggctggc cgtcctattg aattaaaaag    60
ccgggctctg cccccggctt tttttaaaag aaaagattga cagtataata gtcaattact   120
ataataaaat tgttcgtaca aatatttatt tataggttta ttttctatca ttagtacgta   180
tcttttgtat ttgaaagcgt tttatttttat gagaaagggg cagtttacat g           231

<210> SEQ ID NO 102
<211> LENGTH: 231
<212> TYPE: DNA
<213> ORGANISM: Bacillus licheniformis

<400> SEQUENCE: 102
ttctgaaatc tgtcaaaaaa aataaaaaac ataccggaaa ttaaattgac agttttttttc   60 ataatgatat aatgaagttg ttcgtacaaa tatgtttttg atgttagttg tacgtacata   120
taatcgcgat acagtttgag atcaaggtat gattatgtt tttttgtaag cgttttaata   180
gtttgctatt ctacacagac accataaaga cgaggaggag gaagctattt g            231

<210> SEQ ID NO 103
<211> LENGTH: 95
<212> TYPE: DNA
<213> ORGANISM: lambda phage

<400> SEQUENCE: 103
gactcctgtt gatagatcca gtaatgacct cagaactcca tctggatttg ttcagaacgc    60
tcggttgccg ccgggcgttt tttattggtg agaat                              95

<210> SEQ ID NO 104
<211> LENGTH: 4809
<212> TYPE: DNA
<213> ORGANISM: Artificial Sequence
<220> FEATURE:
<223> OTHER INFORMATION: cas9 expression cassette

<400> SEQUENCE: 104
attcctccat tttcttctgc tatcaaaata acagactcgt gattttccaa acgagctttc    60
aaaaaagcct ctgccccttg caaatcggat gcctgtctat aaaattcccg atattggtta   120
aacagcggcg caatggcggc cgcatctgat gtctttgctt ggcgaatgtt catcttattt   180
cttcctccct ctcaataatt ttttcattct atcccttttc tgtaaagttt atttttcaga   240 atactttat catcatgctt tgaaaaata tcacgataat atccattgtt ctcacgaag    300 cacacgcagg tcatttgaac gaattttttc gacaggaatt tgccgggact caggagcatt   360
taacctaaaa aagcatgaca tttcagcata atgaacattt actcatgtct attttcgttc   420
ttttctgtat gaaaatagtt atttcgagtc tctacgaaa tagcgagaga tgatatacct   480
aaatagagat aaaatcatct caaaaaaatg ggtctactaa aatattattc catctattac   540
aataaattca cagaatagtc ttttaagtaa gtctactctg aatttttttta aaggagagg   600 gtaactaatg gataaaaaat acagcattgg tctggatatc ggaaccaaca gcgttgggtg   660

-continued

```
ggcagtaata acagatgaat acaaagtgcc gtcaaaaaaa tttaaggttc tggggaatac    720
agatcgccac agcataaaaa agaatctgat tggggcattg ctgtttgatt cgggtgagac    780
agctgaggcc acgcgtctga aacgtacagc aagaagacgt tacacacgtc gtaaaaatcg    840
tatttgctac ttacaggaaa ttttttctaa cgaaatggcc aaggtagatg atagtttctt    900
ccatcgtctc gaagaatctt ttctggttga ggaagataaa aaacacgaac gtcaccctat    960
ctttggcaat atcgtggatg aagtggccta tcatgaaaaa taccctacga tttatcatct   1020
tcgcaagaag ttggttgata gtacggacaa agcggatctg cgtttaatct atcttgcgtt   1080
agcgcacatg atcaaatttc gtggtcattt cttaattgaa ggtgatctga atcctgataa   1140
ctctgatgtg gacaaattgt ttatacaatt agtgcaaacc tataatcagc tgttcgagga   1200
aaacccatt aatgcctctg gagttgatgc caaagcgatt ttaagcgcga gactttctaa   1260
gtcccggcgt ctggagaatc tgatcgccca gttaccaggg gaaaagaaaa atggtctgtt   1320
tggtaatctg attgccctca gtctggggct taccccgaac ttcaaatcca attttgacct   1380
ggctgaggac gcaaagctgc agctgagcaa agatacttat gatgatgacc tcgacaatct   1440
gctcgcccag attggtgacc aatatgcgga tctgtttctg gcagcgaaga atctttcgga   1500
tgctatcttg ctgtcggata ttctgcgtgt taataccgaa atcaccaaag cgcctctgtc   1560
tgcaagtatg atcaagagat acgacgagca ccaccaggac ctgactcttc ttaaggcact   1620
ggtacgccaa cagcttccgg agaaatacaa agaaatattc ttcgaccagt ccaagaatgg   1680
ttacgcgggc tacatcgatg gtggtgcatc acaggaagag ttctataaat ttattaaacc   1740
aatccttgag aaaatggatg gcacggaaga gttacttgtt aaacttaacc gcgaagactt   1800
gcttagaaag caacgtacat tcgacaacgg ctccatccca caccagattc atttaggtga   1860
acttcacgcc atcttgcgca gacaagaaga tttctatccc ttcttaaaag acaatcggga   1920
gaaaatcgag aagatcctga cgttccgcat tccctattat gtcggtcccc tggcacgtgg   1980
taattctcgg tttgcctgga tgacgcgcaa aagtgaggaa accatcaccc cttgaaactt   2040
tgaagaagtc gtggataaag gtgctagcgc gcagtctttt atagaaagaa tgacgaactt   2100
cgataaaaac ttgcccaacg aaaaagtcct gcccaagcac tctcttttat atgagtactt   2160
tactgtgtac aacgaactga ctaaagtgaa atacgttacg gaaggtatgc gcaaacctgc   2220
cttcttagt ggcgagcaga aaaaagcaat tgtcgatctt ctctttaaaa cgaatcgcaa   2280
ggtaactgta aaacagctga aggaagatta tttcaaaaag atcgaatgct ttgattctgt   2340
cgagatctcg ggtgtcgaag atcgtttcaa cgcttcctta gggacctatc atgatttgct   2400
gaagataata aaagacaaag actttctcga caatgaagaa aatgaagata ttctggagga   2460
tattgttttg accttgacct tattcgaaga tagagagatg atcgaggagc gcttaaaaac   2520
ctatgcccac ctgtttgatg acaaagtcat gaagcaatta aagcgccgca gatatacggg   2580
gtggggccgc ttgagccgca agttgattaa cggtattaga gacaagcaga gcggaaaaac   2640
tatcctggat ttcctcaaat ctgacggatt tgcgaaccgc aattttatgc agcttataca   2700
tgatgattcg cttacattca agaggatat tcagaaggct caggtgtctg gcaaggtga   2760
ttcactccac gaacatatag caaatttggc cggctctcct gcgattaaga aggggatcct   2820
gcaaacagtt aaagttgtgg atgaacttgt aaaagtaatg gccgccaca agccggagaa   2880
tatcgtgata gaaatggcgc gcgagaatca acgacacaa aaaggtcaaa agaactcaag   2940
agagagaatg aagcgcattg aggaggggat aaaggaactt ggatctcaaa ttctgaaaga   3000
acatccagtt gaaaacactc agctgcaaaa tgaaaaattg tacctgtact acctgcagaa   3060
```

```
tggaagagac atgtacgtgg atcaggaatt ggatatcaat agactctcgg actatgacgt   3120
agatcacatt gtccctcaga gcttcctcaa ggatgattct atagataata aagtacttac   3180
gagatcggac aaaaatcgcg gtaaatcgga taacgtccca tcggaggaag tcgttaaaaa   3240
gatgaaaaac tattggcgtc aactgctgaa cgccaagctg atcacacagc gtaagtttga   3300
taatctgact aaagccgaac gcggtggtct tagtgaactc gataaagcag gatttataaa   3360
acggcagtta gtagaaacgc gccaaattac gaaacacgtg gctcagatcc tcgattctag   3420
aatgaataca aagtacgatg aaaacgataa actgatccgt gaagtaaaag tcattacctt   3480
aaaatctaaa cttgtgtccg atttccgcaa agattttcag ttttacaagg tccgggaaat   3540
caataactat caccatgcac atgatgcata tttaaatgcg gttgtaggca cggcccttat   3600
taagaaatac cctaaactcg aaagtgagtt tgtttatggg gattataaag tgtatgacgt   3660
tcgcaaaatg atcgcgaaat cagaacagga atcggtaag gctaccgcta aatactttt   3720 ttattccaac attatgaatt ttttaagac cgaaataact ctcgcgaatg gtgaaatccg   3780
taaacggcct cttatagaaa ccaatggtga acgggagaa atcgtttggg ataaaggtcg   3840
tgactttgcc accgttcgta aagtcctctc aatgccgcaa gttaacattg tcaagaagac   3900
ggaagttcaa acaggggat tctccaaaga atctatcctg ccgaagcgta acagtgataa   3960
acttattgcc agaaaaaaag attgggatcc aaaaaaatac ggaggctttg attcccctac   4020
cgtcgcgtat agtgtgctgg tggttgctaa agtcgagaaa gggaaagca agaaattgaa   4080 atcagttaaa gaactgctgg gtattacaat tatggaaaga tcgtcctttg agaaaaatcc   4140
gatcgacttt ttagaggcca agggtataa ggaagtgaaa aaagatctca tcatcaaatt   4200
accgaagtat agtctttttg agctggaaaa cggcagaaaa agaatgctgg cctccgcggg   4260
cgagttacag aagggaaatg agctggcgct gccttccaaa tatgttaatt ttctgtacct   4320
tgccagtcat tatgagaaac tgaagggcag ccccgaagat aacgaacaga acaattatt   4380 cgtggaacag cataagcact attagatga aattatagag caaattagtg aattttctaa   4440
gcgcgttatc ctcgcggatg ctaatttaga caaagtactg tcagcttata ataaacatcg   4500
ggataagccg attagagaac aggccgaaaa tatcattcat ttgtttacct taaccaacct   4560
tggagcacca gctgccttca aatatttcga taccacaatt gatcgtaaac ggtatacaag   4620
tacaaaagaa gtcttggacg caaccctcat tcatcaatct attactggat tatatgagac   4680
acgcattgat ctttcacagc tgggcggaga ctaagactcc tgttgataga tccagtaatg   4740
acctcagaac tccatctgga tttgttcaga acgctcggtt gccgccgggc gttttttatt   4800
ggtgagaat                                                            4809
```

<210> SEQ ID NO 105
<211> LENGTH: 23
<212> TYPE: DNA
<213> ORGANISM: Bacillus licheniformis

<400> SEQUENCE: 105

```
aatggctgcg gctctggaaa tgg                                              23
```

<210> SEQ ID NO 106
<211> LENGTH: 17
<212> TYPE: DNA
<213> ORGANISM: Artificial Sequence
<220> FEATURE:
<223> OTHER INFORMATION: 17 bp VT

```
<400> SEQUENCE: 106
ggctgcggct ctggaaa                                                       17

<210> SEQ ID NO 107
<211> LENGTH: 18
<212> TYPE: DNA
<213> ORGANISM: Artificial Sequence
<220> FEATURE:
<223> OTHER INFORMATION: 18bp VT

<400> SEQUENCE: 107
tggctgcggc tctggaaa                                                      18

<210> SEQ ID NO 108
<211> LENGTH: 19
<212> TYPE: DNA
<213> ORGANISM: Artificial Sequence
<220> FEATURE:
<223> OTHER INFORMATION: 19bp VT

<400> SEQUENCE: 108
atggctgcgg ctctggaaa                                                     19

<210> SEQ ID NO 109
<211> LENGTH: 20
<212> TYPE: DNA
<213> ORGANISM: Artificial Sequence
<220> FEATURE:
<223> OTHER INFORMATION: 20bp VT

<400> SEQUENCE: 109
aatggctgcg gctctggaaa                                                    20

<210> SEQ ID NO 110
<211> LENGTH: 76
<212> TYPE: DNA
<213> ORGANISM: Artificial Sequence
<220> FEATURE:
<223> OTHER INFORMATION: Cas9 endoncuclease recognition domain

<400> SEQUENCE: 110
gttttagagc tagaaatagc aagttaaaat aaggctagtc cgttatcaac ttgaaaaagt        60
ggcaccgagt cggtgc                                                        76

<210> SEQ ID NO 111
<211> LENGTH: 96
<212> TYPE: DNA
<213> ORGANISM: Artificial Sequence
<220> FEATURE:
<223> OTHER INFORMATION: DNA encoding gRNA targeting duplication

<400> SEQUENCE: 111
aatggctgcg gctctggaaa gttttagagc tagaaatagc aagttaaaat aaggctagtc        60
cgttatcaac ttgaaaaagt ggcaccgagt cggtgc                                  96

<210> SEQ ID NO 112
<211> LENGTH: 368
<212> TYPE: DNA
<213> ORGANISM: Artificial Sequence
<220> FEATURE:
<223> OTHER INFORMATION: duplication gRNA expression cassette

<400> SEQUENCE: 112 ggtagcccctt gcctacctag cttccaagaa agatatccta acagcacaag agcggaaaga      60
```

```
tgtttttgttc tacatccaga acaacctctg ctaaaattcc tgaaaaattt tgcaaaaagt    120
tgttgacttt atctacaagg tgtggcataa tgtgtggaat tgtgagcgct cacaattaat    180
ggctgcggct ctggaaagtt ttagagctag aaatagcaag ttaaaataag gctagtccgt    240
tatcaacttg aaaagtggc accgagtcgg tgcgactcct gttgatagat ccagtaatga     300
cctcagaact ccatctggat tgttcagaa cgctcggttg ccgccgggcg ttttttattg     360
gtgagaat                                                             368

<210> SEQ ID NO 113
<211> LENGTH: 500
<212> TYPE: DNA
<213> ORGANISM: Bacillus licheniformis

<400> SEQUENCE: 113
gtatgaggaa ctgatggcat ctgcaggcta tatcagcgcg tctacagtcc aggaagcaag     60
aagcagctat gattccattt acgacatcgt gtcacagtac gatttagagg accttctct     120 gtttgacagc gaaaagtgga aggtgctttc aaaaaaagac atcgaaaacc tggacaaata    180
tttcgacttt ctcgtgcagg aagcaagcag ccgaaacaaa aactgaatac ttctccgcgg    240
cacactctcc tctctatcat tttcgtctgt ttacgatcct gctgttattt tatcccttat    300
gttaactttt gtcaatattt tcctgtcta agtatttcct atagtcaaca tttgtattaa     360
aatgttcata tcatgaattt gcgggggga tggcgatgac aaggttcggc gagcggctca    420
aagagctgag ggaacaaaga agcctgtcgg ttaatcagct tgccatgtat gccggtgtga    480
gcgccgcagc catttccaga                                                500

<210> SEQ ID NO 114
<211> LENGTH: 500
<212> TYPE: DNA
<213> ORGANISM: Bacillus licheniformis

<400> SEQUENCE: 114
atcgaaaacg gccaccgcgg cgttcccaag cccgcgacga tcagaaaatt ggccgaggct     60
ctgaaaatgc cgtacgagca gctcatggat attgccggtt atatgagagc tgacgagatt    120
cgcgaacagc cgcgcggcta tgtcacgatg caggagatcg cggccaagca cggcgtcgaa    180
gacctgtggc tgtttaaacc cgagaaatgg gactgtttgt cccgcgaaga cctgctcaac    240
ctcgaacagt attttcattt tttggttaat gaagcgaaga agcgccaatc ataaaaagcc    300 gaatttcct tttaggagaa gttcggcttt tttcggctgc cttaagcggc atccggattc      360
ggcgtcttgc ctttatgatg cttaacgggg ctcagcgcac gctcgagcca tcccatgaac    420
agatcggcga tgatcgccat cagcgccgtc gggatcgcgc tgctagaat gatcgctgtt     480 ccgttggtcg cgtttgatcc                                                500

<210> SEQ ID NO 115
<211> LENGTH: 1000
<212> TYPE: DNA
<213> ORGANISM: Artificial Sequence
<220> FEATURE:
<223> OTHER INFORMATION: rghR2 duplication editing template

<400> SEQUENCE: 115
gtatgaggaa ctgatggcat ctgcaggcta tatcagcgcg tctacagtcc aggaagcaag     60
aagcagctat gattccattt acgacatcgt gtcacagtac gatttagagg accttctct    120
```

```
gtttgacagc gaaaagtgga aggtgctttc aaaaaaagac atcgaaaacc tggacaaata       180
tttcgacttt ctcgtgcagg aagcaagcag ccgaaacaaa aactgaatac ttctccgcgg       240
cacactctcc tctctatcat tttcgtctgt ttacgatcct gctgttattt tatcccttat       300 gttaacttt gtcaatattt ttcctgtcta agtatttcct atagtcaaca tttgtattaa        360
aatgttcata tcatgaattt gcggggggga tggcgatgac aaggttcggc gagcggctca      420
aagagctgag ggaacaaaga agcctgtcgg ttaatcagct tgccatgtat gccggtgtga      480
gcgccgcagc catttccaga atcgaaaacg gccaccgcgg cgttcccaag cccgcgacga      540
tcagaaaatt ggccgaggct ctgaaaatgc cgtacgagca gctcatggat attgccggtt      600
atatgagagc tgacgagatt cgcgaacagc cgcgcggcta tgtcacgatg caggagatcg      660
cggccaagca cggcgtcgaa gacctgtggc tgtttaaacc cgagaaatgg gactgtttgt      720
cccgcgaaga cctgctcaac ctcgaacagt attttcattt tttggttaat gaagcgaaga      780
agcgccaatc ataaaaagcc gaatttccct tttaggagaa gttcggcttt ttcggctgc       840 cttaagcggc atccggattc ggcgtcttgc ctttatgatg cttaacgggg ctcagcgcac      900
gctcgagcca tcccatgaac agatcggcga tgatcgccat cagcgccgtc gggatcgcgc      960
ctgctagaat gatcgctgtt ccgttggtcg cgtttgatcc                           1000
```

<210> SEQ ID NO 116
<211> LENGTH: 20
<212> TYPE: DNA
<213> ORGANISM: Bacillus licheniformis

<400> SEQUENCE: 116

```
gcgaatcgaa aacggaaagc                                                   20
```

<210> SEQ ID NO 117
<211> LENGTH: 20
<212> TYPE: DNA
<213> ORGANISM: Artificial Sequence
<220> FEATURE:
<223> OTHER INFORMATION: rghR2 locus forward

<400> SEQUENCE: 117

```
gcgaatcgaa aacggaaagc                                                   20
```

<210> SEQ ID NO 118
<211> LENGTH: 20
<212> TYPE: DNA
<213> ORGANISM: Artificial Sequence
<220> FEATURE:
<223> OTHER INFORMATION: rghR2 locus reverse

<400> SEQUENCE: 118

```
tcatcgcgat cggcattacg                                                   20
```

<210> SEQ ID NO 119
<211> LENGTH: 1146
<212> TYPE: DNA
<213> ORGANISM: Artificial Sequence
<220> FEATURE:
<223> OTHER INFORMATION: Edited rghR2 locus

<400> SEQUENCE: 119

```
gcgaatcgaa aacggaaagc gcggcgtgcc gaagccggcg acgatcagaa aactggcgga       60
cgctttgaaa gtcccgtatg aggaactgat ggcatctgca ggctatatca gcgcgtctac      120
agtccaggaa gcaagaagca gctatgattc catttacgac atcgtgtcac agtacgattt     180
```

-continued

```
agaggacctt tctctgtttg acagcgaaaa gtggaaggtg ctttcaaaaa aagacatcga    240
aaacctggac aaatatttcg actttctcgt gcaggaagca agcagccgaa acaaaaactg    300
aatacttctc cgcggcacac tctcctctct atcattttcg tctgtttacg atcctgctgt    360
tattttatcc cttatgttaa cttttgtcaa tatttttcct gtctaagtat ttcctatagt    420
caacatttgt attaaaatgt tcatatcatg aatttgcggg ggggatggcg atgacaaggt    480
tcggcgagcg gctcaaagag ctgagggaac aaagaagcct gtcggttaat cagcttgcca    540
tgtatgccgg tgtgagcgcc gcagccattt ccagaatcga aaacggccac cgcggcgttc    600
ccaagcccgc gacgatcaga aaattggccg aggctctgaa aatgccgtac gagcagctca    660
tggatattgc cggttatatg agagctgacg agattcgcga acagccgcgc ggctatgtca    720
cgatgcagga gatcgcggcc aagcacggcg tcgaagacct gtggctgttt aaacccgaga    780
aatgggactg tttgtcccgc gaagacctgc tcaacctcga acagtatttt cattttttgg    840
ttaatgaagc gaagaagcgc caatcataaa aagccgaatt tccctttttag gagaagttcg    900 gcttttttcg gctgccttaa gcggcatccg gattcggcgt cttgccttta tgatgcttaa    960
cggggctcag cgcacgctcg agccatccca tgaacagatc ggcgatgatc gccatcagcg   1020
ccgtcgggat cgcgcctgct agaatgatcg ctgttccgtt ggtcgcgttt gatcccctga   1080
caatgatatc cccgaggccg cctgcgccga caaacgtgcc gatggccgta atgccgatcg   1140
cgatga                                                              1146
```

<210> SEQ ID NO 120
<211> LENGTH: 20
<212> TYPE: DNA
<213> ORGANISM: Artificial Sequence
<220> FEATURE:
<223> OTHER INFORMATION: rghR2 sequencing primer

<400> SEQUENCE: 120

```
tttcgacttt ctcgtgcagg                                                20
```

<210> SEQ ID NO 121
<211> LENGTH: 23
<212> TYPE: DNA
<213> ORGANISM: Bacillus licheniformis

<400> SEQUENCE: 121

```
ctttccgatc acaagttgtc cgg                                            23
```

<210> SEQ ID NO 122
<211> LENGTH: 23
<212> TYPE: DNA
<213> ORGANISM: Bacillus licheniformis

<400> SEQUENCE: 122

```
tttccgatca caagttgtcc ggg                                            23
```

<210> SEQ ID NO 123
<211> LENGTH: 23
<212> TYPE: DNA
<213> ORGANISM: Bacillus licheniformis

<400> SEQUENCE: 123

```
aggcccggac aacttgtgat cgg                                            23
```

<210> SEQ ID NO 124

```
<211> LENGTH: 23
<212> TYPE: DNA
<213> ORGANISM: Bacillus licheniformis

<400> SEQUENCE: 124
gagttttaaa tggcgaaagg agg                                         23

<210> SEQ ID NO 125
<211> LENGTH: 23
<212> TYPE: DNA
<213> ORGANISM: Bacillus licheniformis

<400> SEQUENCE: 125
ttaaatggcg aaaggaggcc cgg                                         23

<210> SEQ ID NO 126
<211> LENGTH: 23
<212> TYPE: DNA
<213> ORGANISM: Bacillus licheniformis

<400> SEQUENCE: 126
gcagagtttt aaatggcgaa agg                                         23

<210> SEQ ID NO 127
<211> LENGTH: 23
<212> TYPE: DNA
<213> ORGANISM: Bacillus licheniformis

<400> SEQUENCE: 127
acactcagca gagttttaaa tgg                                         23

<210> SEQ ID NO 128
<211> LENGTH: 23
<212> TYPE: DNA
<213> ORGANISM: Bacillus licheniformis

<400> SEQUENCE: 128
aactctgctg agtgtcgccg ggg                                         23

<210> SEQ ID NO 129
<211> LENGTH: 23
<212> TYPE: DNA
<213> ORGANISM: Bacillus licheniformis

<400> SEQUENCE: 129
aaaactctgc tgagtgtcgc cgg                                         23

<210> SEQ ID NO 130
<211> LENGTH: 23
<212> TYPE: DNA
<213> ORGANISM: Bacillus licheniformis

<400> SEQUENCE: 130
aaactctgct gagtgtcgcc ggg                                         23

<210> SEQ ID NO 131
<211> LENGTH: 23
<212> TYPE: DNA
<213> ORGANISM: Bacillus licheniformis

<400> SEQUENCE: 131
cattgaaatc ggcgtatccc cgg                                         23
```

```
<210> SEQ ID NO 132
<211> LENGTH: 23
<212> TYPE: DNA
<213> ORGANISM: Bacillus licheniformis

<400> SEQUENCE: 132
cggggatacg ccgatttcaa tgg                                          23

<210> SEQ ID NO 133
<211> LENGTH: 23
<212> TYPE: DNA
<213> ORGANISM: Bacillus licheniformis

<400> SEQUENCE: 133
aatcagcttg ccattgaaat cgg                                          23

<210> SEQ ID NO 134
<211> LENGTH: 23
<212> TYPE: DNA
<213> ORGANISM: Bacillus licheniformis

<400> SEQUENCE: 134
ttcaatggca agctgattta agg                                          23

<210> SEQ ID NO 135
<211> LENGTH: 23
<212> TYPE: DNA
<213> ORGANISM: Bacillus licheniformis

<400> SEQUENCE: 135
gattgtgttc aatcatgtac tgg                                          23

<210> SEQ ID NO 136
<211> LENGTH: 23
<212> TYPE: DNA
<213> ORGANISM: Bacillus licheniformis

<400> SEQUENCE: 136
attagaaagg ggagtaatca tgg                                          23

<210> SEQ ID NO 137
<211> LENGTH: 23
<212> TYPE: DNA
<213> ORGANISM: Bacillus licheniformis

<400> SEQUENCE: 137
aaacataaga gattagaaag ggg                                          23

<210> SEQ ID NO 138
<211> LENGTH: 23
<212> TYPE: DNA
<213> ORGANISM: Bacillus licheniformis

<400> SEQUENCE: 138
gaaacataag agattagaaa ggg                                          23

<210> SEQ ID NO 139
<211> LENGTH: 23
<212> TYPE: DNA
<213> ORGANISM: Bacillus licheniformis

<400> SEQUENCE: 139
agaaacataa gagattagaa agg                                          23
```

<210> SEQ ID NO 140
<211> LENGTH: 1748
<212> TYPE: DNA
<213> ORGANISM: Artificial Sequence
<220> FEATURE:
<223> OTHER INFORMATION: amylase expression cassette

<400> SEQUENCE: 140

```
tcgctgataa acagctgaca tcaactaaaa gcttcattaa atactttgaa aaaagttgtt      60
gacttaaaag aagctaaatg ttatagtaat aaaacagaat agtctttaa gtaagtctac     120
tctgaatttt tttaaaagga gagggtaaag aatgaaacaa caaaaacggc tttacgcccg     180
attgctgacg ctgttatttg cgctcatctt cttgctgcct cattctgcag ctagcgcagc     240
agcgacaaac ggaacaatga tgcagtattt cgagtggtat gtacctaacg acggccagca     300
atggaacaga ctgagaacag atgccccta cttgtcatct gttggtatta acgcagtatg     360
gataccgccg gcttataagg gcacgtctca agcagatgtg gggtacggcc cgtacgatct     420
gtatgattta ggcgagttta atcaaaaagg tacagtcaga acgaagtatg gcacaaaagg     480
agaacttaaa tctgctgtca acacgctgca ttcaaatgga atccaagtgt atggtgatgt     540
cgtgatgaat cataaagcag gtgctgatta tacagaaaac gtaacggcgg tggaggtgaa     600
tccgtctaat agatatcagg aaatcagcgg cgaatataat attcaggcat ggacaggctt     660
caactttccg ggcagaggaa caacgtattc taactggaaa tggcagtggt tccattttga     720
tggaacggat tgggaccaga gcagaagcct ctctagaatc ttcaaattcg atggaaaggc     780
gtgggactgg ccggtttctt cagaaaacgg aaattatgac tatctgatgt acgcggacta     840
tgattatgac catccggatg tcgtgaatga aatgaaaaag tggggcgtct ggtatgccaa     900
cgaagttggg ttagatggat acagacttga cgcggtcaaa catattaaat ttagcttct     960
caaagactgg gtggataacg caagagcagc gacgggaaaa gaaatgttta cggttggcga    1020
atattggcaa aatgatttag gcgccctgaa taactacctg gcaaaggtaa attacaacca    1080
atctctttt gatgcgccgt tgcattacaa cttttacgct gcctcaacag ggggtggata    1140
ttacgatatg agaaatattc ttaataacac gttagtcgca agcaatccga caaaggctgt    1200
tacgttagtt gagaatcatg acacacagcc tggacaatca ctggaatcaa cagtccaacc    1260
gtggtttaaa ccgttagcct acgcgtttat tctcacgaga agcggaggct atccttctgt    1320
attttatgga gatatgtacg gtacaaaagg aacgacaaca agagagatcc ctgctcttaa    1380
atctaaatc gaacctttgc ttaaggctag aaaagactat gcttatggaa cacagagaga    1440
ctatattgat aacccggatg tcattggctg gacgagagaa ggggactcaa cgaaagccaa    1500
gagcggtctg gccacagtga ttacagatgg gccgggcggt tcaaaaagaa tgtatgttgg    1560
cacgagcaat gcgggtgaaa tctggtatga tttgacaggg aatagaacag ataaaatcac    1620
gattggaagc gatggctatg caacatttcc tgtcaataag gaatcagttt cagtatgggt    1680
gcagcaatga aagcttctcg aggttaacag aggacggatt tcctgaagga aatccgtttt    1740
tttattttt                                                           1748
```

<210> SEQ ID NO 141
<211> LENGTH: 1759
<212> TYPE: DNA
<213> ORGANISM: Artificial Sequence
<220> FEATURE:
<223> OTHER INFORMATION: amylase expression cassette

<400> SEQUENCE: 141

```
gtcgctgata acagctgac atcaatatcc tattttttca aaaatatatt taaaagttg    60 ttgacttaaa agaagctaaa tgttatagta ataaaacaga atagtctttt aagtaagtct  120
actctgaatt tttttaaaag gagagggtaa agaatgaaac aacaaaaacg gctttacgcc  180
cgattgctga cgctgttatt tgcgctcatc ttcttgctgc ctcattctgc agctagcgca  240
gccgcaccgt ttaacggtac catgatgcag tattttgaat ggtacttgcc ggatgatggc  300
acgttatgga ccaaagtggc caatgaagcc aacaacttat ccagccttgg catcaccgct  360
ctttggctgc cgcccgctta caaaggaaca agccgcagcg acgtagggta cggagtatac  420
gacttgtatg acctcggcga attcaatcaa aaagggaccg tccgcacaaa atatggaaca  480
aaagctcaat atcttcaagc cattcaagcc gcccacgccg ctggaatgca agtgtacgcc  540
gatgtcgtgt tcgaccataa aggcggcgct gacggcacgg aatgggtgga cgccgtcgaa  600
gtcaatccgt ccgaccgcaa ccaagaaatc tcgggcacct atcaaatcca agcatggacg  660
aaatttgatt ttcccgggcg gggcaacacc tactccagct taagtggcg ctggtaccat  720 tttgacggcg ttgattggga cgaaagccga aaattaagcc gcatttacaa attcaggggc  780
atcggcaaag cgtgggattg gccggtagac acagaaaacg gaaactatga ctacttaatg  840
tatgccgacc ttgatatgga tcatcccgaa gtcgtgaccg agctgaaaaa ctgggggaaa  900
tggtatgtca acacaacgaa cattgatggg ttccggcttg atgccgtcaa gcatattaag  960
ttcagttttt ttcctgattg gttgtcgtat gtgcgttctc agactggcaa gccgctattt 1020
accgtcgggg aatattggag ctatgacatc aacaagttgc acaattacat tacgaaaaca 1080
aacggaacga tgtctttgtt tgatgccccg ttacacaaca aattttatac cgcttccaaa 1140
tcagggggcg catttgatat gcgcacgtta atgaccaata ctctcatgaa agatcaaccg 1200
acattggccg tcaccttcgt tgataatcat gacaccgaac ccggccaagc gcttcagtca 1260
tgggtcgacc catggttcaa accgttggct tacgccttta ttctaactcg gcaggaagga 1320
tacccgtgcg tcttttatgg tgactattat ggcattccac aatataacat tccttcgctg 1380
aaaagcaaaa tcgatccgct cctcatcgcg cgcagggatt atgcttacgg aacgcaacat 1440
gattatcttg atcactccga catcatcggg tggacaaggg aagggtcac tgaaaaacca 1500 ggatccgggc tggccgcact gatcaccgat gggccgggag aagcaaatg gatgtacgtt 1560 ggcaaacaac acgctggaaa agtgttctat gaccttaccg gcaaccggag tgacaccgtc 1620
accatcaaca gtgatggatg ggggaattc aaagtcaatg gcggttcggt ttcggtttgg 1680
gttcctagaa aaacgaccta aaagcttctc gaggttaaca gaggacggat ttcctgaagg 1740
aaatccgttt ttttatttt                                              1759
```

<210> SEQ ID NO 142
<211> LENGTH: 1581
<212> TYPE: DNA
<213> ORGANISM: Artificial Sequence
<220> FEATURE:
<223> OTHER INFORMATION: expression cassette, synthetic sequence

<400> SEQUENCE: 142

```
gtcgctgata acagctgac atcaatatcc tattttttca aaaatatatt taaaagttg    60 ttgacttaaa agaagctaaa tgttatagta ataaaacaga atagtctttt aagtaagtct  120
actctgaatt tttttaaaag gagagggtaa agaatgaaac aacaaaaacg gctttacgcc  180
cgattgctga cgctgttatt tgcgctcatc ttcttgctgc ctcattctgc agcttcagca  240
```

```
gctgatcaag caggaaaaag cccggcaggc gtcagatatc atggcggtga tgaaatcatc      300
cttcagggct ttcattggaa cgtcgtcaga gaagcgccgt ataactggta taacatcctg      360
agacaacaag cgagcacaat tgccgctgat ggcttttccg caatctggat gccggttccg      420
tggagagatt ttagcagctg gacggatgga gataaaagcg gaggcggcga aggatatttt      480
tggcatgact ttaacaaaaa cggccgctat ggaagcgatg ctcaactgag acaagcagca      540
ggagcacttg gaggagcagg agtcaaagtc ctgtacgatg tcgtcccgaa ccatatgaac      600 cgctttatc cggacaaaga aatcaatctg ccggcaggcc aaagattttg gagaaacgat       660
tgcccggacc cggaaatgg accgaatgat tgcgatgatg cgatagatt tctgggcggc        720 gaagcggatc tgaatacagg ccatccgcaa atctatggca tgtttcggga cgaatttacg      780
aatctgagaa gcggatatgg agcgggcgga tttcgctttg atttgtcag aggctatgcc        840 ccggaaagag ttgatagctg gatgagcgat tcagcggata gcagcttttg cgtcggcgaa      900
ctttggaaag aaccgagcga atatccgccg tgggattgga gaaatacagc gagctggcag      960
cagatcatca aagattggag cgatagagca aaatgcccgg tctttgactt tgccctgaaa     1020
gaacgcatgc aaaatggaag cgtcgccgat tggaaacatg cctgaacgg aaatccggac      1080 ccgagatgga gagaagtcgc cgtcacgttt gtcgataacc atgacacagg atatagcccg     1140
ggacaaaatg gaggacaaca taaatggccg cttcaagatg ccttatcag acaggcgtat      1200 gcctatatcc ttcatcacc gggaacaccg gttgtttatt ggccgcatat gtatgattgg      1260
ggctatggcg atttcatccg ccaactgatc caggttagaa gaacagcagg agtcagagcg      1320
gatagcgcca ttagctttca tagcggctat agcggacttg tcgctacagt tagcggcagc     1380
caacaaacac tggtcgtcgc cctgaatagc gatctggcaa atccgggaca agttgctagc      1440 ggcagctttta gcaagcagt caatgccagc aatggccaag tcagagtctg gagaagcgga     1500
agcggagatg gaggaggaaa tgacggcggc taaaagagca gagaggacgg atttcctgaa     1560
ggaaatccgt tttttttattt t                                               1581
```

<210> SEQ ID NO 143
<211> LENGTH: 1452
<212> TYPE: DNA
<213> ORGANISM: Artificial Sequence
<220> FEATURE:
<223> OTHER INFORMATION: Synthetic Cytophaga sp. variant #2 amylase
      expression cassette

<400> SEQUENCE: 143

```
gcagcgacaa acggaacaat gatgcagtat ttcgagtggt atgtacctaa cgacggccag       60
caatggaaca gactgagaac agatgcccct tacttgtcat ctgttggtat tacagcagta      120
tggacaccgc cggcttataa gggcacgtct caagcagatg tggggtacgg cccgtacgat      180
ctgtatgatt taggcgagtt taatcaaaaa ggtacagtca gaacgaagta tggcacaaaa      240
ggagaactta aatctgctgt caacacgctg cattcaaatg gaatccaagt gtatggtgat      300
gtcgtgatga atcataaagc aggtgctgat tatacagaaa acgtaacggc ggtggaggtg      360
aatccgtcta atagatatca ggaaacgagc ggcgaatata atattcaggc atggacaggc      420
ttcaactttc cgggcagagg aacaacgtat tctaactgga atggcagtg gttccatttt      480 gatggaacgg attgggacca gagcagaagc ctctctagaa tcttcaaatt ccatggaaag      540
gcgtgggact ggccggtttc ttcagaaaac ggaaattatg actatctgat gtacgcggac      600
tatgattatg accatccgga tgtcgtgaat gaaatgaaaa agtggggcgt ctggtatgcc      660
```

```
aacgaagttg ggttagatgg atacagactt gacgcggtca aacatattaa atttagcttt    720
ctcaaagact gggtggataa cgcaagagca gcgacgggaa aagaaatgtt tacggttggc    780
gaatattggc aaaatgattt aggggccctg aataactacc tggcaaaggt aaattacaac    840
caatctcttt ttgatgcgcc gttgcattac aacttttacg ctgcctcaac aggggtgga    900 gcgtacgata tgagaaatat tcttaataac acgttagtcg caagcaatcc gacaaaggct    960
gttacgttag ttgagaatca tgacacacag cctggacaat cactggaatc aacagtccaa   1020
ccgtggttta aaccgttagc ctacgcgttt attctcacga gaagcggagg ctatcctgcg   1080
gtattttatg gagatatgta cggtacaaaa ggaacgacaa catatgagat ccctgctctt   1140
aaatctaaaa tcgaaccttt gcttaaggct agaaaagact atgcttatgg aacacagaga   1200
gactatattg ataacccgga tgtcattggc tggacgagag aaggggactc aacgaaagcc   1260
aagagcggtc tggccacagt gattacagat gggccgggcg gttcaaaaag aatgtatgtt   1320
ggcacgagca atgcgggtga aatctggtat gatttgacag gaatagaac agataaaatc    1380 acgattggaa gcgatggcta tgcaacattt cctgtcaatg ggggctcagt ttcagtatgg   1440
gtgcagcaat ga                                                       1452

<210> SEQ ID NO 144
<211> LENGTH: 846
<212> TYPE: DNA
<213> ORGANISM: Artificial Sequence
<220> FEATURE:
<223> OTHER INFORMATION: synthetic allele glcT1 sequence

<400> SEQUENCE: 144
gtgaacagat cctttaccgt tgaaaaggta ctcaacaaca acgttttaat cgctctccat     60
gatgattaca gagaagttgt cttgattggc aaaggaatcg gttttggtaa aaagcgcgga    120
gatcttatcg aacatgagaa ctacgaaaaa atgtttatcc tggaaaatga taaggaacaa    180
tcgcagtata agaagctctt cacttatgtc gatgaaaaaa tggttgatat cgccaatgat    240
gtcatctacc atatcgcgca aaaaatcggc cagccgctga acgaacacat tcatgtcgcc    300
ctgacggacc atatcgcatt tgcagttaag cgtctagaaa agggatttga tatgaaaaat    360
ccgtttttgc ttgagacgga atcgctttat ccgaaggaat acgaagtcgc caaggaagcc    420
gtcgatatga ttaatgaaaa atccgacatt cagctgcctg aaggtgaaat cgggttcatc    480
gcgcttcata tccacagtgc gatgacaaac cgcccgcttt ctgaagtcaa tcagcattca    540
caactgatct ccaggcttgt ccaggtcatc gaagattcat tccagatgca agtcaacagg    600
gaaagcgtga actatttgcg gctgatcagg cacttgcgct ttacgattga caggataaaa    660
cgggacgagc cgattcagga accggaaaaa ttaatgttgt tgttgaaaac ggaatatccg    720
ctgtgttaca atactgcttg gaagatgatc aagatcttgc agcaagcgct caagaaaccg    780
gttcatgagg cagaagccgt ttatttgaca ttgcatttgt accgtttgac taataaaatt    840
tcataa                                                               846
```